US012570761B2

(12) United States Patent
Berne et al.

(10) Patent No.: US 12,570,761 B2
(45) Date of Patent: Mar. 10, 2026

(54) ANTI-CEACAM5 ANTIBODIES AND USES THEREOF

(71) Applicant: SANOFI, Paris (FR)

(72) Inventors: Pierre-Francois Berne, Paris (FR); Francis Blanche, Paris (FR); Hervé Bouchard, Paris (FR); Béatrice Cameron, Paris (FR); Tarik Dabdoubi, Paris (FR); Stéphanie Decary, Paris (FR); Paul Ferrari, Paris (FR); Alexey Rak, Paris (FR)

(73) Assignee: SANOFI, Paris (FR)

( * ) Notice: Subject to any disclaimer, the term of this patent is extended or adjusted under 35 U.S.C. 154(b) by 433 days.

(21) Appl. No.: 17/705,016

(22) Filed: Mar. 25, 2022

(65) Prior Publication Data

US 2022/0340682 A1 Oct. 27, 2022

Related U.S. Application Data

(60) Division of application No. 16/558,939, filed on Sep. 3, 2019, now Pat. No. 11,332,542, which is a division of application No. 15/446,465, filed on Mar. 1, 2017, now Pat. No. 10,457,739, which is a division of application No. 14/716,377, filed on May 19, 2015, now Pat. No. 9,617,345, which is a continuation of application No. PCT/EP2013/074291, filed on Nov. 20, 2013.

(30) Foreign Application Priority Data

Nov. 20, 2012 (EP) .................................... 12306444

(51) Int. Cl.

| | |
|---|---|
| ***C07K 16/30*** | (2006.01) |
| ***A61K 31/537*** | (2006.01) |
| ***A61K 47/68*** | (2017.01) |
| ***C07K 16/28*** | (2006.01) |
| ***C07K 16/46*** | (2006.01) |
| ***G01N 33/575*** | (2026.01) |

(52) U.S. Cl.

CPC ........ *C07K 16/3007* (2013.01); *A61K 31/537* (2013.01); *A61K 47/68033* (2023.08); *A61K 47/6849* (2017.08); *A61K 47/6853* (2017.08); *C07K 16/2896* (2013.01); *C07K 16/464* (2013.01); *G01N 33/57565* (2026.01); *C07K 2317/24* (2013.01); *C07K 2317/33* (2013.01); *C07K 2317/34* (2013.01); *C07K 2317/565* (2013.01); *C07K 2317/73* (2013.01); *C07K 2317/77* (2013.01); *C07K 2317/92* (2013.01); *G01N 2333/70503* (2013.01)

(58) Field of Classification Search

CPC ........................ C07K 16/3007; A61K 47/6853
USPC ....................................................... 424/174.1
See application file for complete search history.

(56) References Cited

U.S. PATENT DOCUMENTS

| | | | |
|---|---|---|---|
| 1,045,773 | A | 11/1912 | Cole |
| 4,179,337 | A | 12/1979 | Davis et al. |
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 4,861,719 | A | 8/1989 | Miller |
| 4,975,278 | A | 12/1990 | Senter et al. |
| 5,202,238 | A | 4/1993 | Fell, Jr. et al. |
| 5,204,244 | A | 4/1993 | Fell et al. |
| 5,208,020 | A | 5/1993 | Chari et al. |

(Continued)

FOREIGN PATENT DOCUMENTS

| | | | |
|---|---|---|---|
| CN | 101802012 | A | 8/2010 |
| CN | 108341876 | A | 7/2018 |

(Continued)

OTHER PUBLICATIONS

ClinicalTrials.gov, "SAR408701 in Combination With Ramucirumab in Pre-treated Patients With Non Squamous Non-small Cell Lung Cancer (NSQ NSCLC) (CARMEN-LC04)", May 19, 2020.
International Search Report and Written Opinion received for PCT Patent Application No. PCT/EP2021/081038, dated Feb. 8, 2022.
Sanofi, "Clinical Trials Appendices", Jul. 29, 2020, Retrieved from url: https://www.sanofi.com/dam/jcr:5aa069ad-47d7-43db-a46b-fdc22b1dc7a3/2020_07_29_Q2_2020_RD_Appendix.pdf, p. 59, SAR408701.
Almagro et al. (Jan. 1, 2008) "Humanization of Antibodies", Frontiers in Bioscience, vol. 13, pp. 1619-1633.

(Continued)

*Primary Examiner* — Lynn A Bristol
(74) *Attorney, Agent, or Firm* — MH2 Technology Law Group, LLP

(57) ABSTRACT

Antibodies are provided which bind human and *Macaca fascicularis* CEACAM5 proteins, as well as isolated nucleic acids, vectors and host cells comprising a sequence encoding the antibodies. Also provided are immunoconjugates comprising the antibodies conjugated or linked to a growth-inhibitory agent, and to pharmaceutical compositions comprising the antibodies, or immunoconjugates. The antibodies or immunoconjugates are used for the treatment of cancer or for diagnostic purposes.

21 Claims, 28 Drawing Sheets

Specification includes a Sequence Listing.

(56) References Cited

U.S. PATENT DOCUMENTS

| | | | |
|---|---|---|---|
| 5,215,534 | A | 6/1993 | De Harde et al. |
| 5,225,539 | A | 7/1993 | Winter |
| 5,278,056 | A | 1/1994 | Bank et al. |
| 5,475,092 | A | 12/1995 | Chari et al. |
| 5,500,362 | A | 3/1996 | Robinson et al. |
| 5,530,101 | A | 6/1996 | Queen et al. |
| 5,565,332 | A | 10/1996 | Hoogenboom et al. |
| 5,585,089 | A | 12/1996 | Queen et al. |
| 5,585,499 | A | 12/1996 | Chari et al. |
| 5,821,337 | A | 10/1998 | Carter et al. |
| 5,846,545 | A | 12/1998 | Chari et al. |
| 5,859,205 | A | 1/1999 | Adair et al. |
| 5,882,877 | A | 3/1999 | Gregory et al. |
| 5,994,524 | A | 11/1999 | Matsushima et al. |
| 6,013,516 | A | 1/2000 | Verma et al. |
| 6,018,032 | A | 1/2000 | Koike et al. |
| 6,127,175 | A | 10/2000 | Vigne et al. |
| 6,333,410 | B1 | 12/2001 | Chari et al. |
| 6,464,998 | B1 | 10/2002 | Beuzard et al. |
| 6,629,949 | B1 | 10/2003 | Douglas et al. |
| 6,659,982 | B2 | 12/2003 | Douglas et al. |
| 8,668,910 | B2 | 3/2014 | Bouchard et al. |
| 9,248,242 | B2 | 2/2016 | Verespej et al. |
| 9,427,531 | B2 | 8/2016 | Hourmand et al. |
| 9,566,395 | B2 | 2/2017 | Denny et al. |
| 9,617,345 | B2 | 4/2017 | Berne et al. |
| RE47,123 | E | 11/2018 | Blanc et al. |
| 10,457,739 | B2 | 10/2019 | Berne et al. |
| 11,332,542 | B2 | 5/2022 | Berne et al. |
| 2005/0003403 | A1 | 1/2005 | Rossi et al. |
| 2009/0226444 | A1 | 9/2009 | Rau et al. |
| 2011/0123530 | A1 | 5/2011 | Arron et al. |
| 2011/0123554 | A1 | 5/2011 | Osterroth et al. |
| 2012/0225089 | A1 | 9/2012 | Bouchard et al. |
| 2015/0125386 | A1 | 5/2015 | Hansen et al. |
| 2016/0032004 | A1 | 2/2016 | Govindan et al. |
| 2016/0108131 | A1 | 4/2016 | Berne et al. |
| 2016/0159905 | A1 | 6/2016 | Abdiche et al. |
| 2016/0361360 | A1 | 12/2016 | Chang et al. |
| 2017/0166637 | A1 | 6/2017 | Ben-Moshe et al. |
| 2018/0022817 | A1 | 1/2018 | Berne et al. |
| 2019/0161548 | A1 | 5/2019 | Johnson et al. |
| 2020/0069799 | A1 | 3/2020 | Jezek et al. |
| 2020/0069814 | A1 | 3/2020 | Zhao et al. |
| 2020/0102401 | A1 | 4/2020 | Berne et al. |
| 2020/0262922 | A1 | 8/2020 | Bhattacharya et al. |
| 2021/0093730 | A1 | 4/2021 | Sperber et al. |
| 2021/0261649 | A1 | 8/2021 | Parry |
| 2022/0080053 | A1* | 3/2022 | Allard ................ C07K 16/2827 |
| 2022/0202946 | A1* | 6/2022 | Authelin ............ A61K 47/6849 |
| 2022/0340682 | A1 | 10/2022 | Berne et al. |
| 2023/0087871 | A1* | 3/2023 | Nicolazzi ........... A61K 47/6853 424/134.1 |
| 2023/0149557 | A1* | 5/2023 | Nicolazzi ........... A61K 47/6805 424/133.1 |
| 2023/0151088 | A1 | 5/2023 | Nicolazzi et al. |
| 2023/0181755 | A1* | 6/2023 | Nicolazzi .................. A61P 1/00 424/181.1 |
| 2024/0226313 | A1* | 7/2024 | Baudat ............... A61K 47/6889 |
| 2024/0424126 | A1* | 12/2024 | Baudat ............... C07K 16/3007 |
| 2025/0041434 | A1* | 2/2025 | Chadjaa ................. A61K 45/06 |
| 2025/0154250 | A1 | 5/2025 | Chadjaa et al. |

FOREIGN PATENT DOCUMENTS

| | | | |
|---|---|---|---|
| CN | 104918958 | B | 12/2019 |
| EP | 0125023 | A1 | 11/1984 |
| EP | 0173494 | A2 | 3/1986 |
| EP | 0519596 | A1 | 12/1992 |
| EP | 0592106 | A1 | 4/1994 |
| EP | 0239400 | B1 | 8/1994 |
| EP | 2050764 | A1 | 4/2009 |
| EP | 2922875 | A1 | 9/2015 |
| EP | 2979700 | A1 | 2/2016 |
| EP | 3199552 | A1 | 8/2017 |
| EP | 3243527 | | 6/2019 |
| EP | 3594243 | | 1/2020 |
| EP | 3693023 | A1 | 8/2020 |
| JP | 2016506370 | A | 3/2016 |
| JP | 2018520140 | A | 7/2018 |
| JP | 2018520148 | A | 7/2018 |
| RU | 2607569 | | 1/2017 |
| RU | 2697522 | | 2/2024 |
| WO | WO 1981/001145 | A1 | 4/1981 |
| WO | WO 1987/002671 | A1 | 5/1987 |
| WO | WO 1987/005330 | A1 | 9/1987 |
| WO | WO 1988/007378 | A1 | 10/1988 |
| WO | WO 1991/009967 | A1 | 7/1991 |
| WO | WO 1994/011026 | A2 | 5/1994 |
| WO | WO 1994/019478 | A1 | 9/1994 |
| WO | WO 1995/014785 | A1 | 6/1995 |
| WO | WO 1996/002576 | A1 | 2/1996 |
| WO | WO 1996/022378 | A1 | 7/1996 |
| WO | WO 1997/010354 | A1 | 3/1997 |
| WO | WO 1998/045322 | A2 | 10/1998 |
| WO | WO 2004/016801 | A2 | 2/2004 |
| WO | WO 2004/091668 | A1 | 10/2004 |
| WO | 2005077090 | A2 | 8/2005 |
| WO | WO 2007/071426 | A1 | 6/2007 |
| WO | WO 2008/010101 | A2 | 1/2008 |
| WO | WO 2009/012268 | A1 | 1/2009 |
| WO | WO 2009/032661 | A1 | 3/2009 |
| WO | WO 2009/134977 | A1 | 11/2009 |
| WO | 2011001052 | A1 | 1/2011 |
| WO | 2011039724 | A1 | 4/2011 |
| WO | WO 2012/117002 | A1 | 9/2012 |
| WO | 2014004809 | A2 | 1/2014 |
| WO | WO 2014/079886 | A1 | 5/2014 |
| WO | 2014092804 | A1 | 6/2014 |
| WO | 2014157444 | A1 | 10/2014 |
| WO | 2015012904 | A2 | 1/2015 |
| WO | 2015069430 | A2 | 5/2015 |
| WO | WO 2015/075201 | A1 | 5/2015 |
| WO | 2015168607 | A2 | 11/2015 |
| WO | WO 2016/180941 | A1 | 11/2016 |
| WO | 2016210108 | A1 | 12/2016 |
| WO | 2018204368 | A1 | 11/2018 |
| WO | 2018227023 | A1 | 12/2018 |
| WO | 2020056008 | A1 | 3/2020 |
| WO | WO 2020/053301 | A1 | 3/2020 |
| WO | 2020079209 | A1 | 4/2020 |
| WO | WO 2020/161214 | A1 | 8/2020 |
| WO | 2020190725 | A1 | 9/2020 |
| WO | 2020190731 | A1 | 9/2020 |
| WO | 2020190734 | A1 | 9/2020 |
| WO | 2020190760 | A1 | 9/2020 |
| WO | 2020190762 | A1 | 9/2020 |
| WO | WO 2021/214221 | A1 | 10/2021 |
| WO | WO 2021/214222 | A1 | 10/2021 |
| WO | WO 2021/214223 | A1 | 10/2021 |
| WO | WO 2021/214227 | A1 | 10/2021 |
| WO | 2023079057 | A1 | 5/2023 |
| WO | 2024180192 | A1 | 9/2024 |
| WO | 2024184349 | A1 | 9/2024 |
| WO | 2024194455 | A1 | 9/2024 |
| WO | 2024251733 | A1 | 12/2024 |
| WO | 2025169012 | A1 | 8/2025 |

OTHER PUBLICATIONS

Angal, et al., “A Single Amino Acid Substitution Abolishes the Heterogeneity of Chimeric Mouse/Human (IgG4) Antibody”, Molecular Immunology, vol. 30, No. 1, pp. 105-108, 1993.

Beers et al. (2010) “Cd20 as a Target for Therapeutic Type I and II Monoclonal Antibodies”, Seminars in Hematology, vol. 47, No. 2, pp. 107-114.

Berman et al. (Jan. 1, 2000) “The Protein Data Bank”, Nucleic Acids Research, vol. 28, No. 1, pp. 235-242.

Blumenthal et al. (2005) “Inhibition of Adhesion, Invasion, And Metastasis by Antibodies Targeting CEACA”, Cancer Research, vol. 65, No. 19, XP055022386, pp. 8809-8817.

(56) References Cited

OTHER PUBLICATIONS

Blumenthal et al., "Carcinoembryonic antigen antibody inhibits lung metastasis and augments chemotherapy in a human colonic carcinoma xenograft", Cancer Immunol. Immunother., Apr. 2005, 54(4): 315-327.
Brady et al. (Feb. 1984) "New Cosmid Vectors Developed for Eukaryotic DNA Cloning", Gene vol. 27, Issue 2, pp. 223-232.
Caron et al. (1992) "Biological and Immunological Features of Humanized M195 (Anti-CD33) Monoclonal", Cancer Research, vol. 52, pp. 6761-6767.
Caron et al. (Oct. 1992) "Engineered Humanized Dimeric Forms of IgG Are More Effective Antibodies", Journal of Experimental Medicine, The Rockefeller University Press, vol. 176, pp. 1191-1195.
Clinicaltrials.Gov, "History of Changes for Study: NCT03324113 Evaluation of SAR408701 in Combination With Other Anti-tumor Drug in Japanese Patients With Advanced Malignant Solid Tumors", Jan. 15, 2019.
Cromwell et al. (2006) "Protein Aggregation and Bioprocessing", The AAPS Journal, vol. 8, No. 3, pp. E572-E579.
Decary et al. (Aug. 1, 2015) "Abstract 1688: A Novel Anti-CEACAM5 Maytansinoid-Antibody-Drug Conjugate for the Treatment of Colorectal, Lung and Gastric Tumors", AACR 106th Annual Meeting, Apr. 18-22, 2015, vol. 75, Issue 15, Supplement.
Decary et al., "Abstract 1688: A novel anti-CEACAM5 maytansinoid-antibody-drug conjugate for the treatment of colorectal, lung and gastric tumors", Cancer Research, Aug. 1, 2015, 75(15 Suppl.): 1688.
Dimitrov, "Therapeutic Antibodies Methods and Protocols", Methods in Molecular Biology™ book series (MIMB), 2009, vol. 525, 445 Pages, 2009.
Doern et al. (2009) "Characterization of Inhibitory Anti-Insulin-Like Growth Factor Receptor Antibodies with Different Epitope Specificity and Ligand-Blocking Properties: Implications for Mechanism of Action in Vivo", The Journal of Biological Chemistry, vol. 284, No. 15, pp. 10254-10267.
Ebrahimnejad et al. (2000) "Cell Adhesion Molecule CEACAM1 Associates with Paxillin in Granulocytes and Epithelial and Endothelial Cells", Experimental Cell Research, vol. 260, No. 1, pp. 365-373.
Edge et al. (Nov. 15, 1981) "Deglycosylation of glycoproteins by trifluoromethanesulfonic acid", Analytical Biochemistry, vol. 118, No. 1, pp. 131-137.
European Search Report for European Patent Applicaton No. 2020031521.8, dated Oct. 8, 2020.
Extended European Search Report received for European Patent Application No. 17157890.9, mailed on May 24, 2017, 9 Pages.
Extended European Search Report received for European Patent Application No. 20315449.7, mailed on Apr. 29, 2021.
Foote et al. (Mar. 20, 1992) "Antibody Framework Residues Affecting the Conformation of the Hypervariable Loops", Journal of Molecular Biology, vol. 224, No. 2, pp. 487-499.
Gazzano-Santoro et al. (1997) "A Non-Radioactive Complement-Dependent Cytotoxicity Assay for Anti-Cd20 Monoclonal Antibody", Journal of Immunological Methods, vol. 202, No. 2, pp. 163-171.
GE Healthcare (Apr. 2010) "Resolving a Bottleneck in Screening and Characterization of Recombinant Antibody Fragments using Biacore 4000", Application note 28-9777-72 AA, Biacore™ label-free interaction analysis, 6 Pages.
Genbank (Nov. 1, 1994) "Carcinoembryonic Antigen [*Homo sapiens*]", UniProtKB—P06731 (Ceam5_Human), Accession No. AAA51967.1.
Genbank "Carcinoembryonic Antigen-Related Cell Adhesion Molecule 1 Isoform 1 Precursor [*Homo sapiens* ]", Accession No. NP_001703.2.
Genbank "Carcinoembryonic Antigen-Related Cell Adhesion Molecule 6 Precursor [*Homo sapiens*]", Accession No. NP_002474.3.
Genbank "Carcinoembryonic Antigen-Related Cell Adhesion Molecule 7 Precursor [*Homo sapiens*]", Accession No. NP_008821.1.
Genbank "Carcinoembryonic Antigen-Related Cell Adhesion Molecule 8 Precursor [*Homo sapiens*]", Accession No. NP_001807.2.
Gillies et al. (Jul. 1983) "A Tissue-Specific Transcription Enhancer Element is Located in The Major Intron of a Rearranged Immunoglobulin Heavy Chain Gene", Cell, vol. 33, No. 3, pp. 717-728.
Gold et al. (1965) "Demonstration of Tumor-Specific Antigens in Human Colonic Carcinomata by Immunological Tolerance and Absorption Techniques", The Journal of Experimental Medicine, vol. 121, pp. 439-462.
Govindan et al., "Improving the Therapeutic Index in Cancer Therapy by Using Antibody-Drug Conjugates Designed with a Moderately Cytotoxic Drug", Molecular Pharmaceutics, Jun. 1, 2015, 12(6): 1836-1847.
Hammarström et al., "Gastric Cancer—Chapter 31", Tumor Markers: Physiology, Pathobiology, Technology, and Clinical Applications, vol. 382, 2002, pp. 375-382.
Harmsen et al. (2007) "Properties, Production, and Applications of Camelid Single-Domain Antibody Fragments", Application Microbial Biotechnology, vol. 77, No. 1, pp. 13-22.
Henry et al. (Dec. 2015) "Abstract B145: PK/PD Evaluation of an Anti-CEACAM5 Antibody Drug Conjugate, in a Colon Patient-Derived-Xenografted Mice Model", AACR-NCI-EORTC International Conference: Molecular Targets and Cancer Therapeutics; Nov. 5-9, 2015; Boston, MA, vol. 14, Issue 12, Supplement 2.
International Search Report and Written Opinion received for PCT Patent Application No. PCT/EP2013/074291, mailed on Feb. 24, 2014, 14 Pages.
International Search Report and Written Opinion received for PCT Patent Application No. PCT/EP2020/052932, mailed Apr. 30, 2020.
International Search Report and Written Opinion received for PCT Patent Application No. PCT/EP2021/060535, dated Jul. 26, 2021.
International Search Report and Written Opinion received for PCT Patent Application No. PCT/EP2021/060537, dated Jul. 26, 2021.
International Search Report and Written Opinion received for PCT Patent Application No. PCT/EP2021/060542, dated Jul. 26, 2021.
International Search Report and Written Opinion received for PCT Patent Application No. PCT/EP2021/060536 ,dated Jul. 26, 2021.
Iveson et al., "Review of metastatic colorectal cancer treatment pathways and early clinical experience of trifluridine/tipiracil in the UK named patient programme", BMC Cancer, Feb. 3, 2020, 20(91): 1-8.
Jespers et al. (1994) "Guiding the Selection of Human Antibodies from Phage Display Repertoires to a Single Epitope of An Antigen", Bio/Technology (Nature Publishing Company), vol. 12, No. 9, pp. 899-903.
Julien et al. (2012) "Characterization of a Large Panel of Patient-Derived Tumor Xenografts Representing the Clinical Heterogeneity of Human Colorectal Cancer", Clinical Cancer Research, vol. 18, No. 19, pp. 5314-5328.
Kammerer et al. (2010) "Coevolution of Activating and Inhibitory Receptors Within Mammalian Carcinoembryonic Antigen Families", BMC Biology, vol. 8, No. 12, 21 Pages.
Kilpatrick et al. (Aug. 1997) "Rapid Development of Affinity Matured Monoclonal Antibodies Using RIMMS", Hybridoma, vol. 16, No. 4, pp. 381-389.
Kim, et al., "Immunohistochemistry for Pathologists: Protocols, Pitfalls, and Tips", Journal of Pathology and Translational Medicine, vol. 50, No. 6, pp. 411-418, 2016.
Kranz, et al., "Factors Influencing Polysorbate's Sensitivity Against Enzymatic Hydrolysis and Oxidative Degradation", Journal of Pharmaceutical Sciences, vol. 108, Issue 6, pp. 2022-2032, Jun. 2019.
Kuwana et al. (Dec. 31, 1987) "Expression of Chimeric Receptor Composed of Immunoglobulin-Derived V Regions And T-Cell Receptor-Derived C Regions", Biochemical and Biophysical Research Communications, vol. 149, pp. 960-968.
Langer, "New Methods of Drug Delivery", Science, vol. 249, Issue 4976, pp. 1527-1533, Sep. 28, 1990.
Lefranc et al. (2003) "IMGT Unique Numbering for Immunoglobulin and T Cell Receptor Variable Domains and Ig Superfamily V-like Domains", Developmental & Comparative Immunology, vol. 27, No. 1, pp. 55-77.

(56) References Cited

OTHER PUBLICATIONS

Lefranc et al. (2005) "IMGT, The International Immunogenetics information system", Nucleic Acids Research, 2005, pp. D593-D597.
Liersch, "Safety and efficacy of repeated anJournal of Oncologyti-CEA radioimmunotherapy (RAIT) with 131I-labetuzumab post salvage resection of colorectal liver metastases", Journal of Oncology, 25(18 suppl), Meeting Abstract, Jun. 20, 2007, ASCO Annual Meeting, Tumor Biology and Human Genetics.
Litzen et al. (1993) "Separation and Quantitation of Monoclonal Antibody Aggregates by Asymmetrical Flow Field-Flow Fractionation and Comparison to Gel Permeation Chromatography", Analytical Biochemistry, vol. 212, No. 2, pp. 469-480.
Magge, "Antibody drug conjugate shows promise for metastatic colorectal cancer", Oct. 10, 2017, Retrieved from the Internet: URL: https://www.healio.com/news/hematology-oncology/20171010/antibody-drug-conjugate-shows-pr.omise-for-metastatic-colorectal-cancer.
Mason et al. (Jun. 1985) "Transcription Cell Type Specificity Is Conferred by An Immunoglobulin VH Gene Promoter That Includes A Functional Consensus Sequence", Cell, vol. 41, No. 2, pp. 479-487.
Meehan, et al., "A Microinfusor Device for the Delivery of Therapeutic Levels of Peptides and Macromolecules", Journal of Controlled Release, vol. 46, Issues 1-2, pp. 107-116, May 5, 1997.
Miyaji et al. (Mar. 1990) "Expression of Human Beta-Interferon in Namalwa KJM-1 Which Was Adapted to Serum-Free Medium", Cytotechnology, vol. 3, No. 2, pp. 133-140.
Mizukami et al. (May 1987) "A New SV40-Based Vector Developed for cDNA Expression in Animal Cells", Journal of Biochemistry vol. 101, No. 5, pp. 1307-1310.
Mohsin et al. (Jul. 23, 2004) "Progesterone Receptor by Immunohistochemistry and Clinical Outcome in Breast Cancer: A Validation Study", Modern Pathology: An Official Journal of the United States and Canadian Academy of Pathology, Inc., pp. 1545-1554.
Monsellier et al. (2006) "Improving the Stability of an Antibody Variable Fragment by a Combination of Knowledge-based Approaches: Validation and Mechanisms", Journal of Molecular Biology, vol. 362, pp. 580-593.
Morrison et al. (1984) "Transfer and Expression of Immunoglobulin Genes", Annual Review of immunology, vol. 2, pp. 239-256.
NCBI (Jun. 20, 2016) "CEACAM5 Carcinoembryonic Antigen Related Cell Adhesion Molecule 5 [ *Homo sapiens* (Human)", Gene ID: 1048.
Needleman et al. (Mar. 1970) "A General Method Applicable to The Search for Similarities in The Amino Acid Sequence of Two Proteins", Journal of Molecular Biology, vol. 48, No. 3, pp. 443-453.
Neuberger et al. (1985) "A Hapten-Specific Chimaeric IgE Antibody with Human Physiological Effector Function", Nature, 1985, vol. 314, No. 6008, pp. 268-270.
Oberst et al. (2009) "In Vitro Pharmacological Comparison of a Carcinoembryonic Antigen (CEA)/CD3 Bispecific Cynomolgus-Reactive Biosimilar Bite Antibody (Cys111) Biosimilar with The Clinical Candidate Medi-565 (Mt111)", Abstract# 3247: In Proceedings of the 100th American Association for Cancer Research, vol. 50, XP008167243, p. 786.
O'Hare et al. (Mar. 1, 1981) "Transformation of Mouse Fibroblasts to Methotrexate Resistance by A Recombinant Plasmid Expressing A Prokaryotic Dihydrofolate Reductase", Proceedings of National Academy of Sciences, vol. 78, No. 3, pp. 1527-1531.
Padlan, Eduardo A. (Apr.-May 1991) "A Possible Procedure for Reducing the Immunogenicity of Antibody Variable Domains While Preserving Their Ligand Binding Properties", Molecular Immunology, vol. 28, No. 4-5, pp. 489-498.
Peng et al. (2012) "The CEA/CD3-Bispecific Antibody Medi-565 (MT111) Binds a Nonlinear Epitope in the Full-Length But", PloS One, vol. 7, No. 5, XP002719867, pp. e36412.
Peters et al. (Mar. 2005) "The Immune Epitope Database and Analysis Resource: From Vision to Blueprint", Plos Biology, vol. 3, No. 3, e91, pp. 0379-0381.
Plowman et al. (1997) "Human Tumor Xenograft Models in NCI Drug Development", Anticancer Drug Development Guide, pp. 101-125.
Powell, et al., "Compendium of Excipients For Parenteral Formulations", PDA Journal of Pharmaceutical Science and Technology, vol. 52, No. 5, pp. 238-311, Sep. 1, 1998.
Remington et al. "Remington's Pharmaceutical Sciences", 15th Edition, pp. 1035-1038.
Remington et al. "Remington's Pharmaceutical Sciences", 15th Edition, pp. 1570-1580.
Riechmann et al. (1988) "Expression of an Antibody Fv Fragment in Myeloma Cells", Journal of Molecular Biology, vol. 203, No. 3, pp. 825-828.
Riechmann et al. (Mar. 24, 1988) "Reshaping Human Antibodies for Therapy", Nature, vol. 332, No. 6162, pp. 323-327.
Roguska et al. (Feb. 1, 1994) "Humanization of Murine Monoclonal Antibodies Through Variable Domain Resurfacing", Proceedings of the National Academy of Sciences, vol. 91, No. 3, pp. 969-973.
Sanofi, "Evaluation of SAR408701 in Patients With Advanced Solid Tumors", ClinicalTrials.gov Identifier: NCT02187848, Retrieved from:<<https://clinicaltrials.gov/ct2/show/NCT02187848>>, 9 Pages, Jul. 11, 2014.
Sanofi, "SAR408701 Versus Docetaxel in Previously Treated, Carcinoembryonic Antigen-related Cell Adhesion Molecule 5 (CEACAM5) Positive Metastatic Non-squamous Non-small Cell Lung Cancer Patients (CARMEN-LC03)", ClinicalTrials.gov Identifier: NCT04154956, Retrieved from: <<https://clinicaltrials.gov/ct2/show/NCT04154956>>, 9 Pages, Nov. 7, 2019.
Schmidt et al. (2008) "Kinetics of Anti-Carcinoembryonic Antigen Antibody Internalization: Effects of Affinity. Bivalency and Stability", Cancer Immunology Immunotherapy, vol. 57, XP019654564, pp. 1879-1890.
Sharkey et al. (1990) "Murine Monoclonal Antibodies against Carcinoembryonic Antigen: Immunological", Cancer Research, vol. 50, No. 9, pp. 2823-2831.
Sharkey et al. (1995) "Evaluation of a Complementarity-Determining Region-Grafted (Humanized) Anti-Carcinoembryonic Antigen Monoclonal Antibody in Preclinical and Clinical Studies", Cancer Research, vol. 55, pp. 5935s-5945s.
Shirasu, et al. (Jun. 2016) "CEACAM5 (carcinoembryonic antigen-related cell adhesion molecule 5 (carcinoembryonic antigen", Atlas of Genetics and Cytogenetics in Oncology and Haematology, vol. 20, No. 5, pp. 243-249.
Shitara et al. (Jan. 3, 1994) "A New Vector for The High Level Expression of Chimeric Antibodies in Myeloma Cells", Journal of Immunological Methods, vol. 167, No. 1-2, pp. 271-278.
Shopes, (May 1, 1992) "A Genetically Engineered Human IgG Mutant with Enhanced Cytolytic Activity", Journal of Immunology, vol. 148, No. 9, pp. 2918-2922.
Sojar et al. (Nov. 15, 1987) "A Chemical Method for The Deglycosylation of Proteins", Archives of Biochemistry and Biophysics, vol. 259, No. 1, pp. 52-57.
Steipe et al. (Jul. 15, 1994) "Sequence Statistics Reliably Predict Stabilizing Mutations in a Protein Domain", Journal of Molecular Biology, vol. 240, No. 3, pp. 188-192.
Strickland et al. (2009) "Preclinical Evaluation of Carcinoembryonic Cell Adhesion Molecule (CEACAM) 6 as Potential Therapy Target for Pancreatic Adenocarcinoma", The Journal of Pathology, vol. 218, No. 3, pp. 380-390.
Studnicka et al. (Jun. 1, 1994) "Human-Engineered Monoclonal Antibodies Retain Full Specific Binding Activity by Preserving Non-CDR Complementarity-Modulating Residues", Protein Engineering, vol. 7, No. 6, pp. 805-814.
Taylor, et al., "A Transgenic Mouse That Expresses a Diversity of Human Sequence Heavy and Light Chain Immunoglobulins", Nucleic Acids Research, vol. 20, No. 23, pp. 6287-6295, Dec. 11, 1992.
Thotakura et al. (1987) "[28] Enzymatic Deglycosylation Of Glycoproteins", Methods in Enzymology. vol. 138, Academic Press, pp. 350-359.

(56) References Cited

OTHER PUBLICATIONS

Urlaub et al. (Jul. 1980) "Isolation of Chinese Hamster Cell Mutants Deficient in Dihydrofolate Reductase Activity", Proceedings of the National Academy of Sciences of the United States of America, vol. 77, No. 7, pp. 4216-4220.
Vitetta et al. (1987) "Interaction and Activation of Antigen-Specific T and B Cells", Immunological Reviews, vol. 99, Issue 1, pp. 193-239.
Vitetta et al. (1987) "Redesigning Nature's Poisons to Create Anti-Tumor Reagents", Science, vol. 238, No. 4830, pp. 1098-1104.
Wang et al. (2008) "Fractionation of Monoclonal Antibody Aggregates Using Membrane Chromatography", Journal of Membrane Science, vol. 318, No. 1-2, pp. 311-316.
Wennerberg et al. (1993) "Hepatocyte Paraffin 1: A Monoclonal Antibody That Reacts with Hepatocytes and Can Be Used for Differential Diagnosis of Hepatic Tumors", The American Journal of Pathology, vol. 143, No. 4, pp. 1050-1054.
Wilson, "Novel Therapeutic Developments Other Than EGFR and VEGF Inhibition in Colorectal Cancer", Oncologist, Oct. 1, 2006, 11(9): 1018-1024.
Wu, et al., "Receptor-mediated in Vitro Gene Transformation by a Soluble DNA Carrier System", The Journal of Biological Chemistry, vol. 262, No. 10, pp. 4429-4432, Apr. 1987.
Zhang et al. (Aug. 23, 2011) "Epitope Mapping of A 95 kDa Antigen in Complex with Antibody by Solution-Phase Amide Backbone Hydrogen/Deuterium Exchange Monitored by Fourier Transform Ion Cyclotron Resonance Mass Spectrometry", Analytical Chemistry, vol. 83, No. 18, pp. 7129-7136.
Zhao et al. (2004) "An Enzyme-Linked Immunosorbent Assay for Human Carcinoembryonic Antigen-Related Cell Adhesion Molecule 8, A Biological Marker of Granulocyte Activities In Vivo", Journal of Immunological Methods, vol. 293, Issues 1-2, pp. 207-214.
Zheng et al., "A Novel Anti-CEACAM5 Monoclonal Antibody, CC4, Suppresses Colorectal Tumor Growth and Enhances NK Cells-Mediated Tumor Immunity", PLOS One, Jun. 2011, 6(6): e21146.
U.S. Appl. No. 14/716,377, filed May 19, 2015, Pierre-Francois Berne, Anti-CEACAM5 Antibodies And Uses Thereof.
U.S. Appl. No. 15/446,465, filed Mar. 1, 2017, Pierre-Francois Berne, Anti-CEACAM5 Antibodies And Uses Thereof.
U.S. Appl. No. 16/558,939, filed Sep. 3, 2019, Pierre-Francois Berne, Anti-CEACAM5 Antibodies And Uses Thereof.
U.S. Appl. No. 17/425,603, filed Jul. 23, 2021, Aurore Allard, Use Of Anti-Ceacam5 Immunoconjugates For Treating Lung Cancer.
U.S. Appl. No. 17/552,443, filed Nov. 9, 2021, Jean-René Authelin, CEACAM5 Antibody-Drug Conjugate Formulation.
U.S. Appl. No. 17/916,737, filed Oct. 3, 2022, Céline Nicolazzi, Antitumor Combinations Containing Anti-CEACAM5 Antibody Conjugates, Trifluridine And Tipiracil.
U.S. Appl. No. 17/916,877, filed Oct. 4, 2022, Céline Nicolazzi, Antitumor Combinations Containing Anti-Ceacam5 Antibody Conjugates And Folfiri.
U.S. Appl. No. 17/917,064, filed Oct. 5, 2022, Céline Nicolazzi, Antitumor Combinations Containing Anti-Ceacam5 Antibody Conjugates And Cetuximab.
U.S. Appl. No. 17/917,375, filed Apr. 22, 2021, Céline Nicolazzi, Antitumor Combinations Containing Anti-Ceacam5 Antibody Conjugates And Flfox
Patel et al., "BDB001, an intravenously administered toll-like receptor 7 and 8 (TLR7/8) agonist, in combination with pembrolizumab in advanced solid tumors: Phase 1 safety and efficacy results," presented at the ASCO Annual Meeting, 2021, poster retrieved from https://meetings.asco.org/abstracts-presentations/196042 Jun. 25, 2024.
Sahlmann, MD, C.-O., et al., "Repeated Adjuvant Anti-CEA Radioimmunotherapy After Resection of Colorectal Liver Metastases: Safety, Feasibility, and Long-Term Efficacy Results of a Prospective Phase 2 Study," Cancer, vol. 123, Feb. 15, 2017 (Published online Oct. 20, 2016), pp. 638-649.
Author Unknown, "Tusamitamab Ravtansine (SAR408701) in Combination With Pembrolizumab andTusamitamab Ravtansine (SAR408701) in Combination with Pembrolizumab and Platinum-based Chemotherapy With or Without Pemetrexed in Patients With NSQ NSCLC (CARMEN-LC05) (CARMEN-LC05)," NCTO4524689, Updated May 18, 2022, Retrieved from the Internet: URL: https://clinicaltrials.gov/ct2/show/NCT04524689 on May 19, 2022.
Schofield, D.J., et al., "Activity of murine surrogate antibodies for durvalumab and tremelimumab lacking effector function and the ability to deplete regulatory T cells in mouse models of cancer," MABS, vol. 13, Issue 1, 2021 e1857100, 18 pages.
Segal, N.H., et al., "Abstract LB-159: A Phase I study of IMMU-130 (labetuzumab-SN38) anti-CEACAM5 antibody-drug conjugate (ADC) in patients with metastatic colorectal cancer (mCRC)," Cancer Research, vol. 73, LB-159, Apr. 15, 2013, 2 pages.
Singh, et al. (2009). Antibody-Cytotoxic Agent Conjugates: Preparation and Characterization. In: Dimitrov, A. (eds) Therapeutic Antibodies. Methods in Molecular Biology™, vol. 525. Humana Press. https://doi.org/10.1007/978-1-59745-554-1_23, 28 pages.
Strop et al., "Location Matters: Site of Conjugation Modulates Stability and Pharmacokinetics of Antibody Drug Conjugates," Chemistry & Biology, vol. 20, No. 2, Feb. 21, 2013, pp. 161-167.
Thompson, J.A., "Molecular Cloning and Expression of Carcinoembryonic Antigen Gene Family Members," Tumor Biology, vol. 16, No. 1, 1995, pp. 10-16.
Verma, S., et al., "Trastuzumab Emtansine for HER2-Positive Advanced Breast Cancer," The New England Journal of Medicine, vol. 367, No. 19, Nov. 8, 2012, pp. 1783-1791.
Wittmann-Regis, Agnès (PCT Authorized Officer), International Preliminary Report on Patentability and Written Opinion of the International Searching Authority for International Application No. PCT/EP2013/074291 dated May 26, 2015, 9 pages.
Wittmann-Regis, Agnès (PCT Authorized Officer), International Preliminary Report on Patentability and Written Opinion of the International Searching Authority for International Application No. PCT/EP2022/080776, dated May 2, 2024, 7 pages.
Younes, A., et al., "Results of a Pivotal Phase II Study of Brentuximab Vedotin for Patients With Relapsed or Refractory Hodgkin's Lymphoma," Journal of Clinical Oncology, vol. 30, No. 18, Jun. 20, 2012, pp. 2183-2189.
Zarogoulidis, K., et al., "Treatment of non-small cell lung cancer (NSCLC)," Journal of Thoracic Disease, vol. 5, Suppl. 4, Sep. 2013, pp. S389-S396.
Zhou et al., "Site-Specific Antibody-Drug Conjugation through Glycoengineering," Bioconjugate Chem., vol. 25, No. 3, Feb. 17, 2014, pp. 510-520.
Edelman et al., "The Covalent Structure of an Entire γG Immunoglobulin Molecule," Proc. Natl. Acad. USA, vol. 63, May 1969, pp. 78-85.
Russian Search Report dated Aug. 29, 2024 for Russian Application No. 2022127325, 2 pages (English translation).
Garnett, "Targeted drug conjugates: principles and progress," Advanced Drug Delivery Reviews, vol. 53, Issue 2, Dec. 17, 2001, pp. 171-216.
NCBI—National Center for Biotechnology Information (2024), PubChem Substance Record for SID 405226618, Enoblituzumab (USAN/INN), Source: KEGG; retrieved Jun. 12, 2024 from https://pubchem.ncbi.nlm.nih.gov/substance/405226618, deposited May 18, 2020; structure for SID 405226618 (CAS No. 1353485-38-7-Enoblituzumab) retrieved from https://www.genome.jp/entry/D11752 Jun. 12, 2024, 5 pages.
Adumeau et al., "Thiol-reactive bifunctional chelators for the creation of site-selectively modified radioimmunoconjugates with improved stability," Bioconjugate Chemistry, vol. 29, No. 4., Apr. 18, 2018, pp. 1364-1372.
Agarwal et al., "Hydrazino-Pictet-Spengler ligation as a biocompatible method for the generation of stable protein conjugates," Bioconjugate Chem, vol. 24, No. 6, May 28, 2013, pp. 846-851.
Agarwal et al., "Site-Specific Antibody-Drug Conjugates: The Nexus ofBioorthogonal Chemistry, Protein Engineering, and DrugDevelopment," Bioconjugate Chem., vol. 26, 2015 (Published Dec. 12, 2014), pp. 176-192.

(56) References Cited

OTHER PUBLICATIONS

Author Unknown, structure for CAS number [352439-36-2]—azido-PEG8-OH, Chemical Book Product Catalog, 2016; retrieved from https://www.chemicalbook.com/ProductCatalog_EN/201271.htm; Jun. 12, 2024, 8 pages.
Author Unknown, structure for CAS number [642473-95-8]—3M-012, GLPBio Technology Product Catalog, 2017, retrieved from https://www.glpbio.com/tlr7-8-agonist-3.html Jun. 12, 2024, 5 pages.
Axup et al., "Synthesis of site-specific antibody-drug conjugates using unnatural amino acids," PNAS, vol. 109, No. 40, Oct. 2, 2012, pp. 16101-16106.
Beck et al., "Strategies and challenges for the next generation of antibody-drug conjugates," Nature Reviews—Drug Discovery, vol. 16, May 2017 (Published online Mar. 17, 2017), pp. 315-337.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics, vol. 12, No. 11, Nov. 2, 2015, pp. 3986-3998.
Extended European Search Report dated Mar. 9, 2022 for European Application No. 21306412.4, 8 pages.
Berillon, Laurent (PCT Authorized Officer), International Search Report and Written Opinion of the International Searching Authority dated Jan. 31, 2023 for International Application No. PCT/EP2022/077804, 13 pages.
Bryant et al., "In Vitro and In Vivo Evaluation of Cysteine Rebridged Trastuzumab-MMAE Antibody Drug Conjugates with Defined Drug-to-Antibody Ratios," Molecular Pharmaceutics, vol. 12, No. 6, 2015 (Published Apr. 20, 2015), pp. 1872-1879.
Burema, Shiri (PCT Authorized Officer), International Search Report and Written Opinion for International Application No. PCT/EP2021/060535 dated Jul. 26, 2021, 15 pages.
CAS Registry No. 2254086-60-5, USAN (JK-225): Tusamitamab Ravtansine, Sponsor: Sanofi, Code Designations: SAR408701, UNII: DSS3BE2ZXN, Nov. 24, 2021, 2 pages.
Chang, C.-H., et al., "Combination Therapy with Bispecific Antibodies and PD-1 Blockade Enhances the Antitumor Potency of T Cells," Cancer Research, vol. 77, No. 19, pp. 5384-5394, Oct. 1, 2017, published online Aug. 17, 2017, XP055542212, US ISSN: 0008-5472, DOI: 10.1158/0008-5472.CAN-16-3431.
Chapman, Rob (PCT Authorized Officer), International Search Report for International Application No. PCT/EP2022/084105, dated Feb. 14, 2023, 8 pages.
Chapman, Rob (PCT Authorized Officer), International Search Report for International Application No. PCT/EP2022/080776, dated Feb. 13, 2023, 6 pages.
Criscitiello et al., "Antibody-drug conjugates in solid tumors: a look into novel targets," Journal of Hematology & Oncology, vol. 14, No. 1, Jan. 28, 2021, doi: 10.1186/s13045-021-01035-z, 18 pages.
Eisenhauer, E.A., et al., "New response evaluation criteria in solid tumours: Revised Recist guideline (Version 1.1)," Eur. J. Cancer, vol. 45, No. 2, Jan. 2009, pp. 228-247.
Gandhi, L., et al., "Pembrolizumab plus Chemotherapy in Metastatic Non-Small-Cell Lung Cancer," New England Journal of Medicine, vol. 378, 2018 (ePublished Apr. 16, 2018), pp. 2078-2092.
Genbank Accession No. AAK62676 for murine TLR7 polypeptide; Jul. 15, 2002.
Genbank Accession No. AAK62677 for murine TLR8 polypeptide; Jul. 15, 2002.
Genbank Accession No. AAZ95441 for human TLR8 polypeptide; Nov. 25, 2009.
Genbank Accession No. AAZ99026 for human TLR7 polypeptide; Nov. 25, 2009.
Gold, P., et al., "Specific carcinoembryonic antigens of the human digestive system," Journal of Experimental Medicine, vol. 122, No. 3, Sep. 1, 1965, pp. 467-481.
Hammarström, S., "The carcinoembryonic antigen (CEA) family: structures, suggested functions and expression in normal and malignant tissues," Seminars in Cancer Biology, vol. 9, Issue 2, Apr. 1999, pp. 67-81.
Hermanson, G.T. (2008) Bioconjugate Techniques. 2nd Edition, Academic Press, London, 1323.
Hudak et al., "Synthesis of Heterobifunctional Protein Fusions Using Copper-Free Click Chemistry and the Aldehyde Tag," Angewandte Chemie, International Edition, vol. 51, 2012 (Published online Mar. 12, 2012, pp. 4161-4165.
Jeger et al.,"Site-Specific and Stoichiometric Modification of Antibodies by Bacterial Transglutaminase," Angewandte Chemie, International Edition, vol. 10, 2010 (Published online Nov. 25, 2010), pp. 9995-9997.
Junutula et al., "Site-specific conjugation of a cytotoxic drug to an antibody improves the therapeutic index," Nature Biotechnology, vol. 26, No. 8, Aug. 2008 (Published online Jul. 20, 2008), pp. 925-932 (9 pages total).
Kabat et al., Sequences of proteins of immunological interest. 5th Edition—US Department of Health and Human Services, NIH Publication No. 91-3242, 1991, pp. 662, 680 and 689.
Lunter, Pim (PCT Authorized Officer), International Search Report and Written Opinion of the International Searching Authority dated Mar. 14, 2023 for International Application No. PCT/EP2022/084107.
Johnson, et al., "Phase III trial comparing antibody-drug conjugate (ADC) SAR408701 with docetaxel in patients with metastatic non-squamous non-small cell lung cancer (NSQ NSCLC) failing chemotherapy and immunotherapy," Journal of Clinical Oncology, vol. 38, No. 15., 2020 , ASCO Annual Meeting, Non-Small Cell Metastatic, 4 pages.
Mok, Tony S.K., et al., "Pembrolizumab versus chemotherapy for previously untreated, PD-L1-expressing, locally advanced or metastatic non-small-cell lung cancer (Keynote-042): a randomised, open-label, controlled, phase 3 trial," The Lancet, vol. 393, Issue 10183, May 4, 2019, pp. 1819-1830, epub Apr. 4, 2019.
National Center for Biotechnology Information (2024). PubChem Compound Summary for CID 4614742, 2-[2-[2-(2-Azidoethoxy)ethoxy]ethoxy]ethanol (CAS No. 86770-67-4). Retrieved Jun. 12, 2024 from https://pubchem.ncbi.nlm.nih.gov/compound/Azido-PEG4-alcohol; created Sep. 16, 2005, 15 pages.
NCBI—National Center for Biotechnology Information (2024), PubChem Compound Summary for CID 10940805, Azide-PEG12-alcohol (CAS No. [1821464-55-4), retrieved Jun. 12, 2024 from https://pubchem.ncbi.nlm.nih.gov/compound/Azide-PEG12-alcohol; created Oct. 26, 2006, 11 pages.
NCBI—National Center for Biotechnology Information (2024), PubChem Compound Summary for CID 135403648, 5-Formyltetrahydrofolic acid (CAS No. 58-05-9, Leucovorin (Folinic acid)—$C_{20}H_{23}N_7O_7$), retrieved Aug. 1, 2024 from https://pubchem.ncbi.nlm.nih.gov/compound/135403648, created Jan. 15, 2019, 71 pages.
NCBI—National Center for Biotechnology Information (2024), PubChem Compound Summary for CID 159603, Resiquimod (CAS No. 144875-48-9), retrieved Jun. 12, 2024 from https://pubchem.ncbi.nlm.nih.gov/compound/Resiquimod, created Aug. 1, 2005, 33 pages.
NCBI—National Center for Biotechnology Information (2024), PubChem Compound Summary for CID 3385, 5-Fluorouracil (CAS No. 51-21-8, Fluorouracil—$C_4H_3FN_2O_2$), retrieved Aug. 1, 2024 from https://pubchem.ncbi.nlm.nih.gov/compound/3385, created Mar. 25, 2005, 121 pages.
NCBI—National Center for Biotechnology Information (2024), PubChem Compound Summary for CID 60838, (+)-Irinotecan (CAS No. 97682-44-5, Irinotecan—$C_{33}H_{38}N_4O_6$), retrieved Aug. 1, 2024 from https://pubchem.ncbi.nlm.nih.gov/compound/60838, created Jun. 24, 2005, 79 pages.
NCBI—National Center for Biotechnology Information (2024), PubChem Compound Summary for CID 6256, 5-Trifluorothymidine (CAS No. 70-00-8, Trifluridine—$C_{10}H_{11}F_3N_2O_5$), retrieved Aug. 1, 2024 from https://pubchem.ncbi.nlm.nih.gov/compound/6256, created Jun. 24, 2005, 75 pages.

(56) References Cited

OTHER PUBLICATIONS

NCBI—National Center for Biotechnology Information (2024), PubChem Compound Summary for CID 6323366, 5-chloro-6-[(2-iminopyrrolidin-1-yl)methyl]-1H-pyrimidine-2,4-dione (CAS No. 183204-71-2, Tipiracil—$C_9H_{11}ClN_4O_2$), retrieved Aug. 1, 2024 from https://pubchem.ncbi.nlm.nih.gov/compound/6323266, created Nov. 29, 2005, 35 pages.
NCBI—National Center for Biotechnology Information (2024), PubChem Compound Summary for CID 78798 (CAS No. 5117-19-1) 3,6,9, 12, 15, 18,21-Heptaoxatricosane-1,23-diol, retrieved Jun. 12, 2024 from https://pubchem.ncbi.nlm.nih.gov/compound/Octaethylene-glycol, created Mar. 27, 2005, 33 pages.
"NCBI—National Center for Biotechnology Information (2024), PubChem Compound Summary for CID 8200, Tetraethylene glycol, (CAS No. 112-60-7), retrieved Jun. 12, 2024 from https://pubchem.ncbi.nlm.nih.gov/compound/Tetraethylene-glycol, created Mar. 26, 2005, 80 pages".
NCBI—National Center for Biotechnology Information (2024), PubChem Substance Record for SID 17397410, Trastuzumab (USAN/INN), Source: KEGG, retrieved Jun. 12, 2024 from https://pubchem.ncbi.nlm.nih.gov/substance/17397410, deposited Nov. 22, 2006; structure for SID 17397410 (CAS No. 180288-69-1—Herceptin®), deposited Nov. 22, 2006, retrieved from https://www.genome.jp/entry/D03257 Jun. 12, 2024, 8 pages.
NCBI—National Center for Biotechnology Information (2024), PubChem Substance Record for SID 17397595, Cetuximab (USAN/INN), Source: KEGG; retrieved Jun. 12, 2024 from https://pubchem.ncbi.nlm.nih.gov/substance/17397595, deposited Nov. 22, 2006; structure for SID 17397595 (CAS No. 205923-56-4—Erbitux®) retrieved from https://www.genome.jp/entry/D03455 Jun. 12, 2024, 7 pages.
NCBI—National Center for Biotechnology Information (2024), PubChem Substance Record for SID 481155577, Tusamitamab, Source: BOC Sciences, retrieved Jun. 12, 2024 from https://pubchem.ncbi.nlm.nih.gov/substance/481155577, deposited May 11, 2023, structure for SID 481155577 (CAS No. 2349294-95-5—Tusamitamab) retrieved from https://www.genome.jp/entry/D12309, Jun. 12, 2024, 5 pages.
NCBI—National Center for Biotechnology Information (2024). PubChem Compound Summary for CID 4620597, NSuccinimidyl 3-maleimidopropionate (CAS No. 55750-62-4). Retrieved Jun. 12, 2024 from https://pubchem.ncbi.nlm.nih.gov/compound/N-Succinimidyl-3-maleimidopropionate; created Sep. 16, 2005, 21 pages.
NCBI—National Center for Biotechnology Information (2024). PubChem Compound Summary for CID 77078258, DBCO-amine (CAS No. 1255942-06-3). Retrieved Jun. 12, 2024 from https://pubchem.ncbi.nlm.nih.gov/compound/DBCO-amine; created Sep. 5, 2014, 18 pages.
Patel et al., "BDB001, an intravenously administered toll-like receptor 7 and 8 (TLR7/8) agonist, in combination withpembrolizumab in advanced solid tumors: Phase 1 safety and efficacy results," Journal of Clinical Oncology, vol. 39, Issue 15, Suppl. 2512, May 28, 2021, Abstract and Poster provided, https://doi.org/10.1200/JCO.2021.39.15_suppl.2512.
Colucci et al., "Phase III Randomized Trial of FOLFIRI Versus FOLFOX4 in the Treatment of Advanced Colorectal Cancer: A Multicenter Study of the Gruppo Oncologico Dell'Italia Meridionale," Journal of Clinical Oncology, vol. 23, No. 22, Aug. 1, 2005, pp. 4866-4875.
Daugherty et al., "Formulation and delivery issues for monoclonal antibody therapeutics," Advanced Drug Delivery Reviews, vol. 58, Nos. 5-6, Sep. 2006 (Available online May 22, 2006), pp. 686-706.
Chinese Office Action issued Aug. 31, 2024 for Chinese Patent Application No. 202180030342.6, 5 pages (English translation).
Pertsev, I.M., Pharmaceutical and biomedical aspects of drugs: in 2 volumes. T. 1.—Kharkov: UkrFA, 1999, pp. 253-255 of 464 [see English translation of Office Action dated Sep. 27, 2024 from Russian Application No. 2022130335 for a concise explanation of relevance].
Peters, G.J., "Therapeutic potential of TAS-102 in the treatment of gastrointestinal malignancies," Therapeutic Advances in Medical Oncology, vol. 7, No. 6, 2015 (First published online Sep. 10, 2015), pp. 340-356.
Reckamp et al., "Phase II Randomized Study of Ramucirumab and Pembrolizumab Versus Standard of Care in Advanced Non-Small-Cell Lung Cancer Previously Treated With Immunotherapy-Lung-MAP S1800A," Journal of Clinical Oncology, vol. 40, Issue 21, 2022 (Available online Jun. 3, 2022), pp. 2295-2307, 18 pages.
Trail, P.A., "Antibody Drug Conjugates as Cancer Therapeutics," Antibodies, vol. 2, Issue 1, Feb. 27, 2013, pp. 113-129 [obtained Dec. 18, 2024 at URL: https://www.mdpi.com/2073-4468/2/1/113].
Russian Search Report dated Sep. 27, 2024 for Russian Application No. 2022130335, 3 pages (English translation).
Taiwan Search Report issued Nov. 28, 2024 for Taiwan Patent Application No. 110114496, 1 page (English translation).
Vladimirova et al., "The Role of Histological and Molecular Analysis in the Choice of Treatment for Advanced Non-Small Cell Lung Cancer," Pharmateca, Journal Archive, No. 8, 2012, 11 pages.
Zhang et al., Clinical Glycobiology, Nov. 30, 2017, Science and Technology Literature Publishing House, 3 pages [Supplementary Search Report issued Feb. 17, 2025 for Chinese Patent Application No. 202180029921.9 for explanation of relevance].
Supplementary Search Report issued Feb. 17, 2025 for Chinese Patent Application No. 202180029921.9 (English translation).
Chen, Chengwei, et al., Drugs and Toxic Liver Diseases, 2nd Edition, Shanghai Science and Technology Press, Jan. 31, 2013, p. 778 (4 pages provided) [Supplementary Search Report issued Feb. 14, 2025 for Chinese Patent Application No. 202180029921.9 for explanation of relevance].
Jiang, Yuan, Pharmaceutical Biotechnology, People's Health Publishing House, Dec. 31, 1996, p. 164 (2 pages provided) [Supplementary Search Report issued Feb. 14, 2025 for Chinese Patent Application No. 202180029921.9 for explanation of relevance].
Chen, Zhiwu, et al., Pharmacology Henan Science and Technology Press , Jan. 31, 2013, p. 294 (6 pages provided) [Supplementary Search Report issued Feb. 14, 2025 for Chinese Patent Application No. 202180029921.9 for explanation of relevance].
Supplementary Search Report issued Feb. 14, 2025 for Chinese Patent Application No. 202180030566.7 (English translation).
Russian Office Action dated Sep. 27, 2024 for Russian Application No. 2022130335, 10 pages (English translation).
Center for Drug Evaluation and Research (CDER) et al., "Guidance for Industry, Estimating the Maximum Safe Starting Dose in Initial Clinical Trials for Therapeutics in Adult Healthy Volunteers," Food and Drug Administration (FDA), Office of New Drugs in the CDER, Jul. 2005, pp. 1-27 (30 pages total).
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer," Journal of Clinical Oncology, vol. 35, No. 29, Oct. 10, 2017 (Published at jco.org on Aug. 17, 2017), pp. 3338-3346 (17 pages total).
Jeon et al., "Adjuvant Chemotherapy Using the FOLFOX Regimen in Colon Cancer," Journal of the Korean Society of Coloproctology, vol. 27, No. 3, 2011, pp. 140-146.
Sanofi, "Evaluation of SAR408701 in Japanese Patients With Advanced Malignant Solid Tumors," (Official Title: "A Phase I/Ib Study to Evaluate Safety and Pharmacokinetics of SAR408701 Administered Intravenously as Monotherapy and in Combination With Other Anti-tumor Drug in Japanese Patients With Advanced Malignant Solid Tumors"), History of Changes for Study, Protocol ID: TCD15054, ClinicalTrials. gov Identifier: NCT03324113, Version 10, Mar. 25, 2019, 18 pages.
Tabernero et al., "Administration of Cetuximab Every 2 Weeks in the Treatment of Metastatic Colorectal Cancer: An Effective, More Convenient Alternative to Weekly Administration?", The Oncologist, vol. 13, 2008, pp. 113-119.
Vassileva et al., "Significant Therapeutic Efficacy with Combined Radioimmunotherapy and Cetuximab in Preclinical Models of Colorectal Cancer," The Journal of Nuclear Medicine, vol. 56, No. 8, Aug. 2015 (Published online Jun. 4, 2015), pp. 1239-1245.
US Non-Final Office Action for U.S. Appl. No. 17/917,064 dated Aug. 5, 2025, 95 pages.

(56) References Cited

OTHER PUBLICATIONS

US Non-Final Office Action for U.S. Appl. No. 17/917,375 dated Aug. 26, 2025, 78 pages.
Russian Office Action and Search Report for Russian Application No. 2023115205 dated Feb. 14, 2025, 18 pages (English Translation only provided).
Author Unknown, "OFS. 1.1.0001.18—Rules for the use of pharmacopoeial articles," State Pharmacopoeia of the Russian Federation, XIV Ed., vol. 1, 2018, pp. 122-127 (p. 125 only provided) [see the English Translation of the Russian Office Action dated Feb. 14, 2025 for Russian Application No. 2023115205 for a concise explanation of relevance].
European Search Report for European Patent Application 20315218 dated Oct. 8, 2020, 5 pages.
Burema, Shiri (PCT Authorized Officer), International Search Report and Written Opinion for International Application No. PCT/EP2021/060536 dated Jul. 26, 2021, 11 pages.
Govindan et al., "CEACAM5-Targeted Therapy of Human Colonic and Pancreatic Cancer Xenografts with Potent Labetuzumab-SN-38 Immunoconjugates," Clinical Cancer Research, vol. 15, No. 19, Oct. 1, 2009, pp. 6052-6061.
Hoffmann et al., "Antibody structure and engineering considerations for the design and function of Antibody Drug Conjugates (ADCs)," Oncoimmunology, vol. 7, No. 3, 2018 (Published online Nov. 20, 2017), pp. e1395127-1-e1395127-11.
Jorgensen et al., "Recent trends in stabilizing peptides and proteins in pharmaceutical formulation—considerations in the choice of excipients," Expert Opinion on Drug Delivery, vol. 6, Issue 11, 2009 (Published online Aug. 13, 2009), pp. 1219-1230 [Russian Office Action and Search for Russian Application No. 2023115205 dated Feb. 14, 2025 for explanation of relevance].
Kahl, K., "Antibody drug conjugate shows promise for metastatic colorectal cancer," and Magge, D.R., "Perspective" Oct. 10, 2017, 4 pages, Retrieved from the Internet on Jun. 15, 2025 from https://www.healio.com/news/hematology-oncology/20171010/antibody-drug-conjugate-shows-promise-for-metastatic-colorectal-cancer.
Livesey, Geoffrey, "Health potential of polyols as sugar replacers, with emphasis on low glycaemic properties," Nutrition Research Reviews, vol. 16, 2003, pp. 163-191.
Mohan, Chandra, "Buffers. A Guide for the Preparation and Use of Buffers in Biological Systems," Calbiochem® Biochemicals, EMD CB0052-2006 USD Buffers Booklet, Aug. 2006, 39 pages.
Mohelnikova-Duchonova et al., "FOLFOX/FOLFIRI Pharmacogenetics: The call for a personalized approach in colorectal cancer therapy," World Journal of Gastroenterology, vol. 20, No. 30, Aug. 14, 2014, pp. 10316-10330.
Nair et al., "A simple practice guide for dose conversion between animals and human," Journal of Basic and Clinical Pharmacy, vol. 7, Issue 2, Mar.-May 2016, pp. 27-31.
Rowe et al. (Editors), "Handbook of Pharmaceutical Excipients," Sixth Edition, Pharmaceutical Press and American Pharmacists Association, 2009, pp. 242-243 and 247-248 (6 pages total).
Sanofi, "Evaluation of SAR408701 in Japanese Patients With Advanced Malignant Solid Tumors," (Official Title: "A Phase I/Ib Study to Evaluate Safety and Pharmacokinetics of SAR408701 Administered Intravenously as Monotherapy and in Combination With Other Anti-tumor Drug in Japanese Patients With Advanced Malignant Solid Tumors"), History of Changes for Study, Protocol ID: TCD15054, ClinicalTrials.gov Identifier: NCT03324113, Jan. 15, 2019, 15 pages.
Wang et al., "Antibody Structure, Instability, and Formulation," Journal of Pharmaceutical Sciences, vol. 96, No. 1, Jan. 2007, pp. 1-26.
Chinese Search Report for Chinese Application No. 202180030342.6 dated Aug. 29, 2024, 3 pages (English translation only provided).
US Non-Final Office Action for U.S. Appl. No. 17/522,443 dated Mar. 31, 2025, 25 pages.
US Notice of Allowance for U.S. Appl. No. 17/522,443 dated Jul. 28, 2025, 18 pages.
US Non-Final Office Action for U.S. Appl. No. 17/425,603 dated Mar. 20, 2025, 167 pages.
US Final Office Action for U.S. Appl. No. 17/425,603 dated Aug. 29, 2025, 57 pages.
Adam et al., "Therapeutic targets in non-small cell lung cancer: preclinical and human studies of carcinoembryonic antigen-related cell adhesion molecule 5 (CEACAM5) expression and its associated molecular landscape," Poster presented at the EMSO IO 2021, Geneva, Switzerland, Dec. 8-11, 2021, 1 page.
Aguilera, Miguel, Extended European Search Report for European Application No. 23175455.7 dated Oct. 23, 2023, 7 pages.
Aguilera, Miguel, International Search Report and Written Opinion of the International Searching Authority for International Application No. PCT/EP2024/057737 dated Jul. 5, 2024, 17 pages.
Author Unknown, Comparison Format: Merged "History of Changes for Study: NCT04394624 SAR408701 in Combination With Ramucirumab in Pre-treated Patients With Non Squamous Non-small Cell Lung Cancer (NSQ NSCLC) (CARMEN-LC04)," Jan. 9, 2023, 5 pages, XP093074466, Retrieved from the Internet on Aug. 17, 2023 at: URL: https://classic.clinicaltrials.gov/ct2/history/NCT04394624?A-30&D-30&C-merged#StudyPageTop.
Author Unknown, "Tusamitamab Ravtansine (SAR408701) in Combination With Pembrolizumab and Tusamitamab Ravtansine (SAR408701) in Combination With Pembrolizumab and Platinum-based Chemotherapy With or Without Pemetrexed in Patients with NSQ NSCLC (CARMEN-LC05)," Dec. 12, 2022, 6 pages, XP093074465, Retrieved from the Internet on Aug. 17, 2023: URL: https://classic.clinicaltrials.gov/ct2/history/NCT04524689? A=24&B=24&C=merged#StudyPageTop.
Beauchemin et al., "Carcinoembryonic antigen-related cell adhesion molecules (CEACAMs) in cancer progression and metastasis," Cancer Metastasis Reviews, vol. 32, 2013 (Published online Aug. 1, 2013), pp. 643-671 (30 pages total).
Becht et al., "Estimating the population abundance of tissue-infiltrating immune and stromal cell populations using gene expression," Genome Biology, vol. 17, Article No. 218, 2016 (Published online Oct. 20, 2016), pp. 1-20.
Becht et al., Erratum to: "Estimating the population abundance of tissue-infiltrating immune and stromal cell populations using gene expression," Genome Biology, vol. 17, Article No. 249, 2016 (Erratum published online Dec. 1, 2016), pp. 1-2.
Blumenthal et al., "Expression patterns of CEACAM5 and CEACAM6 in primary and metastatic cancers," BMC Cancer, vol. 7, Article No. 2, Jan. 3, 2007, doi: 10.1186/1471-2407-7-2.
Burema, Shiri (EP Examiner), Extended European Search Report for European Application No. 23305290.1 dated Aug. 28, 2023, 12 pages.
Burema, Shiri (PCT Authorized Officer), International Search Report and Written Opinion of the International Searching Authority for International Application No. PCT/EP2024/055281 dated Apr. 4, 2024, 12 pages.
Burema, Shiri (PCT Authorized Officer), International Search Report and Written Opinion of the International Searching Authority for International Application No. PCT/EP2024/055721 dated Apr. 23, 2024, 19 pages.
Chu, Quincy S., "Targeting non-small cell lung cancer: driver mutation beyond epidermal growth factor mutation and anaplastic lymphoma kinase fusion," Therapeutic Advances in Medical Oncology, vol. 12, Jan. 23, 2020, pp. 1-27.
Conesa et al., "A survey of best practices for RNA-seq data analysis," Genome Biology, vol. 17, Article No. 13, Jan. 26, 2016, pp. 1-19.
Decary et al., "Preclinical Activity of SAR408701: A Novel Anti-CEACAM5-maytansinoid Antibody-drug Conjugate for the Treatment of CEACAM5-positive Epithelial Tumors," Clinical Cancer Research, vol. 26, 2020 (Published Online First Oct. 12, 2020), pages OF1-OF11 (12 pages total).
Delucia et al., "Regulation of CEACAM5 and therapeutic efficacy of an anti-CEACAM5-SN38 antibody-drug conjugate in neuroendocrine prostrate cancer," Clinical Cancer Research, vol. 27, No. 3, Feb. 1, 2021, pp. 759-774.

(56) References Cited

OTHER PUBLICATIONS

Desai et al., "Antibody-Drug Conjugates: A Promising Novel Therapeutic Approach in Lung Cancer," Lung Cancer, vol. 163, No. 23, 2022 (Available online Dec. 15, 2021), pp. 96-106.
Dobin et al., "STAR: ultrafast universal RNA-seq aligner," Bioinformatics, vol. 29, No. 1, 2013 (Advance Access Publication Oct. 25, 2012), pp. 15-21.
Gazzah et al., "Efficacy and safety of the antibody-drug conjugate (ADC) SAR408701 in patients (pts) with non-squamous non-small cell lung cancer (NSQ NSCLC) expressing carcinoembryonic antigen-related cell adhesion molecule 5 (CEACAM5)," Journal of Clinical Oncology, vol. 38, No. 15 Supplement, Abstract No. 9505, May 25, 2020, 3 pages.
Gazzah et al., "Safety, pharmacokinetics, and antitumor activity of the anti-CEACAM5-DM4 antibody-drug conjugate tusamitamab ravtansine (SAR408701) in patients with advanced solid tumors: first-in-human dose-escalation study," Annals of Oncology, vol. 33, Issue 4, 2022 (Available online Jan. 10, 2022), pp. 416-425.
Gherman et al., "Current and New Predictors for Treatment Response in Metastatic Colorectal Cancer. The Role of Circulating miRNAs as Biomarkers," International Journal of Molecular Sciences, vol. 21, Article 2089, 2020 (Published online Mar. 18, 2020), pp. 1-22.
Hack et al., "Augmenting Anticancer Immunity Through Combined Targeting of Angiogenic and PD-1/PD-L1 Pathways: Challenges and Opportunities," Frontiers in Immunology, vol. 11, Article 598877, Nov. 5, 2020, pp. 1-24.
Hu et al., "Quantitative Secretomic Analysis Identifies Extracellular Protein Factors That Modulate the Metastatic Phenotype of Non-Small Cell Lung Cancer," Journal of Proteome Research, vol. 15, No. 2, Feb. 5, 2016, pp. 477-486 (22 pages total).
Kalesse et al., "The Chemistry and Biology of the Leptomycin Family," Synthesis, vol. 8, 2002, pp. 981-1003.
Lapointe et al., "Validation of an immunohistochemical assay, CEACAM5 Ihc 769, under development for use with the antibody-drug conjugate tusamitamab ravtansine (SAR4087001)," Journal of Clinical Oncology, vol. 39, No. 15 Suppl., Abstract No. e21030, May 2021, 2 pages, https://doi.org/10.1200/JCO.2021.39.15_suppl.e21030.
Lee et al., "Systemic surfaceome profiling identifies target antigens for immune-based therapy in subtypes of advanced prostate cancer," PNAS, vol. 115, No. 19, 2018 (Published online Apr. 23, 2018), pp. E4473-E4482.
Li et al., "Treatment wth a VEGFR-2 antiboby results in intra-tumor immune modulation and enhances anti-tumor efficacy of PD-L1 blockade in syngeneic murine tumor models," PLoS One, vol. 17, No. 7, Jul. 18, 2022, Article e0268244, 10 pages.
Locker et al., "ASCO 2006 update of recommendations for the use of tumor markers in gastrointestinal cancer," Journal of Clinical Oncology, vol. 24, No. 33, Nov. 20, 2006 (Epub Oct. 23, 2006), pp. 5313-5377 (16 pages total).
NCBI—National Center for Biotechnology Information (2025), PubChem Compound Summary for CID 9887054, Oxaliplatin (CAS No. 61825-94-3), retrieved Sep. 30, 2025 from https://pubchem.ncbi.nlm.nih.gov/compound/Eloxatin, created Oct. 25, 2006, modified Sep. 27, 2025, 47 pages.
Papadaki et al., "Assessment of the Efficacy and Clinical Utility of Different Circulating Tumor Cell (CTC) Detection Assays in Patients with Chemotherapy-Naïve Advanced or Metastatic Non-Small Cell-Lung Cancer (NSCLC)," International Journal of Molecular Sciences, vol. 22, Jan. 18, 2021, 16 pages.
Paz-Ares et al., "Open-label, Phase 2 study of tusamitamab ravtansine (SAR408701) in combination with pembrolizumab and with pembrolizumab + platinum-based chemotherapy +/- pemetrexed in patients with CEACAM5- positive nonsquamous Nsclc (CARMEN-LC05)," Oncology Pro, European Society of Medical Oncology (ESMO), vol. 33, Issue S2, Apr. 1, 2022, Abstract and Poster, 3 pages.
Pouzin et al., "Integrated multiple analytes and semi-mechanistic population pharmacokinetic model of tusamitamab ravtansine, a DM4 anti-CEACAM5 antibody-drug conjugate," Journal of Pharmacokinetics and Pharmacodynamics, vol. 49, 2022 (Published online Feb. 15, 2022), pp. 381-394.
Ricordel et al., "Safety and efficacy of tusamitamab ravtansine (SAR408701) in long-term treated patients with nonsquamous non-small cell lung cancer (Nsq Nsclc) expressing carcinoembryonic antigen-related cell adhesion molecule 5 (CEACAM5)," Journal of Clinical Oncology, vol. 40, No. 16 Supplement, Jun. 2022, Abstract No. 9039, 1 page.
Rodak et al., "Current Landscape of Non-Small Cell Lung Cancer: Epidemiology, Histological Classification, Targeted Therapies, and Immunotherapy," Cancers, vol. 13, Article 4705, Sep. 20, 2021, 33 pages.
Sefrioui et al., "Cea, CA19-9, circulating DNA and circulating tumour cell kinetics in patients treated for metastatic colorectal cancer (mCRC)," British Journal of Cancer, vol. 125, 2021 (Published online Jun. 10, 2021), pp. 725-733.
Tabernero et al., "Tusamitamab Ravtansine in Patients with Advanced Solid Tumors: Phase I Study of Safety, Pharmacokinetics, and Antitumor Activity Using Alternative Dosing Regimens," Cancer Research Communications, vol. 3, No. 8, Aug. 28, 2023, pp. 1662-1671.
Trapnell et al., "Differential gene and transcript expression analysis of RNA-seq experiments with TopHat and Cufflinks," Nat. Protoc., vol. 7, No. 3, 2012 (Available in PMC Mar. 1, 2012), pp. 562-578 (39 p. total).
Turkdogan et al., "Carcinoembryonic antigen levels correlated with advanced disease in medullary thyroid cancer," Journal of Otolaryngology—Head and Neck Surgery, vol. 47, Article 55, 2018 (Published online Sep. 17, 2018), 7 pages.
Witte et al., "Monoclonal antibodies targeting the VEGF receptor-2 (Flk1/KDR) as an anti-angiogenic therapeutic strategy," Cancer and Metastasis Reviews, vol. 17, Jun. 1998, pp. 155-161.
Yoshino et al., "TAS-102 monotherapy for pretreated metastatic colorectal cancer: a double-blind, randomised, placebo-controlled phase 2 trial," Lancet Oncolology, vol. 13, Oct. 2012 (Published online Aug. 28, 2012), pp. 993-1001.
Zhang et al., "CEACAM5 stimulates the pregression of non-small-cell lung cancer by promoting call proliferation and migration," Journal of International Medical Research, vol. 48, No. 9, Sep. 2020, pp. 1-15.
US Notice of Allowance for U.S. Appl. No. 17/522,443 dated Oct. 21, 2025, 15 pages.
U.S. Non-Final Office Action for U.S. Appl. No. 17/916,737 dated Nov. 3, 2025, 86 pages.
Extended European Search Report for European Application No. 23305883.3 dated Oct. 23, 2023, 5 pages.
International Search Report and Written Opinion of the International Searching Authority for International Application No. PCT/EP2024/065335 dated Aug. 30, 2024, 13 pages.
Isambert et al., "Safety and efficacy of tusamitamab ravtansine in combinaton with pembrolizumab ± chemotherapy in patients with CEACAM5-positive nonsquamous NSCLC (CARMEN-LC05 phase II study)" Journal of Thoracic Oncology, vol. 18, No. 4S, Abstract, Apr. 2023, pp. S46-S47.
Magiera-Mularz et al., "Human and mouse PD-L1: similar molecular structure, but different druggability profiles," iScience, 2021, vol. 24, Article 101960, Jan. 22, 2021, 26 pages.

* cited by examiner

MAb3 VH SEQ ID NO:35 (1) EVKLVESGGGLVKPGGSLTLPCAAS GFTFSRYAMSWVRQTPEKRLEWVASISSGG-DTYY
MAb1 VH SEQ ID NO:31 (1) EVMLVESGGGLVKPGGSLKLSCAAS GFTFSSYAMSWVRQTPEKRLEWVATISSGGSYIYY
MAb4 VH SEQ ID NO:37 (1) EVQLVESGGGLVKPGGSLKLSCAAS GFTFSSYDMSWVRQTPEKRLEWVAFISSYGGRTYY
MAb5 VH SEQ ID NO:39 (1) ELQLVESGGVLVKPGGSLKLSCAAS GFAFSSYDMSWVRQTPEKRLEWVTYINSGGGITYY
MAb2 VH SEQ ID NO:33 (1) EVQLQESGGVLVKPGGSLKLSCAAS GFVFSSYDMSWVRQTPEKRLEWVAYISSGGGITYF

MAb3 VH SEQ ID NO:35 (60) PDSVKGRFTVSRDNARNILFLQMSSLRSEDTGMYYCARVNYYDSSFLDWWGQGTTLTVSS
MAb1 VH SEQ ID NO:31 (61) LDSVKGRFTISRDNAKNTLYLQMSSLRSEDTAMYYCARPAYYGNPAMDYWGQGTSVTVSS
MAb4 VH SEQ ID NO:37 (61) ADTVKGRFTISRDNAKNTLYLQMSSLKSEDTAMFYC AAHYFGTSGPFAYWGQGTLVTVSE
MAb5 VH SEQ ID NO:39 (61) PDTVKGRFTISRDNARNTLYLQMSSLKSEDTAIYYC TAHYFGSSGPFAYWGQGTLVTVSA
MAb2 VH SEQ ID NO:33 (61) PDTVQGRFTVSRDNAKNTLYLQMNSLKSEDTAIYYC AAHYFGSSGPFAYWGQGTLVTVSA

MAb3 VL SEQ ID NO:36 (1) DIVMTQSQRFMSTLEGDRVSVTCKAS QNVGTNVAWYQQKPGQSPKALIYSASYRYSGVPD
MAb1 VL SEQ ID NO:32 (1) DILMTQSQKFMSTSVGDRVSVTCKAS QNVGTNVAWYQQKPGQSPKPLIYSASYRYSGVPD
MAb4 VL SEQ ID NO:38 (1) DIQMTQSPASLSASVGETVTITCRAS ENIYSYFAWYQQKQGKSPQLLVYNAKILAEGVPS
MAb5 VL SEQ ID NO:40 (1) DIQMTQSPASLSASVGETVTITCRAS ENIYSYLAWYQQKQGKSPQLLVYNAKTLTEGVPS
MAb2 VL SEQ ID NO:34 (1) DIQMTQSPASLSASVGETVTITCRAS ENIFSYLAWYQQKQGKSPQLLVYNTKTLAEGVPS

MAb3 VL SEQ ID NO:36 (61) RFTGSGSGTDFTLTISNVQSEDLAEYFC QQYNNYPLYTFGGGTKLEIK
MAb1 VL SEQ ID NO:32 (61) RFTGSGSGTDFTLTISNVQSEDLAEYFC QQYNSYPLYTFGGGTKLEIK
MAb4 VL SEQ ID NO:38 (61) RFSGSGSGTQFSLKINSLQPEDFGTYYC QHHYGIP-FTFGSGTKLELK
MAb5 VL SEQ ID NO:40 (61) RFSGSGSGTQFSLKINSLQPEDFGSYYC QHHYGTP-FTFGSGTKLEIK
MAb2 VL SEQ ID NO:34 (61) RFSGSGSGTQFSLKINSLQPEDFGSYYC QHHYGTP-FTFGSGTKLEIK

FIG. 7

Heavy Chain variable domain alignment

| | | | | | | | | |
|---|---|---|---|---|---|---|---|---|
| Mab2 | SEQ ID NO:33 | (1) | EVQLQESGGVLVKPGGSLKLSCAAS | **GFVFSSYD** | MSWVRQTPEKRLEWVAY | **ISSGGGIT** | YF | (60) |
| Mab4 | SEQ ID NO:37 | (1) | EVQLVESGGGLVKPGGSLKLSCAAS | **GFTFSSYD** | MSWVRQTPEKRLEWVAF | **ISSYGGRT** | YY | (60) |
| Mab5 | SEQ ID NO:39 | (1) | ELQLVESGGVLVKPGGSLKLSCAAS | **GFAFSSYD** | MSWVRQTPEKRLEWVTY | **INSGGGIT** | YY | (60) |
| humanized VH1a | SEQ ID NO:5 | (1) | EVQLQESGPGLVKPGGSLSLSCAAS | **GFVFSSYD** | MSWVRQTPERGLEWVAY | **ISSGGGIT** | YA | (60) |
| humanized VH1 | SEQ ID NO:51 | (1) | EVQLQESGPGLVKPGGSLSLSCAAS | **GFVFSSYD** | MSWVRQTPERRLEWVAY | **ISSGGGIT** | YF | (60) |
| humanized VHg2 | SE Q ID NO:74 | (1) | EVQLVESGGGLVQPGGSLRLSCAAS | GFVFSSYD | MSWVRQAPGKGLEWVSY | ISSGGGIT | YY | (60) |

| | | | | | | |
|---|---|---|---|---|---|---|
| Mab2 | SEQ ID NO:33 | (61) | PDTVQGRFTVSRDNAKNTLYLQMNSLKSEDTAIYYC | **AAHYFGSSGPFAY** | WGQGTLVTVSA | (120) |
| Mab4 | SEQ ID NO:37 | (61) | ADTVKGRFTISRDNAKNTLYLQMSSLKSEDTAMFYC | **AAHYFGTSGPFAY** | WGQGTLVTVSA | (120) |
| Mab5 | SEQ ID NO:39 | (61) | PDTVKGRFTISRDNARNTLYLQMSSLKSEDTAIYYC | **TAHYFGSSGPFAY** | WGQGTLVTVSA | (120) |
| humanized VH1a | SEQ ID NO:5 | (61) | PSTVKGRFTVSRDNAKNTLYLQMNSLTSEDTAVYYC | **AAHYFGSSGPFAY** | WGQGTLVTVSS | (120) |
| humanized VH1 | SEQ ID NO:5 1 | (61) | PSTVKGRFTVSRDNAKNTLYLQMNSLTSEDTAIYYC | **AAHYFGSSGPFAY** | WGQGTLVTVSA | (120) |
| humanized VHg2 | SEQ ID NO:74 | (61) | ADSVKGRFTISRDNSKNTLYLQMNSLRAEDTAVYYC | AAHYFGSSGPFAY | WGQGTLVTVSS | (120) |

In : CDR positions allowing any substitution
In : CDR positions allowing only conservative substitution
In : CDR positions not allowing any substitution

FIG.22

Light Chain variable domain alignment

| | | | | | | |
|---|---|---|---|---|---|---|
| Mab2 | SEQ ID NO: 34 | (1)DIQMTQSPASLSASVGETVTITCRAS | **ENIFSY** | LAWYQQKQGKSPQLLVY | **NTK** | TLAEGVPS (60) |
| Mab4 | SEQ ID NO: 38 | (1)DIQMTQSPASLSASVGETVTITCRAS | **ENIYSY** | FAWYQQKQGKSPQLLVY | **NAK** | ILAEGVPS (60) |
| Mab5 | SEQ ID NO: 40 | (1)DIQMTQSPA SLSASVGETVTITCRAS | **ENIYSY** | LAWYQQKQGKSPQLLVY | **NAK** | TLTEGVPS (60) |
| humanized VL1 | SEQ ID NO: 17 | (1)DIQMTQSPASLSASVGDTVTITCRAS | **ENIFSY** | LAWYQQKPGKSPKLLVY | **NTK** | TLAEGVPS (60) |
| humanized VL1a | SEQ ID NO: 23 | (1)DIQMTQSPASLSASVGDRVTITCRAS | **ENIFSY** | LAWYQQKPGKSPKLLVY | **NTK** | TLAEGVPS (60) |
| humanized VL1c | SEQ ID NO: 29 | (1)DIQMTQSPASLSASVGDRVTITCRAS | **ENIFSY** | LAWYQQKPGKSPKLLVY | **NTR** | TLAEGVPS (60) |
| humanized VL1d | SEQ ID NO: 55 | (1)DIQMTQSPASLSASVGDTVTITCRAS | **ENIFSY** | LAWYQQKPGKSPKLLVY | **NTR** | TLAEGVPS (60) |
| humanized VLg5 | SEQ ID NO: 75 | (1)DIQMTQSPSSLSASVGDRVTITCRAS | ENIFSY | LAWYQQKPGKAPKLLIY | NTR | TLQSGVPS (60) |

| | | | | |
|---|---|---|---|---|
| Mab2 | SEQ ID NO: 34 | (61)RFSGSGSGTQFSLKINSLQPEDFGSYYC | **QHHYGTPFT** | FGSGTKLEIK (107) |
| Mab4 | SEQ ID NO: 38 | (61)RFSGSGSGTQFSLKINSLQPEDFGTYYC | **QHHYGIPFT** | FGSGTKLELK (107) |
| Mab5 | SEQ ID NO: 40 | (61)RFSGSGSGTQ FSLKINSLQPEDFGSYYC | **QHHYGTPFT** | FGSGTKLEIK (107) |
| humanized VL1 | SEQ ID NO: 17 | (61)RFSGSGSGTQFSLTISSLQPEDFGSYYC | **QHHYGTPFT** | FGSGTKLEIK (107) |
| humanized VL1a | SEQ ID NO: 23 | (61)RFSGSGSGTDFSLTISSLQPEDFATYYC | **QHHYGTPFT** | FGSGTKLEIK (107) |
| humanized VL1c | SEQ ID NO: 29 | (61)RFSGS GSGTDFSLTISSLQPEDFATYYC | **QHHYGTPFT** | FGSGTKLEIK (107) |
| humanized VL1d | SEQ ID NO: 55 | (61)RFSGSGSGTQFSLTISSLQPEDFGSYYC | **QHHYGTPFT** | FGSGTKLEIK (107) |
| humanized VLg5 | SEQ ID NO: 75 | (61)RFSGSGSGTDFTLTISSLQPEDFATYYC | QHHYGTPFT | FGQGTKLEIK (107) |

In ▨ : CDR positions allowi ng any substitution
In ▧ : CDR positions allowing only conservative substitution
In □ : CDR positions not allowing any substitution

FIG.23

SEQUENCE LISTING

```
<160> NUMBER OF SEQ ID NOS: 90

<210> SEQ ID NO 1
<211> LENGTH: 8
<212> TYPE: PRT
<213> ORGANISM: Artificial Sequence
<220> FEATURE:
<223> OTHER INFORMATION: CDR

<400> SEQUENCE: 1

Gly Phe Thr Phe Ser Ser Tyr Ala
1               5


<210> SEQ ID NO 2
<211> LENGTH: 8
<212> TYPE: PRT
<213> ORGANISM: Artificial Sequence
<220> FEATURE:
<223> OTHER INFORMATION: CDR
```

```
<400> SEQUENCE: 2

Ile Ser Ser Gly Gly Ser Tyr Ile
1               5


<210> SEQ ID NO 3
<211> LENGTH: 13
<212> TYPE: PRT
<213> ORGANISM: Artificial Sequence
<220> FEATURE:
<223> OTHER INFORMATION: CDR

<400> SEQUENCE: 3

Ala Arg Pro Ala Tyr Tyr Gly Asn Pro Ala Met Asp Tyr
1               5                   10


<210> SEQ ID NO 4
<211> LENGTH: 6
<212> TYPE: PRT
<213> ORGANISM: Artificial Sequence
<220> FEATURE:
<223> OTHER INFORMATION: CDR

<400> SEQUENCE: 4

Gln Asn Val Gly Thr Asn
1               5


<210> SEQ ID NO 5
<211> LENGTH: 120
<212> TYPE: PRT
<213> ORGANISM: Artificial Sequence
<220> FEATURE:
<223> OTHER INFORMATION: VH1a of humanized  MAb2 antibody

<400> SEQUENCE: 5

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser
        115                 120


<210> SEQ ID NO 6
<211> LENGTH: 10
<212> TYPE: PRT
<213> ORGANISM: Artificial Sequence
<220> FEATURE:
<223> OTHER INFORMATION: CDR

<400> SEQUENCE: 6

Gln Gln Tyr Asn Ser Tyr Pro Leu Tyr Thr
1               5                   10
```

<210> SEQ ID NO 7
<211> LENGTH: 8
<212> TYPE: PRT
<213> ORGANISM: Artificial Sequence
<220> FEATURE:
<223> OTHER INFORMATION: CDR

<400> SEQUENCE: 7

Gly Phe Val Phe Ser Ser Tyr Asp
1               5

<210> SEQ ID NO 8
<211> LENGTH: 8
<212> TYPE: PRT
<213> ORGANISM: Artificial
<220> FEATURE:
<223> OTHER INFORMATION: CDR

<400> SEQUENCE: 8

Ile Ser Ser Gly Gly Gly Ile Thr
1               5

<210> SEQ ID NO 9
<211> LENGTH: 13
<212> TYPE: PRT
<213> ORGANISM: Artificial
<220> FEATURE:
<223> OTHER INFORMATION: CDR

<400> SEQUENCE: 9

Ala Ala His Tyr Phe Gly Ser Ser Gly Pro Phe Ala Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: CDR

<400> SEQUENCE: 10

Glu Asn Ile Phe Ser Tyr
1               5

<210> SEQ ID NO 11
<211> LENGTH: 526
<212> TYPE: PRT
<213> ORGANISM: Homo sapiens

<400> SEQUENCE: 11

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

-continued

```
Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510
```

Leu Thr Ala Thr Glu Ile Ile Tyr Ser Glu Val Lys Lys Gln
        515                 520                 525

<210> SEQ ID NO 12
<211> LENGTH: 9
<212> TYPE: PRT
<213> ORGANISM: Artificial Sequence
<220> FEATURE:
<223> OTHER INFORMATION: CDR

<400> SEQUENCE: 12

Gln His His Tyr Gly Thr Pro Phe Thr
1               5

<210> SEQ ID NO 13
<211> LENGTH: 8
<212> TYPE: PRT
<213> ORGANISM: Artificial Sequence
<220> FEATURE:
<223> OTHER INFORMATION: CDR

<400> SEQUENCE: 13

Gly Phe Thr Phe Ser Arg Tyr Ala
1               5

<210> SEQ ID NO 14
<211> LENGTH: 7
<212> TYPE: PRT
<213> ORGANISM: Artificial Sequence
<220> FEATURE:
<223> OTHER INFORMATION: CDR

<400> SEQUENCE: 14

Ile Ser Ser Gly Gly Asp Thr
1               5

<210> SEQ ID NO 15
<211> LENGTH: 13
<212> TYPE: PRT
<213> ORGANISM: Artificial Sequence
<220> FEATURE:
<223> OTHER INFORMATION: CDR

<400> SEQUENCE: 15

Ala Arg Val Asn Tyr Tyr Asp Ser Ser Phe Leu Asp Trp
1               5                   10

<210> SEQ ID NO 16
<211> LENGTH: 6
<212> TYPE: PRT
<213> ORGANISM: Artificial Sequence
<220> FEATURE:
<223> OTHER INFORMATION: CDR

<400> SEQUENCE: 16

Gln Asn Val Gly Thr Asn
1               5

<210> SEQ ID NO 17
<211> LENGTH: 107
<212> TYPE: PRT
<213> ORGANISM: Artificial Sequence
<220> FEATURE:
<223> OTHER INFORMATION: VL1 of humanized MAb2 antibody

<400> SEQUENCE: 17

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Thr Ile Ser Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 18
<211> LENGTH: 10
<212> TYPE: PRT
<213> ORGANISM: Artificial Sequence
<220> FEATURE:
<223> OTHER INFORMATION: CDR

<400> SEQUENCE: 18

Gln Gln Tyr Asn Asn Tyr Pro Leu Tyr Thr
1               5                   10

<210> SEQ ID NO 19
<211> LENGTH: 8
<212> TYPE: PRT
<213> ORGANISM: Artificial Sequence
<220> FEATURE:
<223> OTHER INFORMATION: CDR

<400> SEQUENCE: 19

Gly Phe Thr Phe Ser Ser Tyr Asp
1               5

<210> SEQ ID NO 20
<211> LENGTH: 8
<212> TYPE: PRT
<213> ORGANISM: Artificial Sequence
<220> FEATURE:
<223> OTHER INFORMATION: antibody fragment

<400> SEQUENCE: 20

Ile Ser Ser Tyr Gly Gly Arg Thr
1               5

<210> SEQ ID NO 21
<211> LENGTH: 13
<212> TYPE: PRT
<213> ORGANISM: Artificial Sequence
<220> FEATURE:
<223> OTHER INFORMATION: CDR

<400> SEQUENCE: 21

Ala Ala His Tyr Phe Gly Thr Ser Gly Pro Phe Ala Tyr
1               5                   10

<210> SEQ ID NO 22
<211> LENGTH: 6

<212> TYPE: PRT
<213> ORGANISM: Artificial Sequence
<220> FEATURE:
<223> OTHER INFORMATION: CDR

<400> SEQUENCE: 22

Glu Asn Ile Tyr Ser Tyr
1               5

<210> SEQ ID NO 23
<211> LENGTH: 107
<212> TYPE: PRT
<213> ORGANISM: Artificial Sequence
<220> FEATURE:
<223> OTHER INFORMATION: VL1a of humanized MAb2 antibody

<400> SEQUENCE: 23

Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 24
<211> LENGTH: 9
<212> TYPE: PRT
<213> ORGANISM: Artificial Sequence
<220> FEATURE:
<223> OTHER INFORMATION: CDR

<400> SEQUENCE: 24

Gln His His Tyr Gly Ile Pro Phe Thr
1               5

<210> SEQ ID NO 25
<211> LENGTH: 8
<212> TYPE: PRT
<213> ORGANISM: Artificial Sequence
<220> FEATURE:
<223> OTHER INFORMATION: CDR

<400> SEQUENCE: 25

Gly Phe Ala Phe Ser Ser Tyr Asp
1               5

<210> SEQ ID NO 26
<211> LENGTH: 8
<212> TYPE: PRT
<213> ORGANISM: Artificial Sequence
<220> FEATURE:
<223> OTHER INFORMATION: CDR

<400> SEQUENCE: 26

Ile Asn Ser Gly Gly Gly Ile Thr
1               5

<210> SEQ ID NO 27
<211> LENGTH: 13
<212> TYPE: PRT
<213> ORGANISM: Artificial Sequence
<220> FEATURE:
<223> OTHER INFORMATION: CDR

<400> SEQUENCE: 27

```
Thr Ala His Tyr Phe Gly Ser Ser Gly Pro Phe Ala Tyr
1               5                   10
```

<210> SEQ ID NO 28
<211> LENGTH: 6
<212> TYPE: PRT
<213> ORGANISM: Artificial Sequence
<220> FEATURE:
<223> OTHER INFORMATION: CDR

<400> SEQUENCE: 28

```
Glu Asn Ile Tyr Ser Tyr
1               5
```

<210> SEQ ID NO 29
<211> LENGTH: 107
<212> TYPE: PRT
<213> ORGANISM: Artificial Sequence
<220> FEATURE:
<223> OTHER INFORMATION: VL1c of humanized MAb2 antibody

<400> SEQUENCE: 29

```
Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys
            100                 105
```

<210> SEQ ID NO 30
<211> LENGTH: 9
<212> TYPE: PRT
<213> ORGANISM: Artificial
<220> FEATURE:
<223> OTHER INFORMATION: CDR

<400> SEQUENCE: 30

```
Gln His His Tyr Gly Thr Pro Phe Thr
1               5
```

<210> SEQ ID NO 31
<211> LENGTH: 120
<212> TYPE: PRT
<213> ORGANISM: Artificial
<220> FEATURE:
<223> OTHER INFORMATION: antibody fragment -continued

<400> SEQUENCE: 31

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Ile Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Pro Ala Tyr Tyr Gly Asn Pro Ala Met Asp Tyr Trp Gly Gln
            100                 105                 110

Gly Thr Ser Val Thr Val Ser Ser
        115                 120
```

<210> SEQ ID NO 32
<211> LENGTH: 108
<212> TYPE: PRT
<213> ORGANISM: Artificial
<220> FEATURE:
<223> OTHER INFORMATION: antibody fragment

<400> SEQUENCE: 32

```
Asp Ile Leu Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Tyr Thr Phe Gly Gly Gly Thr Lys Leu Glu Ile Lys
            100                 105
```

<210> SEQ ID NO 33
<211> LENGTH: 120
<212> TYPE: PRT
<213> ORGANISM: Artificial Sequence
<220> FEATURE:
<223> OTHER INFORMATION: antibody fragment

<400> SEQUENCE: 33

```
Glu Val Gln Leu Gln Glu Ser Gly Gly Val Leu Val Lys Pro Gly Gly
1               5                   10                  15

Ser Leu Lys Leu Ser Cys Ala Ala Ser Gly Phe Val Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ile Thr Tyr Phe Pro Asp Thr Val
    50                  55                  60
```

-continued

```
Gln Gly Arg Phe Thr Val Ser Arg Asp Asn Ala Lys Asn Thr Leu Tyr
65                  70                  75                  80

Leu Gln Met Asn Ser Leu Lys Ser Glu Asp Thr Ala Ile Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ala
        115                 120


<210> SEQ ID NO 34
<211> LENGTH: 107
<212> TYPE: PRT
<213> ORGANISM: Artificial Sequence
<220> FEATURE:
<223> OTHER INFORMATION: antibody fragment

<400> SEQUENCE: 34

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105


<210> SEQ ID NO 35
<211> LENGTH: 119
<212> TYPE: PRT
<213> ORGANISM: Artificial Sequence
<220> FEATURE:
<223> OTHER INFORMATION: antibody fragment

<400> SEQUENCE: 35

Glu Val Lys Leu Val Glu Ser Gly Gly Gly Leu Val Lys Pro Gly Gly
1               5                   10                  15

Ser Leu Thr Leu Pro Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Asp Thr Tyr Tyr Pro Asp Ser Val Lys
    50                  55                  60

Gly Arg Phe Thr Val Ser Arg Asp Asn Ala Arg Asn Ile Leu Phe Leu
65                  70                  75                  80

Gln Met Ser Ser Leu Arg Ser Glu Asp Thr Gly Met Tyr Tyr Cys Ala
                85                  90                  95

Arg Val Asn Tyr Tyr Asp Ser Ser Phe Leu Asp Trp Trp Gly Gln Gly
            100                 105                 110

Thr Thr Leu Thr Val Ser Ser
        115


<210> SEQ ID NO 36
```

<211> LENGTH: 108
<212> TYPE: PRT
<213> ORGANISM: Artificial Sequence
<220> FEATURE:
<223> OTHER INFORMATION: antibody fragment

<400> SEQUENCE: 36

```
Asp Ile Val Met Thr Gln Ser Gln Arg Phe Met Ser Thr Leu Glu Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Tyr Thr Phe Gly Gly Gly Thr Lys Leu Glu Ile Lys
            100                 105
```

<210> SEQ ID NO 37
<211> LENGTH: 120
<212> TYPE: PRT
<213> ORGANISM: Artificial Sequence
<220> FEATURE:
<223> OTHER INFORMATION: antibody fragment

<400> SEQUENCE: 37

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Arg Leu Glu Trp Val
        35                  40                  45

Ala Phe Ile Ser Ser Tyr Gly Gly Arg Thr Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Phe Tyr Cys
                85                  90                  95

Ala Ala His Tyr Phe Gly Thr Ser Gly Pro Phe Ala Tyr Trp Gly Gln
            100                 105                 110

Gly Thr Leu Val Thr Val Ser Ala
        115                 120
```

<210> SEQ ID NO 38
<211> LENGTH: 107
<212> TYPE: PRT
<213> ORGANISM: Artificial
<220> FEATURE:
<223> OTHER INFORMATION: antibody fragment

<400> SEQUENCE: 38

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30
```

```
Phe Ala Trp Tyr Gln Gln Lys Gln Gly Lys Ser Pro Gln Leu Leu Val
        35                  40                  45

Tyr Asn Ala Lys Ile Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Ile Pro Phe
                85                  90                  95

Thr Phe Gly Ser Gly Thr Lys Leu Glu Leu Lys
            100                 105


<210> SEQ ID NO 39
<211> LENGTH: 120
<212> TYPE: PRT
<213> ORGANISM: Artificial
<220> FEATURE:
<223> OTHER INFORMATION: antibody fragment

<400> SEQUENCE: 39

Glu Leu Gln Leu Val Glu Ser Gly Gly Val Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Thr Tyr Ile Asn Ser Gly Gly Gly Ile Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Ile Tyr Tyr Cys
                85                  90                  95

Thr Ala His Tyr Phe Gly Ser Ser Gly Pro Phe Ala Tyr Trp Gly Gln
            100                 105                 110

Gly Thr Leu Val Thr Val Ser Ala
        115                 120


<210> SEQ ID NO 40
<211> LENGTH: 107
<212> TYPE: PRT
<213> ORGANISM: Artificial
<220> FEATURE:
<223> OTHER INFORMATION: antibody fragment

<400> SEQUENCE: 40

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105
```

<210> SEQ ID NO 41
<211> LENGTH: 449
<212> TYPE: PRT
<213> ORGANISM: Artificial
<220> FEATURE:
<223> OTHER INFORMATION: antibody fragment

<400> SEQUENCE: 41

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Ile Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Pro Ala Tyr Tyr Gly Asn Pro Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 42
<211> LENGTH: 215
<212> TYPE: PRT
<213> ORGANISM: Artificial Sequence
<220> FEATURE:
<223> OTHER INFORMATION: antibody fragment

<400> SEQUENCE: 42

Asp Ile Leu Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Tyr Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 43
<211> LENGTH: 449
<212> TYPE: PRT
<213> ORGANISM: Artificial
<220> FEATURE:
<223> OTHER INFORMATION: antibody fragment
```

<400> SEQUENCE: 43

Glu Val Gln Leu Gln Glu Ser Gly Gly Val Leu Val Lys Pro Gly Gly
1 5 10 15

Ser Leu Lys Leu Ser Cys Ala Ala Ser Gly Phe Val Phe Ser Ser Tyr
20 25 30

Asp Met Ser Trp Val Arg Gln Thr Pro Glu Lys Arg Leu Glu Trp Val
35 40 45

Ala Tyr Ile Ser Ser Gly Gly Gly Ile Thr Tyr Phe Pro Asp Thr Val
50 55 60

Gln Gly Arg Phe Thr Val Ser Arg Asp Asn Ala Lys Asn Thr Leu Tyr
65 70 75 80

Leu Gln Met Asn Ser Leu Lys Ser Glu Asp Thr Ala Ile Tyr Tyr Cys
85 90 95

Ala Ala His Tyr Phe Gly Ser Ser Gly Pro Phe Ala Tyr Trp Gly Gln
100 105 110

Gly Thr Leu Val Thr Val Ser Ala Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 44
<211> LENGTH: 214
<212> TYPE: PRT
<213> ORGANISM: Artificial Sequence
<220> FEATURE:
<223> OTHER INFORMATION: antibody fragment

<400> SEQUENCE: 44

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Val
        35                  40                  45

Tyr Asn Thr Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 45
<211> LENGTH: 448
<212> TYPE: PRT
<213> ORGANISM: Artificial Sequence
<220> FEATURE:
<223> OTHER INFORMATION: antibody fragment

<400> SEQUENCE: 45

Glu Val Lys Leu Val Glu Ser Gly Gly Gly Leu Val Lys Pro Gly Gly
1               5                   10                  15

Ser Leu Thr Leu Pro Cys Ala Ala Ser Gly Phe Thr Phe Ser Arg Tyr
            20                  25                  30
```

-continued

```
Ala Met Ser Trp Val Arg Gln Thr Pro Glu Lys Arg Leu Glu Trp Val
        35                  40                  45

Ala Ser Ile Ser Ser Gly Gly Asp Thr Tyr Tyr Pro Asp Ser Val Lys
    50                  55                  60

Gly Arg Phe Thr Val Ser Arg Asp Asn Ala Arg Asn Ile Leu Phe Leu
65                  70                  75                  80

Gln Met Ser Ser Leu Arg Ser Glu Asp Thr Gly Met Tyr Tyr Cys Ala
                85                  90                  95

Arg Val Asn Tyr Tyr Asp Ser Ser Phe Leu Asp Trp Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 46
<211> LENGTH: 215
<212> TYPE: PRT
<213> ORGANISM: Artificial
<220> FEATURE:
<223> OTHER INFORMATION: antibody fragment

<400> SEQUENCE: 46

```
Asp Ile Val Met Thr Gln Ser Gln Arg Phe Met Ser Thr Leu Glu Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Tyr Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 47
<211> LENGTH: 449
<212> TYPE: PRT
<213> ORGANISM: Artificial
<220> FEATURE:
<223> OTHER INFORMATION: antibody fragment

<400> SEQUENCE: 47

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Arg Leu Glu Trp Val
        35                  40                  45

Ala Phe Ile Ser Ser Tyr Gly Gly Arg Thr Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Phe Tyr Cys
                85                  90                  95
```

```
Ala Ala His Tyr Phe Gly Thr Ser Gly Pro Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 48
<211> LENGTH: 214
<212> TYPE: PRT
<213> ORGANISM: Artificial Sequence
<220> FEATURE:
<223> OTHER INFORMATION: antibody fragment -continued

<400> SEQUENCE: 48

Asp Ile Gln Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Tyr
20 25 30

Phe Ala Trp Tyr Gln Gln Lys Gln Gly Lys Ser Pro Gln Leu Leu Val
35 40 45

Tyr Asn Ala Lys Ile Leu Ala Glu Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Thr Tyr Tyr Cys Gln His His Tyr Gly Ile Pro Phe
85 90 95

Thr Phe Gly Ser Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 49
<211> LENGTH: 449
<212> TYPE: PRT
<213> ORGANISM: Artificial Sequence
<220> FEATURE:
<223> OTHER INFORMATION: antibody fragment

<400> SEQUENCE: 49

Glu Leu Gln Leu Val Glu Ser Gly Gly Val Leu Val Lys Pro Gly Gly
1 5 10 15

Ser Leu Lys Leu Ser Cys Ala Ala Ser Gly Phe Ala Phe Ser Ser Tyr
20 25 30

Asp Met Ser Trp Val Arg Gln Thr Pro Glu Lys Arg Leu Glu Trp Val
35 40 45

Thr Tyr Ile Asn Ser Gly Gly Gly Ile Thr Tyr Tyr Pro Asp Thr Val
50 55 60

Lys Gly Arg Phe Thr Ile Ser Arg Asp Asn Ala Arg Asn Thr Leu Tyr
65 70 75 80

Leu Gln Met Ser Ser Leu Lys Ser Glu Asp Thr Ala Ile Tyr Tyr Cys
85 90 95

Thr Ala His Tyr Phe Gly Ser Ser Gly Pro Phe Ala Tyr Trp Gly Gln
100 105 110

Gly Thr Leu Val Thr Val Ser Ala Ala Ser Thr Lys Gly Pro Ser Val
115 120 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 50
<211> LENGTH: 214
<212> TYPE: PRT
<213> ORGANISM: Artificial
<220> FEATURE:
<223> OTHER INFORMATION: antibody fragment

<400> SEQUENCE: 50

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30
```

```
Leu Ala Trp Tyr Gln Gln Lys Gln Gly Lys Ser Pro Gln Leu Leu Val
        35                  40                  45

Tyr Asn Ala Lys Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 51
<211> LENGTH: 120
<212> TYPE: PRT
<213> ORGANISM: Artificial Sequence
<220> FEATURE:
<223> OTHER INFORMATION: antibody fragment

<400> SEQUENCE: 51

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Arg Leu Glu Trp Val
        35                  40                  45

Ala Tyr Ile Ser Ser Gly Gly Gly Ile Thr Tyr Phe Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Ile Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ala
        115                 120


<210> SEQ ID NO 52
<211> LENGTH: 702
<212> TYPE: PRT
<213> ORGANISM: Homo sapiens
```

<400> SEQUENCE: 52

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400
```

```
Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700


<210> SEQ ID NO 53
<211> LENGTH: 654
<212> TYPE: PRT
<213> ORGANISM: Macaca fascicularis

<400> SEQUENCE: 53

Gln Leu Thr Ile Glu Ser Arg Pro Phe Asn Val Ala Glu Gly Lys Glu
1               5                   10                  15

Val Leu Leu Leu Ala His Asn Val Ser Gln Asn Leu Phe Gly Tyr Ile
            20                  25                  30

Trp Tyr Lys Gly Glu Arg Val Asp Ala Ser Arg Arg Ile Gly Ser Cys
        35                  40                  45

Val Ile Arg Thr Gln Gln Ile Thr Pro Gly Pro Ala His Ser Gly Arg
    50                  55                  60
```

-continued

```
Glu Thr Ile Asp Phe Asn Ala Ser Leu Leu Ile Gln Asn Val Thr Gln
65                  70                  75                  80

Ser Asp Thr Gly Ser Tyr Thr Ile Gln Val Ile Lys Glu Asp Leu Val
                85                  90                  95

Asn Glu Glu Ala Thr Gly Gln Phe Arg Val Tyr Pro Glu Leu Pro Lys
            100                 105                 110

Pro Tyr Ile Thr Ser Asn Asn Ser Asn Pro Ile Glu Asp Lys Asp Ala
        115                 120                 125

Val Ala Leu Thr Cys Glu Pro Glu Thr Gln Asp Thr Thr Tyr Leu Trp
    130                 135                 140

Trp Val Asn Asn Gln Ser Leu Pro Val Ser Pro Arg Leu Glu Leu Ser
145                 150                 155                 160

Ser Asp Asn Arg Thr Leu Thr Val Phe Asn Ile Pro Arg Asn Asp Thr
                165                 170                 175

Thr Ser Tyr Lys Cys Glu Thr Gln Asn Pro Val Ser Val Arg Arg Ser
            180                 185                 190

Asp Pro Val Thr Leu Asn Val Leu Tyr Gly Pro Asp Ala Pro Thr Ile
        195                 200                 205

Ser Pro Leu Asn Thr Pro Tyr Arg Ala Gly Glu Tyr Leu Asn Leu Thr
    210                 215                 220

Cys His Ala Ala Ser Asn Pro Thr Ala Gln Tyr Phe Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Ala Ile Thr Val Tyr Ala Glu Leu
        275                 280                 285

Pro Lys Pro Tyr Ile Thr Ser Asn Asn Ser Asn Pro Ile Glu Asp Lys
    290                 295                 300

Asp Ala Val Thr Leu Thr Cys Glu Pro Glu Thr Gln Asp Thr Thr Tyr
305                 310                 315                 320

Leu Trp Trp Val Asn Asn Gln Arg Leu Ser Val Ser Ser Arg Leu Glu
                325                 330                 335

Leu Ser Asn Asp Asn Arg Thr Leu Thr Val Phe Asn Ile Pro Arg Asn
            340                 345                 350

Asp Thr Thr Phe Tyr Glu Cys Glu Thr Gln Asn Pro Val Ser Val Arg
        355                 360                 365

Arg Ser Asp Pro Val Thr Leu Asn Val Leu Tyr Gly Pro Asp Ala Pro
    370                 375                 380

Thr Ile Ser Pro Leu Asn Thr Pro Tyr Arg Ala Gly Glu Asn Leu Asn
385                 390                 395                 400

Leu Ser Cys His Ala Ala Ser Asn Pro Ala Ala Gln Tyr Phe Trp Phe
                405                 410                 415

Val Asn Gly Thr Phe Gln Gln Ser Thr Gln Glu Leu Phe Ile Pro Asn
            420                 425                 430

Ile Thr Val Asn Asn Ser Gly Ser Tyr Met Cys Gln Ala His Asn Ser
        435                 440                 445

Ala Thr Gly Leu Asn Arg Thr Thr Val Thr Ala Ile Thr Val Tyr Val
    450                 455                 460

Glu Leu Pro Lys Pro Tyr Ile Ser Ser Asn Asn Ser Asn Pro Ile Glu
465                 470                 475                 480
```

-continued

```
Asp Lys Asp Ala Val Thr Leu Thr Cys Glu Pro Val Ala Glu Asn Thr
                485                 490                 495

Thr Tyr Leu Trp Trp Val Asn Asn Gln Ser Leu Ser Val Ser Pro Arg
            500                 505                 510

Leu Gln Leu Ser Asn Gly Asn Arg Ile Leu Thr Leu Leu Ser Val Thr
        515                 520                 525

Arg Asn Asp Thr Gly Pro Tyr Glu Cys Gly Ile Gln Asn Ser Glu Ser
    530                 535                 540

Ala Lys Arg Ser Asp Pro Val Thr Leu Asn Val Thr Tyr Gly Pro Asp
545                 550                 555                 560

Thr Pro Ile Ile Ser Pro Pro Asp Leu Ser Tyr Arg Ser Gly Ala Asn
                565                 570                 575

Leu Asn Leu Ser Cys His Ser Asp Ser Asn Pro Ser Pro Gln Tyr Ser
            580                 585                 590

Trp Leu Ile Asn Gly Thr Leu Arg Gln His Thr Gln Val Leu Phe Ile
        595                 600                 605

Ser Lys Ile Thr Ser Asn Asn Asn Gly Ala Tyr Ala Cys Phe Val Ser
    610                 615                 620

Asn Leu Ala Thr Gly Arg Asn Asn Ser Ile Val Lys Asn Ile Ser Val
625                 630                 635                 640

Ser Ser Gly Asp Ser Ala Pro Gly Ser Ser Gly Leu Ser Ala
                645                 650


<210> SEQ ID NO 54
<211> LENGTH: 214
<212> TYPE: PRT
<213> ORGANISM: Artificial Sequence
<220> FEATURE:
<223> OTHER INFORMATION: antibody

<400> SEQUENCE: 54

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 55
<211> LENGTH: 107
<212> TYPE: PRT
<213> ORGANISM: Artificial Sequence
<220> FEATURE:
<223> OTHER INFORMATION: antibody

<400> SEQUENCE: 55

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Gln Phe Ser Leu Thr Ile Ser Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys
            100                 105


<210> SEQ ID NO 56
<211> LENGTH: 418
<212> TYPE: PRT
<213> ORGANISM: Homo sapiens
<220> FEATURE:
<221> NAME/KEY: DOMAIN
<222> LOCATION: (1)..(394)
<223> OTHER INFORMATION: extracellular domain of human CEACAM1
<220> FEATURE:
<221> NAME/KEY: MISC_FEATURE
<222> LOCATION: (395)..(418)
<223> OTHER INFORMATION: extension with His-tag

<400> SEQUENCE: 56

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140
```

```
Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
    370                 375                 380

Leu Pro Gln Glu Asn Gly Leu Ser Pro Gly Ser Gly Ser Gly Ser Gly
385                 390                 395                 400

Leu Asn Asp Ile Phe Glu Ala Gln Lys Ile Glu Trp His His His His
                405                 410                 415

His His


<210> SEQ ID NO 57
<211> LENGTH: 418
<212> TYPE: PRT
<213> ORGANISM: Macaca fascicularis
<220> FEATURE:
<221> NAME/KEY: DOMAIN
<222> LOCATION: (1)..(394)
<223> OTHER INFORMATION: extracellular domain of cynomolgus monkey
      CEACAM1
<220> FEATURE:
<221> NAME/KEY: MISC_FEATURE
<222> LOCATION: (395)..(418)
<223> OTHER INFORMATION: extension with His-tag

<400> SEQUENCE: 57

Gln Leu Thr Ile Glu Ser Arg Pro Phe Asn Val Ala Glu Gly Lys Glu
1               5                   10                  15

Val Leu Leu Leu Ala His Asn Leu Ser Gln Asn Leu Ile Gly Tyr Asn
            20                  25                  30

Trp His Lys Gly Glu Arg Val Asp Ala Lys Arg Leu Ile Val Ala Tyr
        35                  40                  45
```

```
Val Ile Glu Thr Lys Gln Thr Thr Pro Gly Pro Ala His Ser Gly Arg
    50                  55                  60

Glu Met Ile Tyr Ser Asn Ala Ser Leu Leu Ile Gln Asn Val Thr Gln
65                  70                  75                  80

Asn Asp Thr Gly Ser Tyr Thr Leu Gln Val Ile Lys Gly Asp Leu Val
                85                  90                  95

Asn Glu Glu Ala Thr Gly Gln Phe Arg Val Tyr Pro Glu Leu Pro Lys
            100                 105                 110

Pro Asn Ile Thr Ile Asn Asn Ser Asn Pro Val Glu Asp Lys Asp Val
        115                 120                 125

Val Thr Phe Thr Cys Glu Ser Glu Ala Gln Asp Thr Thr Tyr Leu Trp
    130                 135                 140

Trp Val Asn Asn Gln Ser Leu Pro Val Ser Ser Arg Leu Gln Leu Ser
145                 150                 155                 160

Asn Gly Asn Lys Thr Leu Thr Leu Leu Ser Val Leu Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Ser Ala Ala Ser Asn Pro Pro Ala Gln Tyr Ser Trp Leu Ile Asn
225                 230                 235                 240

Glu Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Arg Asn Arg Thr Thr Val Lys Met Ile Ile Val Ser Glu Gln Ser
        275                 280                 285

Leu Val Val Ala Gln Pro Gln Ile Lys Ala Ser Lys Thr Thr Val Thr
    290                 295                 300

Glu Asp Lys Asp Tyr Val Asn Leu Thr Cys Ser Thr Asn Asp Thr Gly
305                 310                 315                 320

Ile Ser Ile Ser Trp Phe Phe Lys Asp Gln Ser Leu Pro Ser Ser Glu
                325                 330                 335

Arg Met Lys Leu Ser Gln Asp Asn Ala Thr Leu Ser Ile Asn Pro Val
            340                 345                 350

Lys Arg Glu Asp Ala Gly Asn Tyr Ser Cys Glu Val Phe Asn Leu Ile
        355                 360                 365

Ser Lys Asn Arg Ser Asp Pro Ile Val Leu Ile Val Asn Tyr Asn Asn
    370                 375                 380

Arg Ala Gln Glu Asn Ile Leu Pro Ala Gly Ser Gly Ser Gly Ser Gly
385                 390                 395                 400

Leu Asn Asp Ile Phe Glu Ala Gln Lys Ile Glu Trp His His His His
                405                 410                 415

His His
```

<210> SEQ ID NO 58
<211> LENGTH: 675
<212> TYPE: PRT
<213> ORGANISM: Homo sapiens
<220> FEATURE:
<221> NAME/KEY: DOMAIN

```
<222> LOCATION: (1)..(651)
<223> OTHER INFORMATION: extracellular domain of human CEACAM5
<220> FEATURE:
<221> NAME/KEY: MISC_FEATURE
<222> LOCATION: (652)..(675)
<223> OTHER INFORMATION: extension with His-tag

<400> SEQUENCE: 58

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
        355                 360                 365
```

```
His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Ser Gly Ser Gly Ser
                645                 650                 655

Gly Leu Asn Asp Ile Phe Glu Ala Gln Lys Ile Glu Trp His His His
            660                 665                 670

His His His
        675
```

<210> SEQ ID NO 59
<211> LENGTH: 678
<212> TYPE: PRT
<213> ORGANISM: Macaca fascicularis
<220> FEATURE:
<221> NAME/KEY: DOMAIN
<222> LOCATION: (1)..(654)
<223> OTHER INFORMATION: extracellular domain of cynomolgus monkey
      CEACAM5
<220> FEATURE:
<221> NAME/KEY: MISC_FEATURE
<222> LOCATION: (655)..(678)
<223> OTHER INFORMATION: extension with His-tag

<400> SEQUENCE: 59

```
Gln Leu Thr Ile Glu Ser Arg Pro Phe Asn Val Ala Glu Gly Lys Glu
1               5                   10                  15

Val Leu Leu Leu Ala His Asn Val Ser Gln Asn Leu Phe Gly Tyr Ile
            20                  25                  30

Trp Tyr Lys Gly Glu Arg Val Asp Ala Ser Arg Arg Ile Gly Ser Cys
        35                  40                  45

Val Ile Arg Thr Gln Gln Ile Thr Pro Gly Pro Ala His Ser Gly Arg
    50                  55                  60

Glu Thr Ile Asp Phe Asn Ala Ser Leu Leu Ile Gln Asn Val Thr Gln
65                  70                  75                  80

Ser Asp Thr Gly Ser Tyr Thr Ile Gln Val Ile Lys Glu Asp Leu Val
                85                  90                  95

Asn Glu Glu Ala Thr Gly Gln Phe Arg Val Tyr Pro Glu Leu Pro Lys
            100                 105                 110

Pro Tyr Ile Thr Ser Asn Asn Ser Asn Pro Ile Glu Asp Lys Asp Ala
        115                 120                 125

Val Ala Leu Thr Cys Glu Pro Glu Thr Gln Asp Thr Thr Tyr Leu Trp
    130                 135                 140

Trp Val Asn Asn Gln Ser Leu Pro Val Ser Pro Arg Leu Glu Leu Ser
145                 150                 155                 160

Ser Asp Asn Arg Thr Leu Thr Val Phe Asn Ile Pro Arg Asn Asp Thr
                165                 170                 175

Thr Ser Tyr Lys Cys Glu Thr Gln Asn Pro Val Ser Val Arg Arg Ser
            180                 185                 190

Asp Pro Val Thr Leu Asn Val Leu Tyr Gly Pro Asp Ala Pro Thr Ile
        195                 200                 205

Ser Pro Leu Asn Thr Pro Tyr Arg Ala Gly Glu Tyr Leu Asn Leu Thr
    210                 215                 220

Cys His Ala Ala Ser Asn Pro Thr Ala Gln Tyr Phe Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Ala Ile Thr Val Tyr Ala Glu Leu
        275                 280                 285

Pro Lys Pro Tyr Ile Thr Ser Asn Asn Ser Asn Pro Ile Glu Asp Lys
    290                 295                 300

Asp Ala Val Thr Leu Thr Cys Glu Pro Glu Thr Gln Asp Thr Thr Tyr
305                 310                 315                 320

Leu Trp Trp Val Asn Asn Gln Arg Leu Ser Val Ser Ser Arg Leu Glu
                325                 330                 335

Leu Ser Asn Asp Asn Arg Thr Leu Thr Val Phe Asn Ile Pro Arg Asn
            340                 345                 350

Asp Thr Thr Phe Tyr Glu Cys Glu Thr Gln Asn Pro Val Ser Val Arg
        355                 360                 365

Arg Ser Asp Pro Val Thr Leu Asn Val Leu Tyr Gly Pro Asp Ala Pro
    370                 375                 380

Thr Ile Ser Pro Leu Asn Thr Pro Tyr Arg Ala Gly Glu Asn Leu Asn
385                 390                 395                 400
```

-continued

```
Leu Ser Cys His Ala Ala Ser Asn Pro Ala Ala Gln Tyr Phe Trp Phe
                405                 410                 415

Val Asn Gly Thr Phe Gln Gln Ser Thr Gln Glu Leu Phe Ile Pro Asn
            420                 425                 430

Ile Thr Val Asn Asn Ser Gly Ser Tyr Met Cys Gln Ala His Asn Ser
        435                 440                 445

Ala Thr Gly Leu Asn Arg Thr Thr Val Thr Ala Ile Thr Val Tyr Val
    450                 455                 460

Glu Leu Pro Lys Pro Tyr Ile Ser Ser Asn Asn Ser Asn Pro Ile Glu
465                 470                 475                 480

Asp Lys Asp Ala Val Thr Leu Thr Cys Glu Pro Val Ala Glu Asn Thr
                485                 490                 495

Thr Tyr Leu Trp Trp Val Asn Asn Gln Ser Leu Ser Val Ser Pro Arg
            500                 505                 510

Leu Gln Leu Ser Asn Gly Asn Arg Ile Leu Thr Leu Leu Ser Val Thr
        515                 520                 525

Arg Asn Asp Thr Gly Pro Tyr Glu Cys Gly Ile Gln Asn Ser Glu Ser
    530                 535                 540

Ala Lys Arg Ser Asp Pro Val Thr Leu Asn Val Thr Tyr Gly Pro Asp
545                 550                 555                 560

Thr Pro Ile Ile Ser Pro Pro Asp Leu Ser Tyr Arg Ser Gly Ala Asn
                565                 570                 575

Leu Asn Leu Ser Cys His Ser Asp Ser Asn Pro Ser Pro Gln Tyr Ser
            580                 585                 590

Trp Leu Ile Asn Gly Thr Leu Arg Gln His Thr Gln Val Leu Phe Ile
        595                 600                 605

Ser Lys Ile Thr Ser Asn Asn Asn Gly Ala Tyr Ala Cys Phe Val Ser
    610                 615                 620

Asn Leu Ala Thr Gly Arg Asn Asn Ser Ile Val Lys Asn Ile Ser Val
625                 630                 635                 640

Ser Ser Gly Asp Ser Ala Pro Gly Ser Ser Gly Leu Ser Ala Ser Gly
                645                 650                 655

Ser Gly Ser Gly Leu Asn Asp Ile Phe Glu Ala Gln Lys Ile Glu Trp
            660                 665                 670

His His His His His His
        675


<210> SEQ ID NO 60
<211> LENGTH: 317
<212> TYPE: PRT
<213> ORGANISM: Homo sapiens
<220> FEATURE:
<221> NAME/KEY: DOMAIN
<222> LOCATION: (1)..(293)
<223> OTHER INFORMATION: extracellular domain of human CEACAM6
<220> FEATURE:
<221> NAME/KEY: MISC_FEATURE
<222> LOCATION: (294)..(317)
<223> OTHER INFORMATION: extension with His-tag

<400> SEQUENCE: 60

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45
```

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Met Thr Leu Thr Leu Leu Ser Val Lys Arg Asn Asp Ala
                165                 170                 175

Gly Ser Tyr Glu Cys Glu Ile Gln Asn Pro Ala Ser Ala Asn Arg Ser
            180                 185                 190

Asp Pro Val Thr Leu Asn Val Leu Tyr Gly Pro Asp Gly Pro Thr Ile
        195                 200                 205

Ser Pro Ser Lys Ala Asn Tyr Arg Pro Gly Glu Asn Leu Asn Leu Ser
    210                 215                 220

Cys His Ala Ala Ser Asn Pro Pro Ala Gln Tyr Ser Trp Phe Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Met Ile Thr Val Ser Gly Ser Ala
        275                 280                 285

Pro Val Leu Ser Ala Ser Gly Ser Gly Ser Gly Leu Asn Asp Ile Phe
    290                 295                 300

Glu Ala Gln Lys Ile Glu Trp His His His His His His
305                 310                 315

<210> SEQ ID NO 61
<211> LENGTH: 317
<212> TYPE: PRT
<213> ORGANISM: Macaca fascicularis
<220> FEATURE:
<221> NAME/KEY: DOMAIN
<222> LOCATION: (1)..(293)
<223> OTHER INFORMATION: extracellular domain of cynomolgus monkey
      CEACAM6
<220> FEATURE:
<221> NAME/KEY: MISC_FEATURE
<222> LOCATION: (294)..(317)
<223> OTHER INFORMATION: extension with His-tag

<400> SEQUENCE: 61

Gln Leu Thr Ile Glu Ser Arg Pro Phe Asn Val Ala Glu Gly Lys Glu
1               5                   10                  15

Val Leu Leu Leu Ala His Asn Leu Pro Gln Asn Thr Leu Gly Phe Asn
            20                  25                  30

Trp Tyr Lys Gly Glu Arg Val Asp Ala Lys Arg Leu Ile Val Ala Tyr
        35                  40                  45

```
Val Ile Gly Thr Gln Gln Thr Thr Pro Gly Pro Ala His Ser Gly Arg
    50                  55                  60

Glu Met Ile Tyr Ser Asn Ala Ser Leu Leu Ile Gln Asn Val Thr Gln
65                  70                  75                  80

Asn Asp Thr Gly Ser Tyr Thr Leu Gln Val Ile Lys Gly Asp Leu Val
                85                  90                  95

Thr Glu Glu Ala Thr Gly Arg Phe Trp Val Tyr Pro Glu Leu Pro Lys
            100                 105                 110

Pro Tyr Ile Thr Ser Asn Asn Ser Asn Pro Val Glu Asp Lys Asp Ala
        115                 120                 125

Val Asp Phe Thr Cys Glu Pro Asp Ile His Ser Thr Thr Tyr Leu Trp
    130                 135                 140

Trp Val Asn Asp Gln Ser Leu Pro Val Ser Pro Arg Leu Gln Leu Ser
145                 150                 155                 160

Asn Gly Asn Arg Thr Leu Thr Leu Leu Ser Val Lys Arg Asn Asp Ala
                165                 170                 175

Gly Ala Tyr Glu Cys Glu Ile Gln Asn Pro Val Ser Ala Asn Leu Ser
            180                 185                 190

Asp Pro Val Ile Leu Asn Val Leu Tyr Gly Pro Asp Val Pro Thr Ile
        195                 200                 205

Ser Pro Ser Asn Ser Asn Tyr Arg Pro Gly Glu Asn Leu Asn Leu Ser
    210                 215                 220

Cys His Ala Ala Ser Asn Pro Thr Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala Tyr Asn Ser Ala Thr
            260                 265                 270

Gly Leu Asn Arg Thr Thr Val Met Met Ile Thr Val Ser Gly Ser Ala
        275                 280                 285

Pro Gly Leu Ser Ala Ser Gly Ser Gly Ser Gly Leu Asn Asp Ile Phe
    290                 295                 300

Glu Ala Gln Lys Ile Glu Trp His His His His His His
305                 310                 315


<210> SEQ ID NO 62
<211> LENGTH: 322
<212> TYPE: PRT
<213> ORGANISM: Homo sapiens
<220> FEATURE:
<221> NAME/KEY: DOMAIN
<222> LOCATION: (1)..(298)
<223> OTHER INFORMATION: extracellular domain of human CEACAM8
<220> FEATURE:
<221> NAME/KEY: MISC_FEATURE
<222> LOCATION: (299)..(322)
<223> OTHER INFORMATION: extension with His-tag

<400> SEQUENCE: 62

Gln Leu Thr Ile Glu Ala Val Pro Ser Asn Ala Ala Glu Gly Lys Glu
1               5                   10                  15

Val Leu Leu Leu Val His Asn Leu Pro Gln Asp Pro Arg Gly Tyr Asn
            20                  25                  30

Trp Tyr Lys Gly Glu Thr Val Asp Ala Asn Arg Arg Ile Ile Gly Tyr
        35                  40                  45

Val Ile Ser Asn Gln Gln Ile Thr Pro Gly Pro Ala Tyr Ser Asn Arg
    50                  55                  60
```

```
Glu Thr Ile Tyr Pro Asn Ala Ser Leu Leu Met Arg Asn Val Thr Arg
65                  70                  75                  80

Asn Asp Thr Gly Ser Tyr Thr Leu Gln Val Ile Lys Leu Asn Leu Met
                85                  90                  95

Ser Glu Glu Val Thr Gly Gln Phe Ser Val His Pro Glu Thr Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Val
                165                 170                 175

Gly Pro Tyr Glu Cys Glu Ile Gln Asn Pro Ala Ser Ala Asn Phe Ser
            180                 185                 190

Asp Pro Val Thr Leu Asn Val Leu Tyr Gly Pro Asp Ala Pro Thr Ile
        195                 200                 205

Ser Pro Ser Asp Thr Tyr Tyr His Ala Gly Val Asn Leu Asn Leu Ser
    210                 215                 220

Cys His Ala Ala Ser Asn Pro Pro Ser Gln Tyr Ser Trp Ser Val Asn
225                 230                 235                 240

Gly Thr Phe Gln Gln Tyr Thr Gln Lys Leu Phe Ile Pro Asn Ile Thr
                245                 250                 255

Thr Lys Asn Ser Gly Ser Tyr Ala Cys His Thr Thr Asn Ser Ala Thr
            260                 265                 270

Gly Arg Asn Arg Thr Thr Val Arg Met Ile Thr Val Ser Asp Ala Leu
        275                 280                 285

Val Gln Gly Ser Ser Pro Gly Leu Ser Ala Ser Gly Ser Gly Ser Gly
    290                 295                 300

Leu Asn Asp Ile Phe Glu Ala Gln Lys Ile Glu Trp His His His His
305                 310                 315                 320

His His


<210> SEQ ID NO 63
<211> LENGTH: 322
<212> TYPE: PRT
<213> ORGANISM: Macaca fascicularis
<220> FEATURE:
<221> NAME/KEY: DOMAIN
<222> LOCATION: (1)..(298)
<223> OTHER INFORMATION: extracellular domain of cynomolgus monkey
      CEACAM8
<220> FEATURE:
<221> NAME/KEY: MISC_FEATURE
<222> LOCATION: (299)..(322)
<223> OTHER INFORMATION: extension with His-tag

<400> SEQUENCE: 63

Gln Leu Thr Ile Glu Ala Val Pro Ser Asn Ala Ala Glu Gly Lys Glu
1               5                   10                  15

Val Leu Leu Leu Ala His Asn Leu Pro Gln Asp Pro Leu Gly Tyr Asn
            20                  25                  30

Trp Tyr Lys Gly Glu Thr Val Asp Ala Asn Arg Arg Ile Ile Gly Tyr
        35                  40                  45

Val Ile Ala Thr Gln Val Asn Ile Ser Gly Pro Ala Asp Ser Gly Arg
    50                  55                  60
```

```
Glu Thr Ile Tyr Pro Asn Ala Thr Leu Leu Met Gln Asn Val Thr Arg
65                  70                  75                  80

Asn Asp Thr Gly Ser Tyr Thr Leu Gln Val Ile Thr Leu Asn Leu Val
                85                  90                  95

Asn Glu Glu Val Thr Gly Gln Phe Ser Val His Pro Glu Thr Pro Lys
            100                 105                 110

Pro Ser Ile Ser Ser Asn Asn Ser Asn Pro Val Glu Asp Arg Asp Ala
        115                 120                 125

Val Ala Leu Thr Cys Glu Pro Glu Thr Gln Asn Thr Thr Tyr Leu Trp
    130                 135                 140

Trp Val Asn Gly Gln Ser Leu Pro Val Ser Pro Arg Leu Gln Leu Ser
145                 150                 155                 160

Asp Gly Asn Arg Thr Leu Thr Leu Leu Asn Val Thr Arg Asn Asp Thr
                165                 170                 175

Gly Pro Tyr Glu Cys Glu Ile Gln Asn Pro Val Ser Val Asn Phe Ser
            180                 185                 190

Asp Pro Val Thr Leu Asn Val Leu Tyr Gly Pro Asp Ala Pro Asn Ile
        195                 200                 205

Ser Pro Ser Asp Thr Tyr Tyr Leu Pro Gly Val Asn Leu Asn Leu Ser
    210                 215                 220

Cys His Ala Ala Ser Asn Pro Leu Ala Gln Tyr Ser Trp Ser Val Asn
225                 230                 235                 240

Gly Thr Phe Gln Gln His Thr Gln Asn Leu Phe Ile Pro Asn Ile Thr
                245                 250                 255

Ala Lys Asn Ser Gly Ser Tyr Ala Cys His Ala Thr Asn Ser Ala Thr
            260                 265                 270

Gly His Asn Gly Thr Thr Val Arg Met Ile Thr Val Ser Asp Ala Ser
        275                 280                 285

Val Gln Gly Ser Ser Pro Gly Leu Ser Ala Ser Gly Ser Gly Ser Gly
    290                 295                 300

Leu Asn Asp Ile Phe Glu Ala Gln Lys Ile Glu Trp His His His His
305                 310                 315                 320

His His
```

<210> SEQ ID NO 64
<211> LENGTH: 237
<212> TYPE: PRT
<213> ORGANISM: Homo sapiens
<220> FEATURE:
<221> NAME/KEY: DOMAIN
<222> LOCATION: (1)..(213)
<223> OTHER INFORMATION: extracellular domain of human CEACAM7
<220> FEATURE:
<221> NAME/KEY: DOMAIN
<222> LOCATION: (214)..(237)
<223> OTHER INFORMATION: extension with His-tag

<400> SEQUENCE: 64

```
Thr Asn Ile Asp Val Val Pro Phe Asn Val Ala Glu Gly Lys Glu Val
1               5                   10                  15

Leu Leu Val Val His Asn Glu Ser Gln Asn Leu Tyr Gly Tyr Asn Trp
            20                  25                  30

Tyr Lys Gly Glu Arg Val His Ala Asn Tyr Arg Ile Ile Gly Tyr Val
        35                  40                  45

Lys Asn Ile Ser Gln Glu Asn Ala Pro Gly Pro Ala His Asn Gly Arg
    50                  55                  60
```

-continued

```
Glu Thr Ile Tyr Pro Asn Gly Thr Leu Leu Ile Gln Asn Val Thr His
65                  70                  75                  80

Asn Asp Ala Gly Ile Tyr Thr Leu His Val Ile Lys Glu Asn Leu Val
                85                  90                  95

Asn Glu Glu Val Thr Arg Gln Phe Tyr Val Phe Ser Glu Pro Pro Lys
            100                 105                 110

Pro Ser Ile Thr Ser Asn Asn Phe Asn Pro Val Glu Asn Lys Asp Ile
        115                 120                 125

Val Val Leu Thr Cys Gln Pro Glu Thr Gln Asn Thr Thr Tyr Leu Trp
    130                 135                 140

Trp Val Asn Asn Gln Ser Leu Leu Val Ser Pro Arg Leu Leu Leu Ser
145                 150                 155                 160

Thr Asp Asn Arg Thr Leu Val Leu Leu Ser Ala Thr Lys Asn Asp Ile
                165                 170                 175

Gly Pro Tyr Glu Cys Glu Ile Gln Asn Pro Val Gly Ala Ser Arg Ser
            180                 185                 190

Asp Pro Val Thr Leu Asn Val Arg Tyr Glu Ser Val Gln Ala Ser Ser
        195                 200                 205

Pro Asp Leu Ser Ala Ser Gly Ser Gly Ser Gly Leu Asn Asp Ile Phe
    210                 215                 220

Glu Ala Gln Lys Ile Glu Trp His His His His His His
225                 230                 235


<210> SEQ ID NO 65
<211> LENGTH: 292
<212> TYPE: PRT
<213> ORGANISM: Homo sapiens
<220> FEATURE:
<221> NAME/KEY: DOMAIN
<222> LOCATION: (1)..(286)
<223> OTHER INFORMATION: hCEACAM5 N-A1-B1
<220> FEATURE:
<221> NAME/KEY: MISC_FEATURE
<222> LOCATION: (287)..(292)
<223> OTHER INFORMATION: His-tag

<400> SEQUENCE: 65

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160
```

```
Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala His His
        275                 280                 285

His His His His
    290


<210> SEQ ID NO 66
<211> LENGTH: 184
<212> TYPE: PRT
<213> ORGANISM: Homo sapiens
<220> FEATURE:
<221> NAME/KEY: DOMAIN
<222> LOCATION: (1)..(178)
<223> OTHER INFORMATION: hCEACAM5 A2-B2
<220> FEATURE:
<221> NAME/KEY: MISC_FEATURE
<222> LOCATION: (179)..(184)
<223> OTHER INFORMATION: His-tag

<400> SEQUENCE: 66

Glu Pro Pro Lys Pro Phe Ile Thr Ser Asn Asn Ser Asn Pro Val Glu
1               5                   10                  15

Asp Glu Asp Ala Val Ala Leu Thr Cys Glu Pro Glu Ile Gln Asn Thr
            20                  25                  30

Thr Tyr Leu Trp Trp Val Asn Asn Gln Ser Leu Pro Val Ser Pro Arg
        35                  40                  45

Leu Gln Leu Ser Asn Asp Asn Arg Thr Leu Thr Leu Leu Ser Val Thr
    50                  55                  60

Arg Asn Asp Val Gly Pro Tyr Glu Cys Gly Ile Gln Asn Glu Leu Ser
65                  70                  75                  80

Val Asp His Ser Asp Pro Val Ile Leu Asn Val Leu Tyr Gly Pro Asp
                85                  90                  95

Asp Pro Thr Ile Ser Pro Ser Tyr Thr Tyr Tyr Arg Pro Gly Val Asn
            100                 105                 110

Leu Ser Leu Ser Cys His Ala Ala Ser Asn Pro Pro Ala Gln Tyr Ser
        115                 120                 125

Trp Leu Ile Asp Gly Asn Ile Gln Gln His Thr Gln Glu Leu Phe Ile
    130                 135                 140

Ser Asn Ile Thr Glu Lys Asn Ser Gly Leu Tyr Thr Cys Gln Ala Asn
145                 150                 155                 160

Asn Ser Ala Ser Gly His Ser Arg Thr Thr Val Lys Thr Ile Thr Val
                165                 170                 175

Ser Ala His His His His His His
            180
```

<210> SEQ ID NO 67
<211> LENGTH: 193
<212> TYPE: PRT
<213> ORGANISM: Homo sapiens
<220> FEATURE:
<221> NAME/KEY: DOMAIN
<222> LOCATION: (1)..(187)
<223> OTHER INFORMATION: hCEACAM5 A3-B3
<220> FEATURE:
<221> NAME/KEY: MISC_FEATURE
<222> LOCATION: (188)..(193)
<223> OTHER INFORMATION: His-tag

<400> SEQUENCE: 67

```
Glu Leu Pro Lys Pro Ser Ile Ser Ser Asn Asn Ser Lys Pro Val Glu
1               5                   10                  15

Asp Lys Asp Ala Val Ala Phe Thr Cys Glu Pro Glu Ala Gln Asn Thr
            20                  25                  30

Thr Tyr Leu Trp Trp Val Asn Gly Gln Ser Leu Pro Val Ser Pro Arg
        35                  40                  45

Leu Gln Leu Ser Asn Gly Asn Arg Thr Leu Thr Leu Phe Asn Val Thr
    50                  55                  60

Arg Asn Asp Ala Arg Ala Tyr Val Cys Gly Ile Gln Asn Ser Val Ser
65                  70                  75                  80

Ala Asn Arg Ser Asp Pro Val Thr Leu Asp Val Leu Tyr Gly Pro Asp
                85                  90                  95

Thr Pro Ile Ile Ser Pro Pro Asp Ser Ser Tyr Leu Ser Gly Ala Asn
            100                 105                 110

Leu Asn Leu Ser Cys His Ser Ala Ser Asn Pro Ser Pro Gln Tyr Ser
        115                 120                 125

Trp Arg Ile Asn Gly Ile Pro Gln Gln His Thr Gln Val Leu Phe Ile
    130                 135                 140

Ala Lys Ile Thr Pro Asn Asn Asn Gly Thr Tyr Ala Cys Phe Val Ser
145                 150                 155                 160

Asn Leu Ala Thr Gly Arg Asn Asn Ser Ile Val Lys Ser Ile Thr Val
                165                 170                 175

Ser Ala Ser Gly Thr Ser Pro Gly Leu Ser Ala His His His His His
            180                 185                 190

His
```

<210> SEQ ID NO 68
<211> LENGTH: 310
<212> TYPE: PRT
<213> ORGANISM: Macaca fascicularis
<220> FEATURE:
<221> NAME/KEY: DOMAIN
<222> LOCATION: (1)..(286)
<223> OTHER INFORMATION: domain N-A1-B1 of cynomolgus monkey CEACAM5
<220> FEATURE:
<221> NAME/KEY: MISC_FEATURE
<222> LOCATION: (287)..(310)
<223> OTHER INFORMATION: extension with His-tag

<400> SEQUENCE: 68

```
Gln Leu Thr Ile Glu Ser Arg Pro Phe Asn Val Ala Glu Gly Lys Glu
1               5                   10                  15

Val Leu Leu Leu Ala His Asn Val Ser Gln Asn Leu Phe Gly Tyr Ile
            20                  25                  30

Trp Tyr Lys Gly Glu Arg Val Asp Ala Ser Arg Arg Ile Gly Ser Cys
        35                  40                  45
```

```
Val Ile Arg Thr Gln Gln Ile Thr Pro Gly Pro Ala His Ser Gly Arg
    50                  55                  60

Glu Thr Ile Asp Phe Asn Ala Ser Leu Leu Ile Gln Asn Val Thr Gln
65                  70                  75                  80

Ser Asp Thr Gly Ser Tyr Thr Ile Gln Val Ile Lys Glu Asp Leu Val
                85                  90                  95

Asn Glu Glu Ala Thr Gly Gln Phe Arg Val Tyr Pro Glu Leu Pro Lys
            100                 105                 110

Pro Tyr Ile Thr Ser Asn Asn Ser Asn Pro Ile Glu Asp Lys Asp Ala
        115                 120                 125

Val Ala Leu Thr Cys Glu Pro Glu Thr Gln Asp Thr Thr Tyr Leu Trp
    130                 135                 140

Trp Val Asn Asn Gln Ser Leu Pro Val Ser Pro Arg Leu Glu Leu Ser
145                 150                 155                 160

Ser Asp Asn Arg Thr Leu Thr Val Phe Asn Ile Pro Arg Asn Asp Thr
                165                 170                 175

Thr Ser Tyr Lys Cys Glu Thr Gln Asn Pro Val Ser Val Arg Arg Ser
            180                 185                 190

Asp Pro Val Thr Leu Asn Val Leu Tyr Gly Pro Asp Ala Pro Thr Ile
        195                 200                 205

Ser Pro Leu Asn Thr Pro Tyr Arg Ala Gly Glu Tyr Leu Asn Leu Thr
    210                 215                 220

Cys His Ala Ala Ser Asn Pro Thr Ala Gln Tyr Phe Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Met Cys Gln Ala His Asn Ser Ala Thr
            260                 265                 270

Gly Leu Asn Arg Thr Thr Val Thr Ala Ile Thr Val Tyr Ala Ser Gly
        275                 280                 285

Ser Gly Ser Gly Leu Asn Asp Ile Phe Glu Ala Gln Lys Ile Glu Trp
    290                 295                 300

His His His His His His
305                 310
```

<210> SEQ ID NO 69
<211> LENGTH: 202
<212> TYPE: PRT
<213> ORGANISM: Macaca fascicularis
<220> FEATURE:
<221> NAME/KEY: DOMAIN
<222> LOCATION: (1)..(178)
<223> OTHER INFORMATION: domain A2-B2 of cunomolgus monkey CEACAM5
<220> FEATURE:
<221> NAME/KEY: MISC_FEATURE
<222> LOCATION: (179)..(202)
<223> OTHER INFORMATION: extension with His-tag

<400> SEQUENCE: 69

```
Glu Leu Pro Lys Pro Tyr Ile Thr Ser Asn Asn Ser Asn Pro Ile Glu
1               5                   10                  15

Asp Lys Asp Ala Val Thr Leu Thr Cys Glu Pro Glu Thr Gln Asp Thr
            20                  25                  30

Thr Tyr Leu Trp Trp Val Asn Asn Gln Arg Leu Ser Val Ser Ser Arg
        35                  40                  45

Leu Glu Leu Ser Asn Asp Asn Arg Thr Leu Thr Val Phe Asn Ile Pro
    50                  55                  60
```

-continued

```
Arg Asn Asp Thr Thr Phe Tyr Glu Cys Glu Thr Gln Asn Pro Val Ser
65                  70                  75                  80

Val Arg Arg Ser Asp Pro Val Thr Leu Asn Val Leu Tyr Gly Pro Asp
                85                  90                  95

Ala Pro Thr Ile Ser Pro Leu Asn Thr Pro Tyr Arg Ala Gly Glu Asn
            100                 105                 110

Leu Asn Leu Ser Cys His Ala Ala Ser Asn Pro Ala Ala Gln Tyr Phe
        115                 120                 125

Trp Phe Val Asn Gly Thr Phe Gln Gln Ser Thr Gln Glu Leu Phe Ile
    130                 135                 140

Pro Asn Ile Thr Val Asn Asn Ser Gly Ser Tyr Met Cys Gln Ala His
145                 150                 155                 160

Asn Ser Ala Thr Gly Leu Asn Arg Thr Thr Val Thr Ala Ile Thr Val
                165                 170                 175

Tyr Val Ser Gly Ser Gly Ser Gly Leu Asn Asp Ile Phe Glu Ala Gln
            180                 185                 190

Lys Ile Glu Trp His His His His His His
        195                 200


<210> SEQ ID NO 70
<211> LENGTH: 214
<212> TYPE: PRT
<213> ORGANISM: Macaca fascicularis
<220> FEATURE:
<221> NAME/KEY: DOMAIN
<222> LOCATION: (1)..(190)
<223> OTHER INFORMATION: doamin A3-B3 of cynomolgus monkey CEACAM5
<220> FEATURE:
<221> NAME/KEY: MISC_FEATURE
<222> LOCATION: (191)..(214)
<223> OTHER INFORMATION: extension with His-tag

<400> SEQUENCE: 70

Glu Leu Pro Lys Pro Tyr Ile Ser Ser Asn Asn Ser Asn Pro Ile Glu
1               5                   10                  15

Asp Lys Asp Ala Val Thr Leu Thr Cys Glu Pro Val Ala Glu Asn Thr
            20                  25                  30

Thr Tyr Leu Trp Trp Val Asn Asn Gln Ser Leu Ser Val Ser Pro Arg
        35                  40                  45

Leu Gln Leu Ser Asn Gly Asn Arg Ile Leu Thr Leu Leu Ser Val Thr
    50                  55                  60

Arg Asn Asp Thr Gly Pro Tyr Glu Cys Gly Ile Gln Asn Ser Glu Ser
65                  70                  75                  80

Ala Lys Arg Ser Asp Pro Val Thr Leu Asn Val Thr Tyr Gly Pro Asp
                85                  90                  95

Thr Pro Ile Ile Ser Pro Pro Asp Leu Ser Tyr Arg Ser Gly Ala Asn
            100                 105                 110

Leu Asn Leu Ser Cys His Ser Asp Ser Asn Pro Ser Pro Gln Tyr Ser
        115                 120                 125

Trp Leu Ile Asn Gly Thr Leu Arg Gln His Thr Gln Val Leu Phe Ile
    130                 135                 140

Ser Lys Ile Thr Ser Asn Asn Asn Gly Ala Tyr Ala Cys Phe Val Ser
145                 150                 155                 160

Asn Leu Ala Thr Gly Arg Asn Asn Ser Ile Val Lys Asn Ile Ser Val
                165                 170                 175

Ser Ser Gly Asp Ser Ala Pro Gly Ser Ser Gly Leu Ser Ala Ser Gly
            180                 185                 190
```

```
Ser Gly Ser Gly Leu Asn Asp Ile Phe Glu Ala Gln Lys Ile Glu Trp
        195                 200                 205

His His His His His His
    210


<210> SEQ ID NO 71
<211> LENGTH: 344
<212> TYPE: PRT
<213> ORGANISM: Homo sapiens

<400> SEQUENCE: 71

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340
```

<210> SEQ ID NO 72
<211> LENGTH: 265
<212> TYPE: PRT
<213> ORGANISM: Homo sapiens

<400> SEQUENCE: 72

```
Met Gly Ser Pro Ser Ala Cys Pro Tyr Arg Val Cys Ile Pro Trp Gln
1               5                   10                  15

Gly Leu Leu Leu Thr Ala Ser Leu Leu Thr Phe Trp Asn Leu Pro Asn
            20                  25                  30

Ser Ala Gln Thr Asn Ile Asp Val Val Pro Phe Asn Val Ala Glu Gly
        35                  40                  45

Lys Glu Val Leu Leu Val Val His Asn Glu Ser Gln Asn Leu Tyr Gly
    50                  55                  60

Tyr Asn Trp Tyr Lys Gly Glu Arg Val His Ala Asn Tyr Arg Ile Ile
65                  70                  75                  80

Gly Tyr Val Lys Asn Ile Ser Gln Glu Asn Ala Pro Gly Pro Ala His
                85                  90                  95

Asn Gly Arg Glu Thr Ile Tyr Pro Asn Gly Thr Leu Leu Ile Gln Asn
            100                 105                 110

Val Thr His Asn Asp Ala Gly Phe Tyr Thr Leu His Val Ile Lys Glu
        115                 120                 125

Asn Leu Val Asn Glu Glu Val Thr Arg Gln Phe Tyr Val Phe Ser Glu
    130                 135                 140

Pro Pro Lys Pro Ser Ile Thr Ser Asn Asn Phe Asn Pro Val Glu Asn
145                 150                 155                 160

Lys Asp Ile Val Val Leu Thr Cys Gln Pro Glu Thr Gln Asn Thr Thr
                165                 170                 175

Tyr Leu Trp Trp Val Asn Asn Gln Ser Leu Leu Val Ser Pro Arg Leu
            180                 185                 190

Leu Leu Ser Thr Asp Asn Arg Thr Leu Val Leu Leu Ser Ala Thr Lys
        195                 200                 205

Asn Asp Ile Gly Pro Tyr Glu Cys Glu Ile Gln Asn Pro Val Gly Ala
    210                 215                 220

Ser Arg Ser Asp Pro Val Thr Leu Asn Val Arg Tyr Glu Ser Val Gln
225                 230                 235                 240

Ala Ser Ser Pro Asp Leu Ser Ala Gly Thr Ala Val Ser Ile Met Ile
                245                 250                 255

Gly Val Leu Ala Gly Met Ala Leu Ile
            260                 265
```

<210> SEQ ID NO 73
<211> LENGTH: 349
<212> TYPE: PRT
<213> ORGANISM: Homo sapiens

<400> SEQUENCE: 73

```
Met Gly Pro Ile Ser Ala Pro Ser Cys Arg Trp Arg Ile Pro Trp Gln
1               5                   10                  15

Gly Leu Leu Leu Thr Ala Ser Leu Phe Thr Phe Trp Asn Pro Pro Thr
            20                  25                  30

Thr Ala Gln Leu Thr Ile Glu Ala Val Pro Ser Asn Ala Ala Glu Gly
        35                  40                  45

Lys Glu Val Leu Leu Leu Val His Asn Leu Pro Gln Asp Pro Arg Gly
    50                  55                  60
```

Tyr Asn Trp Tyr Lys Gly Glu Thr Val Asp Ala Asn Arg Arg Ile Ile
65 70 75 80

Gly Tyr Val Ile Ser Asn Gln Gln Ile Thr Pro Gly Pro Ala Tyr Ser
85 90 95

Asn Arg Glu Thr Ile Tyr Pro Asn Ala Ser Leu Leu Met Arg Asn Val
100 105 110

Thr Arg Asn Asp Thr Gly Ser Tyr Thr Leu Gln Val Ile Lys Leu Asn
115 120 125

Leu Met Ser Glu Glu Val Thr Gly Gln Phe Ser Val His Pro Glu Thr
130 135 140

Pro Lys Pro Ser Ile Ser Ser Asn Asn Ser Asn Pro Val Glu Asp Lys
145 150 155 160

Asp Ala Val Ala Phe Thr Cys Glu Pro Glu Thr Gln Asn Thr Thr Tyr
165 170 175

Leu Trp Trp Val Asn Gly Gln Ser Leu Pro Val Ser Pro Arg Leu Gln
180 185 190

Leu Ser Asn Gly Asn Arg Thr Leu Thr Leu Leu Ser Val Thr Arg Asn
195 200 205

Asp Val Gly Pro Tyr Glu Cys Glu Ile Gln Asn Pro Ala Ser Ala Asn
210 215 220

Phe Ser Asp Pro Val Thr Leu Asn Val Leu Tyr Gly Pro Asp Ala Pro
225 230 235 240

Thr Ile Ser Pro Ser Asp Thr Tyr Tyr His Ala Gly Val Asn Leu Asn
245 250 255

Leu Ser Cys His Ala Ala Ser Asn Pro Pro Ser Gln Tyr Ser Trp Ser
260 265 270

Val Asn Gly Thr Phe Gln Gln Tyr Thr Gln Lys Leu Phe Ile Pro Asn
275 280 285

Ile Thr Thr Lys Asn Ser Gly Ser Tyr Ala Cys His Thr Thr Asn Ser
290 295 300

Ala Thr Gly Arg Asn Arg Thr Thr Val Arg Met Ile Thr Val Ser Asp
305 310 315 320

Ala Leu Val Gln Gly Ser Ser Pro Gly Leu Ser Ala Arg Ala Thr Val
325 330 335

Ser Ile Met Ile Gly Val Leu Ala Arg Val Ala Leu Ile
340 345

<210> SEQ ID NO 74
<211> LENGTH: 120
<212> TYPE: PRT
<213> ORGANISM: Artificial Sequence
<220> FEATURE:
<223> OTHER INFORMATION: MAb2_VHg2

<400> SEQUENCE: 74

Glu Val Gln Leu Val Glu Ser Gly Gly Gly Leu Val Gln Pro Gly Gly
1 5 10 15

Ser Leu Arg Leu Ser Cys Ala Ala Ser Gly Phe Val Phe Ser Ser Tyr
20 25 30

Asp Met Ser Trp Val Arg Gln Ala Pro Gly Lys Gly Leu Glu Trp Val
35 40 45

Ser Tyr Ile Ser Ser Gly Gly Gly Ile Thr Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser
        115                 120


<210> SEQ ID NO 75
<211> LENGTH: 107
<212> TYPE: PRT
<213> ORGANISM: Artificial Sequence
<220> FEATURE:
<223> OTHER INFORMATION: MAb2_VLg5

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ala Pro Lys Leu Leu Ile
        35                  40                  45

Tyr Asn Thr Arg Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Gln Gly Thr Lys Leu Glu Ile Lys
            100                 105


<210> SEQ ID NO 76
<211> LENGTH: 7
<212> TYPE: PRT
<213> ORGANISM: Artificial Sequence
<220> FEATURE:
<223> OTHER INFORMATION: residues at positions 109-115 of human
      CEACAM5-A3B3

<400> SEQUENCE: 76

Ser Gly Ala Asn Leu Asn Leu
1               5


<210> SEQ ID NO 77
<211> LENGTH: 13
<212> TYPE: PRT
<213> ORGANISM: Artificial Sequence
<220> FEATURE:
<223> OTHER INFORMATION: residues at positions 131-143 of human
      CEACAM5-A3B3

<400> SEQUENCE: 77

Ile Asn Gly Ile Pro Gln Gln His Thr Gln Val Leu Phe
1               5                   10


<210> SEQ ID NO 78
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (3)..(3)
```

<223> OTHER INFORMATION: Xaa is is T, A or V

<400> SEQUENCE: 78

Gly Phe Xaa Phe Ser Ser Tyr Asp
1 5

<210> SEQ ID NO 79
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (2)..(2)
<223> OTHER INFORMATION: Xaa is S or N (in particular S)
<220> FEATURE:
<221> NAME/KEY: MISC_FEATURE
<222> LOCATION: (4)..(4)
<223> OTHER INFORMATION: Xaa is Y or G (in particular G)
<220> FEATURE:
<221> NAME/KEY: MISC_FEATURE
<222> LOCATION: (7)..(7)
<223> OTHER INFORMATION: Xaa is R or I (in particular I)

<400> SEQUENCE: 79

Ile Xaa Ser Xaa Gly Gly Xaa Thr
1 5

<210> SEQ ID NO 80
<211> LENGTH: 13
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(1)
<223> OTHER INFORMATION: Xaa is A or T (in particular A)
<220> FEATURE:
<221> NAME/KEY: MISC_FEATURE
<222> LOCATION: (7)..(7)
<223> OTHER INFORMATION: Xaa is T or S (in particular S)

<400> SEQUENCE: 80

Xaa Ala His Tyr Phe Gly Xaa Ser Gly Pro Phe Ala Tyr
1 5 10

<210> SEQ ID NO 81
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (6)..(6)
<223> OTHER INFORMATION: Xaa is R or S, in particular S
<220> FEATURE:
<221> NAME/KEY: MISC_FEATURE
<222> LOCATION: (8)..(8)
<223> OTHER INFORMATION: Xaa is A or D

<400> SEQUENCE: 81

Gly Phe Thr Phe Ser Xaa Tyr Xaa
1 5

<210> SEQ ID NO 82
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (6)..(6)
<223> OTHER INFORMATION: Xaa is absent, S or G (in particular G)
<220> FEATURE:
<221> NAME/KEY: MISC_FEATURE
<222> LOCATION: (7)..(7)
<223> OTHER INFORMATION: Xaa is D, Y or I
<220> FEATURE:
<221> NAME/KEY: MISC_FEATURE
<222> LOCATION: (8)..(8)
<223> OTHER INFORMATION: Xaa is T or I (in particular T)

<400> SEQUENCE: 82

Ile Ser Ser Gly Gly Xaa Xaa Xaa
1               5

<210> SEQ ID NO 83
<211> LENGTH: 8
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(6)
<223> OTHER INFORMATION: Xaa is any amino acid

<400> SEQUENCE: 83

Xaa Xaa Xaa Xaa Xaa Xaa Tyr Asp
1               5

<210> SEQ ID NO 84
<211> LENGTH: 13
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is A or S
<220> FEATURE:
<221> NAME/KEY: MISC_FEATURE
<222> LOCATION: (4)..(4)
<223> OTHER INFORMATION: Xaa is Y, F or W
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 84

Xaa Xaa His Xaa Phe Gly Xaa Xaa Gly Pro Xaa Ala Xaa
1               5                   10

<210> SEQ ID NO 85
<211> LENGTH: 6
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Y, F or W
<220> FEATURE:
<221> NAME/KEY: MISC_FEATURE
<222> LOCATION: (5)..(5)
<223> OTHER INFORMATION: Xaa is any amino acid

<400> SEQUENCE: 85

Xaa Xaa Xaa Xaa Xaa Tyr
1               5

<210> SEQ ID NO 86
<211> LENGTH: 9
<212> TYPE: PRT
<213> ORGANISM: Artificial Sequence
<220> FEATURE:
<223> OTHER INFORMATION: CDR
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Y, F or W
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid

<400> SEQUENCE: 86

Xaa Xaa His Xaa Xaa Xaa Pro Xaa Xaa
1               5

<210> SEQ ID NO 87
<211> LENGTH: 449
<212> TYPE: PRT
<213> ORGANISM: Artificial Sequence
<220> FEATURE:
<223> OTHER INFORMATION: heavy chain sequence of huMAb2-3

<400> SEQUENCE: 87

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 88
<211> LENGTH: 214
<212> TYPE: PRT
<213> ORGANISM: Artificial Sequence
<220> FEATURE:
<223> OTHER INFORMATION: light chain sequence of huMAb2-3

<400> SEQUENCE: 88

Asp Ile Gln Met Thr Gln Ser Pro Ala Ser Leu Ser Ala Ser Val Gly
1 5 10 15

-continued

```
Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 89
<211> LENGTH: 449
<212> TYPE: PRT
<213> ORGANISM: Artificial Sequence
<220> FEATURE:
<223> OTHER INFORMATION: MAb2 heavy chain VH1-IgG1

<400> SEQUENCE: 89

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Arg Leu Glu Trp Val
        35                  40                  45

Ala Tyr Ile Ser Ser Gly Gly Gly Ile Thr Tyr Phe Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Ile Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 90
<211> LENGTH: 214
<212> TYPE: PRT
<213> ORGANISM: Artificial Sequence
<220> FEATURE:
<223> OTHER INFORMATION: MAb2 light chain VL1d

<400> SEQUENCE: 90

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60
```

-continued

```
Ser Gly Ser Gly Thr Gln Phe Ser Leu Thr Ile Ser Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-CEACAM5 ANTIBODIES AND USES THEREOF

RELATED APPLICATIONS

This application is a divisional of U.S. patent application Ser. No. 16/558,939, filed Sep. 3, 2019, which is a divisional of U.S. patent application Ser. No. 15/446,465, filed Mar. 1, 2017, now U.S. Pat. No. 10,457,739, which is a divisional of U.S. patent application Ser. No. 14/716,377, filed May 19, 2015, now U.S. Pat. No. 9,617,345, which is a continuation of Inter national Patent Application No. PCT/EP2013/074291, filed Nov. 20, 2013, which claims priority to European Patent Application No. 12306444.6, filed Nov. 20, 2012, all of which are incorporated herein by reference in their entirety.

BACKGROUND

The present invention discloses antibodies which specifically bind human and *Macaca fascicularis* CEACAM5 proteins as well as isolated nucleic acids, vectors and host cells comprising a sequence encoding said antibodies. The invention also discloses immunoconjugates comprising said antibodies conjugated or linked to a growth-inhibitory agent, and to pharmaceutical compositions comprising antibodies or immunoconjugates of the invention. The invention discloses the use of the antibodies or immunoconjugates of the invention for the treatment of cancer or for diagnostic purposes.

Carcino-embryonic antigen (CEA) is a glycoprotein involved in cell adhesion. CEA was first identified in 1965 (Gold and Freedman, J Exp Med, 121, 439, 1965) as a protein normally expressed by fetal gut during the first six months of gestation, and found in cancers of the pancreas, liver and colon. The CEA family belongs to the immunoglobulin superfamily. The CEA family, which consists of 18 genes, is sub-divided in two sub-groups of proteins: the carcinoembryonic antigen-related cell adhesion molecule (CEACAM) sub-group and the pregnancy-specific glycoprotein subgroup (Kammerer & Zimmermann, BMC Biology 2010, 8:12).

In humans, the CEACAM sub-group consists of 7 members: CEACAM1, CEACAM3, CEACAM4, CEACAM5, CEACAM6, CEACAM7, CEACAM8. Numerous studies have shown that CEACAM5, identical to the originally identified CEA, is highly expressed on the surface of colorectal, gastric, lung, breast, prostate, ovary, cervix, and bladder tumor cells and weakly expressed in few normal epithelial tissues such as columnar epithelial and goblet cells in colon, mucous neck cells in the stomach and squamous epithelial cells in esophagus and cervix (Hammarström et al, 2002, in "Tumor markers, Physiology, Pathobiology, Technology and Clinical Applications" Eds. Diamandis E. P. et al., AACC Press, Washington pp 375). Thus, CEACAM5 may constitute a therapeutic target suitable for tumor specific targeting approaches, such as immunoconjugates. The present invention provides monoclonal antibodies directed against CEACAM5, and shows that they can be conjugated to a cytotoxic agent to induce a cytotoxic activity able to kill tumor cells in vitro and to induce tumor regression in vivo. The extracellular domains of CEACAM family members are composed of repeated immunoglobulin-like (Ig-like) domains which have been categorized in 3 types, A, B and N, according to sequence homologies. CEACAM5 contains seven such domains, namely N, A1, B1, A2, B2, A3 and B3.

CEACAM5 A1, A2 and A3 domains, on one hand, and B1, B2 and B3 domains, on the other hand, show high sequence homologies, the A domains of human CEACAM5 presenting from 84 to 87% pairwise sequence similarity, and the B domains from 69 to 80%. Furthermore, other human CEACAM members presenting A and/or B domains in their structure, namely CEACAM1, CEACAM6, CEACAM7 and CEACAM8, show homology with human CEACAM5. In particular, the A and B domains of human CEACAM6 protein display sequence homologies with A1 and A3 domains, and any of B1 to B3 domains of human CEACAM5, respectively, which are even higher than observed among the A domains and the B domains of human CEACAM5.

Numerous anti-CEA antibodies were generated in view of CEA-targeted diagnostic or therapeutic purposes. Specificity towards related antigens has always been mentioned as a concern in this field, as an example by Sharkey et al (1990, Cancer Research 50, 2823). Due to the above mentioned homologies some of previously described antibodies may demonstrate binding to repetitive epitopes of CEACAM5 present in the different immunoglobulin domains show cross-reactivity to other CEACAM members such as CEACAM1, CEACAM6, CEACAM7, or CEACAM8, lacking specificity to CEACAM5. The specificity of the anti-CEACAM5 antibody is desired in view of CEA-targeted therapies such that it binds to human CEACAM5-expressing tumor cells but does not bind to some normal tissues expressing the others CEACAM members. It is noteworthy that CEACAM1, CEACAM6 and CEACAM8 have been described as expressed by neutrophils of human and non-human primates (Ebrahimmnejad et al, 2000, Exp Cell Res, 260, 365; Zhao et al, 2004, J Immunol Methods 293, 207; Strickland et al, 2009 J Pathol, 218, 380) where they have been shown to regulate granulopoiesis and to play a role in immune response.

An anti-CEACAM6 antibody drug conjugate has been described, such as the maytansinoid anti-CEACAM6 antibody developed by Genentech (Strickland et al, 2009 J Pathol, 218, 380), which has been shown to induce CEACAM6-dependent haematopoietic toxicity in non-human primates. This toxicity, attributed to accumulation of the antibody drug conjugate in bone marrow and depletion of granulocytes and their cell precursors, was considered by the authors as a major safety concern. So, more precisely, for therapeutic purposes, cross-reactivity of an anti-CEACAM5 antibody with CEACAM1, CEACAM6, CEACAM7, or CEACAM8 may decrease the therapeutic index of the compound by increased toxicity on normal tissues. Thus, there is a strong advantage in obtaining antibodies specifically directed to CEACAM5 that would not cross-react with other molecules of the CEACAM family, especially for use as an antibody drug conjugate (ADC) or with any other mode of action resulting in killing the target cell.

Moreover, as CEACAM5 is described to be expressed, although at low level, in some normal cell tissues, it is critical to develop anti-CEACAM5 antibodies capable of binding to human CEACAM5 as well as to cynomolgus monkey (*Macaca fascicularis*) CEACAM5, as such antibodies may be readily tested in preclinical toxicological studies in cynomolgus monkeys to evaluate their safety profile. Since it has been shown that the efficiency of therapeutic antibodies may be dependent on the localization of the epitope in the target, both in the case of functional antibodies (Doern et al. 2009, J. Biol. Chem 284 10254) and in the case where effector functions are involved (Beers et al. Semin Hematol 47:107-114), a human/monkey cross-reactive antibody has to be shown to bind epitopes in the same repeated Ig-like homologous domain of human and cynomolgus monkey proteins.

Combining the need for species cross-reactivity of such antibodies with the specificity for human and *Macaca fascicularis* CEACAM5, i.e. no cross reactivity with other *Macaca fascicularis* and human CEACAM members, adds a further degree of complexity, given the overall sequence homologies between human and *Macaca fascicularis* CEACAM proteins.

Indeed, global pairwise alignment of *Macaca fascicularis* CEACAM5 sequence with human CEACAM5 sequence (AAA51967.1/GI:180223, 702 amino acids) indicated only 78.5% identity. *Macaca fascicularis* CEACAM1, CEACAM5, and CEACAM6 genes were cloned and a global alignment of human and *Macaca fascicularis* A, B and N domains was performed. This alignment predicted that there are very few regions, if any, to localize an ideal epitope that would be common to human and macaque CEACAM5 and not shared with any other family member. For these reasons developing antibodies cross-reactive between human and *Macaca fascicularis* CEACAM5 without cross-reactivity with other human and *Macaca fascicularis* CEACAM members was expected to have a low probability of success. Noteworthy, previously described anti-CEACAM5 antibodies are almost never documented for *Macaca fascicularis* cross-reactivity, with very few exceptions (MT111, see below).

Anti-human CEACAM5 antibodies have already been used in clinical trials, such as Immunomedics labetuzumab (also known as hMN14, Sharkey et al, 1995, Cancer Research 55, 5935). This antibody has been shown not to bind to related antigens, but is not cross-reacting with CEACAM5 from *Macaca fascicularis*. Noteworthy, Micromet's MT111 antibody (also known as MEDI-565 antibody of MedImmune) is a bi-specific antibody binding to human CEACAM5 and human CD3 (Peng et al., PLoS ONE 7(5): e3641; WO 2007/071426). MT111 is said to have been created by fusion of a single chain variable fragment (scFv) from an antibody that recognizes human and cynomolgus CEACAM5 with scFv from an antibody that recognize human CD3 (poster of Oberst et al., AACR Annual Meeting April 2009 Denver, CO). It has also been reported that MT111 does not bind other CEACAM family members (Peng et al., PLoS ONE 7(5): e3641). MT111 binds to a conformational epitope in the A2 domain of human CEACAM5. This conformational epitope is missing in a splice variant of human CEACAM5, which is expressed concomitantly with full-length CEACAM5 on tumors (Peng et al., PLoS ONE 7(5): e3641). In addition, there is no evidence that MT111 binds to the same epitope in *Macaca fascicularis* CEACAM5.

Finally, CEACAM5 is described in literature as a poorly internalizing surface protein (reviewed in Schmidt et al, 2008, Cancer Immunol. Immunother. 57, 1879), and therefore may not be a favorable target for antibody drug conjugates.

SUMMARY OF THE INVENTION

In an attempt to produce new antibodies against CEACAM5 surface protein with optimal characteristics for therapeutic purposes, the inventors have immunized mice with recombinant proteins and with tumour cells. They have screened hundreds of hybridoma using ELISA on several recombinant proteins of the CEACAM family, and flow cytometry with relevant cell lines, in order to select only immunoglobulins (IgGs) with the advantageous profile. Unexpectedly, they were able to select hybridoma clones and produce corresponding mature IgGs that comprise all of the desired features. They specifically bind to the A3-B3 domain of human CEACAM5 with a high affinity and do not recognize human CEACAM1, CEACAM6, CEACAM7 and CEACAM8 proteins. In a cellular context, these antibodies display high affinity for tumor cells (in the nanomolar range). Moreover these antibodies also bind to *Macaca fascicularis* CEACAM5 protein with a ratio of affinity monkey/human less than or equal to 10. Antibodies of the invention specifically bind to the A3-B3 domain of *Macaca fascicularis* CEACAM5 and do not recognize other *Macaca fascicularis* CEACAM members.

By targeting the A3-B3 domain of CEACAM5, these antibodies have increased tumour-targeting potential, as they have the capacity to bind both full-length human CEACAM5 and to its splice variant identified by Peng et al. (PLoS ONE 7(5): e3641).

In spite of what has been reported in the prior art, the inventors have shown that the antibodies they have produced are able to internalize the CEACAM5-antibody complex after binding, and to induce cytotoxic activity on tumor cells in vitro when combined to a cytotoxic agent. The same antibodies combined to a cytotoxic agent are also able to markedly inhibit tumor growth in mice bearing human primary colon and stomach tumors.

BRIEF DESCRIPTION OF THE DRAWINGS

FIG. 7: Sequence alignments of the VH and VL regions of the MAb1, MAb2, MAb3, MAb4 and MAb5 antibodies.

FIG. 22: Heavy Chain variable domain alignment of MAb2, MAb4, MAb5, humanized VH1a, humanized VH1 and humanized VHg2.

FIG. 23: Light Chain variable domain alignment of MAb2, MAb4, MAb5, humanized VL1, humanized VL1a, humanized VL1c, humanized VL1d and humanized VLg5.

DETAILED DESCRIPTION

Definitions

Figure 1A:
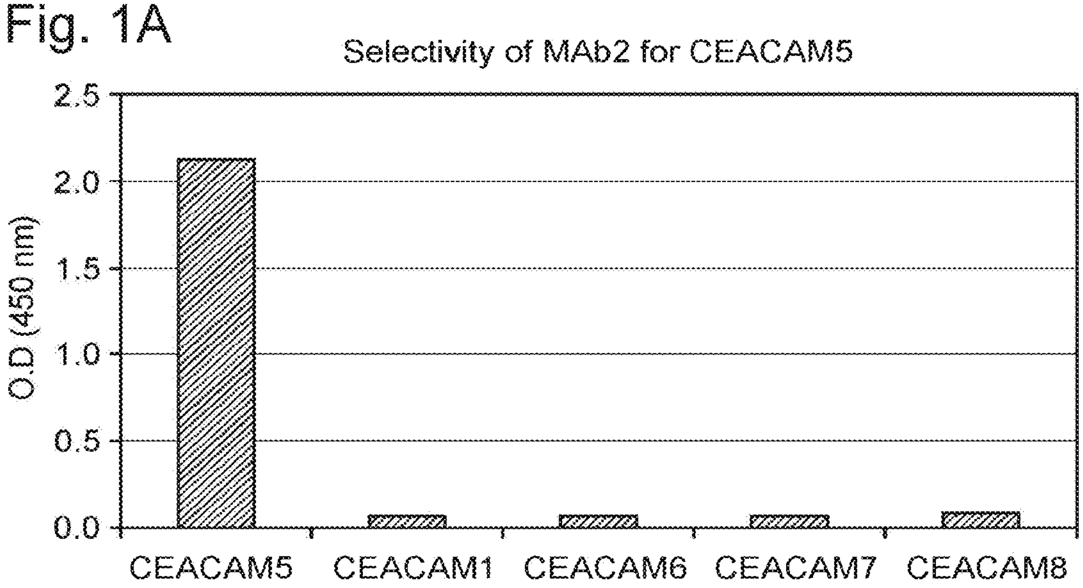
FIGS. 1A-1E: Evaluation of the selectivity of the anti-CEACAM5 antibodies.
Figure 1B:
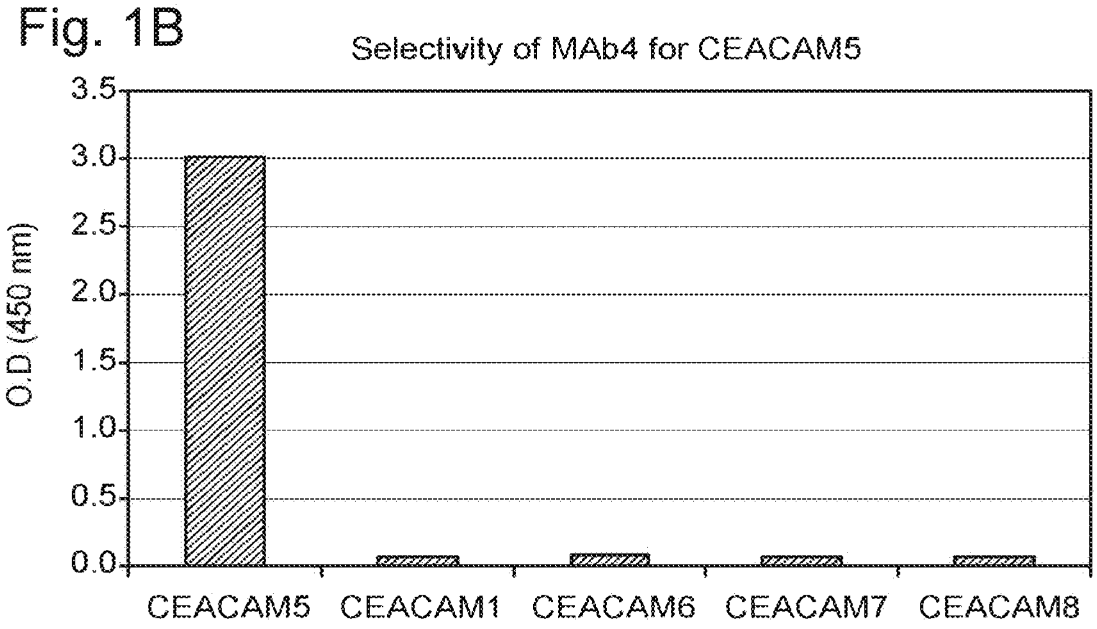

As used herein "CEACAM5" designates the "carcino-embryonic antigen-related cell adhesion molecule 5", also known as "CD66e" (Cluster of Differentiation 66e) or CEA. CEACAM5 is a glycoprotein involved in cell adhesion. CEACAM5 is highly expressed in particular on the surface of colorectal, gastric, lung and uterine tumor cells.

A reference sequence of full length human CEACAM5, including signal peptide (positions 1-34) and propeptide (positions 686-702), is available from the GENBANK® database under accession number AAA51967.1 (SEQ ID NO:52) Five non synonymous SNPs have been identified with a frequency higher than 2% in caucasian population, four of them being localised in the N domain (at positions 80, 83, 112, 113), the last one in the A2 domain (at position 398) of human CECAM5 (SEQ ID NO:58). GENBANK® AAA51967.1 contains the major haplotype (180, V83, 1112, 1113 and E398).

A sequence of the extracellular domain of *Macaca fascicularis* CEACAM5, cloned by the inventors, is disclosed in SEQ ID NO:53.

A "domain" may be any region of a protein, generally defined on the basis of sequence homologies and often related to a specific structural or functional entity. CEACAM family members are known to be composed of Ig-like domains. The term domain is used in this document to designate either individual Ig-like domains, such as "N-domain" or for groups of consecutive domains, such as "A3-B3 domain".

Domain organisation of human CEACAM5 is as follows (based on GENBANK® AAA51967.1 sequence; SEQ ID NO:52):

| Human CEACAM5 domains | Positions on SEQ ID NO: 52 |
|---|---|
| Domain N | 35-142 |
| Domain A1 | 143-237 |
| Domain B1 | 238-320 |
| Domain A2 | 321-415 |
| Domain B2 | 416-498 |

-continued

| Human CEACAM5 domains | Positions on SEQ ID NO: 52 |
|---|---|
| Domain A3 | 499-593 |
| Domain B3 | 594-685 |

Accordingly, the A3-B3 domain of human CEACAM5 consists of amino acids at positions 499-685 of SEQ ID NO:52.

Domain organisation of *Macaca fascicularis* CEACAM5 is as follows (based on cloned extracellular domain sequence; SEQ ID NO:53)

| *Macaca fascicularis* CEACAM5 domains | Positions on SEQ ID NO: 53 |
|---|---|
| Domain N-A1-B1 | −1-286 |
| Domain A2-B2 | −287-64 |
| Domain A3-B3 | 465-654 |

Accordingly, the A3-B3 domain of *Macaca fascicularis* CEACAM5 consists of amino acids at positions 465-654 of SEQ ID NO:53.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., antibodies) can include a polypeptide having a native amino acid sequence, as well as variants and modified forms regardless of their origin or mode of preparation. A protein which has a native amino acid sequence is a protein having the same amino acid sequence as obtained from nature. Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. Native sequence proteins include proteins carrying post-translational modifications such as glycosylation, or phosphorylation, or other modifications of some amino acid residues.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

A sequence "at least 85% identical to a reference sequence" is a sequence having, on its entire length, 85%, or more, for instance 90%, 91%, 92%, 93%, 94%, 95%, 96%, 97%, 98% or 99% sequence identity with the entire length of the reference sequence.

A percentage of "sequence identity" may be determined by comparing the two sequences, optimally aligned over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch J. Mol. Biol. 48:443 (1970). The percentage of sequence identity can be readily determined for instance using the program Needle, with the BLOSUM62 matrix, and the following parameters gap-open=10, gap-extend=0.5.

A "conservative amino acid substitution" is one in which an amino acid residue is substituted by another amino acid residue having a side chain R group with similar chemical properties (e.g., charge, size or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups can also be defined on the basis of amino acid size.

An "antibody" may be a natural or conventional antibody in which two heavy chains are linked to each other by disulfide bonds and each heavy chain is linked to a light chain by a disulfide bond. There are two types of light chain, lambda (I) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties, such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs therefore refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, for instance 90%, 91%, 92%, 93%, 94%, 95%, 96%, 97%, 98% or 99%) to the framework region of a naturally occurring human antibody.

In the context of the invention, CDR/FR definition in an immunoglobulin light or heavy chain is to be determined based on IMGT definition (Lefranc et al. Dev. Comp. Immunol., 2003, 27(1):55-77; www.imgt.org).

As used herein, the term "antibody" denotes conventional antibodies and fragments thereof, as well as single domain antibodies and fragments thereof, in particular variable heavy chain of single domain antibodies, and chimeric, humanised, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit, bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1):13-22).

The term "monoclonal antibody" or "mAb" as used herein refers to an antibody molecule of a single amino acid sequence, which is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which, in its broadest sense, contains one or more regions from one antibody and one or more regions from one or more other antibodies. In an embodiment, a chimeric antibody comprises a VH domain and a VL domain of an antibody derived from a non-human animal, in association with a CH domain and a CL domain of another antibody, in an embodiment, a human antibody. As the non-human animal, any animal such as mouse, rat, hamster, rabbit or the like can be used. A chimeric antibody may also denote a multispecific antibody having specificity for at least two different antigens.

The term "humanised antibody" refers to an antibody which is wholly or partially of non-human origin and which has been modified to replace certain amino acids, for instance in the framework regions of the VH and VL domains, in order to avoid or minimize an immune response in humans. The constant domains of a humanized antibody are most of the time human CH and CL domains.

"Fragments" of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 and antigen binding activity, in which about a half of the N-terminal side of the heavy chain and the entire light chain are bound together through a disulfide bond. It is usually obtained among fragments by treating IgG with a protease, papaine.

The term "F(ab')2" refers to an antibody fragment having a molecular weight of about 100,000 and antigen binding activity, which is slightly larger than 2 identical Fab fragments bound via a disulfide bond of the hinge region. It is usually obtained among fragments by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, for instance by using gene recombination techniques. Divalent and multivalent antibody fragments can form either spontaneously by association of monovalent scFvs, or can be generated by coupling monovalent scFvs by a peptide linker, such as divalent $sc(Fv)_2$. "dsFv" is a VH::VL heterodimer stabilised by a disulphide bond. "(dsFv)2" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains of the same chain, the domains are forced to pair with the complementary domains of another chain and create two antigen-binding sites.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

By "purified" and "isolated" it is meant, when referring to a polypeptide (i.e. the antibody of the invention) or a nucleotide sequence, that the indicated molecule is present in the substantial absence of other biological macromolecules of the same type. The term "purified" as used herein means at least 75%, 85%, 95%, 96%, 97%, or 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Furthermore, a subject according to the invention is a human.

Antibodies

The inventors have succeeded in generating, screening and selecting specific mouse anti-CEACAM5 antibodies displaying high affinity for both human and *Macaca fascicularis* CEACAM5 protein, and which do not significantly cross-react with human CEACAM1, CEACAM6, CEACAM7 and CEACAM8 proteins, and with *Macaca fascicularis* CEACAM1, CEACAM6 and CEACAM8 proteins.

The inventors have determined the sequence of variable heavy and light chains of such monoclonal antibodies, the so-called antibodies MAb1, MAb2, MAb3, MAb4, and MAb5.

The so-called "antibody MAb1" comprises:

a variable domain of heavy chain consisting of sequence EVMLVESGGGLVKPGGSLKLS-CAASGFTFSSYAMSWVRQTPEKRLEWVATIS-SGGSYIYY LDSVKGRFTISRDNAKNTLYLQMSS-LRSEDTAMYYCARPAYYGNPAMDYWGQG-TSVTVS S (SEQ ID NO:31, with CDRs shown in bold characters) in which FR1-H spans amino acid positions 1 to 25, CDR1-H spans amino acid positions 26 to 33 (SEQ ID NO:1), FR2-H spans amino acid positions 34 to 50, CDR2-H spans amino acid positions 51 to 58 (SEQ ID NO:2), FR3-H spans amino acid positions 59 to 96, CDR3-H spans amino acid positions 97 to 109 (SEQ ID NO:3), and FR4-H spans amino acid positions 110 to 120, and a variable domain of light chain consisting of sequence DILMTQSQKFMSTSVGDRVSVTCKASQNVGTN-VAWYQQKPGQSPKPLIYSASYRYSGVPD RFTGSGSGTDFTLTISNVQSEDLAEYFCQQYNSY-PLYTFGGGTKLEIK (SEQ ID NO:32, with CDRs shown in bold characters) in which FR1-L spans amino acid positions 1 to 26, CDR1-L spans amino acid positions 27 to 32 (SEQ ID NO:4), FR2-L spans amino acid positions 33 to 49, CDR2-L spans amino acid positions 50 to 52, FR3-L spans amino acid positions 53 to 88, CDR3-L spans amino acid positions 89 to 98 (SEQ ID NO:6), and FR4-L spans amino acid positions 99 to 108.

The so-called "antibody MAb2" comprises:

a variable domain of heavy chain consisting of sequence EVQLQESGGVLVKPGGSLKLS-CAASGFVFSSYDMSWVRQTPEKRLEWVAYIS-SGGGITYF PDTVQGRFTVSRDNAKNTLYLQM-NSLKSEDTAIYYCAAHYFGSSGP-FAYWGQGTLVTVSA (SEQ ID NO:33, with CDRs shown in bold characters) in which FR1-H spans amino acid positions 1 to 25, CDR1-H spans amino acid positions 26 to 33 (SEQ ID NO:7), FR2-H spans amino acid positions 34 to 50, CDR2-H spans amino acid positions 51 to 58 (SEQ ID NO:8), FR3-H spans amino acid positions 59 to 96, CDR3-H spans amino acid positions 97 to 109 (SEQ ID NO:9), and FR4-H spans amino acid positions 110 to 120, and a variable domain of light chain consisting of sequence DIQMTQSPASLSASVGETVTITCRASENIFSY-LAWYQQKQGKSPQLLVYNTKTLAEGVPSRF SGSGSGTQFSLKIN-SLQPEDFGSYYCQHHYGTPFTFGSGTKLEIK (SEQ ID NO:34, with CDRs shown in bold characters) in which FR1-L spans amino acid positions 1 to 26, CDR1-L spans amino acid positions 27 to 32 (SEQ ID NO:10), FR2-L spans amino acid positions 33 to 49, CDR2-L spans amino acid positions 50 to 52, FR3-L spans amino acid positions 53 to 88, CDR3-L spans amino acid positions 89 to 97 (SEQ ID NO:12), and FR4-L spans amino acid positions 98 to 107.

A variant of antibody MAb2 was also generated by introducing a K52R substitution in the CDR2-L. This variant, which is called herein "Mab2$_{K52R}$", has essentially the same affinity for human and *Macaca fascicularis* CEACAM5 as MAb2.

The so-called "antibody MAb3" comprises:

a variable domain of heavy chain consisting of sequence EVKLVESGGGLVKPGGSLTLP-CAASGFTFSRYAMSWVRQTPEKRLEWVASIS-SGGDTYYP DSVKGRFTVSRDNARNILFLQMS-SLRSEDTGMYYCARVNYYDSSFLDWWGQGT-TLTVSS (SEQ ID NO:35, with CDRs shown in bold characters) in which FR1-H spans amino acid positions 1 to 25, CDR1-H spans amino acid positions 26 to 33 (SEQ ID NO:13), FR2-H spans amino acid positions 34 to 50, CDR2-H spans amino acid positions 51 to 57 (SEQ ID NO:14), FR3-H spans amino acid positions 58 to 95, CDR3-H spans amino acid positions 96 to 108 (SEQ ID NO:15), and FR4-H spans amino acid positions 109 to 119, and a variable domain of light chain consisting of sequence DIVMTQSQRFMSTLEGDRVSVTCKASQNVGTN-VAWYQQKPGQSPKALIYSASYRYSGVPD RFTGSGSGTDFTLTISNVQSEDLAEYFCQQYN-NYPLYTFGGGTKLEIK (SEQ ID NO:36, with CDRs shown in bold characters) in which FR1-L spans amino acid positions 1 to 26, CDR1-L spans amino acid positions 27 to 32 (SEQ ID NO:16), FR2-L spans amino acid positions 33 to 49, CDR2-L spans amino acid positions 50 to 52, FR3-L spans amino acid positions 53 to 88, CDR3-L spans amino acid positions 89 to 98 (SEQ ID NO:18), and FR4-L spans amino acid positions 99 to 108.

The so-called "antibody MAb4" comprises:

a variable domain of heavy chain consisting of sequence EVQLVESGGGLVKPGGSLKLS-CAASGFTFSSYDMSWVRQTPEKRLEWVAFIS-SYGGRTYY ADTVKGRFTISRDNAKNTLYLQM-SSLKSEDTAMFYCAAHYFGTSGP-FAYWGQGTLVTVSA (SEQ ID NO:37, with CDRs shown in bold characters) in which FR1-H spans amino acid positions 1 to 25, CDR1-H spans amino acid positions 26 to 33 (SEQ ID NO:19), FR2-H spans amino acid positions 34 to 50, CDR2-H spans amino acid positions 51 to 58 (SEQ ID NO:20), FR3-H spans amino acid positions 59 to 96, CDR3-H spans amino acid positions 97 to 109 (SEQ ID NO:21), and FR4-H spans amino acid positions 110 to 120, and a variable domain of light chain consisting of sequence DIQMTQSPASLSASVGETVTITCRA-SENIYSYFAWYQQKQGKSPQLLVYNAKILAE-GVPSRF SGSGSGTQFSLKINSLQPEDFGTYYCQ-HHYGIPFTFGSGTKLELK (SEQ ID NO:38, with CDRs shown in bold characters) in which FR1-L spans amino acid positions 1 to 26, CDR1-L spans amino acid positions 27 to 32 (SEQ ID NO:22), FR2-L spans amino acid positions 33 to 49, CDR2-L spans amino acid positions 50 to 52, FR3-L spans amino acid positions 53 to 88, CDR3-L spans amino acid positions 89 to 97 (SEQ ID NO:24), and FR4-L spans amino acid positions 98 to 107.

The so-called "antibody MAb5" comprises:

a variable domain of heavy chain consisting of sequence ELQLVESGGVLVKPGGSLKLS-CAASGFAFSSYDMSWVRQTPEKRLEWVTYIN-SGGGITYY PDTVKGRFTISRDNARNTLYLQM-SSLKSEDTAIYYCTAHYFGSSGP-FAYWGQGTLVTVSA (SEQ ID NO:39, with CDRs shown in bold characters) in which FR1-H spans amino acid positions 1 to 25, CDR1-H spans amino acid positions 26 to 33 (SEQ ID NO:25), FR2-H spans amino acid positions 34 to 50, CDR2-H spans amino acid positions 51 to 58 (SEQ ID NO:26), FR3-H spans amino acid positions 59 to 96, CDR3-H spans amino acid positions 97 to 109 (SEQ ID NO:27), and FR4-H spans amino acid positions 110 to 120, and a variable domain of light chain consisting of sequence DIQMTQSPASLSASVGETVTITCRASENIYSY-LAWYQQKQGKSPQLLVYNAKTLTEGVPSR FSGSGSGTQFSLKIN-SLQPEDFGSYYCQHHYGTPFTFGSGTKLEIK (SEQ ID NO:40, with CDRs shown in bold characters) in which FR1-L spans amino acid positions 1 to 26, CDR1-L spans amino acid positions 27 to 32 (SEQ ID NO:28), FR2-L spans amino acid positions 33 to 49, CDR2-L spans amino acid positions 50 to 52, FR3-L spans amino acid positions 53 to 88, CDR3-L spans amino acid positions 89 to 97 (SEQ ID NO:30), and FR4-L spans amino acid positions 98 to 107.

Therefore, the invention relates to an antibody which binds to human and *Macaca fascicularis* CEACAM5.

In an embodiment the antibody of the invention binds to the A3-B3 domains of human and *Macaca fascicularis* CEACAM5. More specifically, the antibody can bind to the human and *Macaca fascicularis* A3-B3 domains indifferently whether expressed in isolated form, or present in a soluble extracellular domain or membrane-anchored full-length CEACAM5 protein.

The specificity of the antibodies for the A3-B3 domain of human CEACAM5 is advantageous as no SNP with a frequency higher than 2% in caucasian population was reported in this domain, which minimizes the risk that the antibodies' epitope(s) on CEACAM5 be altered in part of the population.

The invention also provides for an antibody which competes for binding to A3-B3 domain of human and *Macaca fascicularis* CEACAM5 proteins with an antibody comprising the variable heavy and light chains of an antibody selected from the group consisting of the so-called antibodies MAb1, MAb2, $MAb2_{K52R}$, MAb3, MAb4, and MAb5, i.e. selected from the group consisting of:

a) an antibody comprising a variable domain of heavy chain of sequence SEQ ID NO:31 and a variable domain of light chain of sequence of sequence SEQ ID NO:32;

b) an antibody comprising a variable domain of heavy chain of sequence SEQ ID NO:33 and a variable domain of light chain of sequence of sequence SEQ ID NO:34;

c) an antibody comprising a variable domain of heavy chain of sequence SEQ ID NO:33 and a variable domain of light chain of sequence of sequence SEQ ID NO:34 in which K at position 52 has been replaced by R;

d) an antibody comprising a variable domain of heavy chain of sequence SEQ ID NO:35 and a variable domain of light chain of sequence of sequence SEQ ID NO:36;

e) an antibody comprising a variable domain of heavy chain of sequence SEQ ID NO:37 and a variable domain of light chain of sequence of sequence SEQ ID NO:38; and f) an antibody comprising a variable domain of heavy chain of sequence SEQ ID NO:39 and a variable domain of light chain of sequence of sequence SEQ ID NO:40.

The ability of a candidate antibody to compete for binding to A3-B3 domain of human and *Macaca fascicularis* CEACAM5 proteins with an antibody comprising the variable heavy and light chains of an antibody selected from the group consisting of the antibodies MAb1, MAb2, MAb3, MAb4, and MAb5 (hereafter a "reference" antibody) may be readily assayed, for instance, by competitive ELISA wherein the antigen (i.e. the A3-B3 domain of human or *Macaca fascicularis* CEACAM5, or a polypeptide comprising or consisting of a fragment of human or *Macaca fascicularis* CEACAM5 including the A3-B3 domain, in particular the extracellular domain of human or *Macaca fascicularis* CEACAM5) is bound to a solid support and two solutions containing the candidate antibody and the reference antibody, respectively, are added and the antibodies are allowed to compete for binding to the antigen. The amount of reference antibody bound to the antigen may then be measured, and compared to the amount of reference antibody bound to the antigen when measured against a negative control (e.g. solution containing no antibody). An amount of bound reference antibody in presence of the candidate antibody decreased as compared to the amount of bound reference antibody in presence of the negative control indicates that the candidate antibody has competed with the reference antibody. Conveniently, the reference antibody may be labeled (e.g. fluorescently) to facilitate detection of bound reference antibody. Repeated measurements may be performed with serial dilutions of the candidate and/or reference antibody.

According to an embodiment, such an antibody, and for instance the antibody which competes for binding to A3-B3 domain of human and *Macaca fascicularis* CEACAM5 proteins with an antibody as defined in b), c), e) and f) above, binds to two regions of the A3-B3 domain of human CEACAM5 protein that consist of amino acids at positions 109-115 (SEQ ID NO:76) and amino acids at positions 131-143 (SEQ ID NO:77) of the A3-B3 domain of human CEACAM5 protein, respectively. Indeed, a conformational epitope for the MAb2 antibody has been identified to belong to the regions 109-115 and 131-143 of the A3-B3 domain of human CEACAM5 protein, and MAb2, MAb4 and MAb5 being structurally closely related, it is assumed by the inventors that said antibodies bind to the same epitope.

According to an embodiment, the antibody according to the invention is specific for the surface human and *Macaca fascicularis* CEACAM5 proteins. In an embodiment, the antibody of the invention does not bind to, or does not significantly cross-react with human CEACAM1, human CEACAM6, human CEACAM7, human CEACAM8, *Macaca fascicularis* CEACAM1, *Macaca fascicularis* CEACAM6 and *Macaca fascicularis* CEACAM8 proteins.

In particular, the antibody does not bind to, or does not significantly cross-react with the extracellular domain of the aforementioned human and *Macaca fascicularis* CEACAM proteins.

Human CEACAM1 full-length protein is available in GENBANK® database under accession number NP_001703.2 (SEQ ID NO:11). The extracellular domain of human CEACAM1 consists of amino acids at positions 35-428 of SEQ ID NO:11. Human CEACAM6 full-length protein is available in GENBANK® database under accession number NP_002474.3 (SEQ ID NO:71). The extracellular domain of human CEACAM6 consists of amino acids at positions 35-327 of SEQ ID NO:71.

Human CEACAM7 full-length protein is available in GENBANK® database under accession number NP_008821.1 (SEQ ID NO:72). The extracellular domain of human CEACAM7 consists of amino acids at positions 36-248 of SEQ ID NO:72.

Human CEACAM8 full-length protein is available in GENBANK® database under accession number NP_001807.2 (SEQ ID NO:73). The extracellular domain of human CEACAM8 consists of amino acids at positions 35-332 of SEQ ID NO:73.

*M. fascicularis* CEACAM1 extracellular domain consists of amino acids at positions 35-428 of full-length protein, i.e. amino acids 1-394 of SEQ ID NO:57.

*M. fascicularis* CEACAM6 extracellular domain consists of amino acids at positions 35-327 of full-length protein, i.e. amino acids 1-293 of SEQ ID NO:61.

*M. fascicularis* CEACAM8 extracellular domain consists of amino acids at positions 35-332 of full-length protein, i.e. amino acids 1-298 of SEQ ID NO:63.

"Affinity" is defined, in theory, by the equilibrium association between the whole antibody and the antigen. It can be experimentally assessed by a variety of known methods, such as measuring association and dissociation rates with surface plasmon resonance or measuring the $EC_{50}$ (or apparent $K_D$) in an immunochemical assay (ELISA, FACS). In these assays, the $EC_{50}$ is the concentration of the antibody which induces a response halfway between the baseline and maximum after some specified exposure time on a defined concentration of antigen by ELISA (enzyme-linked immuno-sorbent assay) or cell expressing the antigen by FACS (Fluorescence Activated Cell Sorting).

A monoclonal antibody binding to antigen 1(Ag1) is "cross-reactive" to antigen 2 (Ag2) when the $EC_{50}$s are in a similar range for both antigens. In the present application, a monoclonal antibody binding to Ag1 is cross-reactive to Ag2 when the ratio of affinity of Ag2 to affinity of Ag1 is equal or less than 10 (for instance 5, 2, 1 or 0.5), affinities being measured with the same method for both antigens.

A monoclonal antibody binding to Ag1 is "not significantly cross-reactive" to Ag2 when the affinities are very different for the two antigens. Affinity for Ag2 may not be measurable if the binding response is too low. In the present application, a monoclonal antibody binding to Ag1 is not significantly cross-reactive to Ag2, when the binding response of the monoclonal antibody to Ag2 is less than 5% of the binding response of the same monoclonal antibody to Ag1 in the same experimental setting and at the same antibody concentration. In practice, the antibody concentration used can be the $EC_{50}$ or the concentration required to reach the saturation plateau obtained with Ag1.

A monoclonal antibody "binds specifically" to, or "is specific for" Ag1 when it is not significantly cross-reactive to Ag2. Accordingly, the antibody according to the invention has a ratio of affinity for human CEACAM5 to the affinity for *Macaca fascicularis* CEACAM5 which is ≤10, for instance ≤5, ≤2, ≤1, or ≤0.5. Thus, the polypeptide according to the invention may be used in toxicological studies performed in monkeys because the toxicity profile observed in monkeys would be relevant to anticipate potential adverse effects in humans An embodiment of the invention has an affinity for human CEACAM5 or *Macaca fascicularis* CEACAM5, or both, which is ≤10 nM, for instance ≤5 nM, ≤3 nM, ≤1 nM or ≤0.1 nM, for instance an affinity of 0.01 nM to 5 nM, or and affinity of 0.1 nM to 5 nM, or of 0.1 nM to 1 nM.

Affinity for human CEACAM5 or for *Macaca fascicularis* CEACAM5 may be determined as the EC50 value in an ELISA using soluble recombinant CEACAM5 as capture antigen.

The antibody of the invention may also have an apparent dissociation constant (apparent KD), as may be determined by FACS analysis on tumor cell line MKN45 (DSMZ, ACC 409) or on xenograft tumor cells deriving from patient (CR-IGR-034P available from Oncodesign Biotechnology, tumor collection CReMEC), which is ≤25 nM, for instance ≤20 nM, ≤10 nM, ≤5 nM, ≤3 nM or ≤1 nM. The apparent KD may be within the range 0.01-20 nM, or may be within the range 0.1-20 nM, 0.1-10 nM, or 0.1-5 nM.

Additionally, antibodies according to the invention have been shown to be able to detect CEACAM5 expression by immunohistochemistry in frozen and formalin-fixed and paraffin embedded (FFPE) tissue sections.

Alignments of the sequences of the VH and VL regions of the MAb1, MAb2, MAb3, MAb4 and MAb5 antibodies are shown in FIG. 7. The comparison of the CRD-H and CDR-L sequences indicates that, structurally, MAb2, MAb4 and MAb5, on one hand, and MAb1 and MAb3, on the other hand, are closely related, said antibodies probably binding to the same epitope. The comparison of the CRD-H and CDR-L sequences further identifies CDR positions that are strictly conserved between the two groups of antibodies and which are thus assumed to be important for specificity, whereas other positions could support substitution.

It has been further identified by the inventors that residues at positions 101-109 of MAb2 VH (i.e. residues of CDR3-H) and residues at positions 47-54 and 88-104 of MAb2 VL (i.e. regions including CDR2-L and CDR3-L, respectively) make part, or form, the antibody paratope for human CEACAM5-A3B3 domain.

Furthermore, residues at positions 27, 28, 29, 31, 51, 52, 89, 90, 93, 94, 96, and 97 of MAb2 VL (i.e. within CDR1-L, CDR2-L and CDR3-L), and residues at positions 26 to 31, 51 to 58, 97, 103, 104, 107, and 109 of MAb2 VH (i.e. within CDR1-H, all of CDR2-H and within CDR3-H) have been identified by single acid substitutions as neutral for binding to human and cynomolgus CEACAM5 extracellular domains. In addition, residues at positions 30 and 92 of MAb2 VL (i.e. within CDR1-L and CDR3-L), and residues at positions 98 and 100 of MAb2 VH (i.e. within CDR3-H), have been shown to tolerate a conservative substitution. Since MAb2, MAb4 and MAb5 carry the same set of 6 CDRs or very closely related ones, it is considered that variations at the same positions of MAb4 or MAb5 in VH or VL or both VH and CL sequences will also result in variant antibodies maintaining the binding specificity and/or affinity for human and cynomolgus CEACAM5.

Noteworthy, all residues of CDR2-H being identified as neutral for binding to human and cynomolgus CEACAM5 extracellular domains, the inventors assumed that CDR2-H might not participate in the interaction. Accordingly, in the antibodies of the invention, CDR2-H could be any sequence of 6 to 10 amino acids, this being the regular length of CDR2-H sequences in human antibodies.

Accordingly, the antibody according to the invention comprises:

a) a CDR1-H consisting of sequence $X_1X_2X_3X_4X_5X_6YD$ (SEQ ID NO:83) wherein each of $X_1$, $X_2$, $X_3$, $X_4$, $X_5$ and $X_6$ is any amino acid; and a CDR2-H consisting of a 6 to 10 amino acid-long sequence, preferably a 8 amino acid long sequence in which any amino acid may be present at any position; and a CDR3-H consisting of sequence $X_1X_2HX_3FGX_4X_5GPX_6AX_7$ (SEQ ID NO:84) wherein each of $X_1$, $X_4$, $X_5$, $X_6$, and $X_7$ is any amino acid, $X_2$ is A or S, and $X_3$ is Y, F or W; and/or b) a CDR1-L consisting of sequence $X_1X_2X_3X_4X_5Y$ (SEQ ID NO:85) wherein each of $X_1$, $X_2$, $X_3$ and $X_5$ is any amino acid, and $X_4$ is Y, F or W; and a CDR2-L consisting of sequence $NX_1X_2$ wherein each of $X_1$ and $X_2$ is any amino acid; and a CDR3-L consisting of sequence $X_1X_2HX_3X_4X_5PX_6X_7$ (SEQ ID NO:86) wherein each of $X_1$, $X_2$, $X_4$, $X_5$, $X_6$ and $X_7$ is any amino acid, $X_3$ is Y, F or W.

In an embodiment, in the CDR1-H consisting of sequence $X_1X_2X_3X_4X_5X_6YD$ (SEQ ID NO:83), $X_1$ is G, or $X_2$ is F, or $X_3$ is T, A or V, or $X_4$ is F, or $X_5$ is S, or $X_6$ is S, or any combination thereof.

In an embodiment, the CDR2-H consists of sequence $IX_1SX_2GGX_3T$ (SEQ ID NO:79) wherein $X_1$ is S or N (in particular S), $X_2$ is Y or G (in particular G), $X_3$ is R or I. In a further embodiment $X_3$ is I.

In an embodiment, in the CDR3-H consisting of sequence $X_1X_2HX_3FGX_4X_5GPX_6AX_7$ (SEQ ID NO:84), $X_1$ is A or T, or $X_4$ is T or S, or $X_5$ is S, or $X_6$ is F, or $X_7$ is Y, or any combination thereof.

In an embodiment, in the CDR1-L consisting of sequence $X_1X_2X_3X_4X_5Y$ (SEQ ID NO:85), $X_1$ is E, or $X_2$ is N, or $X_3$ is I, or $X_5$ is S, or any combination thereof.

In an embodiment, the CDR2-L consists of sequence $NX_1X_2$ wherein $X_1$ is A or T, and $X_2$ is K or R.

In an embodiment, in the CDR3-L consisting of sequence $X_1X_2HX_3X_4X_5PX_6X_7$ (SEQ ID NO:86), $X_1$ is Q, or $X_2$ is H, or $X_4$ is G, or $X_5$ is T, or $X_6$ is F, or $X_7$ is T, or any combination thereof. According to an embodiment, the antibody according to the invention comprises:

a) a CDR1-H consisting of sequence $GFX_1FSSYD$ (SEQ ID NO:78) wherein $X_1$ is T, A or V; and a CDR2-H consisting of sequence $IX_1SX_2GGX_3T$ (SEQ ID NO:79) wherein $X_1$ is S or N (in particular S), $X_2$ is Y or G (in particular G), $X_3$ is R or I; and a CDR3-H consisting of sequence $X_1AHYFGX_2SGPFAY$ (SEQ ID NO:80) wherein $X_1$ is A or T (in particular A), and $X_2$ is T or S; and/or b) a CDR1-L consisting of sequence ENIFSY (SEQ ID NO:10) or ENIYSY (SEQ ID NO:22); and a CDR2-L consisting of sequence $NX_1X_2$ wherein $X_1$ is A or T, and $X_2$ is K or R, in particular R; CDR2-L consisting in particular of NAK, NTK and NTR; and a CDR3-L consisting of sequence QHHYGTPFT (SEQ ID NO:12) or QHHYGIPFT (SEQ ID NO:24).

According to an embodiment, in CDR2-H, $X_1$ is S or N, $X_2$ is G and $X_3$ is I.

According to an embodiment, CDR2-H consists of ISSGGGIT (SEQ ID NO:8), ISSYGGRT (SEQ ID NO:20) or INSGGGIT (SEQ ID NO:26).

According to an embodiment, in CDR3-H, $X_1$ is A or T, and $X_2$ is S.

According to an embodiment, CDR3-H consists of AAHYFGSSGPFAY (SEQ ID NO:9), AAHYFGTSGPFAY (SEQ ID NO:21), or TAHYFGSSGPFAY (SEQ ID NO:27).

Any combination of these embodiments makes part of the invention.

Alternatively, the antibody according to the invention comprises:

a) a CDR1-H consisting of sequence $GFTFSX_1YX_2$ (SEQ ID NO:81) wherein $X_1$ is R or S, in particular S, and $X_2$ is A or D; and a CDR2-H consisting of sequence $ISSGGX_1X_2X_3$ (SEQ ID NO:82) wherein $X_1$ is absent, S or G (in particular G), $X_2$ is D, Y or I, and $X_3$ is T or I; and a CDR3-H consisting of sequence ARPAYYGNPAMDY (SEQ ID NO:3) or ARVNYYDSSFLDW (SEQ ID NO:15); and/or b) a CDR1-L consisting of sequence QNVGTN (SEQ ID NO:4); and a CDR2-L consisting of sequence SAS; and a CDR3-L consisting of sequence QQYNSYPLYT (SEQ ID NO:6) or QQYNNYPLYT (SEQ ID NO:18).

According to an embodiment, CDR2-H consists of sequence ISSGGSYI (SEQ ID NO:2) or ISSGGDT (SEQ ID NO:14).

According to an embodiment, CDR2-H consists of sequence ISSGGSYI (SEQ ID NO:2) and CDR3-H of sequence ARPAYYGNPAMDY (SEQ ID NO:3).

According to an embodiment, CDR2-H consists of ISSGGDT (SEQ ID NO:14) and CDR3-H of sequence ARVNYYDSSFLDW (SEQ ID NO:15).

According to an embodiment, the antibody according to the invention comprises the CDR sequences of the heavy and/or light chains of one of so-called anti-CEACAM5 antibodies MAb1, MAb2, $MAb2_{K52R}$, MAb3, MAb4, and MAb5.

Therefore, the invention relates to an antibody which comprises:

a) CDR1-H of sequence GFTFSSYA (SEQ ID NO:1) or a sequence differing from SEQ ID NO:1 by one amino acid substitution; CDR2-H of sequence ISSGGSYI (SEQ ID NO:2) or a sequence differing from SEQ ID NO:2 by one or more amino acid substitutions; CDR3-H of sequence ARPAYYGNPAMDY (SEQ ID NO:3) or a sequence differing from SEQ ID NO:3 by one amino acid substitution; CDR1-L of sequence QNVGTN (SEQ ID NO:4) or a sequence differing from SEQ ID NO:4 by one amino acid substitution; CDR2-L of sequence SAS or a sequence differing from SAS by one amino acid substitution and CDR3-L of sequence QQYNSYPLYT (SEQ ID NO:6) or a sequence differing from SEQ ID NO:6 by one amino acid substitution; or b) a CDR1-H of sequence GFVFSSYD (SEQ ID NO:7) or a sequence differing from SEQ ID NO:7 by one amino acid substitution; CDR2-H of sequence ISSGGGIT (SEQ ID NO:8) or a sequence differing from SEQ ID NO:8 by one or more amino acid substitutions; CDR3-H of sequence AAHYFGSSGPFAY (SEQ ID NO:9) or a sequence differing from SEQ ID NO:9 by one or more amino acid substitutions; CDR1-L of sequence ENIFSY (SEQ ID NO:10) or a sequence differing from SEQ ID NO:10 by one amino acid substitution; CDR2-L of sequence NTK or NTR or a sequence differing from NTK or NTR by one amino acid substitution and CDR3-L of sequence QHHYGTPFT (SEQ ID NO:12) or a sequence differing from SEQ ID NO:12 by one amino acid substitution; or c) a CDR1-H of sequence GFTFSRYA (SEQ ID NO:13) or a sequence differing from SEQ ID NO:13 by one amino acid substitution; CDR2-H of sequence ISSGGDT (SEQ ID NO:14) or a sequence differing from SEQ ID NO:14 by one or more amino acid substitutions; CDR3-H of sequence ARVNYYDSSFLDW (SEQ ID NO:15) or a sequence differing from SEQ ID NO:15 by one amino acid substitution; CDR1-L of sequence QNVGTN (SEQ ID NO:16) or a sequence differing from SEQ ID NO:16 by one amino acid substitution; CDR2-L of sequence SAS or a sequence differing from SAS by one amino acid substitution and CDR3-L of sequence QQYNNYPLYT (SEQ ID NO:18) or a sequence differing from SEQ ID NO:18 by one amino acid substitution; or d) a CDR1-H of sequence GFTFSSYD (SEQ ID NO:19) or a sequence differing from SEQ ID NO:19 by one amino acid substitution; CDR2-H of sequence ISSYGGRT (SEQ ID NO:20) or a sequence differing from SEQ ID NO:20 by one or more amino acid substitutions; CDR3-H of sequence AAHYFGTSGPFAY (SEQ ID NO:21) or a sequence differing from SEQ ID NO:21 by one or more amino acid substitutions; CDR1-L of sequence ENIYSY (SEQ ID NO:22) or a sequence differing from SEQ ID NO:22 by one amino acid substitution; CDR2-L of sequence NAK or a sequence differing from NAK by one or more amino acid substitutions and CDR3-L of sequence QHHYGIPFT (SEQ ID NO:24) or a sequence differing from SEQ ID NO:24 by one amino acid substitution; or e) an antibody comprising a CDR1-H of sequence GFAFSSYD (SEQ ID NO:25) or a sequence differing from SEQ ID NO:25 by one amino acid substitution; CDR2-H of sequence INSGGGIT (SEQ ID NO:26) or a sequence differing from SEQ ID NO:26 by one or more amino acid substitutions; CDR3-H of sequence TAHYFGSSGPFAY (SEQ ID NO:27) or a sequence differing from SEQ ID NO:27 by one or more amino acid substitutions; CDR1-L of sequence ENIYSY (SEQ ID NO:28) or a sequence differing from SEQ ID NO:28 by one amino acid substitution; CDR2-L of sequence NAK; or a sequence differing from NAK by one or more amino acid substitutions and CDR3-L of sequence QHHYGTPFT (SEQ ID NO:30) or a sequence differing from SEQ ID NO:30 by one amino acid substitution.

One or more individual amino acids may be altered by substitution, in particular by conservative substitution, in one or more of the above CDR sequences. Such an alteration may be intended for example to remove a glycosylation site or a deamidation site, in connection with humanisation of the antibody.

Based on the alignments of the sequences of the VH and VL regions of the MAb1, MAb2, MAb3, MAb4 and MAb5, and based on single acid substitutions in a variant of MAb2 antibody, an amino acid may be substituted:

in CDR1-H: at one or more of positions 1 to 6, for instance at position 3, of CDR1-H of sequence GFVFSSYD (SEQ ID NO:7), GFTFSSYD (SEQ ID NO:19) or GFAFSSYD (SEQ ID NO:25), or at position 6 of CDR1-H of sequence GFTFSSYA (SEQ ID NO:1) or GFTFSRYA (SEQ ID NO:13); and/or in CDR2-H, at one or more of any of the positions, or at one, two or three of positions 2, 4, and 7 of CDR2-H of sequence ISSGGGIT (SEQ ID NO:8), ISSYGGRT (SEQ ID NO:20) or INSGGGIT (SEQ ID NO:26), or at one, two or three of positions 6, 7 and 8 (where the sequence is 8 amino acid long) of CDR2-H of sequence ISSGGSYI (SEQ ID NO:2) or ISSGGDT (SEQ ID NO:14); and/or see above in CDR3-H, at one or more of positions 1, 7, 8, 11 and 13, for instance at one or two of positions 1 and 7 of CDR3-H of sequence AAHYFGSSGPFAY (SEQ ID NO:9), AAHYFGTSGPFAY (SEQ ID NO:21), or TAHYFGSSGPFAY (SEQ ID NO:27), or at position 3, 4, 7, 8, 9, 10, or 11 of sequence ARPAYYGNPAMDY (SEQ ID NO:3) or ARVNYYDSSFLDW (SEQ ID NO:15); and/or in CDR1-L, at one or more of positions 1 to 5, in particular at one or more of positions 1, 2, 3 and 5 or at position 4 of CDR1-L of sequence ENIFSY (SEQ ID NO:10) or ENIYSY (SEQ ID NO:28); and/or in CDR2-L, at positions 2 and/or 3 of sequence NAK, NTK or NTR, in particular at least at position 3 if K is present. In such a case, R for instance can be substituted for K at position 3 of CDR2-L; and/or in CDR3-L, at one or more of positions 1, 2, 5, 6, 8 and 9, for instance at position 6 of CDR3-L of sequence QHHYGIPFT (SEQ ID NO:24) or QHHYGTPFT (SEQ ID NO:30), or at position 5 of CDR3-L of sequence QQYNSYPLYT (SEQ ID NO:6) or QQYNNYPLYT (SEQ ID NO:18).

According to an embodiment, in the antibodies of the invention:

position 5 of CDR3-H of sequence AAHYFGSSGPFAY (SEQ ID NO:9), AAHYFGTSGPFAY (SEQ ID NO:21), or TAHYFGSSGPFAY (SEQ ID NO:27); and/or position 6 of CDR1-L of sequence ENIFSY (SEQ ID NO:10) or ENIYSY (SEQ ID NO:28); and/or position 3 of CDR3-L of sequence QHHYGIPFT (SEQ ID NO:24) or QHHYGTPFT (SEQ ID NO:30)

is (are) unmodified.

According to an embodiment, in CDR1-H of sequence GFVFSSYD (SEQ ID NO:7), GFTFSSYD (SEQ ID NO:19) or GFAFSSYD (SEQ ID NO:25), the amino acid which is substituted for the amino acid at position at position 3 of CDR1-H is selected from the group consisting of T, A or V.

According to an embodiment, in CDR1-H of sequence GFTFSSYA (SEQ ID NO:1) or GFTFSRYA (SEQ ID NO:13), the amino acid which is substituted for the amino acid at position 6 of CDR1-H is R or S.

According to an embodiment, in CDR3-H of sequence AAHYFGSSGPFAY (SEQ ID NO:9), AAHYFGTSGPFAY (SEQ ID NO:21), or TAHYFGSSGPFAY (SEQ ID NO:27), the amino acid which is substituted for the amino acid at position 1 of CDR3-H is A or T and/or the amino acid which is substituted for the amino acid at position 7 of CDR3-H is T or S.

According to an embodiment, in CDR3-H of sequence ARPAYYGNPAMDY (SEQ ID NO:3) or ARVNYYDSSFLDW (SEQ ID NO:15), the amino acid which is substituted for the amino acid at position 3 of CDR3-H is V or P, at position 4 is A or N, at position 7 is D or G, at position 8 is S or N, at position 9 is S or P, at position 10 is F or A, or at position 11 is W or Y.

According to an embodiment, the amino acid which is substituted for the amino acid at position 4 of CDR1-L is Y or F.

According to an embodiment, in CDR2-L of sequence NAK, NTK or NTR, the amino acid which is substituted for the amino acid at position 2 of CDR2-L is A or T.

According to an embodiment, in CDR3-L of sequence QQYNSYPLYT (SEQ ID NO:6) or QQYNNYPLYT (SEQ ID NO:18), the amino acid which is substituted for the amino acid at position 5 of CDR3-L is N or S.

According to an embodiment, in CDR3-L of sequence QHHYGIPFT (SEQ ID NO:24) or QHHYGTPFT (SEQ ID NO:30), the amino acid which is substituted for the amino acid at position 6 of CDR3-L is I or T.

Any combination of the above embodiments makes part of the invention.

In an embodiment the antibody according to the invention is a conventional antibody, such as a conventional monoclonal antibody, or an antibody fragment, a bispecific or multispecific antibody.

In an embodiment the antibody according to the invention comprises or consists of an IgG, or a fragment thereof.

The invention also provides antibodies as defined above further comprising at least the variable domain of heavy chain and/or the variable domain of light chain of one of the five so-called anti-CEACAM5 antibodies MAb1, MAb2, MAb3, MAb4, and MAb5.

Thus an embodiment of the invention relates to a antibody which comprises:

a) a variable domain of heavy chain of sequence SEQ ID NO:31 or a sequence at least 85% identical thereto, and/or a variable domain of light chain of sequence of sequence SEQ ID NO:32, or a sequence at least 85% identical thereto; or b) a variable domain of heavy chain of sequence SEQ ID NO:33, or a sequence at least 85% identical thereto, and/or a variable domain of light chain of sequence of sequence SEQ ID NO:34, or a sequence at least 85% identical thereto; or c) a variable domain of heavy chain of sequence SEQ ID NO:35, or a sequence at least 85% identical thereto, and/or a variable domain of light chain of sequence of sequence SEQ ID NO:36, or a sequence at least 85% identical thereto; or d) a variable domain of heavy chain of sequence SEQ ID NO:37, or a sequence at least 85% identical thereto, and/or a variable domain of light chain of sequence of sequence SEQ ID NO:38, or a sequence at least 85% identical thereto; or e) a variable domain of heavy chain of sequence SEQ ID NO:39, or a sequence at least 85% identical thereto, and/or a variable domain of light chain of sequence of sequence SEQ ID NO:40, or a sequence at least 85% identical thereto. For instance, the sequence of the variable domain of heavy or light chain may differ from the reference sequence SEQ ID NO:31, 32, 33, 34, 35, 36, 37, 38, 39 or 40, as appropriate, by one or more amino acid substitution(s), in particular by one or more conservative amino acid substitution(s) and/or substitution(s) with canonical residues. In an embodiment, the sequence of the variable domain of heavy or light chain may differ from the reference sequence SEQ ID NO:31, 32, 33, 34, 35, 36, 37, 38, 39 or 40 by conservative amino acid substitution(s), only.

The sequence alterations as compared with sequence SEQ ID NO:31, 32, 33, 34, 35, 36, 37, 38, 39 or 40 will be present essentially in one or more of the framework regions, FR1-L, FR2-L, FR3-L, FR4-L and/or FR1-H, FR2-H, FR3-H, FR4-H.

However, amino acid substitutions in one or more CDRs are also possible. In an embodiment, the sequence of the variable domain of light chain may differ from sequence SEQ ID NO:34 at least by a K to R substitution at position 52 of SEQ ID NO:34 (in CDR2-L).

The antibody of the invention and a fragment thereof may be, respectively, a murine antibody and a fragment of a murine antibody.

The antibody may also be a chimeric antibody, and in an embodiment a murine/human antibody, e.g. an antibody comprising murine variable domains of heavy and light chains and a CH domain and a CL domain from a human antibody. The polypeptide may be a fragment of such an antibody.

According to an embodiment, the antibody of the invention is:

a) a chimeric antibody comprising, or consisting of, a heavy chain of sequence SEQ ID NO:41 or a sequence at least 85% identical thereto or a light chain of sequence of sequence SEQ ID NO:42 or a sequence at least 85% identical thereto (i.e heavy and/or light chain of chMAb1 as described in example 5); or a heavy chain and a light chain or, b) a chimeric antibody comprising, or consisting of, a heavy chain of sequence SEQ ID NO:43 or a sequence at least 85% identical thereto or a light chain of sequence of sequence SEQ ID NO:44 or a sequence at least 85% identical thereto; (i.e heavy and/or light chain of chMAb2 as described in example 5); or or a heavy chain and a light chain or, c) a chimeric antibody comprising, or consisting of, a heavy chain of sequence SEQ ID NO:45 or a sequence at least 85% identical thereto or a light chain of sequence of sequence SEQ ID NO:46 or a sequence at least 85% identical thereto; (i.e heavy and/or light chain of chMAb3 as described in example 5); or a heavy chain and a light chain or, d) a chimeric antibody comprising, or consisting of, heavy chain of sequence SEQ ID NO:47 or a sequence at least 85% identical thereto or a light chain of sequence of sequence SEQ ID NO:48 or a sequence at least 85% identical thereto, (i.e heavy and/or light chain of chMAb4 as described in example 5); or or a heavy chain and a light chain or, e) a chimeric antibody comprising, or consisting of, a heavy chain of sequence SEQ ID NO:49 or a sequence at least 85% identical thereto or a light chain of sequence of sequence SEQ ID NO:50 or a sequence at least 85% identical thereto (i.e heavy and/or light chain of chMAb5 as described in example 5), or or a heavy chain and a light chain or, f) a fragment of the chimeric antibody defined in a), b), c), d) or e).

The antibody may also be a humanised antibody or a fragment of a humanised antibody. In an embodiment, the antibody of the invention may result from humanisation of any of the chimeric antibodies defined above in a), b), c), d), e) or f).

Numerous methods for humanisation of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues. Another alternative technique is known as "guided selection" (Jespers et al. (1994) Biotechnology 12, 899) and can be used to derive from a murine antibody a fully human antibody conserving the epitope and binding characteristics of the parental antibody.

For chimeric antibodies, humanisation typically involves modification of the framework regions of the variable region sequences.

Amino acid residues that are part of a CDR will typically not be altered in connection with humanisation, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, for instance by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, for instance Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

Taking the so-called "antibody MAb2" as an example, a humanised antibody or fragment thereof may comprise the following mutations in the variable heavy chain: P instead of G in position 9; and/or G instead of V in position 10; and/or S instead of K in position 19; and/or R instead of K in position 43; and/or G instead of R in position 44; and/or A instead of F in position 60; and/or S instead of D in position 62; and/or K instead of Q in position 65; and/or T instead of K in position 87; and/or V instead of I in position 89; and/or S instead of A in position 113; the positions being given by reference to SEQ ID NO:33.

Still taking the so-called "antibody MAb2" as an example, a humanised antibody or fragment thereof may comprise the following mutations in the variable light chain: D instead of E in position 17; and/or R instead of T in position 18; and/or P instead of Q in position 40; and/or K instead of Q in position 45; and/or R instead of K in position 52; and/or D instead of Q in position 70; and/or T instead of K in position 74; and/or S instead of N in position 76; and/or A instead of G in position 84; and/or T instead of S in position 85; the positions being given by reference to SEQ ID NO:34.

In an embodiment, the antibody of the invention is a humanised antibody comprising, or consisting of, a heavy chain comprising the following mutations, the positions being given by reference to SEQ ID NO:33:

a) P instead of G in position 9; and G instead of V in position 10; and S instead of K in position 19; and R instead of K in position 43; and S instead of D in position 62; and K instead of Q in position 65; and T instead of K in position 87; or b) P instead of G in position 9; and G instead of V in position 10; and S instead of K in position 19; and R instead of K in position 43; and G instead of R in position 44; and A instead of F in position 60; and S instead of D in position 62; and K instead of Q in position 65; and T instead of K in position 87; and V instead of I in position 89; and S instead of A in position 113; and/or a humanised antibody comprising a light chain comprising the following mutations, the positions being given by reference to SEQ ID NO:34:

c) D instead of E in position 17; and P instead of Q in position 40; and K instead of Q in position 45; and T instead of K in position 74; and S instead of N in position 76; or d) D instead of E in position 17; and R instead of T in position 18; and P instead of Q in position 40; and K instead of Q in position 45; and D instead of Q in position 70; and T instead of K in position 74; and S instead of N in position 76; and A instead of G in position 84; and T instead of S in position 85; or e) D instead of E in position 17; and R instead of T in position 18; and P instead of Q in position 40; and K instead of Q in position 45; and R instead of K in position 52; and D instead of Q in position 70; and T instead of K in position 74; and S instead of N in position 76; and A instead of G in position 84; and T instead of S in position 85.

In an embodiment, the antibody of the invention is a humanized antibody obtained by grafting the CDRs of an antibody of the invention into alternative antibody framework regions, more specifically into human framework regions. Taking MAb2 as an example, the 6 CDRs of $MAb2_{K52R}$ have been grafted into a human framework consisting of IGHV3-23 and IGKV1 D-39 genes, and three back-mutations were introduced corresponding to positions 34 and 53 in the VL (SEQ ID NO. 34) and position 50 in the VH (SEQ ID NO. 33) resulting in an antibody comprising a variable domain of heavy chain of sequence SEQ ID NO:74 and a variable domain of light chain of sequence SEQ ID NO:75.

In an embodiment, the antibody of the invention is a humanised antibody comprising, or consisting of, a heavy chain of sequence SEQ ID NO:51, SEQ ID NO:5, or SEQ ID NO: 74, or a sequence at least 85% identical thereto; and/or a light chain of sequence SEQ ID NO:17, SEQ ID NO:23, SEQ ID NO:29, SEQ ID NO:55 or SEQ ID NO: 75 or a sequence at least 85% identical thereto (humanised variable domains of heavy and light chains of MAb2).

In an embodiment, the antibody of the invention is a humanised antibody comprising a heavy chain of sequence SEQ ID NO:51 or a sequence at least 85% identical thereto and a light chain of sequence SEQ ID NO:17 or a sequence at least 85% identical thereto, or a heavy chain of sequence SEQ ID NO:5 or a sequence at least 85% identical thereto and a light chain of sequence SEQ ID NO:23 or a sequence at least 85% identical thereto, or heavy chain of sequence SEQ ID NO:5 or a sequence at least 85% identical thereto and a light chain of sequence SEQ ID NO:29 or a sequence at least 85% identical thereto, or heavy chain of sequence SEQ ID NO:51 or a sequence at least 85% identical thereto and a light chain of sequence SEQ ID NO:55 or a sequence at least 85% identical thereto, or a heavy chain of sequence SEQ ID NO: 74 or a sequence at least 85% identical thereto and a light chain of sequence SEQ ID NO: 75 or a sequence at least 85% identical thereto.

In said humanised antibody or fragment thereof, the variable domains of heavy and light chains may comprise human acceptor framework regions. The humanised antibody further comprises human constant heavy and light chain domains, where present.

In an embodiment, the antibody of the invention is antibody huMAb2-3 or a variant thereof, i.e. an isolated antibody which binds to A3-B3 domain of human and *Macaca fascicularis* CEACAM5 proteins and which comprises:

a) a heavy chain consisting of sequence SEQ ID NO:87 or a sequence at least 85% identical thereto; or b) a light chain consisting of sequence SEQ ID NO:88 or a sequence at least 85% identical thereto or a heavy chain and a light chain.

In an embodiment, the antibody of the invention is antibody huMAb2-4 (MAb2_VL1d VH1-IgG1) or a variant thereof, i.e. an isolated antibody which binds to A3-B3 domain of human and *Macaca fascicularis* CEACAM5 proteins and which comprises:

c) a heavy chain consisting of sequence SEQ ID NO:89 or a sequence at least 85% identical thereto; and/or d) a light chain consisting of sequence SEQ ID NO:90 or a sequence at least 85% identical thereto.

The antibody according to the invention may also be a single domain antibody or a fragment thereof. In an embodiment of the invention, a single domain antibody fragment may consist of a variable heavy chain (VHH) which comprises the CDR1-H, CDR2-H and CDR3-H of the antibodies as described above. The antibody may also be a heavy chain antibody, i.e. an antibody devoid of light chain, which may or may not contain a CH1 domain.

The single domain antibody or a fragment thereof may also comprise the framework regions of a camelid single domain antibody, and optionally the constant domain of a camelid single domain antibody.

The antibody according to the invention may also be an antibody fragment for instance a humanised antibody fragment, selected from the group consisting of Fv, Fab, F(ab')2, Fab', dsFv, (dsFv)2, scFv, sc(Fv)2, and diabodies.

The antibody may also be a bispecific or multispecific antibody formed from antibody fragments, at least one antibody fragment being an antibody fragment according to the invention. Multispecific antibodies are polyvalent protein complexes as described for instance in EP 2 050 764 A1 or US 2005/0003403 A1.

The bispecific or multispecific antibodies according to the invention can have specificity for (a) the A3-B3 epitope on human/*Macaca fascicularis* CEACAM5 targeted by one of the so-called MAb1, MAb2, MAb3, MAb4 and MAb5 antibodies and (b) at least one other antigen. According to an embodiment the at least one other antigen is not a human or *Macaca fascicularis* CEACAM family member, and in an embodiment not at least one or all of human and *Macaca fascicularis* CEACAM1, human and monkey CEACAM6, human and *Macaca fascicularis* CEACAM7, and human and *Macaca fascicularis* CEACAM8. According to another embodiment, the at least one other antigen may be an epitope on human *Macaca fascicularis* CEACAM5 other than said A3-B3 epitope targeted by one of the so-called MAb1, MAb2, MAb3, MAb4 and MAb5 antibodies.

Said antibodies can be produced by any technique well known in the art. In an embodiment said antibodies are produced by techniques as hereinafter described.

Antibodies and fragments thereof according to the invention can be used in an isolated (e.g., purified) from or contained in a vector, such as a membrane or lipid vesicle (e.g. a liposome).

Nucleic Acids, Vectors and Recombinant Host Cells

A further object of the invention relates to a nucleic acid sequence comprising or consisting of a sequence encoding an antibody of the invention as defined above.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for an animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce a recombinant antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC® CRL1581), mouse P3X63-Ag8.653 cell (ATCC® CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC® CRL1662, hereinafter referred to as "YB2/0 cell"), and the like. In an embodiment the YB2/0 cell is used, since ADCC activity of chimeric or humanised antibodies is enhanced when expressed in this cell.

For expression of humanised antibody, the expression vector may be either of a type in which a gene encoding an antibody heavy chain and a gene encoding an antibody light chain exists on separate vectors or of a type in which both genes exist on the same vector (tandem type). In respect of easiness of construction of a humanised antibody expression vector, easiness of introduction into animal cells, and balance between the expression levels of antibody H and L chains in animal cells, the humanised antibody expression vector is of the tandem type Shitara K et al. J Immunol Methods. 1994 Jan. 3; 167(1-2):271-8). Examples of tandem type humanised antibody expression vector include pKANTEX93 (WO 97/10354), pEE18 and the like.

The present invention also relates to a method of producing a recombinant host cell expressing an antibody according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody.

Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or immunoglobulin chains, by standard techniques for production of polypeptides. For instance, they can be synthesized using well-known solid phase method using a commercially available peptide synthesis apparatus (such as that made by Applied Biosystems, Foster City, California) and following the manufacturer's instructions. Alternatively, antibodies and immunoglobulin chains of the invention can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

The invention further relates to a method of producing an antibody of the invention, which method comprises the steps consisting of: (i) culturing a transformed host cell according to the invention; (ii) expressing said antibody or polypeptide; and (iii) recovering the expressed antibody or polypeptide.

Antibodies of the invention are suitably separated from the culture medium by conventional immunoglobulin purification procedures such as, for example, protein A-SEPHAROSE®, hydroxylapatite chromatography, gel electrophoresis, dialysis, or affinity chromatography.

In an r embodiment, a humanised chimeric antibody of the present invention can be produced by obtaining nucleic sequences encoding humanised VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin heavy chains, but those of IgG class are suitable and any one of subclasses belonging to IgG class, such as IgG1, IgG2, IgG3 and IgG4, can also be used. Also, as the CL of a human chimeric antibody, it may be any region which belongs to human immunoglobulin light chains, and those of kappa class or lambda class can be used.

Methods for producing humanised or chimeric antibodies involve conventional recombinant DNA and gene transfection techniques are well known in the art (See Morrison S L. et al. (1984) and patent documents U.S. Pat. Nos. 5,202,238; and 5,204,244).

Methods for producing humanised antibodies based on conventional recombinant DNA and gene transfection techniques are well known in the art (See, e. g., Riechmann L. et al. 1988; Neuberger M S. et al. 1985). Antibodies can be humanised using a variety of techniques known in the art including, for example, the technique disclosed in the application WO2009/032661, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with CEACAM5 with a protease, such as papaine. Also, the Fab can be produced by inserting DNA sequences encoding both chains of the Fab of the antibody into a vector for prokaryotic expression, or for eukaryotic expression, and introducing the vector into procaryotic or eukaryotic cells (as appropriate) to express the Fab.

The F(ab')2 of the present invention can be obtained treating an antibody which specifically reacts with CEACAM5 with a protease, pepsin. Also, the F(ab')2 can be produced by binding Fab' described below via a thioether bond or a disulfide bond.

The Fab' of the present invention can be obtained treating F(ab')2 which specifically reacts with CEACAM5 with a reducing agent, such as dithiothreitol. Also, the Fab' can be produced by inserting DNA sequences encoding Fab' chains of the antibody into a vector for prokaryotic expression, or a vector for eukaryotic expression, and introducing the vector into prokaryotic or eukaryotic cells (as appropriate) to perform its expression.

The scFv of the present invention can be produced by taking sequences of the CDRs or VH and VL domains as previously described, constructing a DNA encoding an scFv fragment, inserting the DNA into a prokaryotic or eukaryotic expression vector, and then introducing the expression vector into prokaryotic or eukaryotic cells (as appropriate) to express the scFv. To generate a humanised scFv fragment, a well known technology called CDR grafting may be used, which involves selecting the complementary determining regions (CDRs) according to the invention, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Modification of the Antibodies of the Invention

Amino acid sequence modification(s) of the antibodies described herein are contemplated. For example, it may be desirable to improve the binding affinity and/or other biological properties of the antibody. It is known that when a humanised antibody is produced by simply grafting only CDRs in VH and VL of an antibody derived from a non-human animal in FRs of the VH and VL of a human antibody, the antigen binding activity may be reduced in comparison with that of the original antibody derived from a non-human animal. It is considered that several amino acid residues of the VH and VL of the non-human antibody, not only in CDRs but also in FRs, may be directly or indirectly associated with the antigen binding activity. Hence, substitution of these amino acid residues with different amino acid residues derived from FRs of the VH and VL of the human antibody would reduce the binding activity. In order to solve the problem, in human antibodies grafted with non-human CDRs, attempts have to be made to identify, among amino acid sequences of the FR of the VH and VL of human antibodies, an amino acid residue which is directly associated with binding of the antibody, or which interacts with an amino acid residue of a CDR, or which maintains the three-dimensional structure of the antibody and which is directly associated with binding to the antigen. The reduced antigen binding activity could be increased by replacing the identified amino acids with amino acid residues of the original antibody derived from a non-human animal.

In one embodiment of the present invention, the six CDRs of a murine antibody of the invention and three amino acids from its framework were grafted onto a human framework, resulting in a humanized antibody (MAb2_VLg5VHg2) having a heavy chain of sequence SEQ ID NO:74 and a light chain of sequence SEQ ID NO:75, which maintained the binding characteristics to human and cynomolgus CEACAM5.

Modifications and changes may be made in the structure of the antibodies of the present invention, and in the DNA sequences encoding them, and still result in a functional antibody or polypeptide with desirable characteristics.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate-3.5); asparagine (−3.5); lysine (−3.9); and arginine (−4.5).

A further object of the present invention also encompasses function-conservative variants of the polypeptides of the present invention.

For example, certain amino acids may be substituted by other amino acids in a protein structure without appreciable loss of activity. Since the interactive capacity and nature of a protein define its biological functional activity, certain amino acid substitutions can be made in a protein sequence, and of course in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody or polypeptide of the invention, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody or polypeptide of the invention.

This was illustrated in the current invention by an alanine-scanning approach made on the CDRs of MAb2$_{K52R}$, showing that several positions of these CDRs appear as neutral, since an alanine could indeed be substituted without significant effect on the binding to human and cynomolgus CEACAM5. Antibody variants resulting from such neutral substitutions are therefore expected to remain functionally identical to the parental antibody. In the provided example 6.4, substitutions were done in a humanized variant of MAb2, but it is predictable that the same variations would also maintain the biological function when introduced into any variant of MAb2, Mab4 or Mab5, since these related antibodies all carry the same set of 6 CDRs or very closely related ones. The neutral positions can be defined as residues 27, 28, 29, 31, 51, 52, 89, 90, 93, 94, 96, 97 in VL sequences of this antibody family (SEQ ID NO:34 or SEQ ID NO:38 or SEQ ID NO:40 or SEQ ID NO:17 or SEQ ID NO:23 or SEQ ID NO:29 or SEQ ID NO:55 or SEQ ID NO:75) and residues 26 to 31, 51 to 58, 97, 103, 104, 107, 109 in VH sequences of this antibody family (SEQ ID NO:33 or SEQ ID NO:37 or SEQ ID NO:39 or SEQ ID NO:5 or SEQ ID NO:51 or SEQ ID NO:74).

Neutral positions can be seen as positions where any amino acid substitution could be incorporated to Mab2, Mab4 or Mab5 CDRs. Indeed, in the principle of alanine-scanning, alanine is chosen since it this residue does not carry specific structural or chemical features. It is generally admitted that if an anlanine can be substituted for a specific amino acid without changing the properties of a protein, many other, if not all amino acid substitutions are likely to be also neutral. In the opposite case where alanine is the wild-type amino acid, if a specific substitution can be shown as neutral, it is likely that other substitutions would also be neutral.

In the provided example 6.4, four positions in the CDRs of Mab2, Mab4 or Mab5 are also identified, that were not found neutral in the context of the alanine-scanning, but where a conservative type of amino acid substitutions has a neutral effect (residues 30 and 92 in VL sequences and residues 98 and 100 in VH sequences of this antibody family)

It is also expected that two or more neutral mutations at different positions in any or in both of the two antibody chain sequences, when combined, would usually result in an antibody which essentially keeps the functional activities of the parental antibody. This has been illustrated for instance with the combined subsitutions LC_T51A and LC_T94A_VL_S31A and VH_G54Y, or VL_T531 and VH_S53A in MAb2_VLg5VHg2.

As outlined above, amino acid substitutions are generally therefore based on the relative similarity of the amino acid side-chain substituents, for example, their hydrophobicity, hydrophilicity, charge, size, and the like. Exemplary substitutions which take any of the foregoing characteristics into consideration are well known to those of skill in the art and include: arginine and lysine; glutamate and aspartate; serine and threonine; glutamine and asparagine; and valine, leucine and isoleucine.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992).

Another type of amino acid modification of the antibody of the invention may be useful for altering the original glycosylation pattern of the antibody, i.e. by deleting one or more carbohydrate moieties found in the antibody, and/or adding one or more glycosylation sites that are not present in the antibody. The presence of either of the tripeptide sequences asparagine-X-serine, and asparagine-X-threonine, where X is any amino acid except proline, creates a potential glycosylation site. Addition or deletion of glycosylation sites to the antibody is conveniently accomplished by altering the amino acid sequence such that it contains one or more of the above-described tripeptide sequences (for N-linked glycosylation sites).

Another type of modification involves the removal of sequences identified, either in silico or experimentally, as potentially resulting in degradation products or heterogeneity of antibody preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an antibody or polypeptuide of the invention, it may therefore be desirable to remove the site, typically by conservative substitution to remove one of the implicated residues. Such substitutions in a sequence to remove one or more of the implicated residues are also intended to be encompassed by the present invention.

Another type of covalent modification involves chemically or enzymatically coupling glycosides to the antibody. These procedures are advantageous in that they do not require production of the antibody in a host cell that has glycosylation capabilities for N- or 0-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Immunoconjugates

The present invention also includes cytotoxic conjugates, or immunoconjugates, or antibody-drug conjugates, or conjugates. As used herein, all these terms have the same meaning and are interchangeable.

The murine antibodies, MAb1, MAb2, MAb3, MAb4, and MAb5, have been conjugated to a maytansinoid (DM4) through a SPDB linker (N-succinimidyl pyridyldithiobutyrate). The resulting antibody-drug-conjugates (ADC) were found to have cytotoxic activity on MKN45 human gastric cancer cells, with $IC_{50}$ values s 1 nM.

Similarly, antibody-SPDB-DM4 conjugates were prepared based on a chimeric form of each of MAb1, MAb2, MAb4, and MAb5. The resulting chMAb1-SPDB-DM4, chMAb2-SPDB-DM4, chMAb3-SPDB-DM4, and chMAb4-SPDB-DM4 were evaluated at two doses against measurable primary colon CR-IGR-034P tumors implanted s.c. in female SCID mice. Analysis of changes in tumor volume for each treated and control and % of tumor regression indicated that chMAb2-SPDB-DM4, chMAb4-SPDB-DM4, and chMAb5-SPDB-DM4 were highly active, at least at the highest dose assayed, and that chMAb2-SPDB-DM4 was active at both assayed doses. Percentages of tumor regression up to 82% were notably obtained.

Antibody-SPDB-DM4 conjugates were also prepared using the humanised variants of MAb2 (huMAb2-1-SPDB-DM4, huMAb2-2-SPDB-DM4, and huMAb2-3-SPDB-DM4). ADC including the chimeric (chMAb2-SPDB-DM4) or humanised variants of MAb2 were compared with an irrelevant antibody-SPDB-DM4 for cytotoxic activity on MKN45 cells. All chimeric and humanised variants of MAb2 ADCs displayed $IC_{50}$ values s 1 nM, i.e. $IC_{50}$ values 53 to 35 fold lower than the measured cytotoxic activity of the irrelevant DM4 conjugate, thereby indicating CEACAM5-mediated cytotoxic activities of the anti-CEACAM5 conjugates.

Anti-tumor activity of huMAb2-3-SPDB-DM4 and huMAb2-4-SPDB-DM4 was evaluated and compared to the chMAb2-SPDB-DM4 against measurable primary colon CR-IGR-034P tumors implanted s.c. in female CD-1 nude mice. All conjugates were highly active at the highest dose assayed (10 mg/kg).

Anti-tumor activity of huMAb2-3-SPDB-DM4 and huMAb2-3-sulfo-SPDB-DM4 was further evaluated against measurable primary colon CR-IGR-034P tumors implanted s.c. in female SCID mice. huMAb2-3-SPDB-DM4 was active at 5 and 2.5 mg/kg, huMAb2-3-sulfo-SPDB-DM4 was highly active at 5 mg/kg and active at 2.5 mg/kg.

Anti-tumor activity of huMAb2-3-SPDB-DM4 was further evaluated against measurable primary lung LUN-NIC-0014 tumors implanted s.c. in female SCID mice and was found to be was highly active at 10 and 5 mg/kg.

Each DM4 conjugate included a mean number of DM4 molecules (or “drug-to-antibody ratio” or “DAR”) ranging from 2 to 5.

Accordingly, the invention relates to “immunoconjugates” comprising an antibody of the invention linked or conjugated to at least one growth inhibitory agent, such as a cytotoxic agent or or a radioactive isotope.

A “growth inhibitory agent”, or “anti-proliferative agent”, which can be used indifferently, refers to a compound or composition which inhibits growth of a cell, especially tumour cell, either in vitro or in vivo.

The term “cytotoxic agent” as used herein refers to a substance that inhibits or prevents the function of cells and/or causes destruction of cells. The term “cytotoxic agent" is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anticancer agents disclosed below. In some embodiments, the cytotoxic agent is a taxoid, vincas, a maytansinoid or maytansinoid analog such as DM1 or DM4, a small drug, a tomaymycin or pyrrolobenzodiazepine derivative, a cryptophycin derivative, a leptomycin derivative, an auristatin or dolastatin analog, a prodrug, topoisomerase II inhibitors, a DNA alkylating agent, an anti-tubulin agent, a CC-1065 or CC-1065 analog.

As used herein "maytansinoids" denotes maytansinoids and maytansinoid analogs. Maytansinoids are drugs that inhibit microtubule formation and that are highly toxic to mammalian cells.

Examples of suitable maytansinoids include maytansinol and maytansinol analogs.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from Trewia nudiflora);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

In an embodiment of the invention, the cytotoxic conjugates of the present invention utilize the thiol-containing maytansinoid (DM1), formally termed $F^{2'}$-deacetyl-$F^{2'}$-(3-mercapto-1-oxopropyl)-maytansine, as the cytotoxic agent. DM1 is represented by the following structural formula (I):

(I)

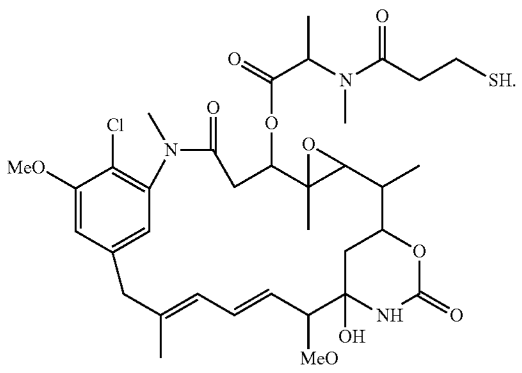

In another embodiment, the cytotoxic conjugates of the present invention utilize the thiol-containing maytansinoid DM4, formally termed $N^{2'}$-deacetyl-N-$^{2'}$(4-methyl-4-mercapto-1-oxopentyl)-maytansine, as the cytotoxic agent. DM4 is represented by the following structural formula (II):

(II)

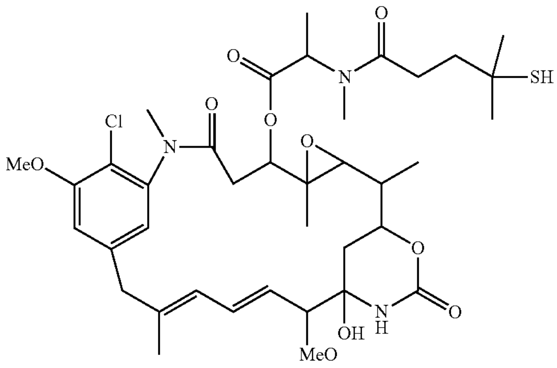

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 reagents and any aggregate which may be present in the solution.

Examples of these cytotoxic agents and of methods of conjugation are further given in the application WO2008/010101 which is incorporated by reference.

The term "radioactive isotope" is intended to include radioactive isotopes suitable for treating cancer, such as $At^{211}$, $Bi^{212}$, $Er^{169}$, $I^{131}$, $I^{125}$, $Y^{90}$, $In^{111}$, $P^{32}$, $Re^{186}$, $Re^{188}$, $Sm^{153}$, $Sr^{89}$, and radioactive isotopes of Lu. Such radioisotopes generally emit mainly beta-radiation. In an embodiment the radioactive isotope is alpha-emitter isotope, more precisely Thorium 227 which emits alpha-radiation. The immunoconjugates according to the present invention can be prepared as described in the application WO2004/091668.

In some embodiments, the antibodies of the present invention are covalently attached, directly or via a cleavable or non-cleavable linker, to at least one growth inhibitory agent.

"Linker", as used herein, means a chemical moiety comprising a covalent bond or a chain of atoms that covalently attaches a polypeptide to a drug moiety.

The conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Conjugation of an antibody of the invention with cytotoxic agents or growth inhibitory agents may be made using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

The linker may be a "cleavable linker" facilitating release of the cytotoxic agent or growth inhibitory agent in the cell. For example, an acid-labile linker, a peptidase-sensitive linker, an esterase labile linker, a photolabile linker or a disulfide-containing linker (See e.g. U.S. Pat. No. 5,208, 020) may be used. The linker may be also a "non-cleavable linker" (for example SMCC linker) that might led to better tolerance in some cases.

Alternatively, a fusion protein comprising the antibody of the invention and a cytotoxic or growth inhibitory polypeptide may be made, by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention may also be used in Dependent Enzyme Mediated Prodrug Therapy by conjugating the polypeptide to a prodrug-activating enzyme which converts a prodrug (e.g. a peptidyl chemotherapeutic agent, see WO81/01145) to an active anti-cancer drug (See, for example, WO 88/07378 and U.S. Pat. No. 4,975,278). The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anticancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. The enzymes can be covalently bound to the polypeptides of the invention by techniques well known in the art such as the use of the heterobifunctional crosslinking reagents discussed above.

According to an embodiment, in the conjugate of the invention, the growth inhibitory agent is a maytansinoid, in an embodiment DM1 or DM4.

In said conjugate, the antibody is conjugated to said at least one growth inhibitory agent by a linking group. In an embodiment said linking group is a cleavable or a non-cleavable linker, such as SPDB, sulfo-SPDB, or SMCC.

The conjugate may be selected from the group consisting of:

i) an antibody-SPDB-DM4 conjugate of formula (III)

(III)

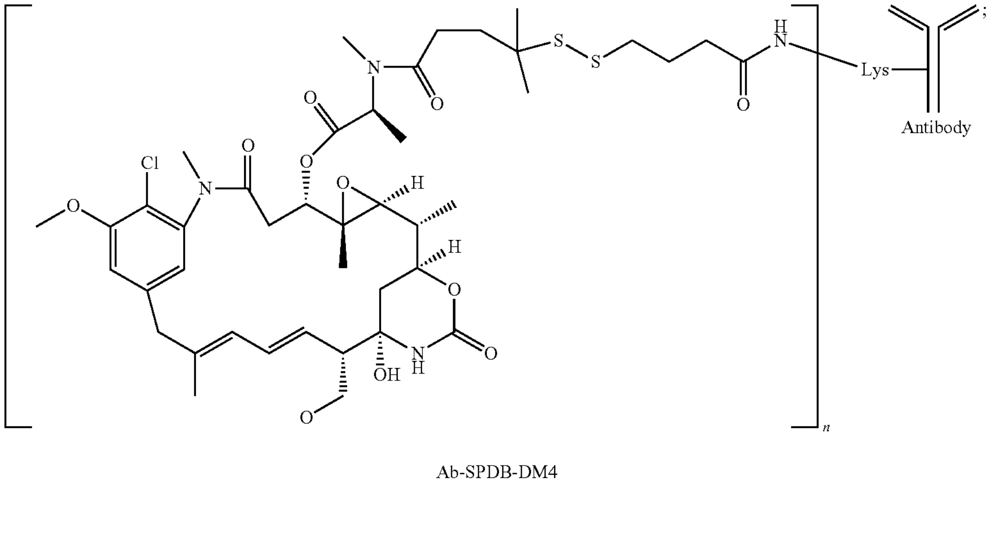

Ab-SPDB-DM4 ii) an antibody-sulfo-SPDB-DM4 conjugate of formula (IV)

(IV)

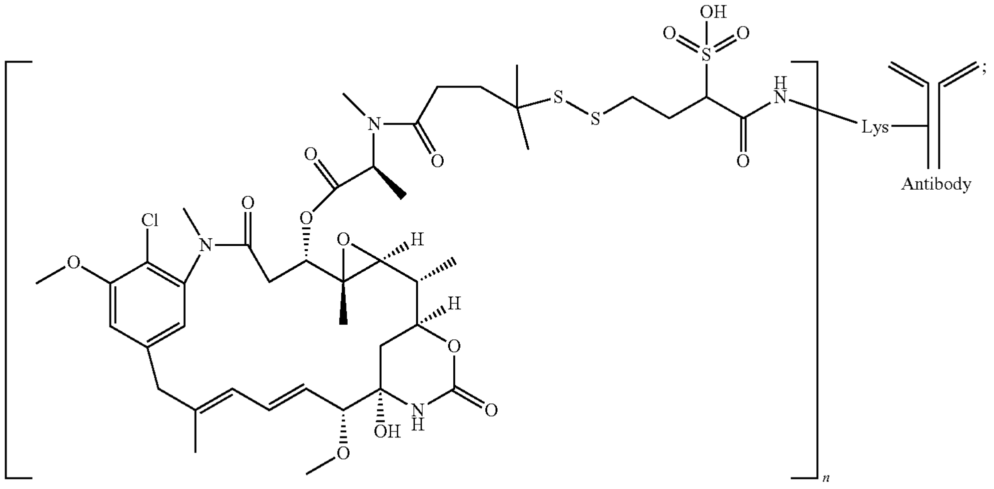

Ab-SulfoSPDB-DM4 and iii) an antibody-SMCC-DM1 conjugate of formula (V)

(V)

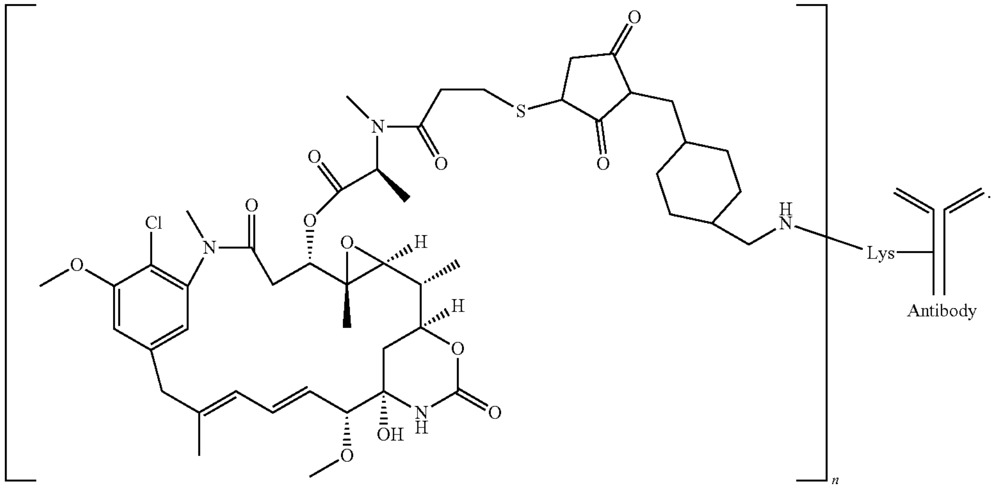

Ab-SMCC-DM1

In said embodiment, the antibody included in the conjugate is selected from the group consisting of:

i) a humanised antibody comprising a heavy chain of sequence SEQ ID NO:51 and a light chain of sequence SEQ ID NO:17, ii) a humanised antibody comprising a heavy chain of sequence SEQ ID NO:5 and a light chain of sequence SEQ ID NO:23, iii) a humanised antibody comprising heavy chain of sequence SEQ ID NO:5 and a light chain of sequence SEQ ID NO:29, and iv) a humanised antibody comprising heavy chain of sequence SEQ ID NO:51 and a light chain of sequence SEQ ID NO:55.

In an embodiment the conjugate is a conjugate of formula (III), (IV) or (V) as defined above, in which the antibody is a humanised antibody comprising heavy chain of sequence SEQ ID NO:5 and a light chain of sequence SEQ ID NO:29.

In general, the conjugate can be obtained by a process comprising the steps of:

(i) bringing into contact an optionally-buffered aqueous solution of a cell-binding agent (e.g. an antibody according to the invention) with solutions of a linker and a cytotoxic compound;

(ii) then optionally separating the conjugate which was formed in (i) from the unreacted cell-binding agent.

The aqueous solution of cell-binding agent can be buffered with buffers such as, e.g. potassium phosphate, acetate, citrate or N-2-Hydroxyethylpiperazine-N'-2-ethanesulfonic acid (Hepes buffer). The buffer depends upon the nature of the cell-binding agent. The cytotoxic compound is in solution in an organic polar solvent, e.g. dimethyl sulfoxide (DMSO) or dimethylacetamide (DMA).

The reaction temperature is usually comprised between 2° and 40° C. The reaction time can vary from 1 to 24 hours. The reaction between the cell-binding agent and the cytotoxic agent can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (ii): the conjugate can be purified e.g. by SEC, adsorption chromatography (such as ion exchange chromatography, IEC), hydrophobic interaction chromatograhy (HIC), affinity chromatography, mixed-support chromatography such as hydroxyapatite chromatography, or high performance liquid chromatography (HPLC). Purification by dialysis or diafiltration can also be used.

As used herein, the term "aggregates" means the associations which can be formed between two or more cell-binding agents, said agents being modified or not by conjugation. The aggregates can be formed under the influence of a great number of parameters, such as a high concentration of cell-binding agent in the solution, the pH of the solution, high shearing forces, the number of bonded dimers and their hydrophobic character, the temperature (see Wang & Gosh, 2008, J. Membrane Sci., 318: 311-316, and references cited therein); note that the relative influence of some of these parameters is not clearly established. In the case of proteins and antibodies, the person skilled in the art will refer to Cromwell et al. (2006, AAPS Journal, 8(3): E572-E579). The content in aggregates can be determined with techniques well known to the skilled person, such as SEC (see Walter et al., 1993, Anal. Biochem., 212(2): 469-480).

After step (i) or (ii), the conjugate-containing solution can be submitted to an additional step (iii) of chromatography, ultrafiltration and/or diafiltration.

The conjugate is recovered at the end of these steps in an aqueous solution.

According to an embodiment, the conjugate according to the invention is characterised by a "drug-to-antibody ratio" (or "DAR") ranging from 1 to 10, for instance from 2 to 5, in particular from 3 to 4. This is generally the case of conjugates including maytansinoid molecules.

This DAR number can vary with the nature of the antibody and of the drug (i.e. the growth-inhibitory agent) used along with the experimental conditions used for the conjugation (like the ratio growth-inhibitory agent/antibody, the reaction time, the nature of the solvent and of the cosolvent if any). Thus the contact between the antibody and the growth-inhibitory agent leads to a mixture comprising several conjugates differing from one another by different drug-to-antibody ratios; optionally the naked antibody; optionally aggregates. The DAR that is determined is thus a mean value.

A method which can be used to determine the DAR consists in measuring spectrophotometrically the ratio of the absorbance at of a solution of substantially purified conjugate at $\lambda_D$ and 280 nm. 280 nm is a wavelength generally used for measuring protein concentration, such as antibody concentration. The wavelength $\lambda_D$ is selected so as to allow discriminating the drug from the antibody, i.e. as readily known to the skilled person, $\lambda_D$ is a wavelength at which the drug has a high absorbance and $\lambda_D$ is sufficiently remote from 280 nm to avoid substantial overlap in the absorbance peaks of the drug and antibody. $\lambda_D$ may be selected as being 252 nm in the case of maytansinoid molecules. A method of DAR calculation may be derived from Antony S. Dimitrov (ed), LLC, 2009, Therapeutic Antibodies and Protocols, vol 525, 445, Springer Science:

The absorbances for the conjugate at $\lambda_D$ ($A_{\lambda D}$) and at 280 nm ($A_{280}$) are measured either on the monomeric peak of the size exclusion chromatography (SEC) analysis (allowing to calculate the "DAR(SEC)" parameter) or using a classic spectrophotometer apparatus (allowing to calculate the "DAR(UV)" parameter). The absorbances can be expressed as follows:

$$A_{\lambda D}=(c_D\times\varepsilon_{D\lambda D})+(c_A\times\varepsilon_{A\lambda D})$$

$$A_{280}=(c_D\times\varepsilon_{D280}d)+(c_A\times\varepsilon_{A280})$$

wherein:

$c_D$ and $c_A$ are respectively the concentrations in the solution of the drug and of the antibody $\varepsilon_{D\lambda D}$ and $\varepsilon_{D280}$ are respectively the molar extinction coefficients of the drug at $\lambda_D$ and 280 nm $\varepsilon_{A\lambda D}$ and $\varepsilon_{A280}$ are respectively the molar extinction coefficients of the antibody at $\lambda_D$ and 280 nm.

Resolution of these two equations with two unknowns leads to the following equations:

$$c_D=[(\varepsilon_{A280}\times A_{\lambda D})-(\varepsilon_{A\lambda D}\times A_{280})]/[(\varepsilon_{D\lambda D}\times\varepsilon_{A280})-(\varepsilon_{A\lambda D}\times\varepsilon_{D280})]$$

$$c_A=[A_{280}-(c_D\times\varepsilon_{D280})]/\varepsilon_{A280}$$

The average DAR is then calculated from the ratio of the drug concentration to that of the antibody: DAR=$c_D/c_A$.

Pharmaceutical Compositions

The antibodies or immunoconjugates of the invention may be combined with pharmaceutically acceptable excipients, and optionally sustained-release matrices, such as biodegradable polymers, to form therapeutic compositions.

Thus, another object of the invention relates to a pharmaceutical composition comprising an antibody or an immunoconjugate of the invention and a pharmaceutically acceptable carrier or excipient.

The invention also relates to a polypeptide or an immunoconjugate according to the invention, for use as a medicament.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, amino acids, saline, phosphate buffered saline, buffer phosphate, acetate, citrate, succinate; amino acids and derivates such as histidine, arginine, glycine, proline, glycylglycine; inorganic salts NaCl, calcium chloride; sugars or polyalcohols such as dextrose, glycerol, ethanol, sucrose, trehalose, mannitol; surfactants such as Polysorbate 80, polysorbate 20, poloxamer 188; and the like, as well as combination thereof. In many cases, it will be preferable to include isotonic agents, such as sugars, polyalcohols, or sodium chloride in the composition, and formulation may also contain an antioxidant such as tryptamine and a stabilizing agent such as TWEEN® 20.

The form of the pharmaceutical compositions, the route of administration, the dosage and the regimen naturally depend upon the condition to be treated, the severity of the illness, the age, weight, and gender of the patient, etc.

The pharmaceutical compositions of the invention can be formulated for a topical, oral, parenteral, intranasal, intravenous, intramuscular, subcutaneous or intraocular administration and the like.

In an embodiment, the pharmaceutical compositions contain vehicles which are pharmaceutically acceptable for a formulation capable of being injected. These may be isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical composition can be administrated through drug combination devices.

The doses used for the administration can be adapted as a function of various parameters, and for instance as a function of the mode of administration used, of the relevant pathology, or alternatively of the desired duration of treatment.

To prepare pharmaceutical compositions, an effective amount of the antibody or immunoconjugate of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and injectable with the appropriate device or system for delivery without degradation. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

A polypeptide, antibody or immunoconjugate of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, glycine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with any of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more concentrated, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibody or immunoconjugate of the invention may be formulated within a therapeutic mixture to comprise about 0.01 to 100 milligrams, per dose or so.

In addition to the antibody or immunoconjugate formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of polypeptides into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles, or biodegradable polylactide or polylactide co glycolide nanoparticules that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Therapeutic Methods and Uses

The inventors have shown that the five antibodies they have produced are able to internalize the CEACAM5-antibody complex after binding. Furthermore, they have shown that these antibodies, combined with a cytotoxic maytansinoid (DM4), induce cytotoxic activity on human MKN45 tumor cells in vitro. They have also shown that these immunoconjugates induce a marked anti-tumor activity in vivo in a murine model of human primary colon tumor xenografts derived from patient, when used at a dose of 5 mg/kg and 2.5 mg/kg, with a single injection at day 14 post tumor implantation.

Thus, polypeptides, antibodies, immunoconjugates, or pharmaceutical compositions of the invention may be useful for treating cancer.

The cancer to be treated with antibodies, immunoconjugates, or pharmaceutical compositions of the invention is a cancer expressing CEACAM5, in particular overexpressing CEACAM5 as compared to normal (i.e. non tumoral) cells of the same tissular origin. Expression of CEACAM5 by cancer cells may be readily assayed for instance by using an antibody according to the invention, as described in the following section "Diagnostic uses", and in particular by an immunohistochemical method for instance as described in Example 8.

In an embodiment, the cancer may be a colorectal, stomach, lung, uterus cervix, pancreas, oesophagus, ovary, thyroid, bladder, endometrium, breast, liver (for instance cholangiocarcinoma), prostate, or skin cancer. Screening of a panel of human tumors by immunohistochemistry using a mouse anti-human CEACAM5 antibody according to the invention indeed showed antibody staining in these types of cancers, as described in further details in Example 8.

The antibodies or immunoconjugates of the invention may be used alone or in combination with any suitable growth-inhibitory agent.

The antibodies of the invention may be conjugated or linked to a growth inhibitory agent, cytotoxic agent, or a prodrug-activating enzyme as previously described. Antibodies of the invention may be indeed useful for targeting said growth inhibitory agent, cytotoxic agent, or a prodrug to the cancerous cells expressing or over-expressing CEACAM5 on their surface.

It is also well known that therapeutic monoclonal antibodies can lead to the depletion of cells bearing the antigen specifically recognized by the antibody. This depletion can be mediated through at least three mechanisms: antibody mediated cellular cytotoxicity (ADCC), complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed.

Thus, an object of the invention relates to a method for treating a cancer comprising administering a subject in need thereof with a therapeutically effective amount of a polypeptide, an antibody, an immunoconjugate or a pharmaceutical composition of the invention.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth of malignant cells of a tumour and/or the progression of metastases from said tumor. Such treatment can also lead to the regression of tumor growth, i.e., the decrease in size of a measurable tumor. In particular, such treatment leads to the complete regression of the tumor or metastase.

According to the invention, the term "patient" or "patient in need thereof" is intended for a human or non-human mammal affected or likely to be affected with a malignant tumor. In particular, said patient may be a patient who has been determined to be susceptible to a therapeutic agent targeting CEACAM5, in particular to an antibody or immunoconjugate according to the invention, for instance according to a method as described herebelow.

By a "therapeutically effective amount" of the polypeptide of the invention is meant a sufficient amount of the polypeptide to treat said cancer disease, at a reasonable benefit/risk ratio applicable to any medical treatment. It will be understood, however, that the total daily usage of the polypeptides and compositions of the present invention will be decided by the attending physician within the scope of sound medical judgment. The specific therapeutically effective dose level for any particular patient will depend upon a variety of factors including the disorder being treated and the severity of the disorder; activity of the specific polypeptide employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

Another object of the invention relates to a polypeptide, an antibody, an immunoconjugate or a pharmaceutical composition of the invention for use in the treatment of a malignant tumour.

The polypeptide, antibody, immunoconjugate or pharmaceutical composition may be used for inhibiting the progression of metastases of a malignant tumour.

Polypeptides of the invention may be used in combination with any other therapeutical strategy for treating malignant tumour (e.g. adjuvant therapy), and/or for reducing the growth of the metastatic tumour.

Efficacy of the treatment with an antibody or immunoconjugate according to the invention may be readily assayed in vivo, for instance on a mouse model of cancer and by measuring e.g. changes in tumor volume between treated and control groups, % tumor regression, partial regression and/or complete regression as defined in Example 5.3.

Diagnostic Uses

CEACAM5 has been reported to be highly expressed on the surface of colorectal, gastric, lung, uterine tumor cells and weakly expressed in few normal epithelial cells such as colon and esophagus epithelial cells. Additionally, screening of a panel of human tumors by immunohistochemistry using a mouse anti-human CEACAM5 antibody according to the invention showed antibody staining in colorectal, stomach, lung, uterus cervix, pancreas, oesophagus, ovary, thyroid, bladder, endometrium, breast, liver (in particular cholangiocarcinoma), prostate, and skin cancers.

Therefore, CEACAM5 constitutes a cancer marker and, therefore, has the potential to be used to indicate the effectiveness of an anti-cancer therapy or detecting recurrence of the disease.

In an embodiment, the antibody of the invention is used as component of an assay in the context of a therapy targeting CEACAM5 expressing tumours, in order to determine susceptibility of the patient to the therapeutic agent, monitor the effectiveness of the anti-cancer therapy or detect recurrence of the disease after treatment. In particular, the same antibody of the invention is used both as component of the therapeutic agent and as component of the diagnostic assay.

Thus, a further object of the invention relates to an antibody according to the invention for use for in vivo detecting CEACAM5 expression in a subject, or for use for ex vivo detecting CEACAM5 expression in biological sample of a subject. Said detection may be intended in particular for a) diagnosing the presence of a cancer in a subject, or
b) determining susceptibility of a patient having cancer to a therapeutic agent targeting CEACAM5, in particular an immunoconjugate according to the invention, or
c) monitoring effectiveness of anti-CEACAM5 cancer therapy or detecting cancer relapse after anti-CEACAM5 cancer therapy, in particular for therapy with an immunoconjugate according to the invention;

by detecting expression of the surface protein CEACAM5 on tumor cells.

In an embodiment, the antibody is intended for an in vitro or ex vivo use. For example, CEACAM5 may be detected in vitro or ex vivo in a biological sample obtained from a subject, using an antibody of the invention. The use according to the invention may also be an in vivo use. For example, an antibody according to the invention is administered to the subject and antibody-cells complexes are detected and/or quantified, whereby the detection of said complexes is indicative of a cancer.

The invention further relates to an in vitro or ex vivo method of detecting the presence of a cancer in a subject, comprising the steps consisting of:

(a) contacting a biological sample of a subject with an antibody according to the invention, in particular in conditions sufficient for the antibody to form complexes with said biological sample;
(b) measuring the level of antibody bound to said biological sample,
(c) detecting the presence of a cancer by comparing the measured level of bound antibody with a control, an increased level of bound antibody compared to control being indicative of a cancer.

The invention also relates to an in vitro or ex vivo method of determining susceptibility of a patient having cancer to a therapeutic agent targeting CEACAM5, in particular to an immunoconjugate according to the invention, which method comprises the steps consisting of:

(a) contacting a biological sample of a patient having cancer with an antibody according to the invention, in particular in conditions sufficient for the antibody to form complexes with said biological sample;
(b) measuring the level of antibody bound to said biological sample sample,
(c) comparing the measured level of bound antibody to said biological sample sample with the level of antibody bound to a control;

wherein an increased level of bound antibody to said biological sample sample compared to control is indicative of a patient susceptible to a therapeutic agent targeting CEACAM5.

In the above methods, said control can be a normal, non cancerous, biological sample of the same type, or a reference value determined as representative of the antibody binding level in normal biological sample of the same type.

In an embodiment, the antibodies of the invention are useful for diagnosing a CEACAM5 expressing cancer, such as a colorectal, stomach, lung, uterus cervix, pancreas, oesophagus, ovary, thyroid, bladder, endometrium, breast, liver (in particular cholangiocarcinoma), prostate, or skin cancer.

The invention further relates to an in vitro or ex vivo method of monitoring effectiveness of anti-CEACAM5 cancer therapy, comprising the steps consisting of:

(a) contacting a biological sample of a subject undergoing anti-CEACAM5 cancer therapy, with an antibody according to the invention, in particular in conditions sufficient for the antibody to form complexes with said biological sample;
(b) measuring the level of antibody bound to said biological sample,
(c) comparing the measured level of bound antibody with the level of antibody bound to a control;

wherein a decreased level of bound antibody to said biological sample compared to control is indicative of effectiveness of said anti-CEACAM5 cancer therapy.

In said method, an increased level of bound antibody to said biological sample compared to control is indicative of ineffectiveness of said anti-CEACAM5 cancer therapy.

In an embodiment said control is a biological sample of the same type as the biological sample submitted to analysis, but which was obtained from the subject previously in time, during the course of the anti-CEACAM5 cancer therapy.

The invention further relates to an in vitro or ex vivo method of detecting cancer relapse after anti-CEACAM5 cancer therapy, comprising the steps consisting of:

(a) contacting a biological sample of a subject having completed anti-CEACAM5 cancer therapy, with an antibody according to the invention, in particular in conditions sufficient for the antibody to form complexes with said biological sample;
(b) measuring the level of antibody bound to said biological sample,
(c) comparing the measured level of bound antibody with the level of antibody bound to a control;
wherein an increased level of bound antibody to said biological sample compared to control is indicative of cancer relapse after anti-CEACAM5 cancer therapy.

Said control is in particular a biological sample of the same type as the biological sample submitted to analysis, but which was obtained from the subject previously in time, upon or after completion of the anti-CEACAM5 cancer therapy.

Said anti-CEACAM5 cancer therapy is in particular a therapy using an antibody or immunoconjugate according to the invention. Said anti-CEACAM5 cancer therapy targets a CEACAM5 expressing cancer, in particular a colorectal, stomach, lung, uterus cervix, pancreas, oesophagus, ovary, thyroid, bladder, endometrium, breast, liver (in particular cholangiocarcinoma), prostate, or skin cancer.

In an embodiment, antibodies of the invention may be labelled with a detectable molecule or substance, such as a fluorescent molecule, a radioactive molecule or any other labels known in the that provide (either directly or indirectly) a signal.

As used herein, the term “labeled”, with regard to the antibody according to the invention, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the polypeptide, as well as indirect labeling of the polypeptide by reactivity with a detectable substance.

An antibody of the invention may be labelled with a radioactive molecule by any method known to the art. For example radioactive molecules include but are not limited radioactive atom for scintigraphic studies such as $I^{123}$, $I^{124}$, $In^{111}$, $Re^{186}$, $Re^{188}$, $Tc^{99}$. Polypeptides of the invention may be also labelled with a spin label for nuclear magnetic resonance (NMR) imaging (also known as magnetic resonance imaging, MRI), such as iodine-123, indium-111, fluorine-19, carbon-13, nitrogen-15, oxygen-17, gadolinium, manganese or iron.

A “biological sample” encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. Therefore, biological samples encompass clinical samples, cells in culture, cell supernatants, cell lysates, serum, plasma, biological fluid, and tissue samples, in particular tumor sample.

In an embodiment, the biological sample may be formalin-fixed and paraffin embedded (FFPE) tissue sample. Indeed, antibodies according to the invention can advantageously be used on FFPE tissues which is the format used by most hospitals to collect and archive tissue samples.

The invention also relates to an in vivo method of detecting the presence of a cancer in a subject, comprising the steps consisting of:

a) administering an antibody according to the invention detectably labelled to a patient;
b) detecting localisation of said detectably labelled antibody in the patient by imaging.

Antibodies of the invention may be useful for staging of cancer (e.g., in radioimaging). They may be used alone or in combination with other cancer markers.

The terms “detection” or “detected” as used herein includes qualitative and/or quantitative detection (measuring levels) with or without reference to a control.

In the content of the invention, the term “diagnosing”, as used herein, means the determination of the nature of a medical condition intended to identify a pathology which affects the subject from a number of collected data.

In said method, the cancer is a CEACAM5 expressing cancer, in particular a colorectal, stomach, lung, uterus cervix, pancreas, oesophagus, ovary, thyroid, bladder, endometrium, breast, liver (in particular cholangiocarcinoma), prostate, or skin cancer.

Kits

Finally, the invention also provides kits comprising at least one antibody or immunoconjugate of the invention. Kits containing antibodies of the invention find use in detecting the surface protein CEACAM5, or in therapeutic or diagnostic assays. Kits of the invention can contain a polypeptide or antibody coupled to a solid support, e.g., a tissue culture plate or beads (e.g., SEPHAROSE® beads). Kits can be provided which contain antibodies for detection and quantification of the surface protein CEACAM5 in vitro, e.g. in an ELISA or a Western blot. Such an antibody useful for detection may be provided with a label such as a fluorescent or radiolabel.

BRIEF DESCRIPTION OF THE SEQUENCES

SEQ ID NO:1-4, and 6 show the sequences of the CDR1-H, CDR2-H, CDR3-H, CDR1-L and CDR3-L of the so-called “MAb1” antibody.

SEQ ID NO:5 shows the VH variant sequence VH1a of humanized MAb2 antibody.

SEQ ID NO:7-10, and 12 show the sequences of the CDR1-H, CDR2-H, CDR3-H, CDR1-L and CDR3-L of the so-called “MAb2” antibody.

SEQ ID NO:11 shows the sequence of human CEACAM1 as available from GENBANK® NP_001703.2.

SEQ ID NO:13-16, and 18 show the sequences of the CDR1-H, CDR2-H, CDR3-H, CDR1-L and CDR3-L of the so-called “MAb3” antibody.

SEQ ID NO:17 shows the VL variant sequence VL1 of humanized MAb2 antibody.

SEQ ID NO:19-22, and 24 show the sequences of the CDR1-H, CDR2-H, CDR3-H, CDR1-L and CDR3-L of the so-called “MAb4” antibody.

SEQ ID NO:23 shows the VL variant sequences VL1a of humanized MAb2 antibody.

SEQ ID NO:25-28, and 30 show the sequences of the CDR1-H, CDR2-H, CDR3-H, CDR1-L and CDR3-L of the so-called “MAb5” antibody.

SEQ ID NO:29 shows the VL variant sequences VL1c of humanized MAb2 antibody.

SEQ ID NO:31 shows the VH sequence of the “MAb1” antibody.

SEQ ID NO:32 shows the VL sequence of the "MAb1" antibody.

SEQ ID NO:33 shows the VH sequence of the "MAb2" antibody.

SEQ ID NO:34 shows the VL sequence of the "MAb2" antibody.

SEQ ID NO:35 shows the VH sequence of the "MAb3" antibody.

SEQ ID NO:36 shows the VL sequence of the "MAb3" antibody.

SEQ ID NO:37 shows the VH sequence of the "MAb4" antibody.

SEQ ID NO:38 shows the VL sequence of the "MAb4" antibody.

SEQ ID NO:39 shows the VH sequence of the "MAb5" antibody.

SEQ ID NO:40 shows the VL sequence of the "MAb5" antibody.

SEQ ID NO:41 shows the heavy chain sequence of chMAb1 antibody.

SEQ ID NO:42 shows the light chain sequence of chMAb1 antibody.

SEQ ID NO:43 shows the heavy chain sequence of chMAb2 antibody.

SEQ ID NO:44 shows the light chain sequence chMAb2 antibody.

SEQ ID NO:45 shows the heavy chain sequence chMAb3 antibody.

SEQ ID NO:46 shows the light chain sequence chMAb3 antibody.

SEQ ID NO:47 shows the heavy chain sequence chMAb4 antibody.

SEQ ID NO:48 shows the light chain sequence of chMAb4 antibody

SEQ ID NO:49 shows the heavy chain sequence of chMAb5 antibody.

SEQ ID NO:50 shows the light chain sequence of chMAb5 antibody.

SEQ ID NO:51 shows the VH variant sequence VH1 of humanized MAb2 antibody.

SEQ ID NO:52 shows the sequence of full-length human CEACAM5 as available from GENBANK® database under accession number AAA51967.1.

SEQ ID NO:53 shows the sequence of the extracellular domain of *Macaca fascicularis* CEACAM5.

SEQ ID NO:54 shows the sequence of the light chain of a chimeric antibody (derived from the "MAb2" antibody) comprising a K52 to R52 mutation.

SEQ ID NO: 55 shows the VL variant sequence VL1d of humanized MAb2 antibody.

SEQ ID NO:56 shows the sequence of hCEACAM1 extracellular domain (positions 35-428 of full length hCEACAM1 (NP_001703.2), followed by a 24 amino acid extension containing a His-Tag).

SEQ ID NO:57 shows the sequence of cCEACAM1 extracellular domain followed by a 24 amino acid extension containing a His-Tag.

SEQ ID NO:58 shows the sequence of hCEACAM5 extracellular domain (positions 35-685 of full length hCEACAM5 (AAA51967.1) followed by a 24 amino acid extension containing a His-Tag).

SEQ ID NO:59 shows the sequence of cCEACAM5 extracellular domain followed by a 24 amino acid extension containing a His-Tag.

SEQ ID NO:60 shows the sequence of hCEACAM6 extracellular domain (positions 35-327 of full length hCEACAM6 (NP_002474.3), followed by a 24 amino acid extension containing a His-Tag).

SEQ ID NO:61 shows the sequence of cCEACAM6 extracellular domain followed by a 24 amino acid extension containing a His-Tag.

SEQ ID NO:62 shows the sequence of hCEACAM8 extracellular domain (positions 35-332 of full length hCEACAM8 (NP_001807.2), followed by a 24 amino acid extension containing a His-Tag.

SEQ ID NO:63 shows the sequence of cCEACAM8 extracellular domain, followed by 24 amino acid extension containing a His-Tag.

SEQ ID NO:64 shows the sequence of hCEACAM7 extracellular domain (positions 36-248 of full length hCEACAM7 (NP_008821.1), followed by 24 amino acid extension containing a His-Tag).

SEQ ID NO:65 shows the sequence of hCEACAM5 N-A1-B1 (positions 35-320 of full length hCEACAM5 (AAA51967.1.)) followed by 6 amino acid His-Tag.

SEQ ID NO:66 shows the sequence of hCEACAM5-A2-B2 (positions 321-498 of full length hCEACAM5 (AAA51967.1.)) followed by 6 amino acid His-Tag.

SEQ ID NO:67 shows the sequence of hCEACAM5 A3-B3 (positions 499-685 of full length hCEACAM5 (AAA51967.1.)) followed by 6 amino acid His-Tag-.

SEQ ID NO:68 shows the sequence of cCEACAM5 N-A1-B1, followed by 24 amino acid extension containing a His-Tag.

SEQ ID NO:69 shows the sequence of cCEACAM5 A2-B2, followed by 24 amino acid extension containing a His-Tag.

SEQ ID NO:70 shows the sequence of cCEACAM5 A3-B3, followed by 24 amino acid extension containing a His-Tag.

SEQ ID NO:71 shows the sequence of human CEACAM6 full-length protein as available from GENBANK® NP_002474.3.

SEQ ID NO:72 shows the sequence of human CEACAM7 full-length protein as available from GENBANK® NP_008821.1.

SEQ ID NO:73 shows the sequence of human CEACAM8 full-length protein as available in GENBANK® NP_001807.2.

SEQ ID NO: 74 shows the VH sequence of the variant humanized MAb2_VLg5VHg2.

SEQ ID NO: 75 shows the VL sequence of the variant humanized MAb2_VLg5VHg2.

SEQ ID NO: 76 shows the sequence of amino acids at positions 109-115 of human CEACAM5 A3-B3.

SEQ ID NO: 77 shows the sequence of amino acids at positions 131-143 of human CEACAM5 A3-B3.

SEQ ID NO: 78 shows a consensus sequence for CDR1-H of MAb2/MAb4/MAb5 antibody family based on sequence comparisons.

SEQ ID NO: 79 shows a consensus sequence for CDR2-H of MAb2/MAb4/MAb5 antibody family based on sequence comparisons.

SEQ ID NO: 80 shows a consensus sequence for CDR3-H of MAb2/MAb4/MAb5 antibody family based on sequence comparisons.

SEQ ID NO: 81 shows a consensus sequence for CDR1-H of MAb1/MAb3 antibody family.

SEQ ID NO: 82 shows a consensus sequence for CDR2-H of MAb1/MAb3 antibody family.

SEQ ID NO:83 shows a consensus sequence for CDR1-H of MAb2/MAb4/MAb5 antibody family based on residues identified as neutral in the binding of human and *Macaca fascicularis* CEACAM5 extracellular domains.

SEQ ID NO:84 shows a consensus sequence for CDR3-H of MAb2/MAb4/MAb5 antibody family based on residues identified as neutral in the binding of human and *Macaca fascicularis* CEACAM5 extracellular domains.

SEQ ID NO:85 shows a consensus sequence for CDR1-L of MAb2/MAb4/MAb5 antibody family based on residues identified as neutral in the binding of human and *Macaca fascicularis* CEACAM5 extracellular domains.

SEQ ID NO:86 shows a consensus sequence for CDR3-L of MAb2/MAb4/MAb5 antibody family based on residues identified as neutral in the binding of human and *Macaca fascicularis* CEACAM5 extracellular domains.

SEQ ID NO:87 shows the heavy chain sequence of huMAb2-3 (MAb2_VL1cVH1a-IgG1).

SEQ ID NO:88 shows the light chain sequence of huMAb2-3 (MAb2_VL1cVH1a-IgG1).

SEQ ID NO:89 shows the heavy chain sequence of huMAb2-4 (MAb2_VL1d VH1-IgG1).

SEQ ID NO:90 shows the light chain sequence of huMAb2-4 (MAb2_VL1d VH1-IgG1).

EXAMPLES

The present invention is further illustrated by the following examples which should not be construed as further limiting.

The contents of the Sequence Listing, figures and all references, *patens* and published patent applications cited throughout this application are expressly incorporated herein by reference in their entirety.

Example 1: Preparation of Recombinant Extracellular Domains of CEACAM Proteins In this example, the extracellular protein domains (ECD) of CEACAM from human (h) or cynomolgus monkey (c) origin have been prepared by transient expression in human embryonic kidney HEK293 cells with plasmids allowing expression of the respective cDNA as outlined on Table 1.

Each expression plasmid was complexed with 293fectin™ (Life Technologies) and added to suspension-cultivated 293-F cells (derived from HEK293 cells). Eight days post-transfection, the culture supernatants were collected and the corresponding soluble protein was purified by IMAC (GE Healthcare) to generate a protein batch (see Table 1).

TABLE 1

Description of the recombinant extracellular domains of CEACAM proteins

| Protein name | Protein desription | cDNA sequence origin | Sequence identifier |
|---|---|---|---|
| hEACAM1 | human CEACAM1 ECD (35-428) | NP_001703.2 | SEQ ID NO: 56 |
| cCEACAM1 | *M. fascicularis* CEACAM1 ECD (35-428) | cloned internally | SEQ ID NO: 57 |
| hCEACAM5 | human CEACAM5 ECD (35-685) | AAA51967.1 | SEQ ID NO: 58 |
| cCEACAM5 | *M. fascicularis* CEACAM5 ECD (35-688) | cloned internally | SEQ ID NO: 59 |

TABLE 1-continued

Description of the recombinant extracellular domains of CEACAM proteins

| Protein name | Protein desription | cDNA sequence origin | Sequence identifier |
|---|---|---|---|
| hCEACAM6 | human CEACAM6 ECD (35-327) | NP_002474.3 | SEQ ID NO: 60 |
| cCEACAM6 | *M. fascicularis* CEACAM6 ECD (35-327) | cloned internally | SEQ ID NO: 61 |
| hCEACAM8 | human CEACAM8 ECD (35-332) | NP_001807.2 | SEQ ID NO: 62 |
| cCEACAM8 | *M. fascicularis* CEACAM8 ECD (35-332) | cloned internally | SEQ ID NO: 63 |
| hCEACAM7 | human CEACAM7 ECD (36-248) | NP_008821.1 | SEQ ID NO: 64 |
| hCEACAM5 NA1B1 | human CEACAM5 N-A1-B1 domain (35-320) | AAA51967.1 | SEQ ID NO: 65 |
| CEACAM5 A2B2 | human CEACAM5 A2-B2 domain (321-498) | AAA51967.1 | SEQ ID NO: 66 |
| CEACAM5 A3B3 | human CEACAM5 A3-B3 domain (499-685) | AAA51967.1 | SEQ ID NO: 67 |
| cCEACAM5 NA1B1 | *M. fascicularis* CEACAM5 N-A1-B1 domain (35-320) | cloned internally | SEQ ID NO: 68 |
| cCEACAM5 A2B2 | *M. fascicularis* CEACAM5 A2-B2 domain (321-498) | cloned internally | SEQ ID NO: 69 |
| cCEACAM5 A3B3 | *M. fascicularis* CEACAM5 A3-B3 domain (499-688) | cloned internally | SEQ ID NO: 70 |

Example 2: Generation of Monoclonal Mouse Anti-CEACAM5 Antibodies

In this example, monoclonal antibodies have been generated following mice immunization according to a protocol that led to the generation of antiCEACAM5 mAb.

Example 2.1: Immunization & Hybridoma Generation

Immunizations, fusion and screening were performed using $P3X_{63}$-Ag8.653 myeloma cells with either the extracellular domain of human CEACAM5, the extracellular domain of cynomolgus CEACAM5 or with human tumoral UMC11 cells as described in Wennerberg A. E et al., 1993. Am. J. Pathol., 143(4), 1050-1054 and Kilpatrick et al. 1997. Hybridoma 16: 381389.

Using the RIMMS method as described by Kilpatrick et al. (1997. Hybridoma 16: 381389), 6-8 weeks old female BALB/c mice (S082342; Charles River Labs, Bar Harbor, ME) each received four rounds of immunization over a course of 14 days at intervals of 3-4 days. Antigens emulsified in TITERMAX®'s adjuvant (TITERMAX® Gold Adjuvant; Sigma #T2684) was administered subcutaneously to six sites proximal to draining lymph nodes, along the back of the mice and to six juxtaposed sites along abdomen. Four days after the last injection, mice were sacrified. Bilateral popliteal, superficial inguinal, axillary and branchial lymph nodes were isolated aseptically and washed with fresh RPMI medium.

Using the classical method as described by Wennerberg A. E et al. (1993. Am. J. Pathol., 143(4), 1050-1054), 6-8 weeks old female BALB/c mice (S082342; Charles River Labs, Bar Harbor, ME) each received three rounds of immunization over a course of 41 days. Antigens were administered intraperitonealy to ventral site of mice. Three days after the last injection, mice were sacrified and spleens were isolated aseptically and washed with fresh RPMI medium.

Lymphocytes were released from the lymph nodes or from the spleens and single-cell suspension was washed twice with RPMI medium before being fused with P3X63-AG8.653 myeloma cells using polyethylene glycol. After fusion, the cell mixture was incubated in an incubator at 37° C. for 16-24 hours. The resulting cells preparation was transferred into selective semi-solid medium and aseptically plated out into 100 mm Petri plates and incubated at 37° C. Ten days after initiation of selection, the plates were examined for hybridoma growth, and visible colonies were picked-up and placed into 96-well plates containing 200 μL of growth medium. The 96-well plates were kept in an incubator at 37° C. for 2 to 4 days.

Example 2.2: Screening and In Vitro Characterization of Murine Anti-CEACAM5 Antibodies Primary screening for anti-CEACAM5 IgG production was performed by Enzyme-linked immunosorbent assay (ELISA) using human CEACAM5 protein (prepared as described in Example 1) as capturing antigen and by FACS using several human tumoral cells (H460, MKN45, SW1463, SKMEL28 and UMC11). For ELISA assay, plates were coated with human CEACAM5 protein at 0.25 μg/well in PBS and 100 μL/well of anti-CEACAM5 antibodies were added to the plate. The plate was incubated at 37° C. for 1 h and washed five times with PBS containing 0.05% TWEEN® 20 (PBS-T). Then, 100 μL of a 1:50,000 dilution of rabbit anti-mouse IgG conjugated with horseradish peroxidase (Sigma; #A9044) was added to each well. Following incubation at 37° C. for 1 h in darkness, plates were washed with PBS-T five times. Antibody binding was visualized by adding TMB-H2O2 buffer and read at a wavelength of 450 nm. For FACS assay, human tumoral cells were coated at 40,000 cells/well on 96-well High Bind plate (MSD L15XB-3) and 100 μL/well of anti-CEACAM5 antibodies were added for 45 min at 4° C. and washed three times with PBS 1% BSA. 100 μL/well of goat anti-mouse IgG conjugated with Alexa647 (Invitrogen; #A2135) was added for 45 min at 4° C. and washed three times with PBS 1% BSA. Antibody binding was evaluated after centrifugation and resuspension of cells by adding 200 μl/well PBS 1% BSA and read using Guava® easyCyte™ 8HT Flow Cytometry System.

For evaluating specificity to CEACAM5 of anti-CEACAM5 antibodies, 96-well plates were coated with recombinant human CEACAM1, CEACAM6, CEACAM7 and CEACAM8 proteins (prepared as described in Example 1) using the same coating conditions described previously. Anti-CEACAM5 antibodies were added to the plates and detected by using rabbit anti-mouse IgG conjugated with horseradish peroxidase (Sigma; #A9044). Antibody binding was visualized by adding TMB-H2O2 buffer and read at a wavelength of 450 nm. The results presented on FIGS. 1A-1E show that the anti-CEACAM5 antibodies are selective for human CEACAM5 v. human CEACAM1, CEACAM6, CEACAM7 and CEACAM8.

Example 2.3: MAb Binding Characterization

The apparent affinity of anti-CEACAM5 antibodies to hCEACAM5 expressed on the surface of human MKN45 (DSMZ, ACC 409) tumoral cells were determined by Guava® easyCyte™ 8HT Flow Cytometry System. MKN45 tumoral cells were coated at 40,000 cells/well on 96-well High Bind plate (MSD L15XB-3) and 100 μL/well of anti-CEACAM5 antibodies were added in 2-fold serial dilutions starting at 20 μg/ml up to 12 dilutions in assay diluant for 45 min at 4° C. and and washed three times with PBS 1% BSA. 100 μL/well of goat anti-mouse IgG conjugated with Alexa647 (Invitrogen; #A2135) was added for 45 min at 4° C. and washed three times with PBS 1% BSA. The antibody binding was evaluated after centrifugation and resuspension of cells by adding 200 μl/well PBS 1% BSA and read using Guava® easyCyte™ 8HT Flow Cytometry System. Apparent KD and EC50 values were estimated using BIOST@T-BINDING and BIOST@T-SPEED softwares, respectively.

TABLE 2

EC50 values obtained on MKN45 cells

| Antibodies | MAb1 | MAb2 | MAb3 | MAb4 | MAb5 |
|---|---|---|---|---|---|
| EC50 values | 16 nM | 3.4 nM | 6.2 nM | 4.9 nM | 0.73 nM |

Domain mapping of anti-CEACAM5 antibodies to human CEACAM5 and cynomolgus CEACAM5 proteins was determined by ELISA. 96-well plates were coated with recombinant human A1 (143-237), A1-B1 (143-320), A2-B2 (321-498) and A3-B3 (499-685) domains of CEACAM5 protein (prepared as described in Example 1) and with recombinant cynomolgus N-A1-B1 (1-320), A1-B1 (143-320), A2-B2 (321-498) and A3-B3 (499-688) domains of CEACAM5 protein (prepared as described in Example 1) using the same coating conditions described previously. Purified antibodies were added to the plates and detected by using rabbit anti-mouse IgG conjugated with horseradish peroxidase (Sigma; #A9044). Antibody binding was visualized by adding TMB-H2O2 buffer and read at a wavelength of 450 nm. The results are presented on FIGS. 2A-2E and FIGS. 3A-3E and show that the anti-CEACAM5 antibodies bind to the A3-B3 domain of human and cynomolgus CEACAM5 proteins.

Isotypes of individual mAbs were determined using a mouse IgG isotyping kit according to the manufacuturer's instructions (SEROTEC ref. MMT1). The five CEACAM5-specific mAbs were of the IgG1, k isotype.

Example 3: Characterization of Murine Anti-CEACAM5 Antibodies

Example 3.1: In Vitro Characterization of Murine Anti-CEACAM5 Antibodies

Mouse hybridoma expressing CEACAM5-specific Abs were produced into T500 flask and conditioned media collected after 7 days of growth. CEACAM5-specific Abs were purified by passing the conditioned media through a Protein-G column, washed and eluted with Glycine/HCl 100 mM pH 2.7 buffer. The eluate was dialyzed against PBS before sterile filtration and stored at 4° C.

All CEACAM5-specific mAbs were assessed for their ability to bind human and primate CEACAM5 protein by ELISA. Plates were coated with human or primate CEACAM5 protein, anti-hCEACAM5 mAbs were added to the plate and detected with rabbit anti-mouse IgG conjugated with horseradish peroxidase (Sigma; #A9044). The antibody binding was visualized by adding TMB-H2O2 buffer and read at a wavelength of 450 nm.

TABLE 3

| EC50 values corresponding to binding ability of CEACAM5-specific mAbs to primate CEACAM5 proteins | | | | | |
|---|---|---|---|---|---|
| Antibodies | MAb1 | MAb2 | MAb3 | MAb4 | MAb5 |
| EC50 (nM) hCEACAM5 | 0 53 | 0.14 | 0.36 | 0.08 | 0.40 |
| EC50 (nM) cCEACAM5 | 1.18 | 0.07 | 3.72 | 0.05 | 0.45 |
| Ratio c/h | 2.2 | 0.5 | 10 | 0.6 | 1.1 |

Example 3.2: Apparent Affinity and Antibody Binding Capacity of Anti-CEACAM5 Antibodies to Advanced Human Primary Colon Tumor Cells CR-IGR-034P by Flow Cytometry Advanced human primary colon tumor CR-IGR-034P (Julien et al., Clin Cancer Res Oct. 1, 2012 18:5314-5328) was obtained from Patient-derived xenograft in mice. Tumor CR-IGR-034P was enzymatically dissociated using collagenase Type IV (Invitrogen; #17104-019) and deoxyribonuclease I (Invitrogen; #18047-019) for 1 h at 4° C. Cell viability was estimated by Viacount application using Guava® easyCyte™ 8HT Flow Cytometry System. For apparent affinity estimation, CR-IGR-034P tumoral cells were coated at 40,000 cells/well on 96-well High Bind plate (MSD L15XB-3) and 100 μL/well of anti-CEACAM5 antibodies were added in 2-fold serial dilutions starting at 20 μg/ml up to 12 dilutions in assay diluant for 45 min at 4° C. and washed three times with PBS 1% BSA. 100 μL/well of goat anti-mouse IgG conjugated with Alexa647 (Invitrogen; #A2135) or goat anti-human IgG conjugated with Alexa488 (Invitrogen; #A11013) was added for 45 min at 4° C. and washed three times with PBS 1% BSA. The antibody binding was evaluated after centrifugation and resuspension of cells by adding 200 μl/well PBS 1% BSA and read using Guava® easyCyte™ 8HT Flow Cytometry System. Apparent KD and EC50 values were estimated using BIOST@T-BINDING and BIOST@T-SPEED softwares, respectively.

Antibody binding capacity of anti-CEACAM5 antibodies was determined using Mouse IgG Calibrator kit (Biocytex #7208) or Human IgG Calibrator Kit (Biocytex #CP010) according to the manufacturer's instructions.

TABLE 4

| KD and EC50 values obtained on advanced human primary colon tumor cells CR-IGR-034P | | | | | |
|---|---|---|---|---|---|
| Antibodies | MAb1 | MAb2 | MAb3 | MAb4 | MAb5 |
| KD value | 1.92 nM | 0.38 nM | 1.01 nM | 0.16 nM | 0.5 nM |
| EC50 value | 1 nM | 0.53 nM | 2.8 nM | 0.2 nM | 1.4 nM |

Example 3.3: Internalization Activity of Murine CEACAM5-Specific Antibodies

To evaluate the internalization of the anti-CEACAM5 antibodies MAb1, MAb2, MAb3, MAb4 and MAb5, viable MKN45 cells were incubated for 24 h at 37° C./5% CO2 (or 4° C. on ice for negative control) with 10 μg/ml of ALEXAFLUOR® 488-pre-labeled anti-CEACAM5 antibodies. Then, one part of the wells were rinced with culture medium and the extracellular AF-labeled antibodies bound to the cells were quenched by incubating the cells with anti-ALEXAFLUOR® 488 antibody (50 μg/mL) on ice for 30 min (intracellular fluorescence level). The other part of the wells was only incubated with culture medium in the same time condition (total fluorescence level).

The cells were then detached and washed, and collected in culture medium before flow cytometry analysis using a MACSQUANT™ Vyb analyzer. The cellular-associated fluorescence of $1\times10^4$ cells was measured, and the mean fluorescent intensity of gated viable cells was quantified. The internalization ratio (%) is defined by dividing the quenched cell-associated fluorescence by the total cell-associated fluorescence multiplicated by 100. Data are expressed as the mean±standard deviation (SD)

TABLE 5

| Anti-CEACAM5 murine antibody internalization at 24 hrs in MKN45 cell line | |
|---|---|
| Antibody | Internalization 24hrs, 37° C./5% CO2 % ± StD |
| MAb1 | 49.9 ± 5.1 |
| MAb2 | 45.0 ± 5.5 |
| MAb3 | 51.1 ± 3.5 |
| MAb4 | 42.5 ± 6.7 |
| MAb5 | 51.7 ± 3.1 |

The five CEACAM5-specific antibodies undergo internalization after binding of CEACAM5 expressed at the cell surface membrane, supporting their use in the field of antibody immunoconjugates to specifically address cytotoxic to cancer cells. The anti-CEACAM5 antibodies MAb1, MAb2, MAb3, MAb4 and MAb5 showed internalization in MKN45 human cancer cell line of 49.9%, 45%, 51.1%, 42.5%, 51.7%, respectively, after 24 hours of incubation.

Example 3.4: Cytotoxic Activity of the Corresponding Murine ADCs on MKN45 Cell Line The murine antibodies were conjugated in order to define their in vitro cytotoxic activity. In a 15 ml tube, at room temperature (23° C.), mAb, Buffer A/HEPES (4%), DMA (dimethylacetamide, 20% v/v), then 6 equivalent of SPDB linker are successively introduced under magnetic stirring. After one night at room temperature, DM4 (maytansinoid, 9.6 equivalent) in 15 mM DMA solution is added, and reacted 5 hours. Crude conjugation mixture is purified on SUPERDEX®200 pg 16/60 or G25 26/10 columns (PBS-Na pH7.4/5% NMP), concentrated on AMICON® 15 @5000 g and filtered on Millex 0.22 μm.

The effect of the anti-CEACAM5 maytansinoid conjugates were then tested on tumor cell viability using the CELL TITER-GLO® kit (Promega). To do so, MKN45 human gastric cancer cells were plated in 96-well plates and allowed to adhere during 4 hours in 37° C./5% CO2 atmosphere. Different concentrations of anti-CEACAM5 conjugates were added to the seeded cells. The cells were then incubated for 96 hours in the same atmosphere. CELL TITER-GLO® reagent was then added to the wells for 10 min at room temperature and the luminescent signal was measured using an ENVISION™ plate counter (Perkin-Elmer).

TABLE 6

Cytotoxic activities of the CEACAM5-specific murine ADCs on CEACAM5 + MKN45 cell line

| Antibody Drug Conjugate | Cytotoxic activity $IC_{50}$ (nM) |
|---|---|
| MAb1-SPDB-DM4 | 0.89 ± 0.23 |
| MAb2-SPDB-DM4 | 0.14 ± 0.01 |
| MAb3-SPDB-DM4 | 0.53 ± 0.15 |
| MAb4-SPDB-DM4 | 0.96 ± 0.02 |
| MAb5-SPDB-DM4 | 0.24 ± 0.04 |

The anti-CEACAM5 antibodies conjugated to maytansinoid (DM4) MAb1-SPDB-DM4, MAb2-SPDB-DM4, MAb3-SPDB-DM4, MAb4-SPDB-DM4 and MAb5-SPDB-DM4 showed in vitro cytotoxic activities with an IC50 of 0.89, 0.14, 0.53, 0.96 and 0.24 nM, respectively.

Example 4: Sequence Determination of Heavy and Light Chains of the Anti-CEACAM5 mAbs The sequences of the variable domains of the mAb were retrieved from the hybridoma and cloned into an expression vector to ensure that the cloned mAbs had the same characteristics as the initial murine mAbs.

The derived amino acid sequences provided information in agreement with the data obtained on purified mAbs derived from the hybridoma by N-terminal sequencing and mass spectrometry (LC/MS) of the heavy and light chains (LC, HC) (see Table 7).

TABLE 7

Mass spectrometry analysis of anti-CEACAM5 mAbs from hybridoma

| | | Mass (Da) | |
|---|---|---|---|
| Clone ID | Chain | by LC/MS from batch | in silico value retrieved sequence |
| MAb1 | LC | 23837 | 23836 |
| | HC (GOF) | 50328 | 50330 |
| MAb2i* | LC | 23467 | 23467 |
| | HC (GOF) | 50288 | 50286 |
| MAb3 | LC | 23907 | 23907 |
| | HC (GOF) | 50372 | 50373 |
| MAb4 | LC | 23731 | 23731 |
| | HC (GOF) | 50370 | 50370 |

TABLE 7-continued

Mass spectrometry analysis of anti-CEACAM5 mAbs from hybridoma

| | | Mass (Da) | |
|---|---|---|---|
| Clone ID | Chain | by LC/MS from batch | in silico value retrieved sequence |
| MAb5 | LC | 23659 | 23659 |
| | HC (GOF) | 50329 | 50330 |

*MAb2i is the antibody produced by one of the cloned hybridoma and from which the so-called "MAb2" has been derived by introducing canonical residues in the framework regions of VL and VH, as explained in example 5.

Example 5: Antibody Drug Conjugate (ADC) (Chimer)

Example 5.1: Naked Chimer mAb

The nucleic acid sequences of the variable domains VH, VL were cloned into expression vectors in fusion with the human IgG1 or the human Ckappa constant domain coding sequences respectively to then generate batches of chimer mAbs by transient expression in HEK293 as described in Example 1. Affinities to human and cynomolgus CEACAM5 remained similar for murine and chimer mAbs. On Table 8, affinities are illustrated by the EC50 obtained by ELISA with human or cynomolgus CEACAM5.

TABLE 8

EC50 obtained with CEACAM5 for murine hybridoma and corresponding chimer mAbs

| EC50 obtained for murine hybridoma mAbs | | | EC50 obtained for chimeric mAbs | | |
|---|---|---|---|---|---|
| clone ID | hCEACAM5 | cCEACAM5 | clone ID | hCEACAM5 | cCEACAM5 |
| MAb1 | 0.53 | 1.18 | chMAb1 | 0.51 | 1.57 |
| MAb2i | 0.14 | 0.07 | chMAb2 (lot 1) | 0.16 | 0.13 |
| | | | chMAb2 (lot 2) | 0.14 | 0.17 |
| | | | chMab2$_{K52R}$ | 0.11 | 0.15 |
| MAb3 | 0.36 | 3.72 | chMAb3 | Not done | Not done |
| MAb4 | 0.08 | 0.05 | chMAb4 | 0.14 | 0.12 |
| MAb5 | 0.4 | 0.45 | chMAb5 | 0.18 | 0.13 |

The sequences for the CDR regions were deduced from the protein sequence using the IMGT nomenclature. They correspond to SEQ ID NO: 1-4, 6, 7-10, 12, 13-16, 18, 19-22, 24, 25-28, 30.

Of note, compared to the antibody produced by the cloned hybridoma (MAb2i) canonical residues have been introduced into clone MAb2 at positions 41G, 42K, and 45Q on VL, and at positions 5Q and 7S on VH.

In addition, lysine at position 52 on the VL of clone MAb2 CEA-4 is located in the CDR2, has been replaced by arginine in clone Mab2$_{K52R}$. A batch was generated in the same conditions as that corresponding to clone MAb2 and led to similar affinity to human and cynomolgus CEACAM5 extracellular domain as shown on Table 7. It highlighted that this point mutation in the CDR can be made without any impact on binding.

The LC and HC sequences of the chimer mAb for clone MAb2 and clone Mab2$_{K52R}$ correspond to SEQ ID NO:43, 44, 54.

chMAb2 was constructed as described in example 4. It is a chimer mAb derived from clone MAb2 with a human IgG1, Ck isotype. The sequences correspond to SEQ ID NO:43, and 44. A batch was prepared at 300 mg scale by transient expression in HEK293 followed by protein An affinity chromatography purification, see Table 7 for the binding data. It was the naked mAb used for the production of the ADC.

Example 5.2: Production and Characterisation of ADC

In this example, immunoconjugates were prepared from naked chimer mAb. in vivo efficacy were then assessed.

DAR Calculation:

A conjugate comprises generally from 1 to 10 molecule(s) of the maytansinoid attached covalently to the antibody (so called, "drug-to-antibody ratio" or "DAR"). This number can vary with the nature of the antibody and of the maytansinoid used along with the experimental conditions used for the conjugation (like the ratio maytansinoid/antibody, the reaction time, the nature of the solvent and of the cosolvent if any). Thus the contact between the antibody and the maytansinoid leads to a mixture comprising several conjugates differing from one another by different drug-to-antibody ratios; optionally the naked antibody; optionally aggregates. The DAR that is determined is thus a mean value.

The method used herein to determine the DAR consists in measuring spectrophotometrically the ratio of the absorbance at 252 nm and 280 nm of a solution of the substantially purified conjugate. In particular, said DAR can be determined spectrophotometrically using the measured extinction coefficients at respectively 280 and 252 nm for the antibody and for the maytansinoid ($\varepsilon_{D280}$=5,180 $M^{-1}$ $cm^{-1}$ and $\varepsilon_{D252}$=26,159 $M^{-1}$ $cm^{-1}$). The method of calculation is derived from Antony S. Dimitrov (ed), LLC, 2009, Therapeutic Antibodies and Protocols, vol 525, 445, Springer Science and is described in more details below:

The absorbances for the conjugate at 252 nm (A252) and at 280 nm (A280) are measured either on the monomeric peak of the size exclusion chromatography (SEC) analysis (allowing to calculate the "DAR(SEC)" parameter) or using a classic spectrophotometer apparatus (allowing to calculate the "DAR(UV)" parameter). The absorbances can be expressed as follows:

$$A_{252}=(c_D\times\varepsilon_{D252})+(c_A\times\varepsilon_{A252})$$

$$A_{280}=(c_D\times\varepsilon_{D280})+(c_A\times\varepsilon_{A280})$$

wherein:

- $c_D$ and $c_A$ are respectively the concentrations in the solution of the maytansinoid and of the antibody
- $\varepsilon_{D252}$ and $\varepsilon_{D280}$ dare respectively the molar extinction coefficients of the maytansinoid at 252 nm and 280 nm
- $\varepsilon_{A252}$ and $\varepsilon_{A280}$ are respectively the molar extinction coefficients of the antibody at 252 nm and 280 nm.

Resolution of these two equations with two unknowns leads to the following equations:

$$c_D=[(\varepsilon_{A280}\times A_{252})-(\varepsilon_{A252}\times A_{280})]/[(\varepsilon_{D252}\times\varepsilon_{A280})-(\varepsilon_{A252}\times\varepsilon_{D280})]$$

$$c_A=[A_{280}-(c_D\times\varepsilon_{D280})]/\varepsilon_{A280}$$

The average DAR is then calculated from the ratio of the drug concentration to that of the antibody: DAR=$c_D/c_A$ Deglycosylation and High Resolution Mass Spectrometry of Conjugates (HRMS)

Deglycosylation is a technique of enzymatic digestion by means of glycosidase. The deglycosylation is made from 500 µl of conjugated+100 µl of TRIS® buffer HCl 50 mM+10 µl of glycanase-F enzyme (100 units of freeze-dried enzyme/100 µl of water). The medium is vortexed and maintained one night at 37° C. The deglycosylated sample is then ready to be analyzed in HRMS. Mass spectra were obtained on a Waters Q-Tof-2 system in electrospray positive mode (ES+). Chromatographic conditions are the following: column: 4 µm BioSuite 250 URH SEC 4,6×300 mm (Waters); solvents: A: ammonium formate 25 mM+1% formic acid: B: CH3CN; column temperature: 30° C.; flow rate 0.4 ml/min; isocratic elution 70% A+30% B (15 min).

Analytical Size Exclusion Chromatography (SEC)

Column: TSKGEL® G3000 SWXL 5 µm column, 7.8 mm×30 cm, TOSOH BIOSCIENCE, LLC Part #08541+guard column TSK-GEL® SWXL 7 µM, 40 mm×6 mm, TOSOH BIOSCIENCE, LLC Part #08543

Mobile Phase: KCl (0.2M), KH2PO4 (0.052 M), K2HPO4 (0.107 M), iPrOH (20% in volume)

Analysis Conditions: isocratic elution at 0.5 ml/min for 30 min

Analysis performed on a Lachrom Elite HPLC system (Merck) using a L2455 DAD spectrophotometer detector.

Buffers Contents

Buffer A (pH 6.5): NaCl (50 mM), Potassium Phosphate buffer (50 mM), EDTA (2 mM)

Buffer HGS (pH 5.5): histidine (10 mM), glycine (130 mM), sucrose 5% (w/v), HCl (8 mM)

Abbreviations Used

CV: Column Volume; DAR: Drug Antibody Ratio; DMA: dimethylacetamide; HEPES: 4-(2-hydroxyethyl)-1-piperazine-ethanesulfonic acid; HRMS: High Resolution Mass Spectroscopy; NHS: N-hydroxysuccinimide; Nitro-SPDB: butanoic acid, 4-[(5-nitro-2-pyridinyl)dithio]-, 2,5-dioxo-1-pyrrolidinyl ester (could be prepared as described in WO2004016801 patent); NMP: N-methylpyrrolidinone; RT: room temperature; SEC: Size Exclusion Chromatography ADC (chimers):

chMAb1-SPDB-DM4

Analytical Data:

MW(Ab)=148438 g/mol; MW(DM4)=780.38 g/mol $\varepsilon_{280\ nm}$(Ab)=213320; $\varepsilon_{252\ nm}$ (Ab)=73473

$\varepsilon_{280\ nm}$(DM4)=5180 et $\varepsilon_{252\ nm}$(DM4)=26159

Under stirring, at RT, 3.59 ml of chMAb1 (C=5.72 mg/ml in PBS pH=7.4 buffer) are introduced in a vessel, followed by 0.312 ml of DMA and 0.046 ml of nitro-SPDB linker solution (5.0 Eq-15 mM solution in DMA). Solution is vortexed for 30 sec and then slowly stirred at RT for 3 hours. Under magnetic stirring, 3.8 ml of PBS pH7.5 buffer, 0.389 ml of DMA and 0.074 ml of DM4 solution (15 mM solution in DMA) were sucessively added. After 2.5 hours at RT, crude reaction mixture is purified on HILOAD 26/60 desalting column (SUPERDEX®200 pg; GE Healthcare), preconditioned with 1 CV of NaOH 1M, 2 CV of water and 2 CV of PBS pH7.4 buffer containing 5% of NMP in volume. Conjugate is eluted with PBS pH7.4 buffer containing 5% of NMP, and monomeric conjugate fractions are pooled, concentrated on AMICON® Ultra-15 (Ultracel 10 k, Millipore) and filtered on 0.22 µm filter.

7.6 ml of chMAb1-SPDB-DM4 conjugate (c=2.19 mg/ml) was thus obtained as a colorless clear solution. The conjugate is then analyzed for final drug load and monomeric purity: DAR (UV)=3.38; DAR (SEC)=3.34; RT=17.54 min; monomeric purity=99.8%.

Figure 8:
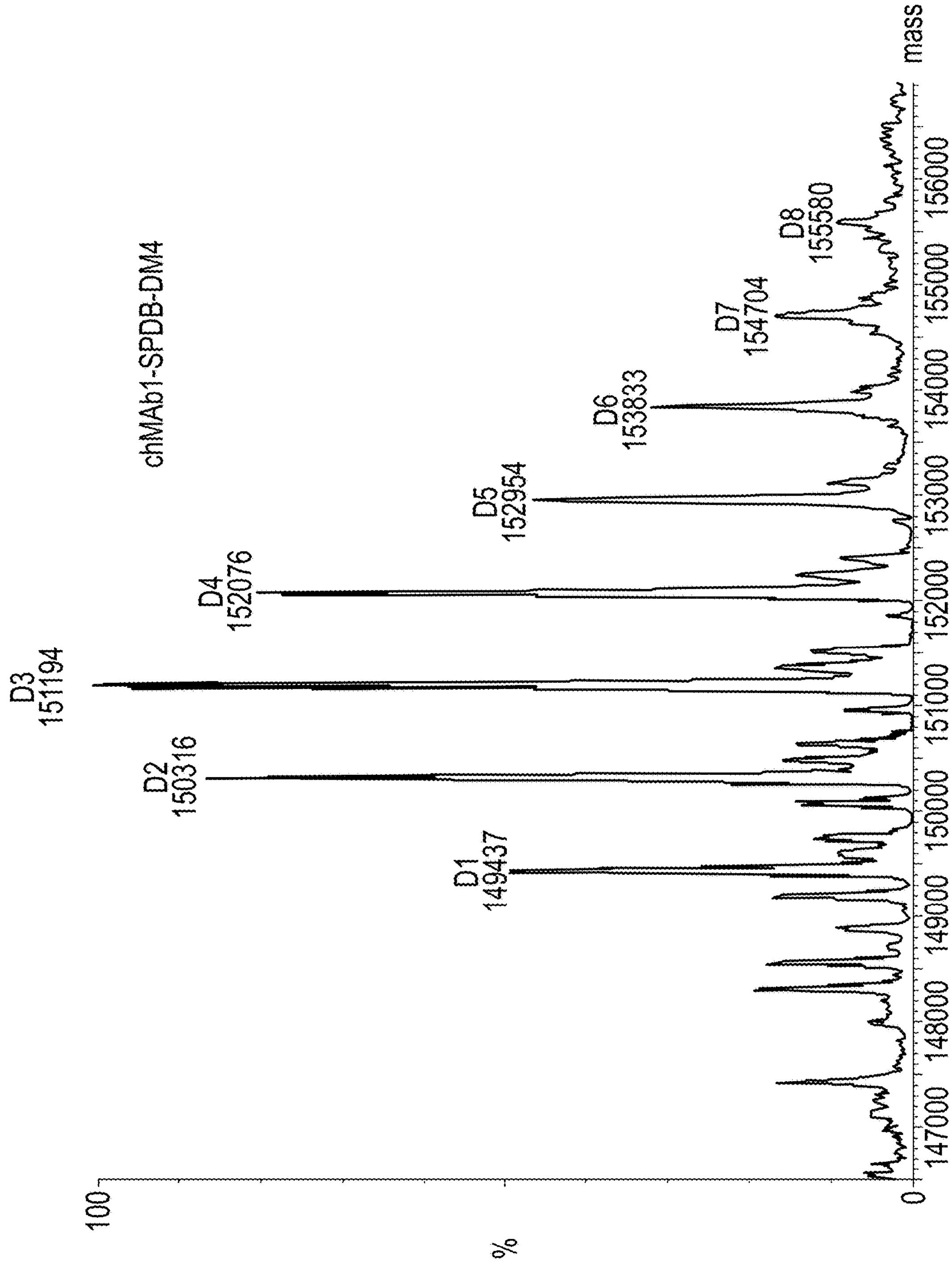
FIG. 8: HRMS analysis of chMAb1-SPDB-DM4 conjugate.

The result of HRMS analysis is shown on FIG. 8.

chMAb2-SPDB-DM4

Analytical Data:

MW(Ab)=147900 g/mol; MW(DM4)=780.38 g/mol $\varepsilon_{280\ nm}$(Ab)=201400; $\varepsilon_{252\ nm}$(Ab)=70889

$\varepsilon_{280\ nm}$(DM4)=5180 et $\varepsilon_{252\ nm}$(DM4)=26159

Under stirring, at RT, 3.8 ml of chMAb2 (C=5.08 mg/ml in PBS pH=7.4 buffer) are introduced in a vessel, followed by 0.337 ml of DMA and 0.0433 ml of nitro-SPDB linker solution (5.0 Eq-15 mM solution in DMA). Solution is vortexed for 30 sec and then slowly stirred at RT for 3 hours. Under magnetic stirring, 3.12 ml of PBS pH7.5 buffer, 0.319 ml of DMA and 0.069 ml of DM4 solution (15 mM solution in DMA) were sucessively added. After 2 hours at RT, crude reaction mixture is filtered on 0.45 μm filter and purified on HILOAD 26/60 desalting column (SUPERDEX®200 pg; GE Healthcare), pre-conditioned with 1 CV of NaOH 1 M, 2 CV of water and 2 CV of PBS pH7.4 buffer containing 5% of NMP in volume. Conjugate is eluted with PBS pH7.4 buffer containing 5% of NMP, and monomeric conjugate fractions are pooled, concentrated on AMICON® Ultra-15 (Ultracel 10 k, Millipore) and filtered on 0.22 μm filter.

7.5 ml of chMAb2-SPDB-DM4 conjugate (c=1.8 mg/ml) was thus obtained as a colorless clear solution. The conjugate is then analyzed for final drug load and monomeric purity: DAR (UV)=4.10; DAR (SEC)=4.05; RT=17.52 min; monomeric purity=99.9%.

Figure 9:
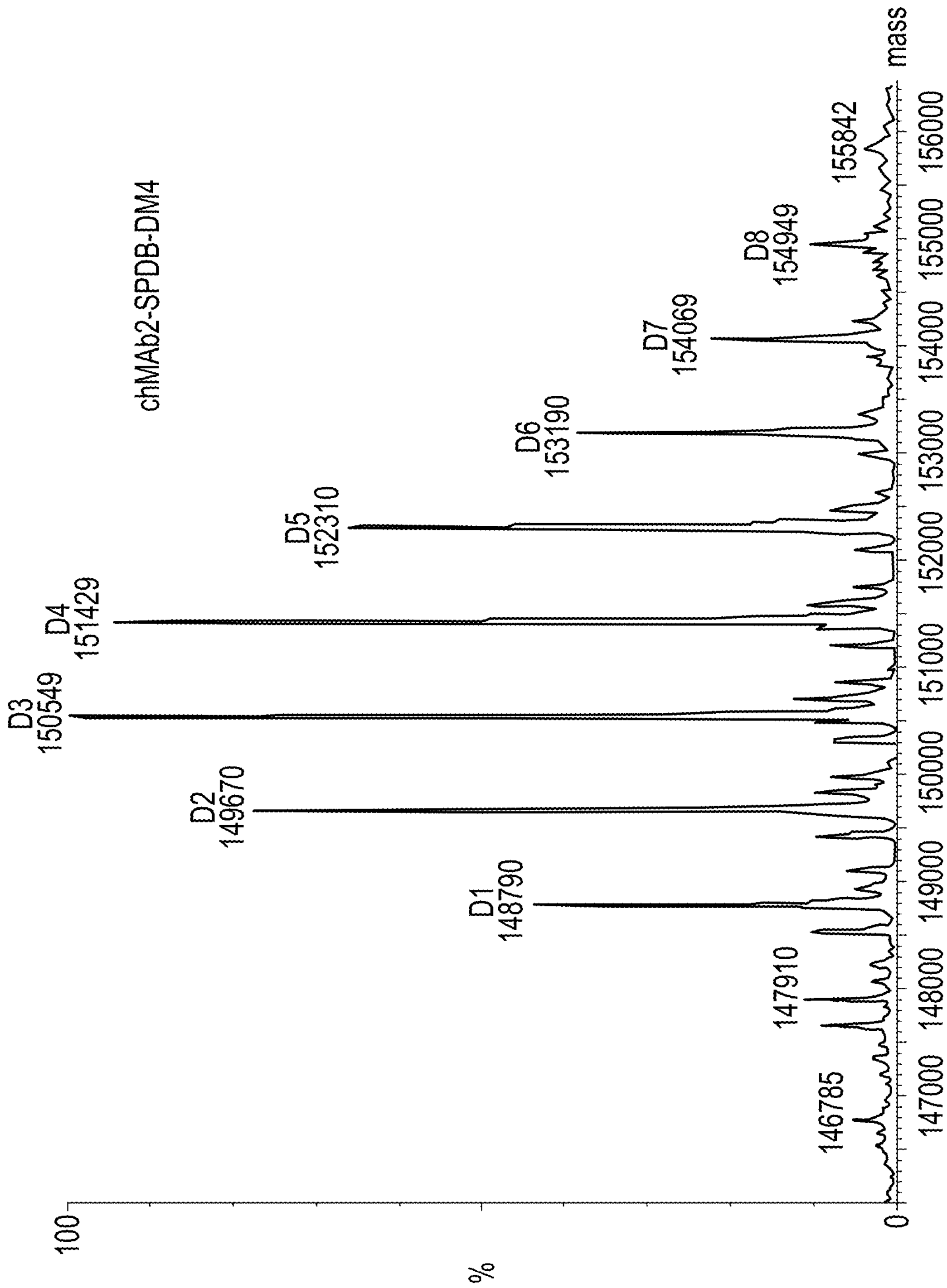
FIG. 9: HRMS analysis of chMAb2-SPDB-DM4 conjugate.

The result of HRMS analysis is shown on FIG. 9.

chMAb4-SPDB-DM4

Analytical Data:

MW(Ab)=148124 g/mol; MW(DM4)=780.38 g/mol $\varepsilon_{280\ nm}$ 280 nm(Ab)=204380; $\varepsilon_{280\ nm}$ 252 nm(Ab)=73142

$\varepsilon_{280\ nm}$ 280 nm(DM4)=5180 et $\varepsilon_{280\ nm}$ 252 nm(DM4)=26159

Under stirring, at RT, 3.63 ml of chMAb4 (C=5.69 mg/ml in PBS pH=7.4 buffer) are introduced in a vessel, followed by 0.316 ml of DMA and 0.0465 ml of nitro-SPDB linker solution (5.0 Eq-15 mM solution in DMA). Solution is vortexed for 30 sec and then slowly stirred at RT for 3 hours. Under magnetic stirring, 3.8 ml of PBS pH7.5 buffer, 0.389 ml of DMA and 0.074 ml of DM4 solution (15 mM solution in DMA) were sucessively added. After 2 hours at RT, crude reaction mixture is purified on HILOAD 26/60 desalting column (SUPERDEX®200 pg; GE Healthcare), pre-conditioned with 1 CV of NaOH 1M, 2 CV of water and 2 CV of PBS pH7.4 buffer containing 5% of NMP in volume. Conjugate is eluted with PBS pH7.4 buffer containing 5% of NMP, and monomeric conjugate fractions are pooled, concentrated on AMICON® Ultra-15 (Ultracel 10 k, Millipore) and filtered on 0.22 μm filter.

6.5 ml of chMAb4-SPDB-DM4 conjugate (c=2.20 mg/ml) was thus obtained as a colorless clear solution. The conjugate is then analyzed for final drug load and monomeric purity: DAR (UV)=3.87; DAR (SEC)=3.85; RT=17.52 min; monomeric purity=99.8%.

Figure 10:
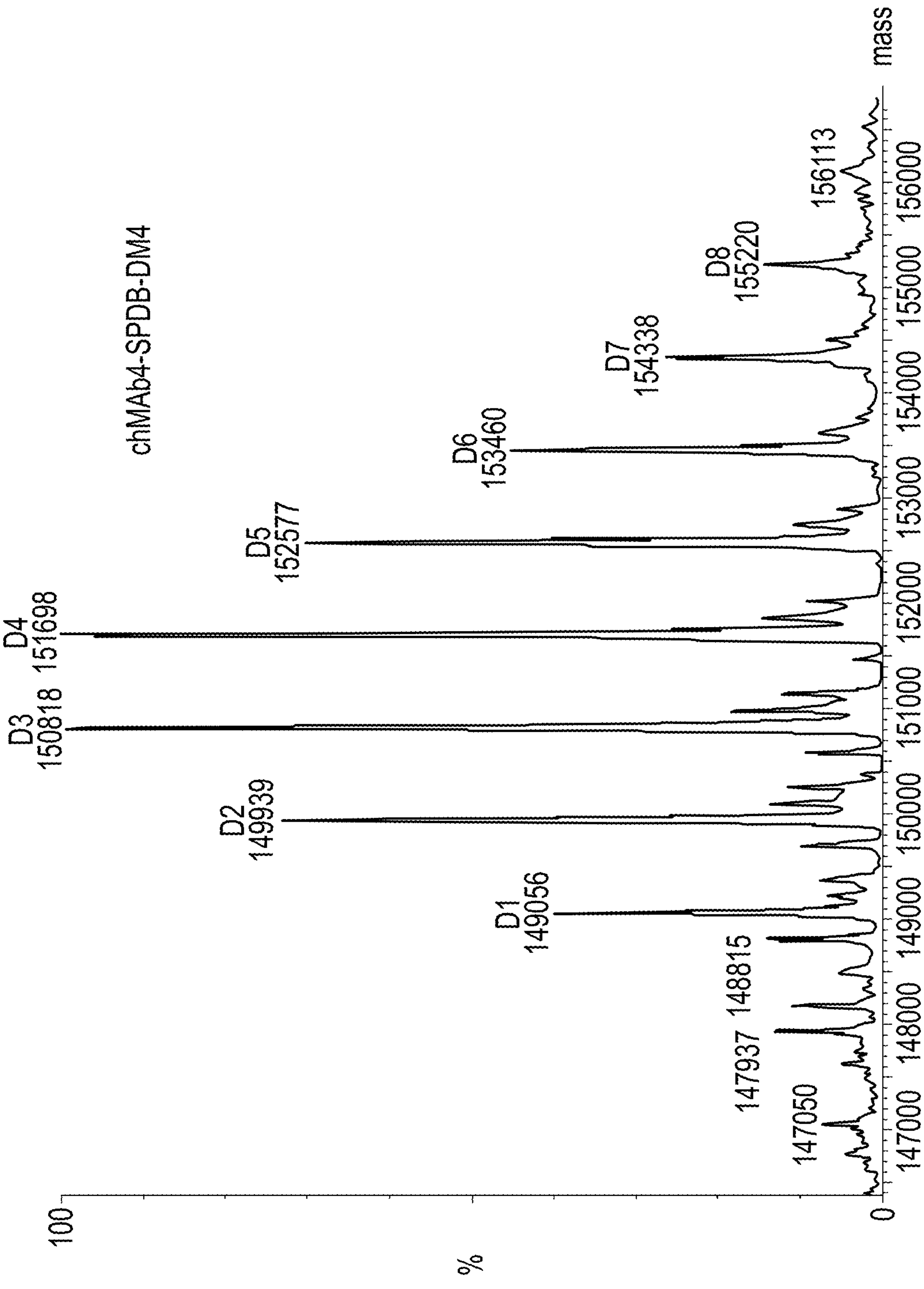
FIG. 10: HRMS analysis of chMAb4-SPDB-DM4 conjugate.

The result of HRMS analysis is shown on FIG. 10.

chMAb5-SPDB-DM4

Analytical Data:

MW(Ab)=148040 g/mol; MW(DM4)=780.38 g/mol $\varepsilon_{280\ nm}$ 280 nm(Ab)=207360; $\varepsilon_{280\ nm}$ 252 nm(Ab)=72288

$\varepsilon_{280\ nm}$ 280 nm(DM4)=5180 et $\varepsilon_{280\ nm}$ 252 nm(DM4)=26159

Under stirring, at RT, 3.15 ml of chMAb5 (C=6.38 mg/ml in PBS pH=7.4 buffer) are introduced in a vessel, followed by 0.269 ml of DMA and 0.0453 ml of nitro-SPDB linker solution (5.0 Eq-15 mM solution in DMA). Solution is vortexed for 30 sec and then slowly stirred at RT for 3 hours. Under magnetic stirring, 4.1 ml of PBS pH7.5 buffer, 0.317 ml of DMA and 0.072 ml of DM4 solution (15 mM solution in DMA) were sucessively added. After 2 hours at RT, crude reaction mixture is filtered on 0.45 μm filter and purified on HILOAD 26/60 desalting column (SUPERDEX®200 pg; GE Healthcare), pre-conditioned with 1 CV of NaOH 1M, 2 CV of water and 2 CV of PBS pH7.4 buffer containing 5% of NMP in volume. Conjugate is eluted with PBS pH7.4 buffer containing 5% of NMP, and monomeric conjugate fractions are pooled, concentrated on AMICON® Ultra-15 (Ultracel 10 k, Millipore) and filtered on 0.22 μm filter.

7.5 ml of AntiCEACAM5_hyb_1917CEA4_VH5Q7S_VL41G42K45Q_IgG1-SPDB-DM4 conjugate (c=3.4 mg/ml) was thus obtained as a colorless clear solution. The conjugate is then analyzed for final drug load and monomeric purity: DAR (UV)=3.4; DAR (SEC)=3.4; RT=17.49 min; monomeric purity=99.8%.

Figure 11:
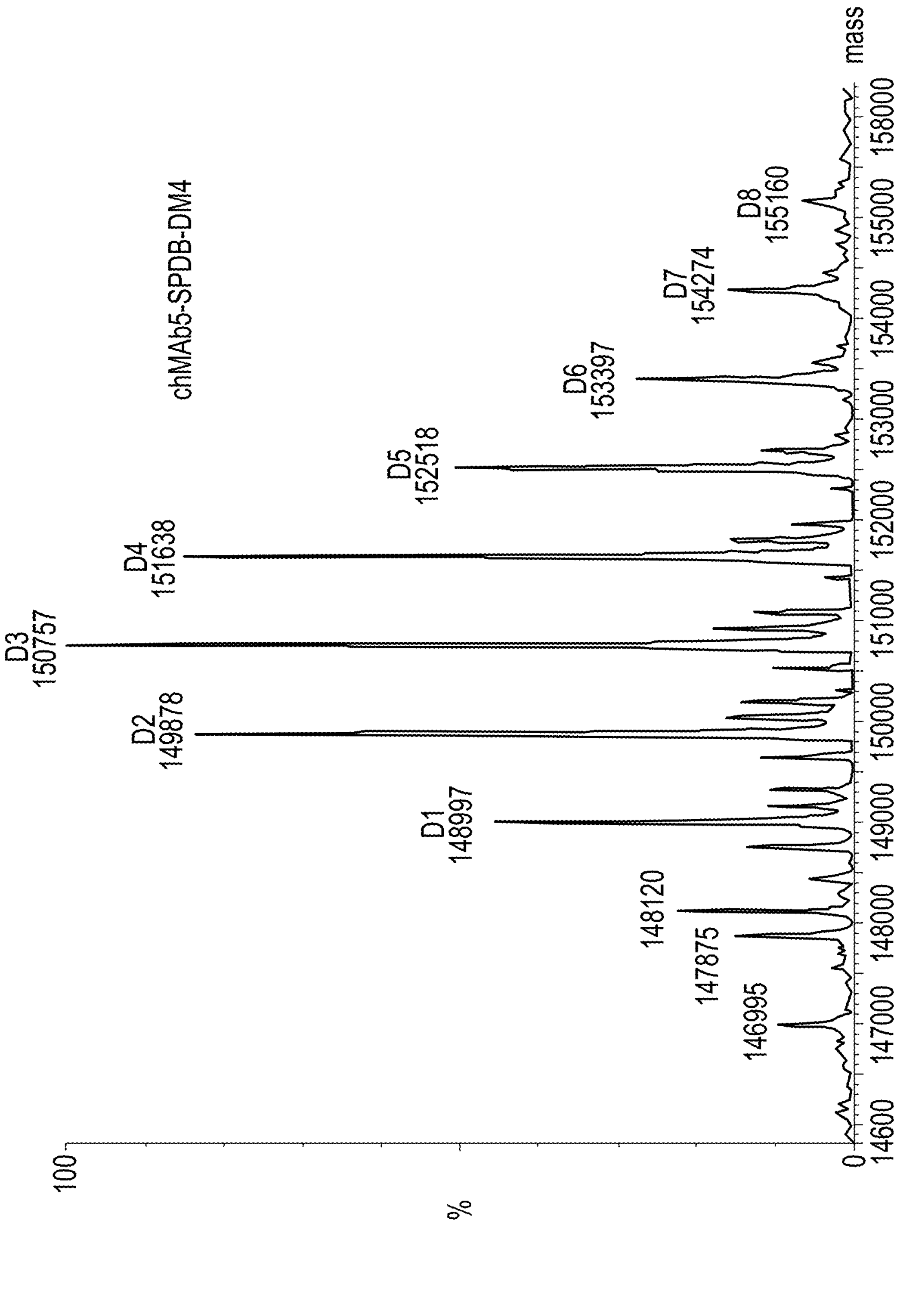
FIG. 11: HRMS analysis of chMAb5-SPDB-DM4 conjugate.

The result of HRMS analysis is shown on FIG. 11.

Example 5.3: In Vivo Efficacy

Four chimeric conjugates (chMAb4-SPDB-DM4, chMAb1-SPDB-DM4, chMAb5-SPDB-DM4 and chMAb2-SPDB-DM4) were evaluated at 2 doses against measurable primary colon CR-IGR-034P tumors implanted s.c. in female SCID mice. Control groups were left untreated. The doses conjugates were given in mg/kg. They were administered at 5 and 2.5 by an intravenous (IV) bolus injection, on day 14 after tumor implantation.

For the evaluation of anti-tumor activity of conjugates, animals were weighed daily and tumors were measured 2 times weekly by caliper. A dosage producing a 20% weight loss at nadir (mean of group) or 10% or more drug deaths, was considered an excessively toxic dosage. Animal body weights included the tumor weights. Tumor volume were calculated using the formula mass (mm$^3$)=[length (mm)×width (mm)2]/2. The primary efficacy end points are ΔT/ΔC, percent median regression, partial and complete regressions (PR and CR).

Changes in tumor volume for each treated (T) and control (C) are calculated for each tumor by subtracting the tumor volume on the day of first treatment (staging day) from the tumor volume on the specified observation day. The median ΔT is calculated for the treated group and the median ΔC is calculated for the control group. Then the ratio ΔT/ΔC is calculated and expressed as a percentage: ΔT/ΔC=(delta T/delta C)×100.

The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (Plowman J, Dykes D J, Hollingshead M, Simpson-Herren L and Alley M C. Human tumor xenograft models in NCI drug development. In: Feibig H H B A, editor. Basel: Karger.; 1999 p 101-125):

% tumor regression is defined as the % of tumor volume decrease in the treated group at a specified observation day compared to its volume on the first day of first treatment.

At a specific time point and for each animal, % regression is calculated. The median % regression is then calculated for the group:

$$\%\ \text{regression (at } t) = \frac{\text{volume}_{t0} - \text{volume}_t}{\text{volume}_{t0}} \times 100$$

Partial regression (PR): Regressions are defined as partial if the tumor volume decreases to 50% of the tumor volume at the start of treatment.

Complete regression (CR): Complete regression is achieved when tumor volume=0 $mm^3$ (CR is considered when tumor volume cannot be recorded).

Results

Figure 4:
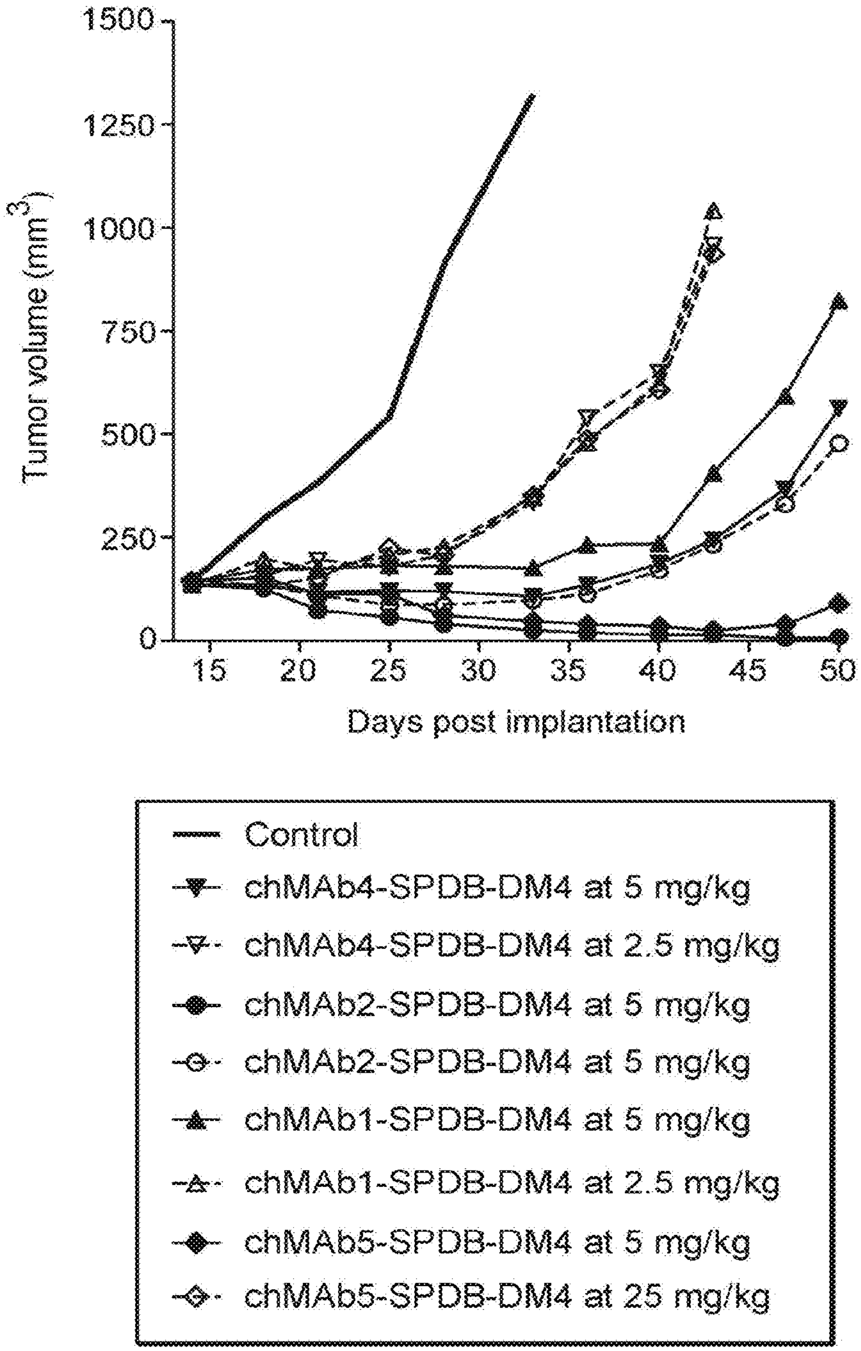
FIG. 4: Evaluation of the anti-tumor activity of chMAb4-SPDB-DM4, chMAb1-SPDB-DM4, chMAb5-SPDB-DM4, and chMAb2-SPDB-DM4 conjugates against primary human colon adenocarcinoma CR-IGR-034P in SCID female mice.

The results are presented on FIG. 4 and Table 9 (below). Using a single administration schedule at 2.5 and 5 mg/kg, all conjugates tested in this study did not induce toxicity.

chMAb1-SPDB-DM4 was very active at 5 and 2.5 mg/kg with a ΔT/ΔC of 0 and 7% ($p<0.0001$ and $p=0.0170$ vs control), respectively. chMAb4-SPDB-DM4 and chMAb5-SPDB-DM4 were highly active at 5 mg/kg with ΔT/ΔC of −5 and −7% ($p<0.0001$ vs control), respectively and tumor regression of 25 and 65%, respectively. They were very active at 2.5 mg/kg with ΔT/ΔC of 7 and 2% ($p=0.0152$ and $p=0.0020$ vs control), respectively. chMAb2-SPDB-DM4 was highly active at 5 and 2.5 mg/kg with ΔT/ΔC of −10 and −8% ($p<0.0001$ vs control), respectively, tumor regression of 82 and 39%, respectively and 3 and 1 CR/6, respectively.

From these results, all chimeric conjugates chMAb4-SPDB-DM4, chMAb1-SPDB-DM4, chMAb5-SPDB-DM4 and chMAb2-SPDB-DM4 were usable to develop a therapeutic ADC.

TABLE 9

Evaluation of the anti-tumor activity of chMAb1-SPDB-DM4, chMAb2-SPDB-DM4, chMAb4-SPDB-DM4, and chMAb5-SPDB-DM4 conjugates against primary human colon adenocarcinoma CR-IGR-034P in SCID female mice,

| Agent[1] | Route/ Dosage in mL/kg | Dosage in mg/kg per injection | Schedule in days | Drug death (Day) | Average body weight change in % per mouse at nadir (day of nadir) | Median ΔT/ΔC in % (day) | Median % of regression (day) | Regressions Partial | Regressions Complete | Biostatistic p value[2] | Comments |
|---|---|---|---|---|---|---|---|---|---|---|---|
| chMAb1- | IV | 5 | 14 | 0/6 | -0.3 (D23) | 0 (D33) | — | 2/6 | 0/6 | <0.0001 | Very active |
| SPDB-DM4 | (10 mL/Kg) | 2.5 | 14 | 0/6 | -1.2 (D22) | 7 (D21) | — | 0/6 | 0/6 | =0.0170 | Very active |
| chMAb2-SPDB-DM4 | IV (10 mL/Kg) | 5 | 14 | 0/6 | -1.1 (D29) | -10 (D33) | 82 (D33) | 6/6 | 3/6 | <0.0001 | Highly active |
| | | 2.5 | 14 | 0/6 | -1.3 (D57) | -8 (D28) | 39 (D28) | 2/6 | 1/6 | <0.0001 | Highly active |
| chMAb4-SPDB-DM4 | IV (10 mL/Kg) | 5 | 14 | 0/6 | -1.9 (D22) | -5 (D28) | 25 (D28) | 2/6 | 0/6 | <0.0001 | Highly active |
| | | 2.5 | 14 | 0/6 | -1.8 (D21) | 7 (D25) | — | 0/6 | 0/6 | <0.0152 | Very active |
| chMAb5-SPDB-DM4 | IV (10 mL/Kg) | 5 | 14 | 0/6 | -1.8 (D29) | -7 (D33) | 65 (D33) | 4/6 | 0/6 | <0.0001 | Highly active |
| | | 2.5 | 14 | 0/6 | -0.8 (D23) | 2 (D21) | — | 0/6 | 0/6 | =0.0020 | Very active |
| Control | — | — | 14 | — | -3.6 (D29) | — | — | — | — | — | — |

[1]drug formulation: HGS(10 mM Histidine, 130 mMGlycine, 5% v/v Sucrose, 0.01% Tween 80) pH 7.4

[2]p-value: Dunett's test versus control after 2-way Anova with repeated measures on rank transformed changes of tumour volume from baseline.

Example 6: Humanization of the Anti-CEACAM5_MAb2 mAb

In this example, humanized variants of parental murine IgG MAb2 have been designed in silico. The resulting mAbs were produced and provided similar characteristics as the chimeric IgG ch-MAb2.

Example 6.1: 4D-Humanization Protocol a) Humanization Based on Molecular Dynamic Trajectories The VL & VH sequences of the murine MAb2 clone were compared against the protein data base (PDB) (Berman et al., Nucleic Acids Research, 2000, 28:235-242). The following templates were used: light and heavy chain framework-3EHB (90.9% Framework light chain identity and 90.8% Framework heavy chain identity), L1-1I8M, L2-1F6L, L3-1 P7K, H1-2QHR, H2-1IGT and H3-1 P4B to build a homology model of anti-CEACAM5 LC and HC using Molecular Operating Environment (MOE) (v. 2011.10-Chemical Computing Group, Quebec, Canada). The homology model was subsequently energy minimized using the standard procedures implemented in MOE.

A molecular dynamics (MD) simulation of the minimized 3D homology model of the murine MAb2 was subsequently performed, with constraints on the protein backbone at 500 K temperature for 1.1 nanoseconds (ns) in Generalized Born implicit solvent. 10 diverse conformations were extracted from this first MD run every 100 picoseconds (ps) for the last 1 ns. These diverse conformations were then each submitted to a MD simulation, with no constraints on the protein backbone and at 300 K temperature, for 2.3 ns. For each of the 10 MD runs, the last 2,000 snapshots, one every ps, from the MD trajectory were then used to calculate, for each murine MAb2 amino acid, its root mean square deviations (rmsd) compared to a reference medoid position. By comparing the average rmsd on the 10 separate MD runs of a given amino acid to the overall average rmsd of all MAb2 murine amino acids, one decides if the amino acid is flexible enough, as seen during the MD to be considered as likely to interact with T-cell receptors and responsible for activation of the immune response. 32 amino acids were identified as flexible in the murine MAb2 antibody, excluding the CDR and its immediate 5 Å vicinity.

The motion of the 60 most flexible murine MAb2 amino acids, during the 20 ns (10×2 ns) of molecular dynamic simulation, were then compared to the motion of the corresponding flexible amino acids of 49 human 3D homology models, for each of which were run the same MD simulations. These 49 human germline models have been built by systematically combining a representative pannel of 7 human light chains (namely vk1, vk2, vk3, vk4, vlambda1, vlambda2, vlambda3) with a representative pannel of 7 human heavy chains (namely vh1a, vh1b, vh2, vh3, vh4, vh5, vh6) (Nucleic Acid Research, 2005, Vol. 33, Database issue D593-D597).

The vk1-vh6 combination showed the highest (72.6%) 4D similarity of its flexible amino acids compared to the flexible amino acids of the murine MAb2 antibody; this model was therefore used to humanize the MAb2 antibody focusing on the flexible amino acids. For the pairwise amino acid association between the murine MAb2 and vk1-vh6 amino acids, the 2 sequences were aligned based on the optimal 3D superposition of the alpha carbons f the 2 corresponding homology models.

b) Stabilizing Mutations

To improve the stability of VL and VH regions of the anti-CEACAM5 antibody, the amino acids of the light and heavy chains with low frequency of occurrence vs. their respective canonical sequences, excluding the CDRs, are originally proposed to be mutated into the most frequently found amino acids (ΔΔGth>0.5 kcal/mol; (Monsellier et al. J. Mol. Biol. 2006, 362,580-593). A first list of consensus mutations for the LC and for the HC has been restricted to the amino acids found in the closest human model (i.e vk1-vh6). None of these mutations are located in the "Vernier" zone (Foote et al., J. Mol. Biol. 1992, 224, 487-499). Other criteria are taken into account to consider these consensus mutations for potentially stabilizing the anti-CECAM5 MAb2 antibody. These criteria are a favourable change of hydropathy at the surface or a molecular mechanics based predicted stabilization of the mutant. Stabilizing mutations reported to be successful in the literature (Bedouelle, H. J. Mol. Biol. 2006, 362,580-593; Steipe B. J. Mol. Biol. 1994, 240, 188-192) were considered.

c) Removal of Unwanted Sequence Motifs

The following motifs of sequences were considered: Asp-Pro (acide labile bond), Asn-X-Ser/Thr (glycosylation, X=any amino acid but Pro), Asp-Gly/Ser/Thr (succinimide/iso-asp formation in flexible areas), Asn-Gly/His/Ser/Ala/Cys (exposed deamidation sites), Met (oxidation in exposed area). The resulting humanized sequences were blasted for sequence similarity against the Immune Epitope Data Base (IEDB) database ((PLos Biol (2005) 3(3)e91) www.immuneepitope.org) to ensure that none of the sequences contain any known B- or T-cell epitope listed in.

d) Humanized VH and VL Regions

Three versions for the light chain (VL1, VL1a, and VL1c) and three versions for the heavy chain are proposed (VH1, VH1a and VH1b). The particular combination of amino acid residues altered in each humanized MAb2 VL and VH variant are set forth in Table 10 and Table 11, respectively. The complete amino acid sequences of the humanized VH and VL domains are set forth in Table 12.

The VL1 variant displays 5 mutations which derive from the direct comparison between the non-CDR most flexible amino acids of the anti-CEACAM5 MAb2 light chain and the vk1 human light chain sequence.

The VL1a variant derives from VL1 and includes 4 new mutations that are consensus (vk1 sequence) and potentially stabilizing. Moreover, 1 of these mutations addresses a potentially problematic deamidation site ($D_{17}T_{18}$).

The VL1c variant derives from VL1a with the introduction of 1 mutation R instead of K at position 52. Indeed, this K52 is located in the CDR L2 and could be a "target" for the conjugation process.

The VH1 variant displays 7 mutations which derive from the direct comparison between the non-CDR most flexible amino acids of the anti-CEACAM5 heavy chain and the vh6 human heavy chain sequence.

The VH1a variant derives from VH1 and includes 4 new mutations that are consensus (vh6 sequence) and potentially stabilizing.

The humanized anti-CEACAM5 MAb2 antibody VL and VH domains were combined as follows: VL1 and VH1; VL1a and VH1a; VL1c and VH1a; VL1a and VH1b

TABLE 10

Mutations of the VL variants of the anti-CEACAM5 MAb2 antibody

| Mouse MAb2 VL | VL1 | VL1d | VL1a | VL1c |
|---|---|---|---|---|
| E17 | D | D | D | D |
| T18 | | | R | R |
| Q40 | P | P | P | P |
| Q45 | K | K | K | K |
| K52 | | R | | R |
| Q70 | | | D | D |
| K74 | T | T | T | T |
| N76 | S | S | S | S |
| G84 | | | A | A |
| S85 | | | T | T |

TABLE 11

Mutations of the VH variants of the anti-CEACAM5 MAb2 antibody

| Mouse MAb2 VH | VH1 | VH1a |
|---|---|---|
| G9 | P | P |
| V10 | G | G |
| K19 | S | S |
| K43 | R | R |
| R44 | | G |
| F60 | | A |
| D62 | S | S |
| Q65 | K | K |
| N84 | | |
| K87 | T | T |
| I89 | | V |
| A113 | | S |

TABLE 12

VH and VL amino acid sequences of exemplary humanized anti-CEACAM5 antibodies.

| VH or VL variant | Sequence | SEQ ID NO. |
|---|---|---|
| clone MAb2 VH1 | EVQLQESGPGLVKPGGSLSLSCAASGFVFS SYDMSVWRQTPERRLEWVAYISSGGGITYF PSTVKGRFTVSRDNAKNTLYLQMNSLTSED TAIYYCAAHYFGSSGPFAYWGQGTLVTVSA | SEQ ID NO: 51 |
| clone MAb2 VH1a | EVQLQESGPGLVKPGGSLSLSCAASGFVFS SYDMSVWRQTPERGLEWWAYISSGGGITYA PSTVKGRFTVSRDNAKNTLYLQMNSLTSED TAVYYCAAHYFGSSGPFAYWGQGTLVTVSS | SEQ ID NO: 5 |

TABLE 12-continued

| VH and VL amino acid sequences of exemplary humanized anti-CEACAM5 antibodies. | | |
|---|---|---|
| VH or VL variant | Sequence | SEQ ID NO. |
| clone MAb2 VL1 | DIQMTQSPASLSASVGDTVTITCRASENIF SYLAWYQQKPGKSPKLLVYNTKTLAEGVPS RFSGSGSGTQFSLTISSLQPEDFGSYYCQH HYGTPFTFGSGTKLEIK | SEQ ID NO: 17 |
| clone MAb2 VL1a | DIQMTQSPASLSASVGDRVTITCRASENIF SYLAWYQQKPGKSPKLLVYNTKTLAEGVPS RFSGSGSGTDFSLTISSLQPEDFATYYCQH HYGTPFTFGSGTKLEIK | SEQ ID NO: 23 |
| clone MAb2 VL1c | DIQMTQSPASLSASVGDRVTITCRASENIF SYLAWYQQKPGKSPKLLVYNTRTLAEGVPS RFSGSGSGTDFSLTISSLQPEDFATYYCQH HYGTPFTFGSGTKLEIK | SEQ ID NO: 29 |
| clone MAb2 VL1d | DIQMTQSPASLSASVGDTVTITCRASENIF SYLAWYQQKPGKSPKLLVYNTRTLAEGVPS RFSGSGSGTQFSLTISSLQPEDFGSYYCQH HYGTPFTFGSGTKLEIK | SEQ ID NO: 55 |

Example 6.2: Sequence of Humanized Anti CEACAM5 mAb

From the amino acid sequences of in silico VL and VH variants, the nucleic acid sequences were derived and synthesized by Geneart. The sequences were cloned into expression vectors in fusion with the human IgG1 or the human Ckappa constant domain coding sequences respectively.

Example 6.3: Production and In Vitro Characterization

Batches of humanized mAbs were produced by transient expression in HEK293 and purified by protein A affinity chromatography. Structure and identity were confirmed by SDS-PAGE analysis, Size Exclusion Chromatography and Mass Spectrometry.

Affinity to human and cynomolgus CEACAM5 was verified by ELISA, EC50 are provided on Table 13.

TABLE 13

Affinity of humanized anti-CEACAM5 mAb to human and cynomolgus CEACAM5

| | | Human CEACAM5 | | Cynomolgus CEACAM5 | |
|---|---|---|---|---|---|
| code | mAb | EC50 (nM) | CV | EC50 (nM) | CV |
| huMAb2-1 | MAb2VL1VH1-IgG1 | 0.22 | 4.7% | 0.20 | 7.9% |
| huMAb2-2 | MAb2_VL1aVH1a-IgG1 | 0.20 | 9.2% | 0.17 | 5.0% |
| huMAb2-3 | MAb2_VL1cVH1a-IgG1 | 0.18 | 11% | 0.19 | 4.3% |
| huMAb2-4 | MAb2_VLId VH1-IgG1 | 0.22 | 4.3% | 0.17 | 5.0% |
| chMAb2 | MAb2-IgG1 | 0.16 | 9.9% | 0.17 | 3.0% |

Specificity to human CEACAM5 versus human CEACAM1, CEACAM6, CEACAM7 and CEACAM8 was verified by ELISA. It was reported as the percentage of binding compared to full binding with human CEACAM5, see Table 14.

TABLE 14

Percentage of binding of humanized anti-CEACAMS mAb to human CEACAMs

| | | hCEA | | | | |
|---|---|---|---|---|---|---|
| code | mAb | CAM5 | CAM1 | CAM6 | CAM7 | CAM8 |
| huMAb2-1 | MAb2VL1VH1-IgG1 | 100% | 0.3% | 0.2% | 0.3% | 0.9% |
| huMAb2-2 | MAb2_VL1aVH1a-IgG1 | 100% | 0.3% | 0.3% | 0.3% | 0.5% |
| huMAb2-3 | MAb2_VL1cVH1a-IgG1 | 100% | 0.3% | 0.3% | 0.3% | 0.6% |
| huMAb2-4 | MAb2_VL1d VH1-IgG1 | 100% | 0.3% | 0.3% | 0.3% | 1.4% |
| chMAb2 | MAb2-IgG1 | 100% | 0.3% | 0.3% | 0.3 % | 0.6% |

Epitope binding domain was verified by ELISA and showed that humanized variants recognized the A3-B3 domain specifically. It was reported as the percentage of binding compared to full binding with human CEACAM5 on Table 15.

TABLE 15

Percentage of binding of humanized anti-CEACAM5 mAh to human CEACAM5 domains

| | | hCEACAM5 | | |
|---|---|---|---|---|
| code | mAb | N-ter-A1-B1 | A2-B2 | A3-B3 |
| huMAb2-1 | MA2_VL1VH1-IgG1 | 0.4% | 0.3% | 100% |
| huMAb2-2 | MA2_VL1aVH1a-IgG1 | 0.4% | 0.3% | 100% |
| huMAb2-3 | MAb2_VL1cVH1a-IgG1 | 0.4% | 0.4% | 100% |
| huMAb2-4 | MAb2_VL1d VH1-IgG1 | 0.3% | 0.3% | 100% |
| chMAb2 | MAb2-IgG1 | 0.5% | 0.3% | 100% |

The binding kinetics of humanized anti-CEACAM5_MAb2 variants, compared with chimeric MAb2, to recombinant human CEACAM5 (hCEACAM5) and cynomolgus monkey CEACAM5 (cCEACAM5) were determined by surface plasmon resonance assay using a BIACORE®2000 (BIAcore Inc., Uppsala, NJ).

Briefly, a CM5 BIACORE®biosensor chip was docked into the instrument and activated with 70 μL of 1:1 NHS/EDC at room temperature. A mouse anti-αhuman Fc IgG1 (BIACORE®#BR-1008-39) (50 μg/mL in 1 M acetate buffer, pH5) were immobilized on the activated chips in all flow cells. The immobilization was carried out at a flow rate of 10 μL/min up to saturation. The chip was then blocked by injection of 70 μL of ethanolamine-HCl, pH8.5, followed by one wash with 3M MgCl2. To measure the binding of anti-CEACAM5 mAbs to the human CEACAM5 protein or cynomolgus CEACAM5 protein, antibodies were used at 1-5 μg/mL in BIACORE® running buffer (HBS-EP). Antigens (human CEACAM5 or cynomolgus CEACAM5) were injected from 1 to 500 nM. Following completion of the injection phase, dissociation was monitored in a BIACORE® running buffer at the same flow rate for 600 sec. The surface was regenerated between injections using 2×5 μL MgCl2 3M (2×30 s). Individual sensorgrams were analyzed using BIAevaluation software.

TABLE 16 binding of humanized anti-CEACAM5 mAb to human and monkey CEACAM5

| mAb | Human CEACAM5 KD (nM) | Cynomolgus CEACAMS KD (nM) |
|---|---|---|
| huMAb2-1 | 9.8 | 41.7 |
| huMAb2-2 | 24.5 | 96.0 |
| huMAb2-3 | 11.7 | 73.5 |
| huMAb2-4 | 6.9 | 38.6 |
| chMAb2 | 9.9 | 52.3 |

Specificity of humanized anti-CEACAM5_MAb2 variants, compared with chimeric MAb2, to cynomolgus CEACAM5 versus cynomolgus CEACAM1, CEACAM6 and CEACAM8 was verified by ELISA. It was reported as the percentage of binding compared to full binding with CEACAM5 or binding at the $EC_{50}$, see Table 17 below

TABLE 17

Percentage of binding of humanized anti-CEACAM5 mAb to cynomolgus CEACAMs

| | | Cynomolgus CEA | | | |
|---|---|---|---|---|---|
| code | mAb | CAM 5 | CAM1 | CAM6 | CAM 8 |
| huMAb2-1 | MAb2_VL1VH1-IgG1 | 100% | 0.3% | 0.3% | 3.6% |
| huMAb2-2 | MAb2_VL1aVH1a-IgG1 | 100% | 0.3% | 0.3% | 0.9% |
| huMAb2-3 | MAb2_VL1cVH1a-IgG1 | 100% | 0.3% | 0.4% | 1.2% |
| huMAb2-4 | MAb2_VL1dVH1-IgG1 | 100% | 0.3% | 0.3% | 3.2% |
| chMAb2 | MAb2-IgG1 | 100% | 0.2% | 0.3% | 1.2% |

Example 6.4: Characterization of Humanized Variants of Mab2 Obtained by Grafting to Human Germline Frameworks In this example, humanized variants of Mab2 were obtained by a CRD-grafting approach. Further, the CDRs of the humanized antibody were submitted to an alanine-scanning approach to show that several positions could be substituted without affecting the binding to human and *Macaca fascicularis* CEACAM5.

The sequence of a humanized version of Mab2 was generated first in silico by selecting human germline frameworks on the basis of structural homology with the murine antibody Mab2. For the light chain, the selected human frameworks are defined by genes IGKV1 D-39*01 and IGKJ2*02 and for the heavy chain, by genes IGHV3-23*04 and IGHJ4*01. The six CDRs of $Mab2_{K52R}$ were grafted into these human frameworks. Three back-mutations were introduced, corresponding to positions 34 and 53 in the VL (SEQ ID NO. 34) (FR2-L and FR3-L regions, respectively) and position 50 in the VH (SEQ ID NO. 33) (FR2-H region), resulting in the following sequence, defined as MAb2_VLg5VHg2.

TABLE 18

VH and VL sequences of MAb2_VLg5VHg2

| VH or VL variant | Sequence | SEQ ID NO. |
|---|---|---|
| MAb2_VHg2 | EVQLVESGGGLVQPGGSLRLSCAASGFVFSSYDMSVWR QAPGKGLEWVSYISSGGGITYYADSVKGRFTISRDNSKNT LYLQMNSLRAEDTAVYYCAAHYFGSSGPFAYWGQGTLVT VSS | SEQ ID NO: 74 |

TABLE 18-continued

| VH and VL sequences of MAb2_VLg5VHg2 | | |
|---|---|---|
| VH or VL variant | Sequence | SEQ ID NO. |
| MAb2_VLg5 | DIQMTQSPSSLSASVGDRVTITCRASENIFSYLAWYQQKP GKAPKLLIYNTRTLQSGVPSRFSGSGSGTDFTLTISSLQPE DFATYYCQHHYGTPFTFGQGTKLEIK | SEQ ID NO: 75 |

Several variants of MAb2_VLg5VHg2 were obtained by the single replacement of each amino acid of the six CDRs, preferentially by an alanine. When alanine is already found in MAb2_VLg5VHg2 CDRs, which occurs in H-CDR3, another amino acid was substituted (Val at residue 97, Arg at residue 98 and Asp at residue 108 of SEQ ID NO:74).

From the in silico amino acid sequences of VL and VH variants, the nucleic acid sequences were derived and generated by gene synthesis. The sequences were cloned into a mammalian expression vector in fusion with the human IgG1 or the human Ckappa constant domain coding sequences respectively. Humanized MAb2_VLg5VHg2, single variants differing from it by one position, and a limited number of combination mutants, were produced by transient expression in HEK293 cells. Cell supernatants containing the secreted IgGs (20 to 70 μg/ml) were diluted to 1 μg/ml for use in binding assays to human CEACAM5 ECD, *Macaca fascicularis* ECD and A3-B3 domain of human CEACAM5.

To evaluate impact of these modifications, IgGs binding was determined by measuring SPR signals with a BIACORE® T200 unit (GE Healthcare). Anti-human Fc antibodies were coupled to a Series S CM5 chip via amine coupling kit to reach a level of 10,000 response units (RU). Approximately 300 to 600 RU of each variant were captured by injecting supernatants at 1 μg/mL with a contact time of 60 seconds and a flow rate of 10 μL/min. All experiments were performed at 25° C. with HBS-EP+ (10 mM Hepes, 150 mM NaCl, 3 mM EDTA, 0.05% surfactant P20) as the running buffer. In a screening mode, the human CEACAM5/cynomolgus CEACAM5/human A3B3 domain was injected at 50 nM over the captured IgG variants at a flow rate of 30 μL/min for 1 minute. A dissociation phase of 60 seconds was held before the surface was regenerated with 1 pulse injection of 3 M $MgCl_2$ at a flow rate of 10 μL/minute and a contact time of 30 seconds.

Figure 16:
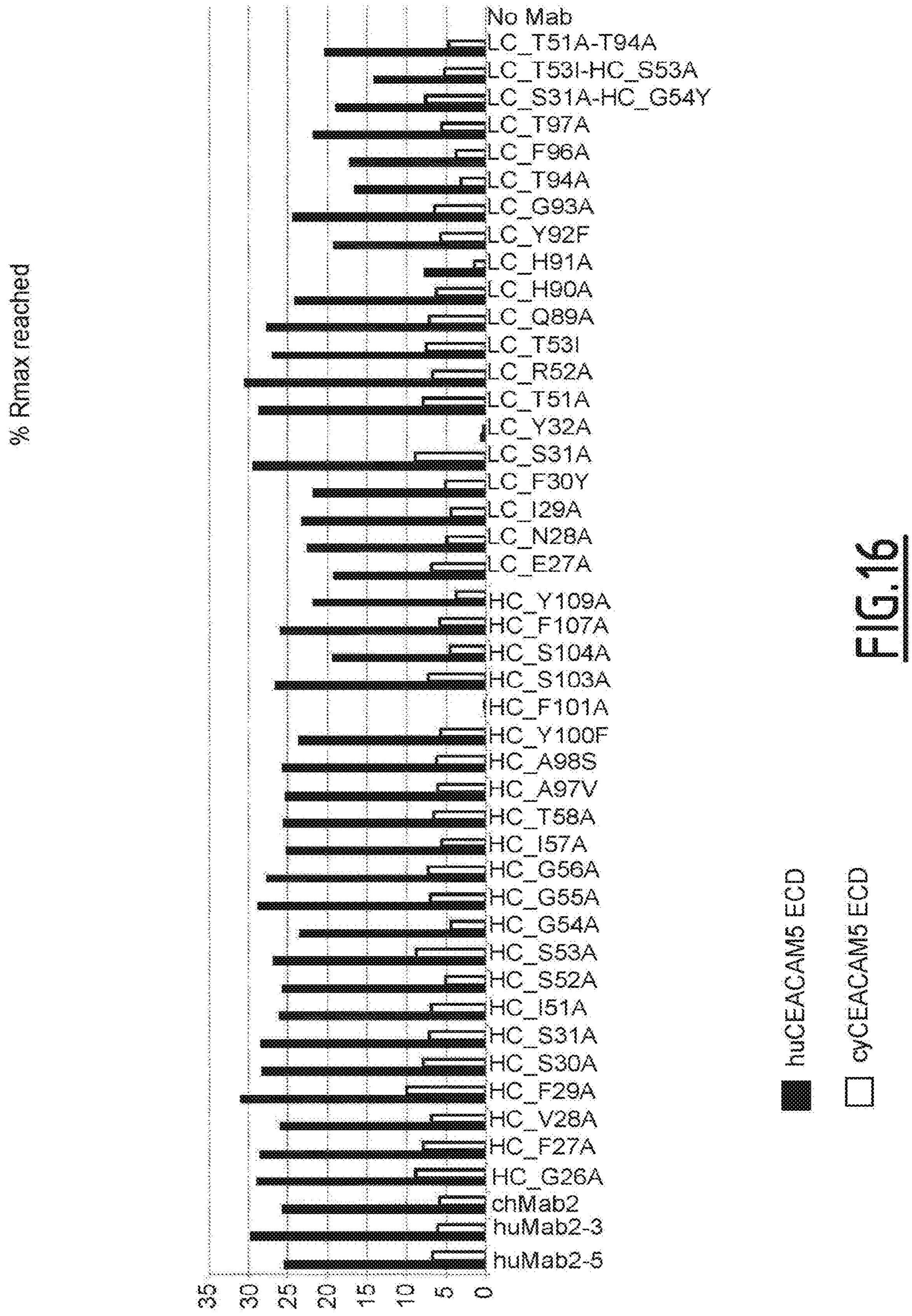
FIG. 16: Binding activity of humanized variants of MAb2 to human and monkey CEACAM5 extracellular domain.
Figure 17:
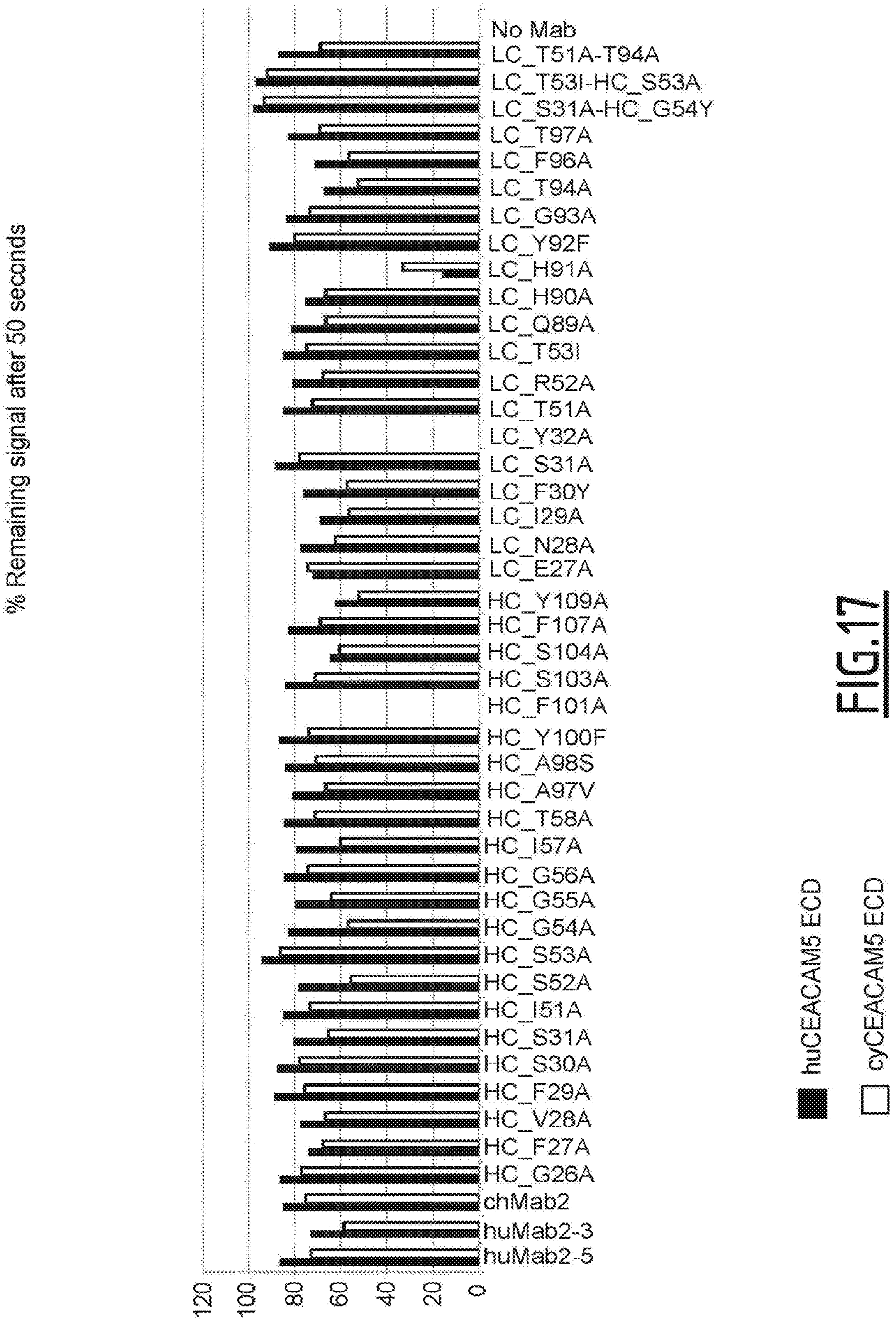
FIG. 17: Stability of binding of humanized variants of MAb2 to human and monkey CEACAM5 extracellular domain.

For each experiment, response data were processed using a reference surface, thereby allowing correction for bulk refractive index changes and any non-specific binding. Data were double referenced using response from blank injections. According to the screening method described in an application note from GE Healthcare (Application note 28-9777-72 AA), two parameters were considered to rank the variants with respect to binding characteristics. First, the binding activity is estimated by the proportion of the theoretical maximum signal measured (percentage of Rmax, see FIG. 16). Second, the percentage of remaining signal is calculated using dissociation report points (the first one 10 seconds after the end of the injection and the second one 50 seconds after the end of injection) and reflects the stability of binding (see FIG. 17).

Single alanine variants at the following positions demonstrated equivalent binding parameters, as compared to the original antibody, suggesting that the CDR amino acids at these positions are neutral for the binding: LC residues 27, 28, 29, 31, 51, 52, 89, 90, 93, 94, 96, 97 and HC residues 26 to 31, 51 to 58, 97, 103, 104, 107, 109. Behaviors of these variants are similar with human and monkey CEACAM5, thus maintaining their cross-reactivity. Binding to A3-B3 domain of CEACAM5 was also found unaffected. Some combinations of two neutral substitutions were also generated and were found to result in unaltered binding parameters, as illustrated with association of LC_T51A with LC_T94A, LC_S31A with HC_G54Y, or LC_T531 with HC_S53A.

Conversely, at all the other CDR positions, substitution of alanine for the original amino acid was found to induce a complete loss of binding or dramatically altered binding parameters. Position 101 of the heavy chain or positions 32 and 91 of the light chain are examples shown on FIGS. 16 and 17), A second set of variants consisted in testing more conservative mutations at some such positions. Doing that, we found that the following conservative substitution were neutral for antigen binding: Tyr for Phe at residue 30 of MAb2_VLg5, Phe for Tyr at residue 92 of the MAb2_VLg5, Ser for Ala at residue 98 of MAb2_VHg2 and Phe for Tyr at residue 100 of MAb2_VHg2 (shown on figures)

Example 7: Humanized Variants of MAb2 Drug Conjugates

Example 7.1: Production and Characterisation huMAb2-2-SPDB-DM4
Analytical Data:

MW(Ab)=147360 g/mol; MW(DM4)=780.38 g/mol
$\varepsilon_{280\ nm}$ (Ab)=201400; $\varepsilon_{280\ nm}$ (Ab)=71693
$\varepsilon_{280\ nm}$ (DM4)=5180; $\varepsilon_{280\ nm}$ (DM4)=26159

Under stirring, at RT, 19.4 mg of huMAb2-2 (C=5.1 mg/ml in PBS pH=7.4 buffer) are introduced in a vessel, followed by 0.375 ml of DMA and 0.0439 ml of nitro-SPDB linker solution (5.0 Eq-15 mM solution in DMA). Solution is vortexed for 30 sec and then slowly stirred at RT for 2 hours. An extra volume of 0.0044 ml of nitro-SPDB linker solution (5.0 Eq-15 mM solution in DMA) is added. After 2 hours at RT under magnetic stirring, 2 ml of PBS pH=7.5 buffer and 0.0702 ml of DM4 solution (15 mM solution in DMA) were successively added. After 2 hours at RT, crude reaction mixture is filtered on 0.45 μm filter and purified on HiPrep 26/10 desalting column (Sephadex G25, GE Healthcare), pre-conditioned with 1 CV of NaOH 1M, 2 CV of water and 2 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled and filtered on 0.22 μm filter.

10.3 ml of huMAb2-2-SPDB-DM4 conjugate (c=1.35 mg/ml) was thus obtained as a colorless clear solution. The conjugate is then analyzed for final drug load and monomeric purity: DAR (UV)=3.7; DAR (SEC)=3.6; RT=17.29 min; monomeric purity=97.9%.

Figure 12:
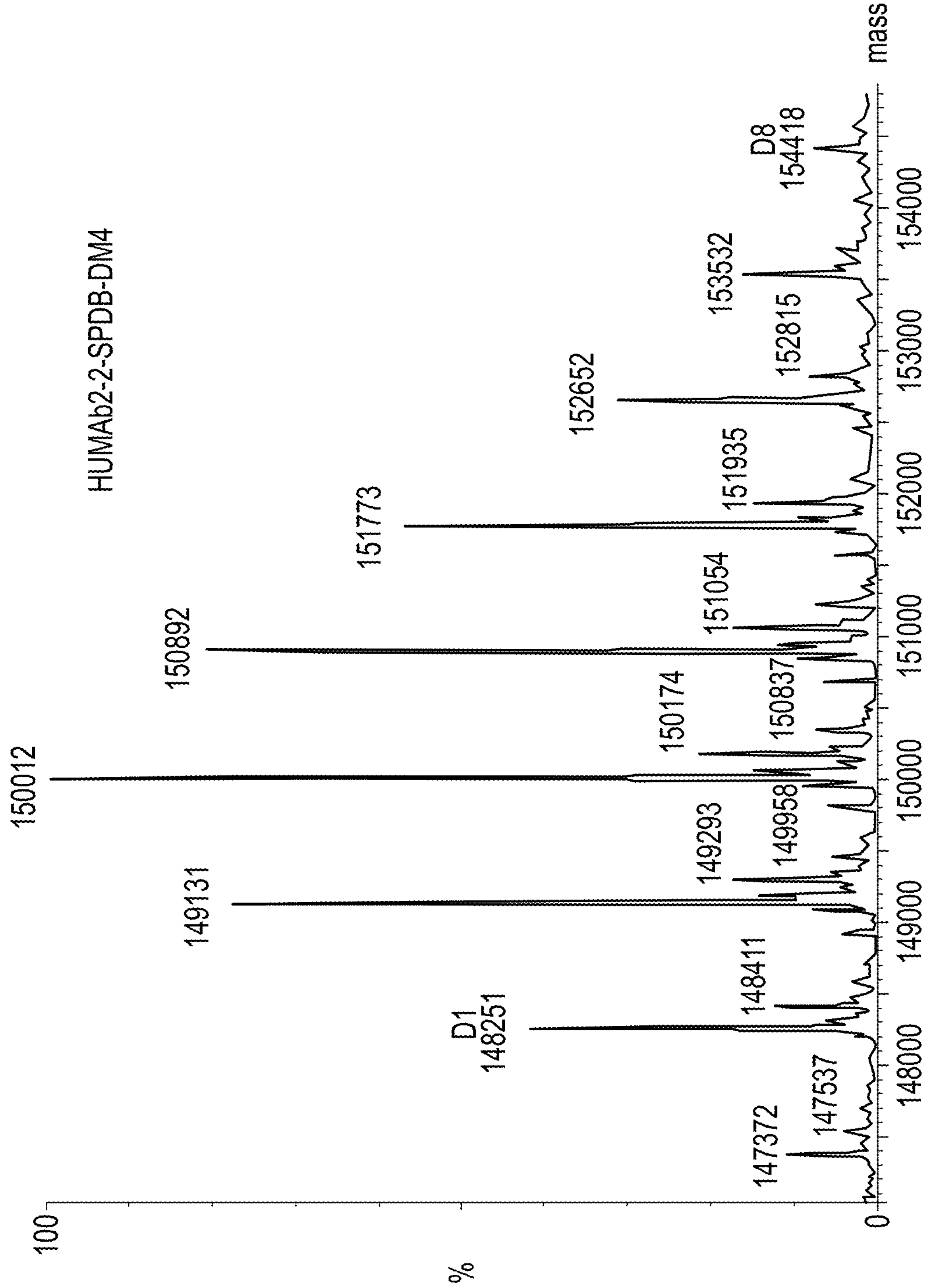
FIG. 12: HRMS analysis of huMAb2-2-SPDB-DM4 conjugate.

Result of HRMS analysis is shown on FIG. 12.

huMAb2-1-SPDB-DM4

Analytical Data:

MW(Ab)=147563 g/mol; MW(DM4)=780.38 g/mol $\varepsilon_{280\ nm}$(Ab)=201400; $\varepsilon_{252\ nm}$(Ab)=69669

$\varepsilon_{280\ nm}$(DM4)=5180; $\varepsilon_{252}$ nm(DM4)=26159

Under stirring, at RT, 3.8 ml of a solution of huMAb2-1 (C=5.08 mg/ml in PBS pH=7.4 buffer) are introduced in a vessel, followed by 0.341 ml of DMA and 0.0392 ml of nitro-SPDB linker solution (4.5 Eq-15 mM solution in DMA). Solution is vortexed for 30 sec and then slowly stirred at RT for 3 hours. An extra volume of 0.0087 ml of nitro-SPDB linker solution (1.0 Eq-15 mM solution in DMA) is added. After 2 hours at RT under magnetic stirring, 2.62 ml of PBS pH7.5 buffer, 0.254 ml of DMA and 0.076 ml of DM4 solution (15 mM solution in DMA) were successively added. After 1 hour at RT, crude reaction mixture is filtered on 0.45 μm filter and purified on HiPrep 26/10 desalting column (Sephadex G25, GE Healthcare), pre-conditioned with 1 CV of NaOH 1M, 2 CV of water and 2 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled and filtered on 0.22 μm filter.

9.5 ml of huMAb2-1-SPDB-DM4 conjugate (c=1.35 mg/ml) was thus obtained as a colorless clear solution. The conjugate is then analyzed for final drug load and monomeric purity: DAR (UV)=4.1; DAR (SEC)=4.0; RT=17.39 min; monomeric purity=96.7%.

Figure 13:
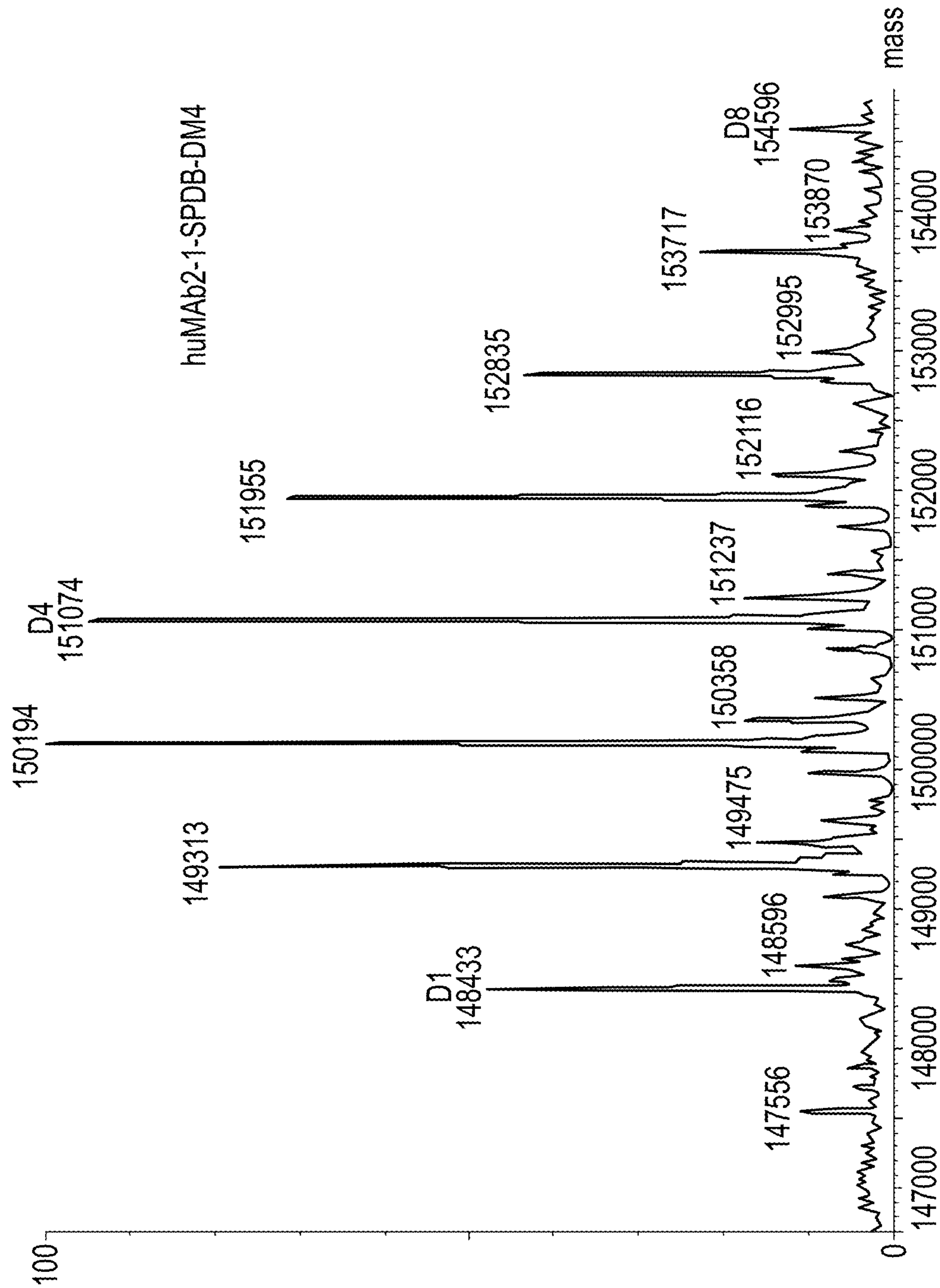
FIG. 13: HRMS analysis of huMAb2-1-SPDB-DM4 conjugate.

Result of HRMS analysis is shown on FIG. 13.

huMAb2-3-SPDB-DM4

Analytical Data:

MW(Ab)=147417 g/mol; MW(DM4)=780.38 g/mol $\varepsilon_{280\ nm}$(Ab)=201400; $\varepsilon_{252\ nm}$(Ab)=71451

$\varepsilon_{280\ nm}$(DM4)=5180; $\varepsilon_{252\ nm}$(DM4)=26159

Under stirring, at RT, 3.8 ml of a solution of huMAb2-3 (C=5.09 mg/ml in PBS pH=7.4 buffer) are introduced in a vessel, followed by 0.336 ml of DMA and 0.0437 ml of nitro-SPDB linker solution (5 Eq-15 mM solution in DMA). Solution is vortexed for 30 sec and then slowly stirred at RT for 3 hours. An extra volume of 0.0035 ml of nitro-SPDB linker solution (0.4 Eq-15 mM solution in DMA) is added. After 1 hour at RT under magnetic stirring, 2.60 ml of PBS pH7.5 buffer, 0.248 ml of DMA and 0.074 ml of DM4 solution (15 mM solution in DMA) were successively added. After 1 hour at RT, crude reaction mixture is filtered on 0.45 μm filter and purified on HiPrep 26/10 desalting column (Sephadex G25, GE Healthcare), pre-conditioned with 1 CV of NaOH 1M, 2 CV of water and 2 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled and filtered on 0.22 μm filter.

11 ml of huMAb2-3-SPDB-DM4 conjugate (c=1.08 mg/ml) was thus obtained as a colorless clear solution. The conjugate is then analyzed for final drug load and monomeric purity: DAR (UV)=3.9; DAR (SEC)=3.8; RT=17.44 min; monomeric purity=98.4%.

Figure 14:
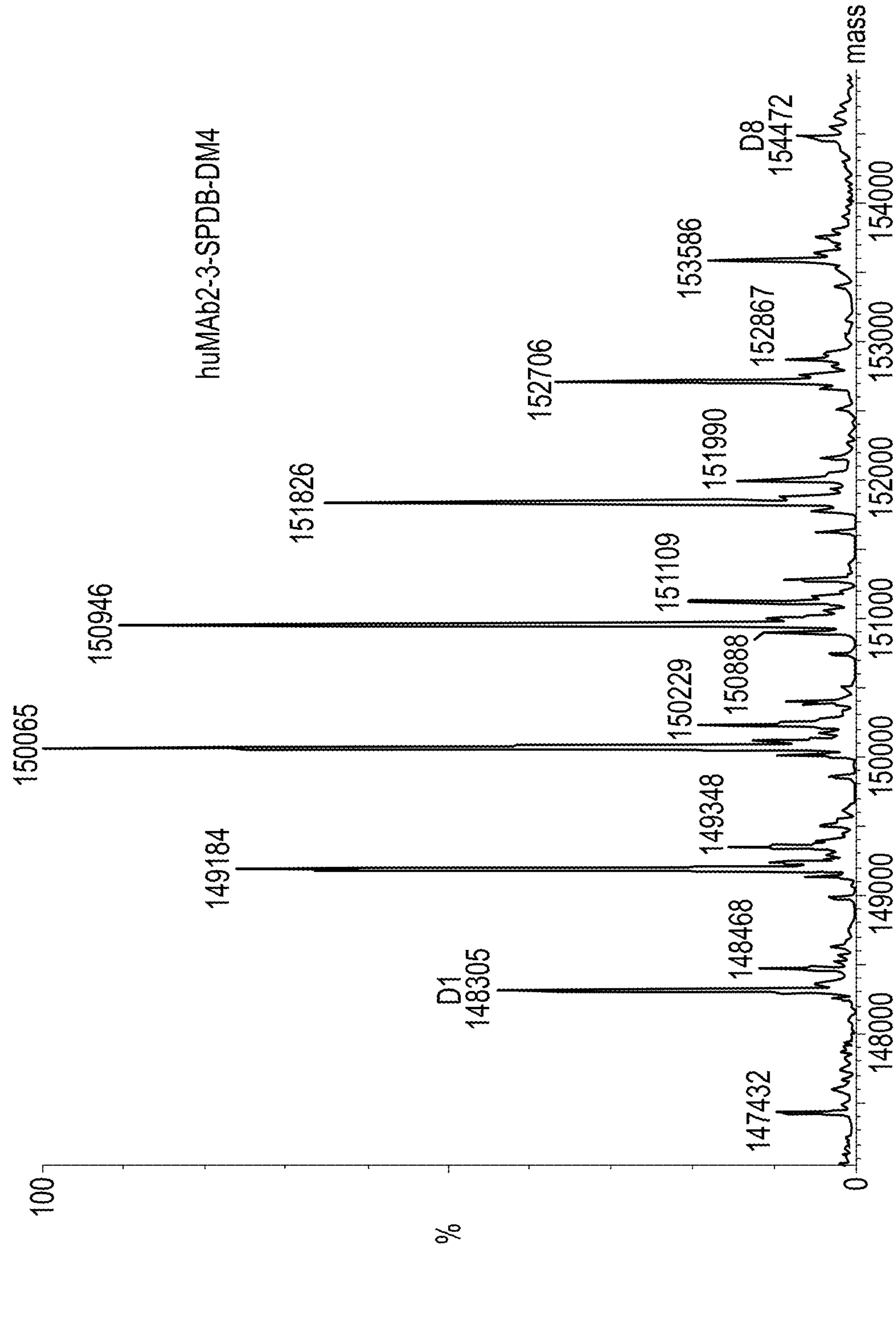
FIG. 14: HRMS analysis of huMAb2-3-SPDB-DM4 conjugate.

Result of HRMS analysis is shown on FIG. 14.

huMAb2-4-SPDB-DM4

Analytical Data:

MW(Ab)=147628 g/mol; MW(DM4)=780.38 g/mol $\varepsilon_{280\ nm}$(Ab)=201400; $\varepsilon_{252\ nm}$(Ab)=70628

$\varepsilon_{280\ nm}$(DM4)=5180; $\varepsilon_{252\ nm}$(DM4)=26159

Under stirring, at RT, 3.8 ml of a solution of huMAb2-4 (C=5.09 mg/ml in PBS pH=7.4 buffer) are introduced in a vessel, followed by 0.345 ml of DMA and 0.0448 ml of nitro-SPDB linker solution (5 Eq-15 mM solution in DMA). Solution is vortexed for 30 sec and then slowly stirred at RT for 3 hours. An extra volume of 0.0027 ml of nitro-SPDB linker solution (0.3 Eq-15 mM solution in DMA) is added. After 1 hour at RT under magnetic stirring, 2.70 ml of PBS pH7.5 buffer, 0.263 ml of DMA and 0.075 ml of DM4 solution (15 mM solution in DMA) were successively added. After 1 hour at RT, crude reaction mixture is filtered on 0.45 μm filter and purified on HiPrep 26/10 desalting column (Sephadex G25, GE Healthcare), pre-conditioned with 1 CV of NaOH 1M, 2 CV of water and 2 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled and filtered on 0.22 μm filter.

11 ml of huMAb2-4-SPDB-DM4 conjugate (c=1.23 mg/ml) was thus obtained as a colorless clear solution. The conjugate is then analyzed for final drug load and monomeric purity: DAR (UV)=3.8; DAR (SEC)=3.8; RT=17.53 min; monomeric purity=99.3%.

Figure 15:
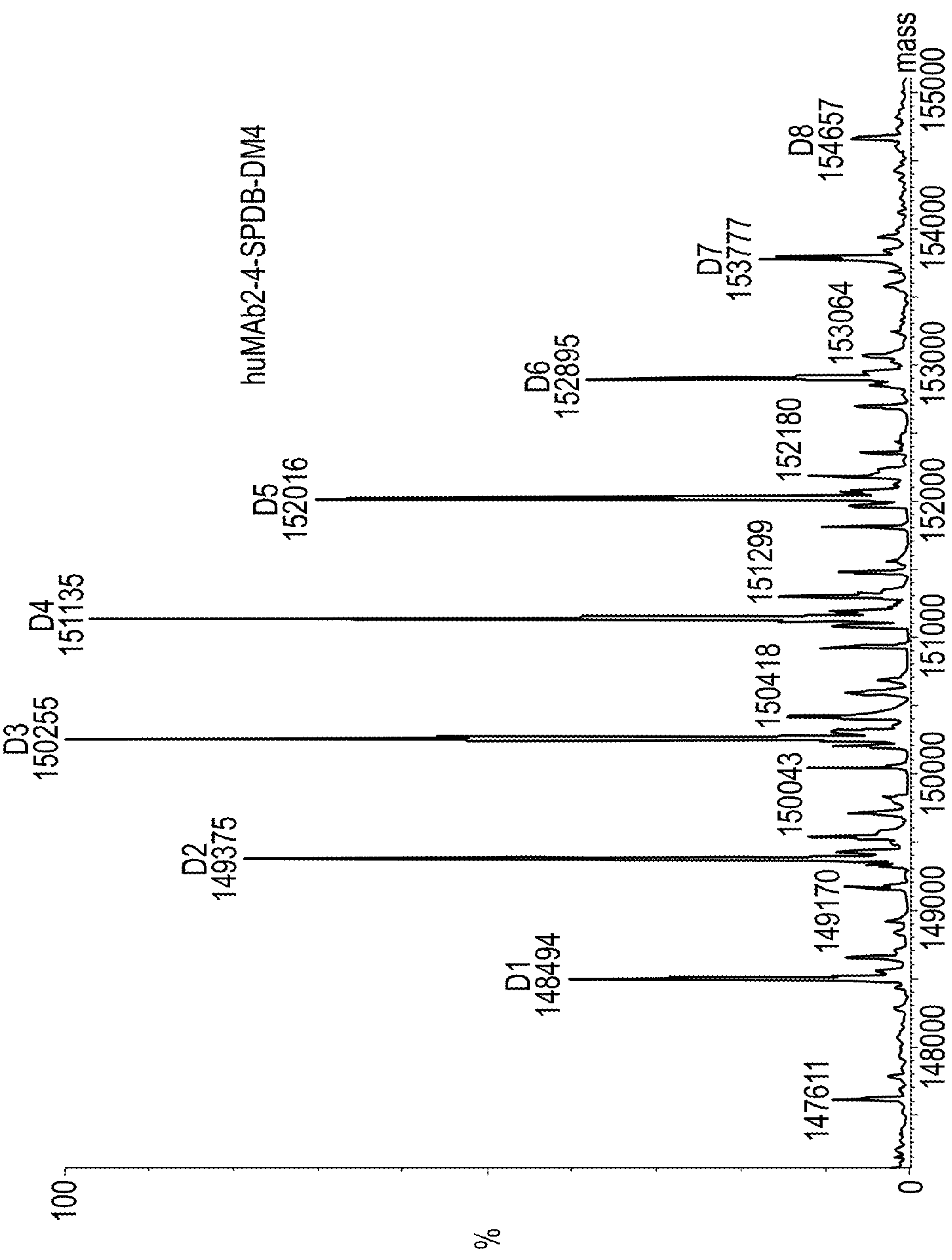
FIG. 15: HRMS analysis of huMAb2-4-SPDB-DM4 conjugate.

Result of HRMS analysis is shown on FIG. 15.

Example 7.2: In Vitro Cytotoxicity

Material and Methods

The effect of the anti-CEACAM5 maytansinoid conjugates on tumor cell viability was assessed as described in example 3.4.

Results

TABLE 19

Cytotoxic activities of the CEACAM5-specific humanized ADCs on CEACAM5 + MKN45 cell line

| ADC | Cytotoxic activity $IC_{50}$ (nM) ± StD |
|---|---|
| chMAb2-SPDB-DM4 | 0.24 ± 0.02 |
| huMAb2-1-SPDB-DM4 | 0.18 ± 0.01 |
| huMAb2-2-SPDB-DM4 | 0.23 ± 0.02 |
| huMAb2-3-SPDB-DM4 | 0.16 ± 0.01 |
| Irrelevant ADC | 8.52 ± 2.07 |

These chMAb2-SPDB-DM4, huMAb2-1-SPDB-DM4, huMAb2-2-SPDB-DM4, and huMAb2-3-SPDB-DM4 conjugates and the DM4 irrelevant conjugate showed in vitro cytotoxic activities on MKN45 cells in culture with an IC50 of 0.24, 0.18, 0.23, 0.16, and 8.52 nM respectively. The cytotoxic activities of the anti-CEACAM5 conjugates was 53 to 35 fold lower than the measured activity of the irrelevant DM4 conjugate indicating CEACAM5-mediated cytotoxic activities of the anti-CEACAM5 conjugates.

Example 73: In Vivo Efficacy Against Primary Colon CR-IGR-034P Tumors Implanted s.c. In Female CD-1 Nude Mice

Material and Method

Two humanized sequences as conjugates huMAb2-3-SPDB-DM4 and huMAb2-4-SPDB-DM4 were evaluated at 4-dose levels compared to the chMAb2-SPDB-DM4, against measurable primary colon CR-IGR-034P tumors implanted s.c. in female CD-1 nude mice. Control groups were left untreated. The doses conjugates were given in mg/kg. They were administered at 10, 5, 2.5 and 1.25 mg/kg by an intravenous (IV) bolus injection, on day 19 after tumor implantation.

Toxicity and efficacy evaluation were performed as reported in example 5.

Results

Figure 5:
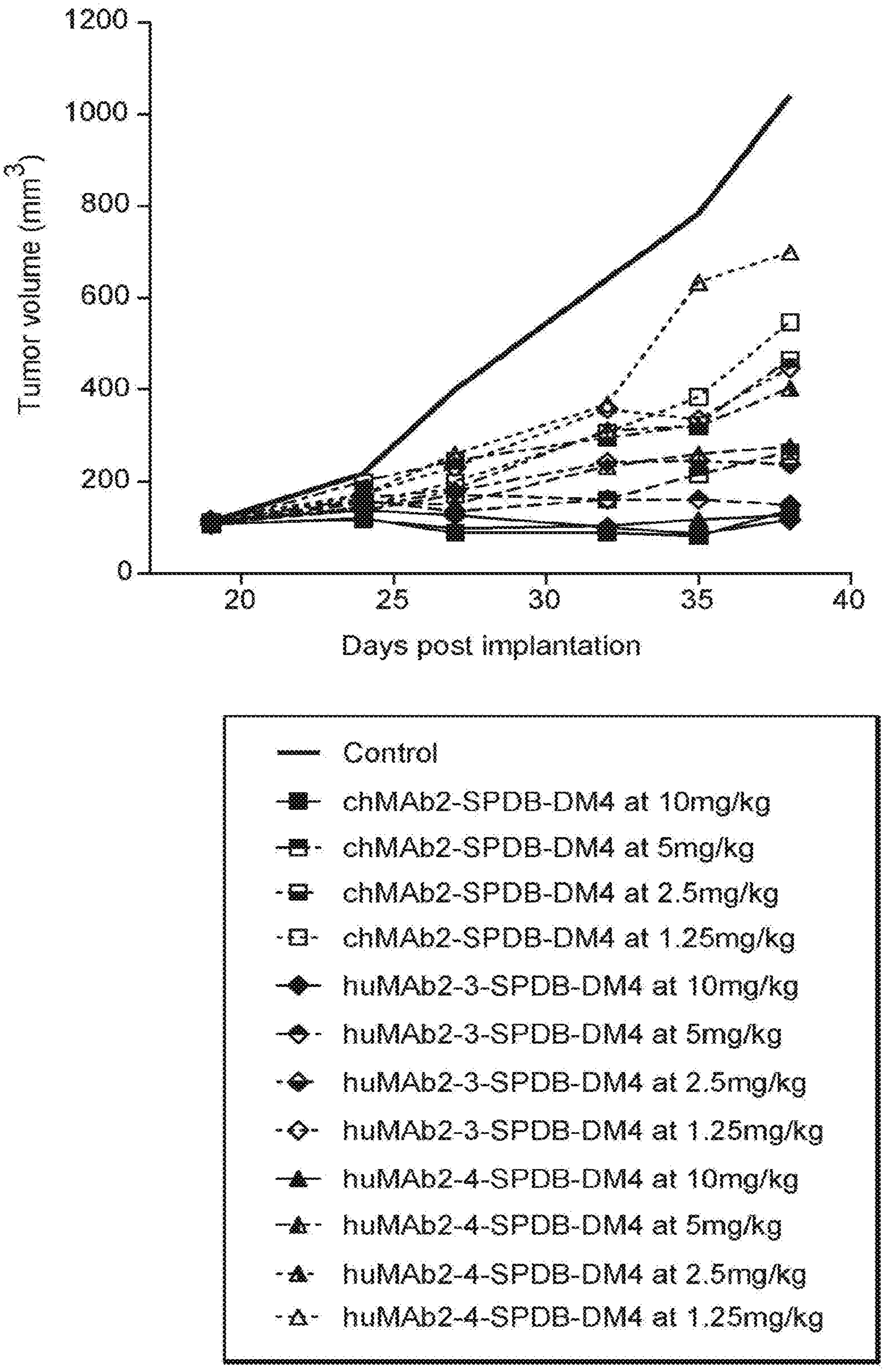
FIG. 5: Evaluation of the anti-tumor activity of huMAb2-3-SPDB-DM4, huMAb2-4-SPDB-DM4 and chMAb2-SPDB-DM4 conjugates against primary human colon adenocarcinoma CR-IGR-034P in SCID female mice.

The results are presented in FIG. 5 and Table 20 (below).

Using a single administration schedule at 1.25, 2.5, 5 and 10 mg/kg, all conjugates tested in this study did not induce toxicity.

huMAb2-4-SPDB-DM4 and chMAb2-SPDB-DM4 were highly active at 10 mg/kg with ΔT/ΔC of −4% ($p<0.0001$ vs control) and tumor regression of 21 and 19%, respectively, active at 5 mg/kg with ΔT/ΔC of 12 ($p=0.0105$ vs control) and 17% ($p=0.0417$ vs control), respectively and marginally active at 2.5 mg/kg with ΔT/ΔC of 36 and 37% (ns vs control), respectively, and inactive at 1.25 mg/kg. huMAb2-3-SPDB-DM4 was highly active at 10 mg/kg with ΔT/ΔC of −6% ($p<0.0001$ vs control) and tumor regression of 31%, very active at 5 mg/kg with ΔT/ΔC of 4% ($p<0.0001$ vs control), active at 2.5 mg/kg with ΔT/ΔC of 12 ($p=0.0322$ vs control) and marginally active at 1.25 mg/kg ΔT/ΔC of 34% (ns vs control).

From these results, both humanized sequences huMAb2-3-SPDB-DM4 and huMAb2-4-SPDB-DM4 were usable to develop a therapeutic ADC. huMAb2-3-SPDB-DM4 was the best of the both sequence.

Example 7.4: In Vivo Efficacy Against Primary Stomach STO-IND-006 Tumors Implanted s.c. In Female SCID Mice Material and Method The humanized conjugate huMAb2-3-SPDB-DM4 was evaluated at 3-dose levels against measurable primary stomach STO-IND-006 tumors implanted s.c. in female SCID mice. Control groups were left untreated. The doses conjugates were given in mg/kg. They were administered at 10, 5 and 2.5 mg/kg by an intravenous (IV) bolus injection, on day 27 after tumor implantation.

Toxicity and efficacy evaluation were performed as reported in example 5.

Results

Using a single administration schedule at 2.5, 5 and 10 mg/kg, huMAb2-3-SPDB-DM4 did not induce toxicity.

Figure 6:
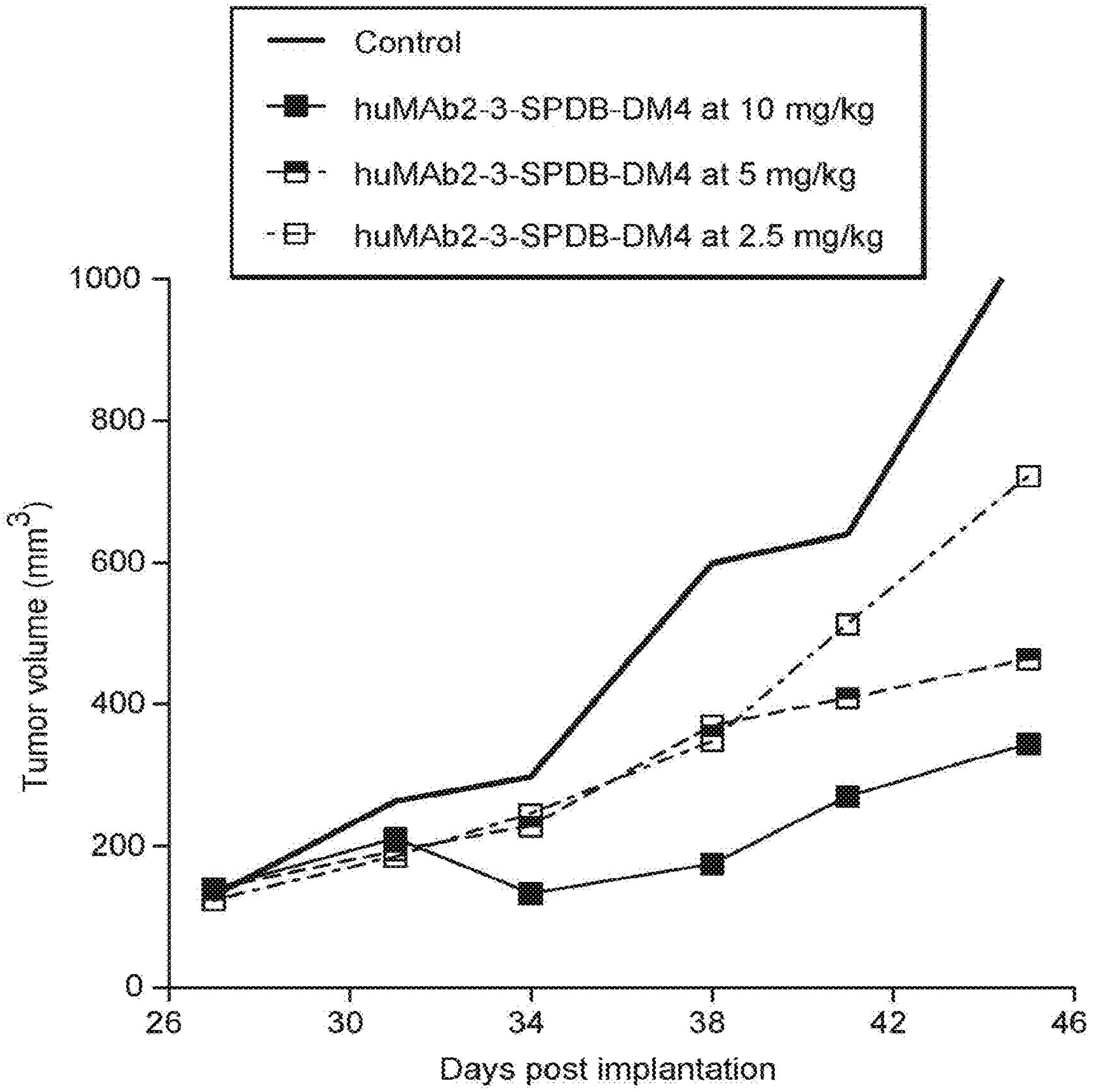
FIG. 6: Evaluation of the anti-tumor activity of huMAb2-3-SPDB-DM4 conjugate against primary human stomach adenocarcinoma STO-IND-006 in SCID female mice.

As shown on FIG. 6 and in Table 21, huMAb2-3-SPDB-DM4 was very active at 10 mg/kg with ΔT/ΔC of 7% ($p<0.0001$ vs control), active at 5 mg/kg with ΔT/ΔC of 36% ($p=0.0281$ vs control) and inactive at 2.5 mg/kg.

TABLE 20

Evaluation of the anti-tumor activity of huMAb2-3-SPDB-DM4 and huMAb2-4-SPDB-DM4 and chMAb2-SPDB-DM4 conjugates against primary human colon adenocarcinoma CR-IGR-034P in CD-1 female mice.

| Agent[1] | Route/ Dosage in mL/kg | Dosage in mg/kg per injection | Schedule in days | Drug death (Day) | Average body weight change in % per mouse at nadir (day of nadir) | Median ΔT/ΔC in % (day) | Median % of regression (day) | Regressions Partial | Regressions Complete | Biostatistic p value[2] | Comments |
|---|---|---|---|---|---|---|---|---|---|---|---|
| chMAb2-SPDB-DM4 | IV (10 mL/Kg) | 10 | 19 | 0/6 | -7.3 (D20) | -4 (D32) | 19 (D32) | 2/6 | 0/6 | <0.0001 | Highly active |
| | | 5 | 19 | 0/6 | -4.5 (D45) | 12 (D32) | — | 0/6 | 0/6 | =0.0105 | Active |
| | | 2.5 | 19 | 0/6 | -4.2 (D20) | 36 (D32) | — | 0/6 | 0/6 | ns | Marginally active |
| | | 1.25 | 19 | 0/6 | -4.1 (D20) | 42 (D32) | — | 0/6 | 0/6 | ns | Inactive |
| huMAb2-3-SPDB-DM4 | IV (10 mL/Kg) | 10 | 19 | 0/6 | -4.3 (D27) | -6 (D35) | 31 (D35) | 2/6 | 0/6 | <0.0001 | Highly active |
| | | 5 | 19 | 0/6 | -3.3 (D20) | 4 (D38) | — | 0/6 | 0/6 | <0.0001 | Very active |
| | | 2.5 | 19 | 0/6 | -5.4 (D45) | 12 (D38) | — | 0/6 | 0/6 | =0.0322 | Active |
| | | 1.25 | 19 | 0/6 | -3.0 (D27) | 34 (D38) | — | 0/6 | 0/6 | ns | Marginally active |
| huMAb2-4-SPDB-DM4 | IV (10 mL/Kg) | 10 | 19 | 0/6 | -3.7 (D23) | -4 (D35) | 21 (D35) | 2/6 | 0/6 | <0.0001 | Very active |
| | | 5 | 19 | 0/6 | -3.2 (D27) | 17 (D38) | — | 0/6 | 0/6 | =0.0417 | Very active |
| | | 2.5 | 19 | 0/6 | -3.4 (D20) | 37 (D38) | — | 0/6 | 0/6 | ns | Marginally active |
| | | 1.25 | 19 | 0/6 | -2.8 (D27) | 50 (D38) | — | 0/6 | 0/6 | ns | Inactive |
| Control | — | — | 19 | — | -3.9 (D27) | — | — | — | — | — | — |

[1]drug formulation: HGS (10 mM Histidine, 130 mM Glycine, 5% v/v Sucrose, 0.01% Tween80) pH7.4;

[2]p-value: Dunnett's test versus control after 2-way Anova with repeated measures on rank transformed changes of tumour volume from baseline;

ns: no significant

TABLE 21

Evaluation of the anti-tumor activity of huMAb2-3-SPDB-DM4 conjugates against primary human stomach adenocarcinoma STO-IND-006 in SCID female mice

| Agent[1] | Route/ Dosage in mL/kg | Dosage in mg/kg per injection | Schedule in days | Drug death (Day) | Average body weight change in % per mouse at nadir (day of nadir) | Median ΔT/ΔC in % (day) | Median % of regression (day) | Regressions Partial | Regressions Complete | Biostatistic p value[2] | Comments |
|---|---|---|---|---|---|---|---|---|---|---|---|
| huMAb2-3-SPDB-DM4 | IV (10 mL/Kg) | 10 | 27 | 0/6 | -10.5 (D45) | 7 (D34) | — | 0/6 | 0/6 | <0.0001 | Very active |
| | | 5 | 27 | 0/6 | -8.4 (D45) | 36 (D45) | — | 0/6 | 0/6 | =0.0281 | Active |
| | | 2.5 | 27 | 0/6 | -5.8 (D45) | 50 (D38) | — | 0/6 | 0/6 | ns | Inactive |
| Control | — | — | 27 | — | -2.5 (D38) | — | — | — | — | — | — |

[1]drug formulation: HGS (10 mM Histidine, 130 mM Glycine, 5% v/v Sucrose, 0.01% Tween80) pH7.4;

[2]p-value: Dunnett's test versus control after 2-way Anova with repeated measures on rank transformed changes of tumour volume from baseline;

ns: no signiiicant

Example 7.5: In Vivo Efficacy Against Primary Lung LUN-NIC-0014 Tumors Implanted s.c. In Female SCID Mice

Material and Method

The humanized conjugate huMAb2-3-SPDB-DM4 was evaluated at 3-dose levels against measurable primary lung LUN-NIC-0014 tumors implanted s.c. in female SCID mice. Control groups were left untreated. The doses conjugates were given in mg/kg. It was administered at 10, 5 and 2.5 mg/kg by an intravenous (IV) bolus injection, on day 29 after tumor implantation.

Toxicity and efficacy evaluation were performed as reported in example 5.

Results

Using a single administration schedule at 2.5, 5 and 10 mg/kg, huMAb2-3-SPDB-DM4 did not induce toxicity.

Figure 18:
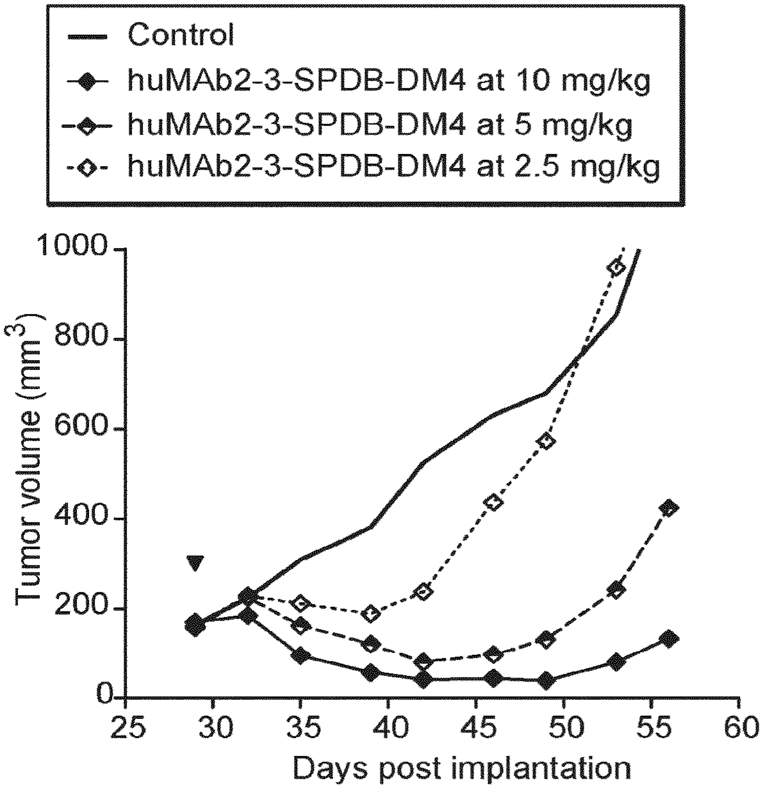
FIG. 18: Evaluation of the anti-tumor activity of huMAb2-3-SPDB-DM4 conjugate against primary human lung adenocarcinoma LUN-NIC-0014 in SCID female mice.

As shown on FIG. 18 and in Table 22, huMAb2-3-SPDB-DM4 was highly active at 10 and 5 mg/kg with ΔT/ΔC inferior to 0% ($p<0.0001$ vs control) and tumor regression of 67 and 57% respectively and active at 2.5 mg/kg with ΔT/ΔC of 12% ($p=0.0363$ vs control).

Example 7.6: In Vivo Efficacy Against Primary Colon CR-IGR-034P Tumors Implanted s.c. in Female SCID Mice

Material and Method

Three conjugates, constituted by the humanized huMAb2-3 conjugated to the DM4 through two different linkers (SPDB and sulfo-SPDB), were evaluated at 2-dose levels against measurable primary colon CR-IGR-034P tumors implanted s.c. in female SCID mice. Control groups were left untreated. The doses conjugates were given in mg/kg. They were administered at 5 and 2.5 mg/kg by an intravenous (IV) bolus injection, on day 19 after tumor implantation.

Toxicity and efficacy evaluation were performed as reported in example 5.

Results

Using a single administration schedule at 2.5 and 5 mg/kg, huMAb2-3-SPDB-DM4 and huMAb2-3-sulfo-SPDB-DM4 did not induce toxicity.

Figure 19:
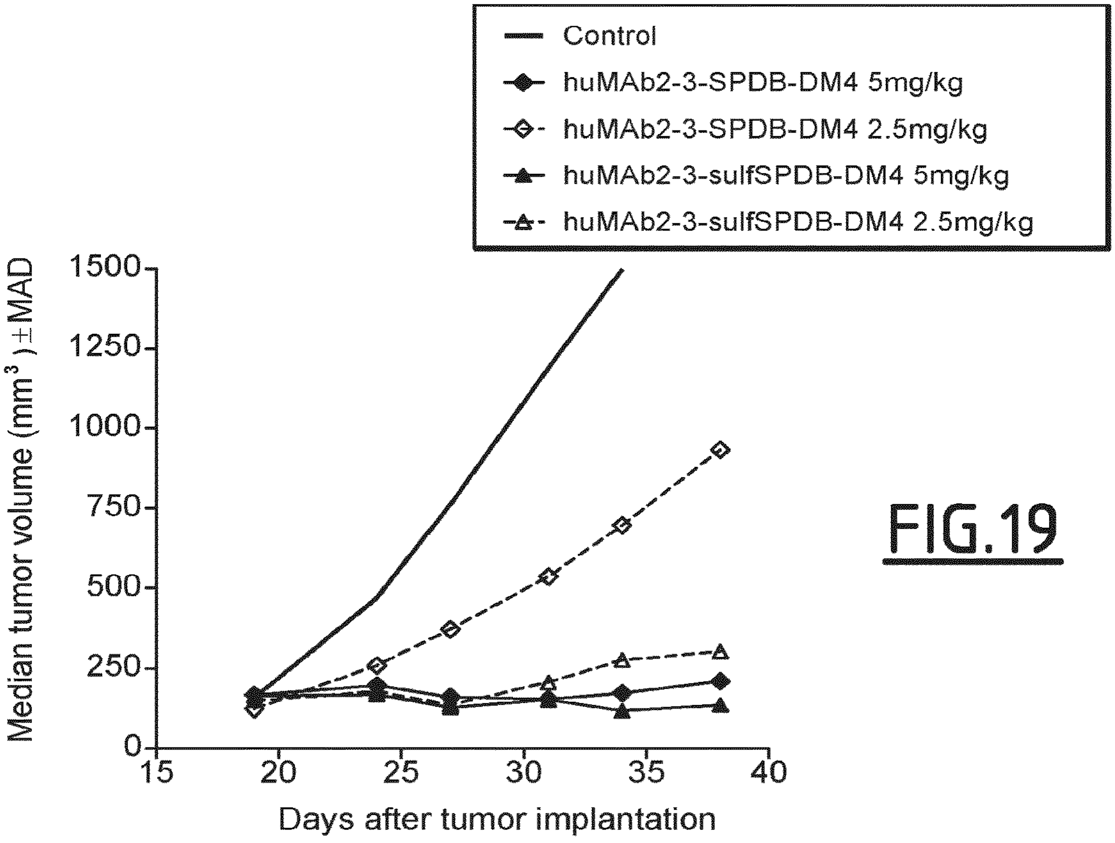
FIG. 19: Evaluation of the anti-tumor activity of huMAb2-3-SPDB-DM4 and huMAb2-3-sulfo-SPDB-DM4 conjugates against primary human colon adenocarcinoma CR-IGR-034P in CD1 nude female mice.

As shown on FIG. 19 and in Table 23, huMAb2-3-SPDB-DM4 was active at 5 and 2.5 mg/kg with ΔT/ΔC of 12% and

TABLE 22

Evaluation of the anti-tumor activity of huMAb2-3-SPDB-DM4 conjugate against primary human stomach adenocarcinoma LUN-NIC-0014 in SCID female mice

| Agent[1] | Route/ Dosage in mL/kg | Dosage in mg/kg per injection | Schedule in days | Drug death (Day) | Average body weight change in % per mouse at nadir (day of nadir) | Median ΔT/ΔC in % (day 42) | Median % of regression (day 42) | Regressions Partial | Regressions Complete | Biostatistic p value[2] | Comments |
|---|---|---|---|---|---|---|---|---|---|---|---|
| huMAb2-3-SPDB-DM4 | IV (10 mL/Kg) | 10 | 29 | 0/6 | +1.7 (D32) | <0 | 67 | 5/6 | 2/6 | <0.0001 | Highly active |
| | | 5 | 29 | 0/6 | -1.1 (D36) | <0 | 57 | 4/6 | 0/6 | <0.0001 | Highly active |
| | | 2.5 | 29 | 0/6 | -0.5 (D32) | 12 (D39) | — | 0/6 | 0/6 | 0.0363 (D39) | Active |
| Control | — | — | — | — | -0.1 (D34) | — | — | — | — | — | — |

[1]drug formulation: HGS (10 mM Histidine, 13 0mM Glycine, 5% v/v Sucrose, 0.01% Tween80) pH7.4;

[2]p-value: Dunnet's test versus control after 2-way Anova with repeated measures on rank transformed changes of tumour volume from baseline.

40%, respectively (p<0.0001 vs control), huMAb2-3-sulfo-SPDB-DM4 was highly active at 5 mg/kg with ΔT/ΔC inferior to 0% (p<0.0001 vs control) and a tumor regression of 12% and active at 2.5 mg/kg with ΔT/ΔC of 1% (p<0.0001 vs control).

TABLE 23

Evaluation of the anti-tumor activity of huMAb2-3-SPDB-DM4 and huMAb2-4-SPDB-DM4 conjugates against primary human colon adenocarcinoma CR-IGR-034P in CD-1 female mice

| Agent[1] | Route/ Dosage in mL/kg | Dosage in mg/kg per injection | Schedule in days | Drug death (Day) | Average body weight change in % per mouse at nadir (day of nadir) | Median ΔT/ΔC in % (day 34) | Median % of regression (day 34) | Regressions Partial | Regressions Complete | Biostatistic p value[2] | Comments |
|---|---|---|---|---|---|---|---|---|---|---|---|
| huMAb2-3-SPDB-DM4 | IV (10 mL/Kg) | 5 | 19 | 0/6 | +1.6 (D20) | 12 | — | 0/6 | 0/6 | <0.0001 | Very |
| | | 2.5 | 19 | 0/6 | -1.5 (D38) | 40 | — | 0/6 | 0/6 | <0.0001 | Marginally active |
| huMAb2-3-sulfo-SPDB-DM4 | IV (10 mL/Kg) | 5 | 19 | 0/6 | +0.1 (D20) | <0 | 12 | 0/6 | 0/6 | <0.0001 | Highly active |
| | | 2.5 | 19 | 0/6 | +0.7 (D20) | 11 | — | 0/6 | 0/6 | <0.0001 | Active |
| | | 2.5 | 19 | 0/6 | +2.5 (D34) | 66 | — | 0/6 | 0/6 | <0.0306 | Inactive |
| Control | — | — | — | — | + 0.5 (D34) | — | — | — | — | — | — |

[1]drug formulation: HGS (10 mM Histidine, 130 mM Glycine, 5% v/v Sucrose, 0.01% Tween80) pH7.4;

[2]p-value : Dunnet's test versus control after 2-way Anova wfth repeated measures on rank transformed changes of tumour volume from baseline.

Example 8: Development of an Immunohistochemistry (IHC) Protocol Dedicated to the Detection of Human and Monkey CEACAM5 Protein in Formalin-Fixed and Paraffin Embedded (FFPE) Tissues

Materials and Methods

Tissues

FFPE tissue microarrays (TMA, Table 24) were used as source of human (tumor and non tumor) as well as cynomolgus monkey (normal) tissues.

TABLE 24 formalin-fixed and paraffin embedded tissue micro-arrays used as tissue sources

| Reference | Provider | Description |
|---|---|---|
| ASM 221 | Pantom ics | Cyno monkey, 22 organs, 22 samples |
| CyFDA | US Biomax | Cyno monkey normal tissue microarray, 33 organs, taken from 6 normal individual (99 cases) |
| COC1501 | Pantomics | Colon cancer tissue array, 150 cores from normal/benign (5 cases) and cancer (70 cases) tissues |
| COC1502 | Pantomics | Colon cancer tissue array, 150 cores from normal/benign (5 cases) and cancer (70 cases) tissues |
| COC1503 | Pantomics | Colon cancer tissue array, 150 cores from normal/benign (5 cases) and cancer (70 cases) tissues |
| MTU951 | Pantomics | 40 types of tumors covering benign, malignant and metastatic entities of 27 anatomic sites |
| LUC1501 | Pantomics | Lung cancer tissue array, 150 cores from normal/benign (5 cases) and cancer (70 cases) tissues |
| LUC1502 | Pantomics | Lung cancer tissue array, 150 cores from normal/benign (5 cases) and cancer (70 cases) tissues |
| LUC1503 | Pantomics | Lung cancer tissue array, 150 cores from normal/benign (5 cases) and cancer (70 cases) tissues |
| MNO961 | Pantomics | 35 types of normal tissues based on the FDA recommendation for antibody cross-reactivity testing. |
| MNO661 | Pantomics | 33 types of normal tissues based on the FDA recommendation for antibody cross-reactivity testing. |
| MNO341 | Pantomics | 33 types of normal tissues based on the FDA recommendation for antibody cross-reactivity testing. |
| PAC481 | Pantomics | Pancreatic cancer tissue array contains 20 cases of cancers and 4 cases of normal and non-malignant pancreatic tissues |

TABLE 24-continued

| formalin-fixed and paraffin embedded tissue micro-arrays used as tissue sources | | |
|---|---|---|
| Reference | Provider | Description |
| CC4 | Superbiochips | 59 cores array including 59 cases of lung cancer |
| A218(III) | Accumax | Esophagus cancer tissue array contains 40 cases of tumors and 8 non-neoplastic |
| A219(II) | Accumax | Head&Neck cancer tissue array contains 45 cases of tumors and 8 non-neoplastic |
| A213(I) | Accumax | Ovary cancer tissue array contains 43 cases of tumors and 8 non-neoplastic |
| A301(IV) | Accumax | Various cancer tissues array with corresponding normal tissues (30 cancer cases, 30 non-neoplastic cases) |
| A103(V) | Accumax | Various normal tissues array in duplicate (45 cases) |
| MAN2 | Superbiochips | 59 cores array including 9 or 10 normal cases of stomach, esophagus, lung, colorectal, thyroid and kidney |
| MA2 | Superbiochips | 59 cores array including 9 or 10 cases of stomach, esophagus, lung, colorectal, thyroid and kidney cancers |
| MBN4 | Superbiochips | 59 cores array including 9 or 10 normal cases of breast, liver, urinary bladder, ovary, pancreas, prostate |
| MB4 | Superbiochips | 59 cores array including 9 or 10 cases of breast, liver, urinary bladder, ovary, pancreas, prostate cancers |
| MCN4 | Superbiochips | 59 cores array including 9 or 10 normal cases of endometrium, gallbladder, larynx, uterine cervix, skin |
| MC4 | Superbiochips | 59 cores array including 9 or 10 cases of endometrium, gallbladder, larynx, cervix, lymphoma, melanoma cancers |
| CJ1 | Superbiochips | 59 cores array including 59 cases of ovary cancer |
| CDN3 | Superbiochips | 59 cores array including 59 cases of normal colon and rectum |
| CCN2 | Superbiochips | 59 cores array including 59 cases of normal lung (matching CC4) |
| BB5 | Superbiochips | 60 cores, 30 human various cancer types |
| AA9 | Superbiochips | 59 cores array including 59 cases of normal organs |
| TMAhu3a | Asterand | Various cancer tissues array (76 cases) |
| STC1501 | Pantomics | Stomach cancer tissue array, 150 cores including 75 cases of normal, reactive and canceroustissues of the stomach |
| STC1502 | Pantomics | Stomach cancer tissue array, 150 cores including 75 cases of normal, reactive and canceroustissues of the stomach |
| STC1503 | Pantomics | Stomach cancer tissue array, 150 cores including 75 cases of normal, reactive and canceroustissues of the stomach |
| STC481 | Pantomics | Stomach cancer tissue array, 16 cases, 48 cores, one normal paired with two tumor tissue cores from each patient |

Antibodies

MAb2 was used as primary mouse anti-human CEACAM5 monoclonal antibody. A biotin-conjugated goat anti-mouse IgG1 (γ1 chain specific) (reference 1070-08, batch L4309-X761, Southern Biotech, USA) was used as secondary antibody.

Immunostaining

Antigen retrieval procedure was applied with Cell Conditioning 1 (CC1) buffer at 95° C. for 8 min and then at 100° C. for 28 min. After endogen biotins blocking step, slides were incubated with the primary anti-antibody diluted in phosphate buffer saline (PBS) at 5 μg/mL for 2 hours at 24° C. The secondary antibody biotin-conjugated goat anti-mouse was incubated at 24° C. for 32 minutes at 0.5 μg/mL. Immunostaining was done with 3,3-diaminobenzidine tetrahydrochloride (DAB) from DABMap™ chromogenic detection kit (760-124, Ventana Medical Systems, Inc, USA) according to manufacturer's recommendations. A couterstaining step was done with hematoxylin (760-2037, Ventana Medical Systems, Inc, USA) and bluing reagent was applied (760-2037, Ventana Medical Systems, Inc, USA). Stained slides were dehydrated and coverslipped with CYTOSEAL™ XYL (8312-4, Richard-Allan Scientific, USA).

IHC Scoring

Immunostained slides were scanned using the ScanScope XT system (Aperio Technologies, Vista, CA). Digitized images were captured using the ImageScope software (version 10.2.2.2319, Aperio Technologies) at ×20 magnification.

Staining evaluation included the histologic site of reactivity, main type of reactive cell, staining intensity and cell staining frequency. The negative samples were scored as 0+. The positive samples were scored with a scale of intensity from 1+ to 4+. Ranges of intensities were described as weak ]0;2+[, moderate [2+;3+[and strong [3+;4+]. Cell frequency was the percentage of immunostained cells and was estimated by the histologist observation as a median by sample. The cell frequency was ordered in 5 categories of proportion score: 1 (0-5%), 2 (6-25%), 3 (26-50%), 4 (51-75%) and 5 (76-100%).

For tumors, a global expression score was adapted from the Allred score (AS) (Mohsin S, Weiss H, Havighurst T, Clark G M, Berardo M, Roanh L D, et al. Progesterone receptor by immunohistochemistry and clinical outcome in breast cancer: a validation study. Mod. Pathol. 2004; 17:1545-1554). This AS was obtained by adding the intensity and the proportion scores to obtain a total score that ranged from 0-9. The AS was reported as a percent of the maximum global score and ranged in 5 categories: very low (0-25%), weak (26-50%), moderate (51-75%), and high (76-100%). The prevalence was defined as the percent of positive cases for the indication Descriptive Statistical Analysis Descriptive statistics were calculated with Microsoft Excel 2003 software. For each indication, number of cases, positive cases number, prevalence, intensity score median, frequency median, Allred score mean, intensity range, frequency range and Allred score range were described.

Example 8.1: Use of an Anti-CEACAM5 Monoclonal Antibody for Evaluation of CEACAM5 Protein in FFPE Human Tumors by Immunohistochemistry (IHC)

Figure 1C:
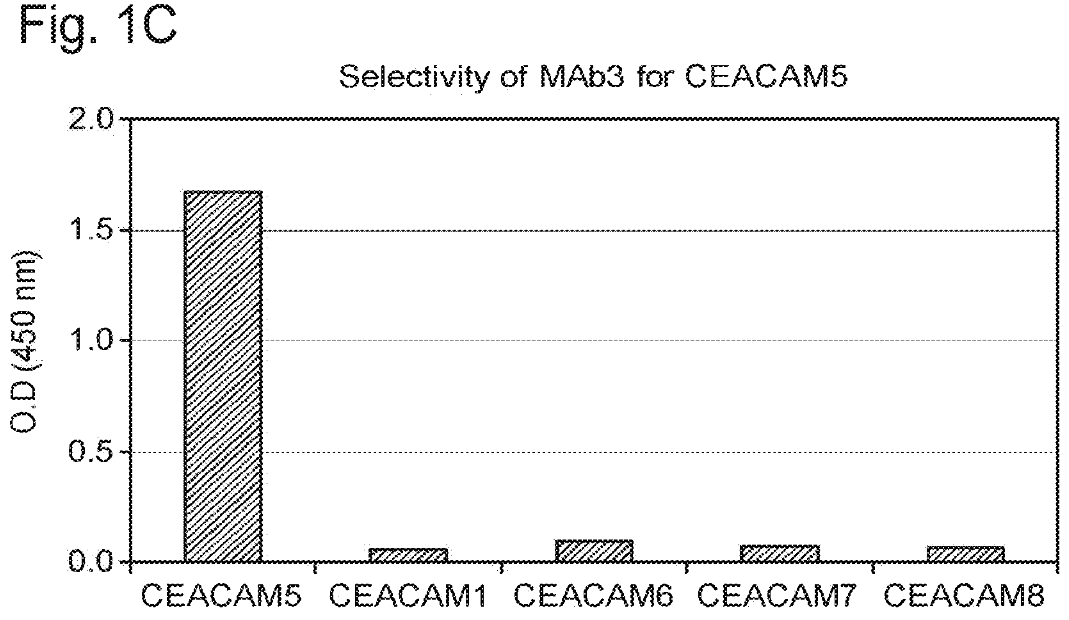
Figure 1D:
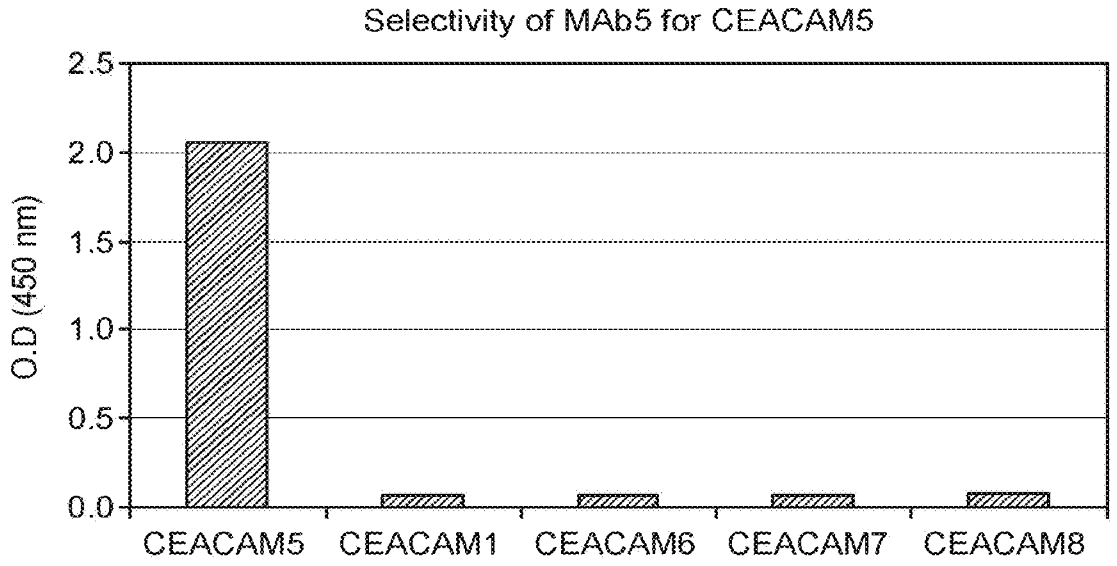
Figure 1E:
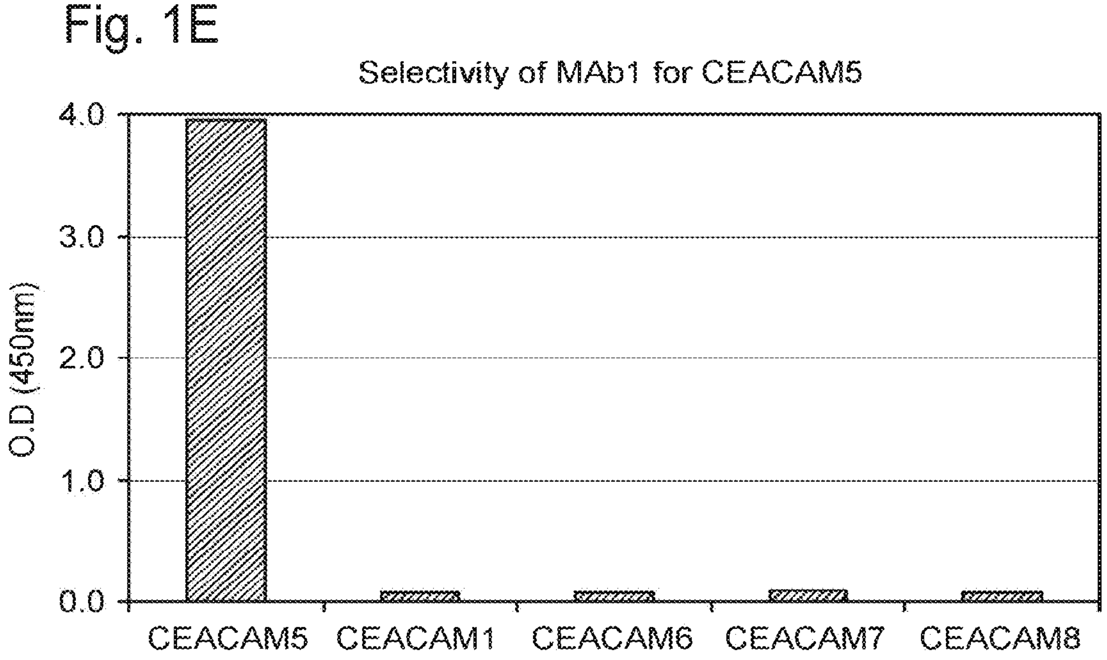
Figure 2A:
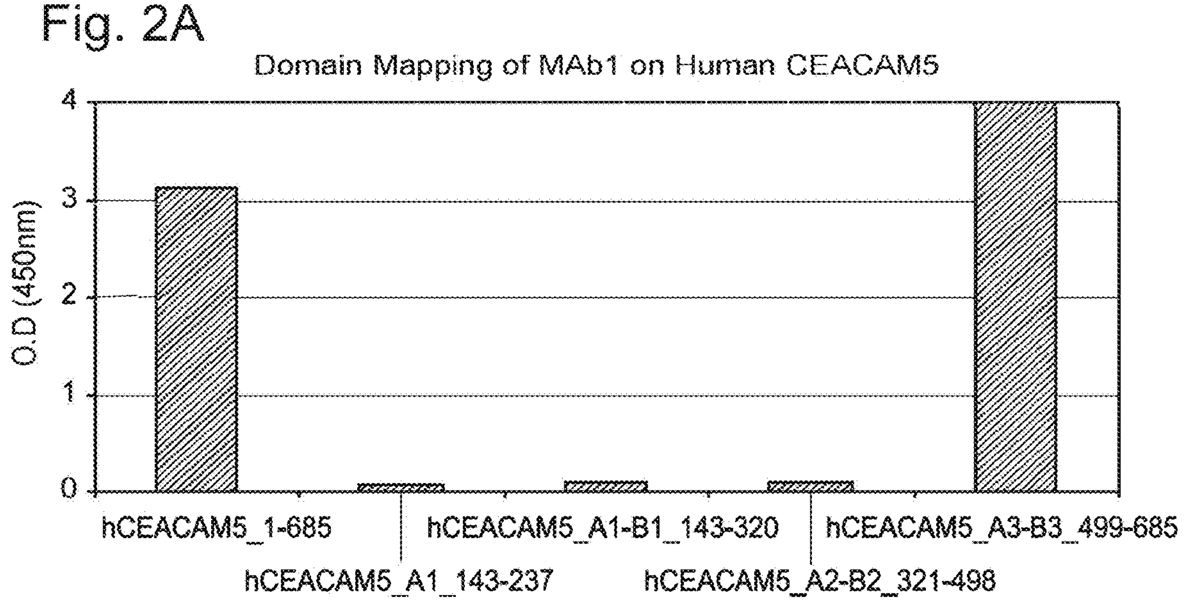
FIGS. 2A-2E: Domain mapping of the anti-CEACAM5 antibodies on human CEACAM5.
Figure 2B:
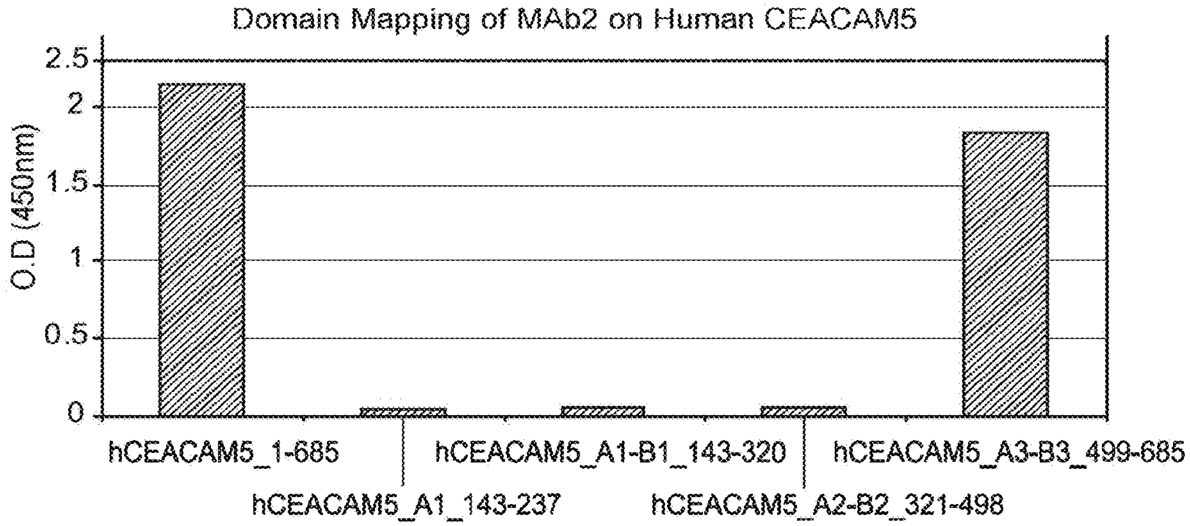
Figure 2C:
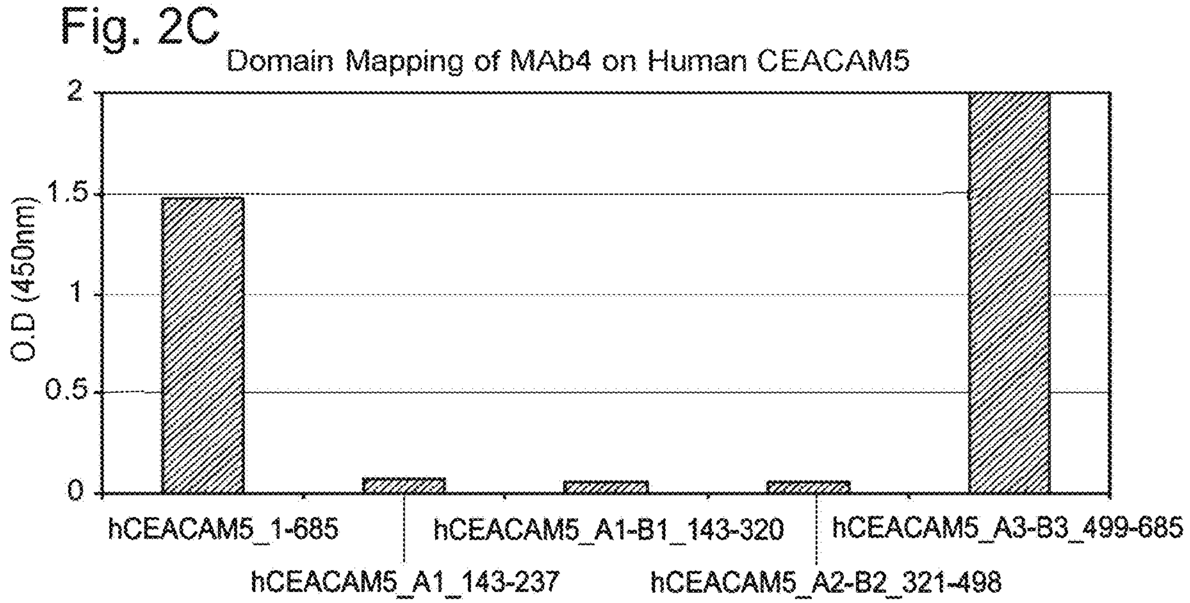
Figure 2D:
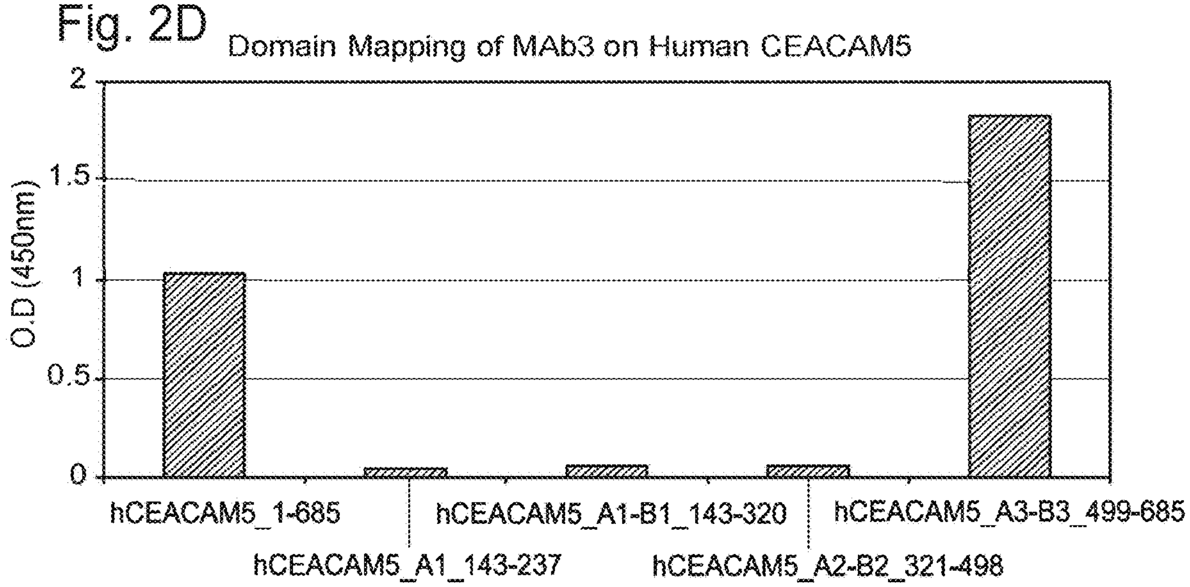
Figure 2E:
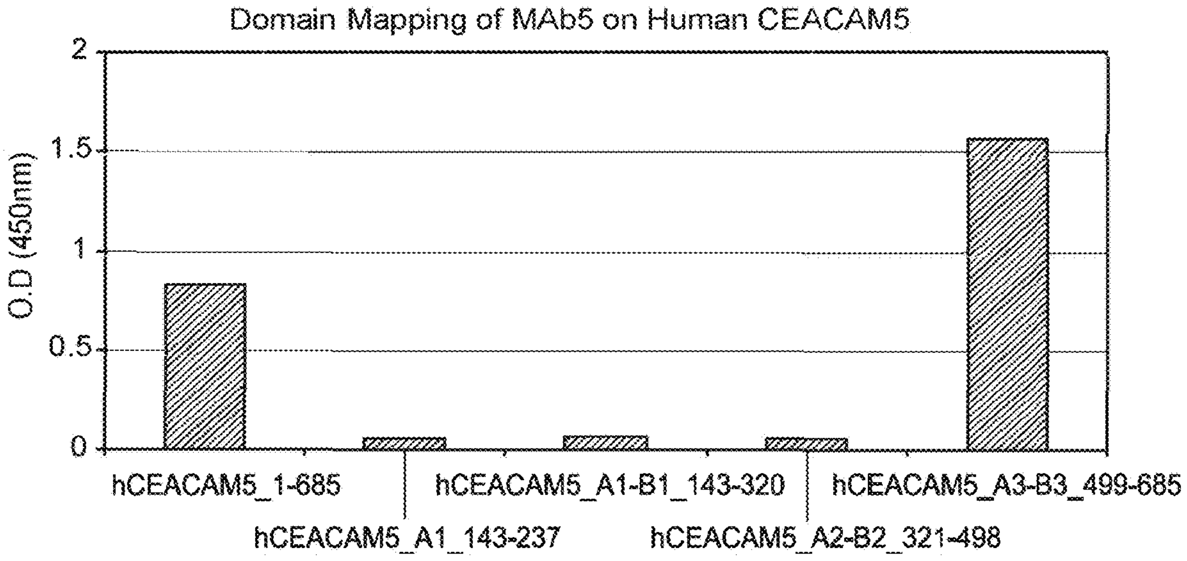
Figure 3A:
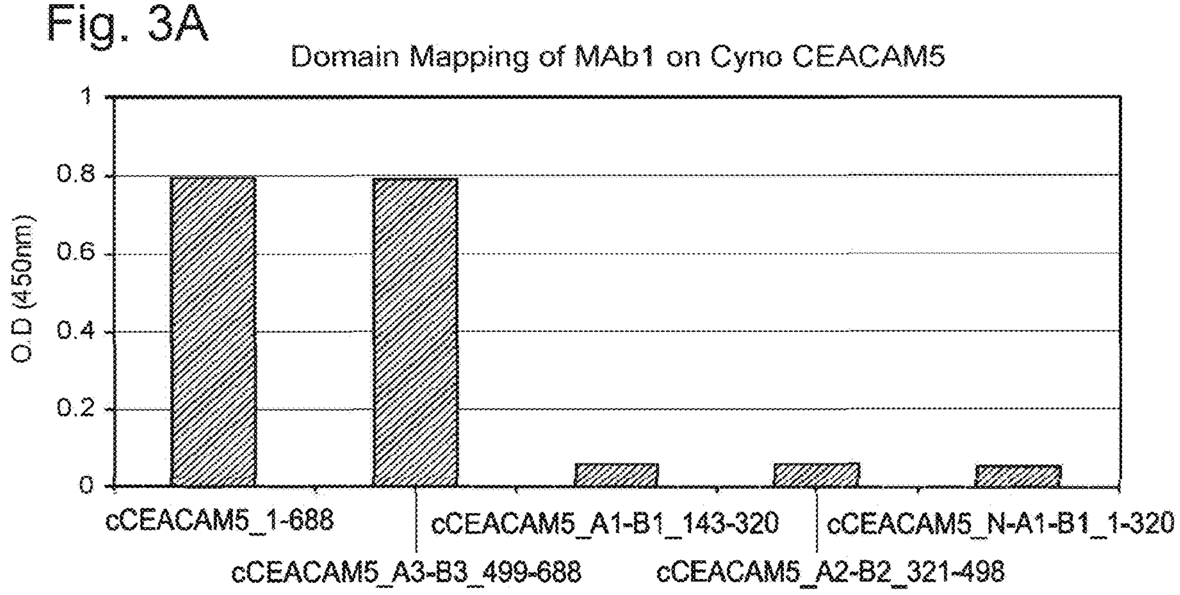
FIGS. 3A-3E: Domain mapping of the anti-CEACAM5 antibodies on cynomolgus CEACAM5.
Figure 3B:
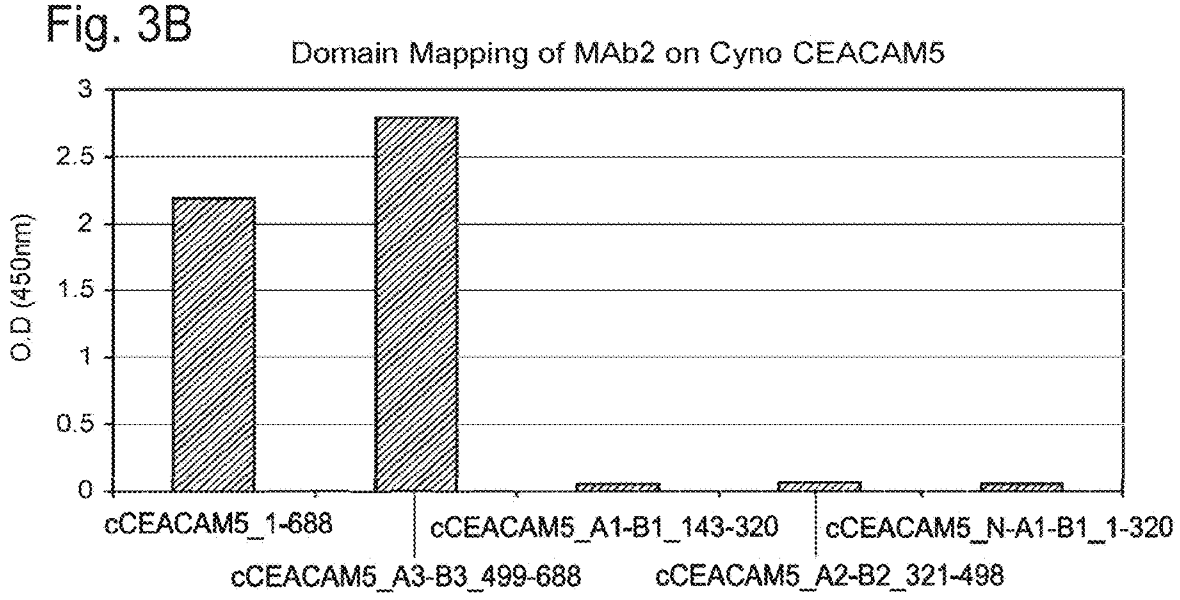
Figure 3C:
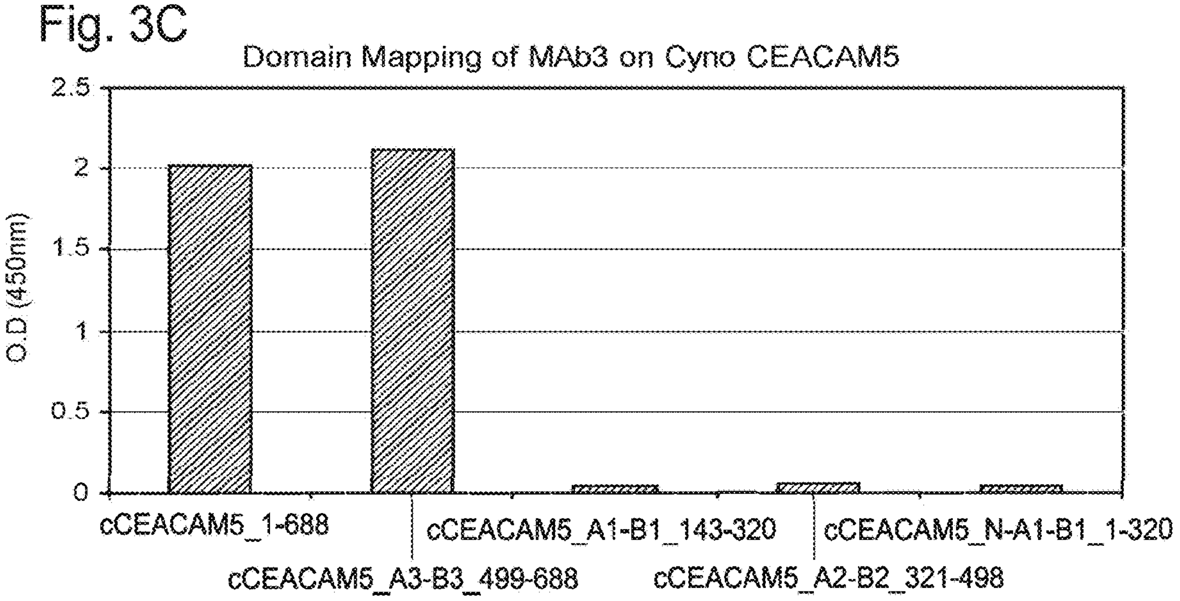
Figure 3D:
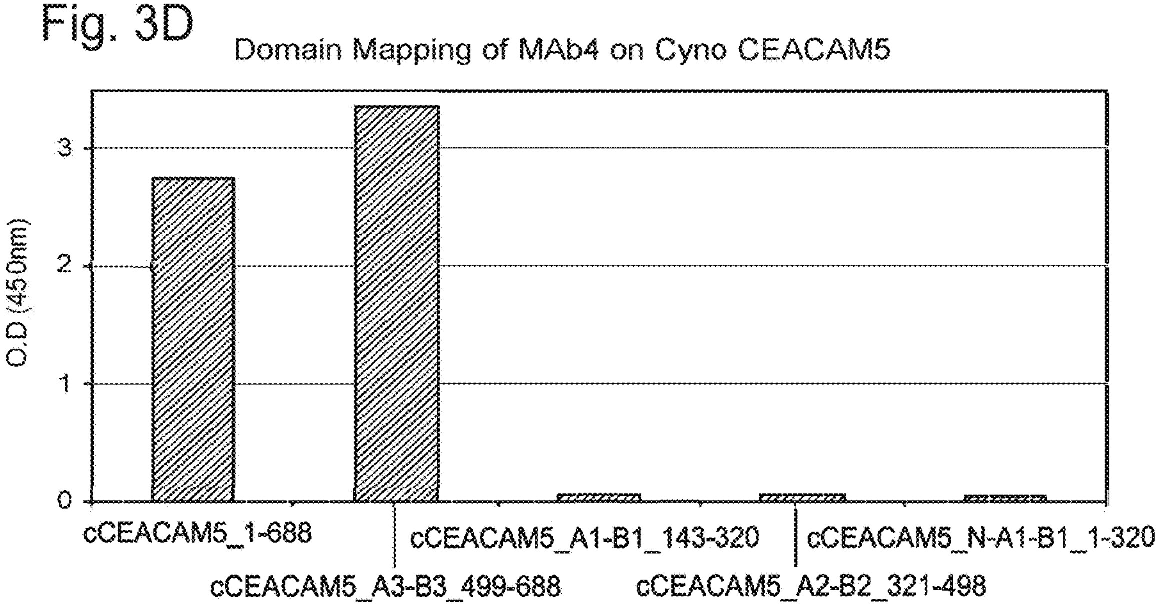
Figure 3E:
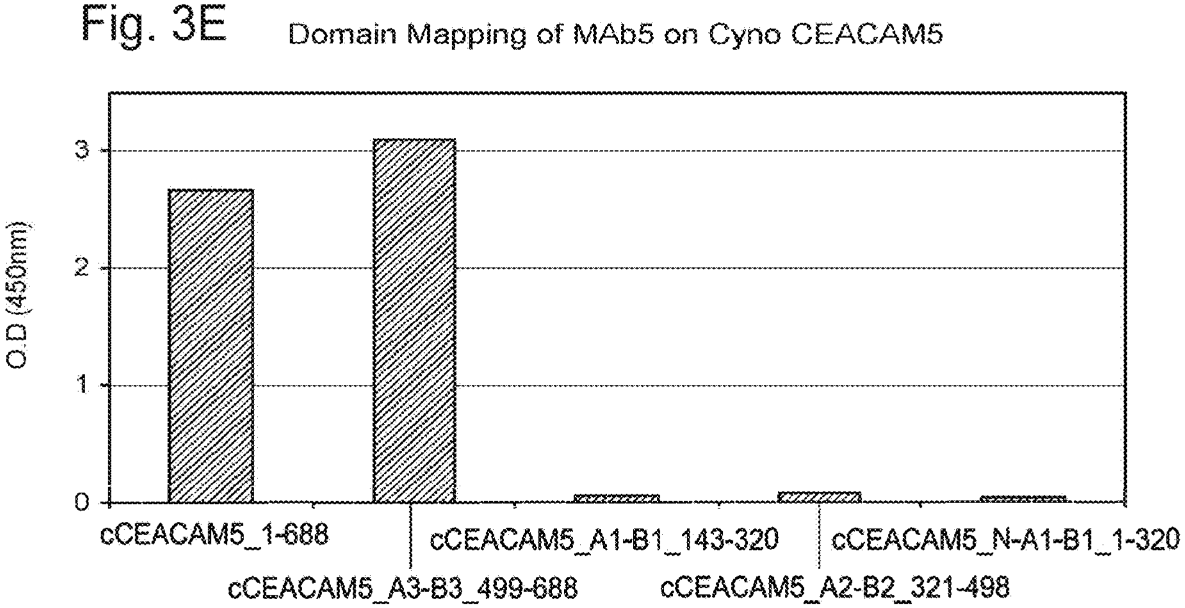

Large panel of human tumors were studied using commercial tissue array slides (FFPE format). Expression of CEACAM5 protein was located in membrane +/− cytoplasm of tumor cells (FIG. 1C, FIG. 1D). Some membrane staining was polarized at apical pole of cells in the more differentiated tumors. CEACAM5 protein was found to be expressed in:

- 89% of colon adenocarcinoma cases (194/219, intensity 2-2.5+, frequency 53-59%, AS 60-66%)
- 49% of stomach adenocarcinoma cases (95/195, intensity 2.5+, frequency 53%, AS 62%)
- 41% of lung adenocarcinoma cases (24/58, intensity 1.8-2+, frequency 50-53%, AS 54-58%)
- 79% of uterus cervix squamous carcinoma cases (11/14, intensity 2+, frequency 22%, AS 46%)
- 53% of pancreas adenocarcinoma cases (18/34, intensity 2+, frequency 23%, AS 42%)
- 37% of esophagus squamous cell carcinoma cases (23/62, intensity 2+, frequency 16%, AS 38%)
- 4% of ovary carcinoma cases (3/77, intensity 2+, frequency 43%, AS 54%)
- 11% of thyroid carcinoma cases (2/18, intensity 1.5+, frequency 63%, AS 56%)
- 25% of bladder carcinoma cases (5/20, intensity 1.5+, frequency 61%, AS 56%)
- 7% of endometrium adenocarcinoma cases (1/14, intensity 2+, frequency 50%, AS 56%)
- 11% of breast ductal carcinoma cases (2/18, intensity 1.5+, frequency 53%, AS 50%)
- 53% of cholangiocarcinoma cases (2/6, intensity 1.5+, frequency 75%, AS 50%)
- 53% of lung squamous cell carcinoma cases (31/148, intensity 1.5+, frequency 22%, AS 39%)
- 8% of prostate adenocarcinoma cases (1/13, intensity 2+, frequency 50%, AS 44%)
- 25% of skin squamous carcinoma cases (2/8, intensity 1.5+, frequency 23%, AS 39%)

Example 8.2: Tissue Cross-Reactivity of an Anti-CEACAM5 Monoclonal Antibody in Cynomolgus Monkey (*Macaca fascicularis*) and Comparison with Human Expression Pattern The extracellular protein domain of CEACAM5 from human (h) or cynomolgus monkey (c) origin have been prepared by transient expression in human embryonic kidney HEK293 cells with CEACAM5 cDNA plasmid (example 1, Table 1). Cell pellets were fixed in 10% formalin (Sigma Aldrich, USA) for 16 hours, and embedded in paraffin as a piece of tissue according to standard histological procedure.

Commercial TMA were used as human and monkey normal tissues source (Table 21).

Crossreactivity of Mab2 was shown by immunostaining in both human and monkey CEACAM5 transfected cells (membrane and cytoplasm localization).

In cynomolgus normal tissues, CEACAM5 protein expression was found in columnar absorptive epithelial cells (2/3 positive cases, median intensity 1.5+, mean frequency 55%).

In human non tumor tissues, CEACAM5 expression was also observed in columnar absorptive epithelial cells (62/64 positive cases, median intensity 2+, mean frequency 90%). In human tissues, CEACAM5 expression was observed in less extent in esophagus epithelial cells, head&neck epithelial cells, stomach gastric pit epithelial cells and uterus cervix epithelial cells.

Example 9: Antibody Drug Conjugate (Variant)

AntiCEACAM5 huMAb2-3-sulfoSPDB-DM4

Analytical Data:

MW(Ab)=147417 g/mol; MW(DM4)=780.38 g/mol $\varepsilon_{280\ nm}$(Ab)=201400; $\varepsilon_{252\ nm}$(Ab)=71451

$\varepsilon_{280\ nm}$(DM4)=5180; $\varepsilon_{252\ nm}$(DM4)=26159

Under stirring, at RT, 7.0 ml of a solution of anti-CEACAM5 huMAb2-3 (C=5.32 mg/ml in PBS pH=7.4 buffer) are introduced in a vessel, followed by 1.6 ml of DMA and 168.4 μl of nitro-sulfoSPDB linker (described in WO2009134977) solution (10 Eq-15 mM solution in DMA). Solution is slowly stirred at RT for 3 hours. An extra volume of 3.4 μl of nitro-sulfoSPDB linker solution (2.0 Eq-15 mM solution in DMA) is added. After 2 hours at RT under magnetic stirring, 2.90 ml of PBS pH 7.4 buffer, 0.407 ml of DMA and 0.322 ml of DM4 solution (15 mM solution in DMA) were sucessively added. After 1 hour at RT, and 16 hours at 5° C., crude reaction mixture is purified on HiPrep 26/10 desalting column (Sephadex G25, GE Healthcare), pre-conditioned with 1 CV of NaOH 1M, 2 CV of water and 2 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled and filtered on 0.22 μm filter.

Figure 20:
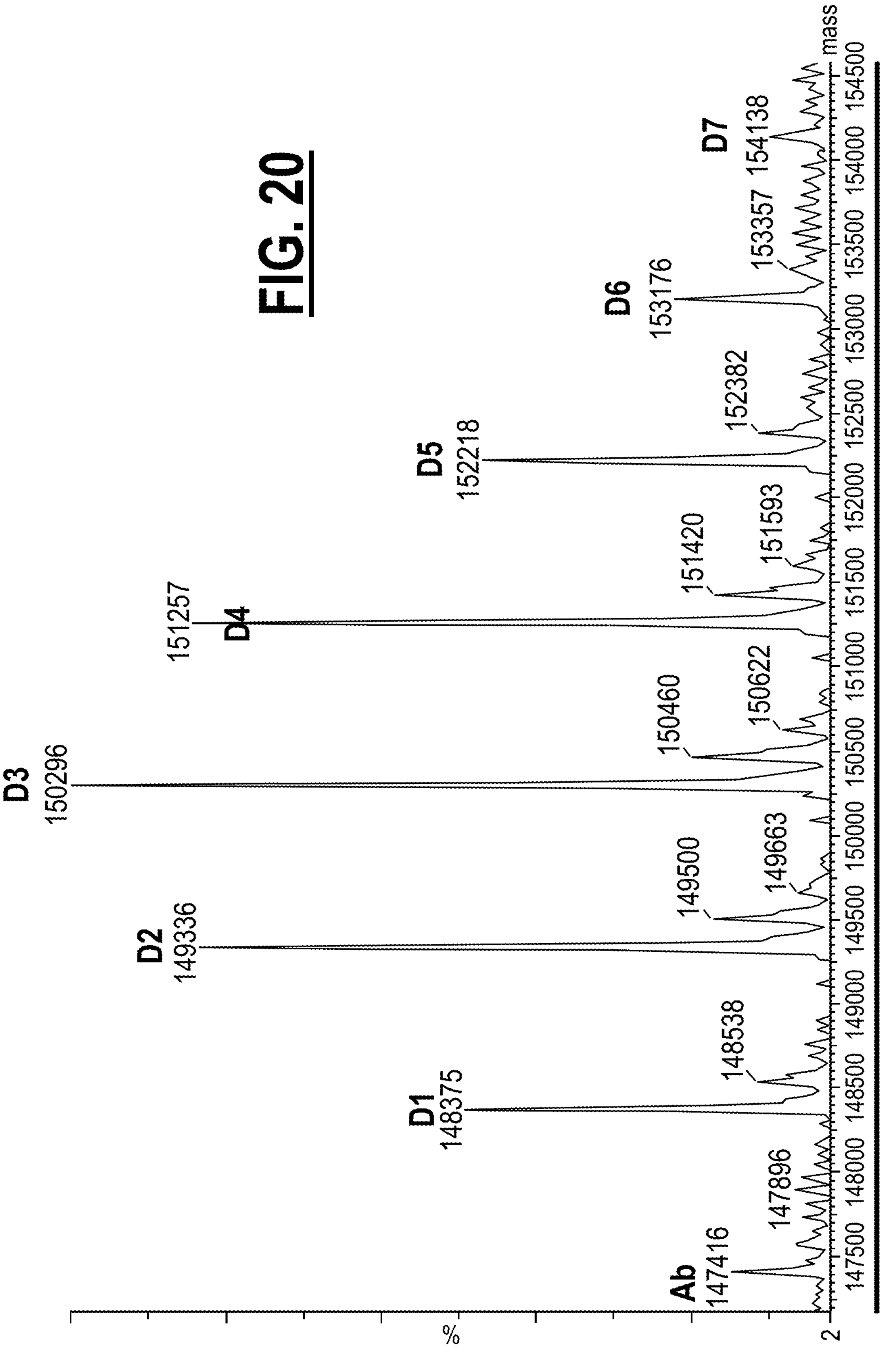
FIG. 20: HRMS analysis of huMAb2-3-sulfoSPDB-DM4.

19 ml of antiCEACAM5 huMAb2-3-sulfoSPDB-DM4 conjugate (c=1.51 mg/ml) was thus obtained as a colorless clear solution. The conjugate is then analyzed for final drug load and monomeric purity: DAR (UV)=3.4; DAR (SEC)=3.3; monomeric purity=99.8%; HRMS data: see FIG. 20.

AntiCEACAM5 huMAb2-3-SMCC-DM1

Analytical Data:

MW(Ab)=147417 g/mol; MW(DM1)=738 g/mol $\varepsilon_{280\ nm}$(Ab)=201400; $\varepsilon_{252\ nm}$(Ab)=71451

$\varepsilon_{280\ nm}$(DM1)=5180; $\varepsilon_{252}$ nm(DM1)=26159

Under stirring, at RT, 11.3 ml of a solution of anti-CEACAM5 huMAb2-3 (C=3.47 mg/ml in buffer A pH=6.5) are introduced in a vessel, followed by 0.387 ml of DMA and 178 μl of SMCC linker solution (10 Eq-15 mM solution in DMA). Solution is slowly stirred at RT for 2 hours. Crude reaction mixture is buffer exchanged on HiPrep 26/10 desalting column (Sephadex G25, GE Healthcare), pre-conditioned with 2 CV of NaOH 0.2M, 5 CV of water and 5 CV of citrate buffer (pH 5.5). Conjugate is eluted with citrate buffer (pH 5.5) and monomeric conjugate fractions are pooled and filtered on 0.22 μm filter. To this solution are sucessively added, under stirring, at RT, 0.476 ml of DMA and 0.124 ml of DM1 solution (15 mM solution in DMA). After 2 hours at RT, crude reaction mixture is purified twice on HiPrep 26/10 desalting column (Sephadex G25, GE Healthcare), pre-conditioned with 2 CV of NaOH 0.2M, 5 CV of water and 5 CV of histidine (10 mM), glycine (130 mM), sucrose (5%), pH=5.5 buffer. Conjugate is eluted with histidine (10 mM), glycine (130 mM), sucrose (5%), pH=5.5 buffer, and monomeric conjugate fractions are pooled, filtered on 0.22 μm filter.

Figure 21:
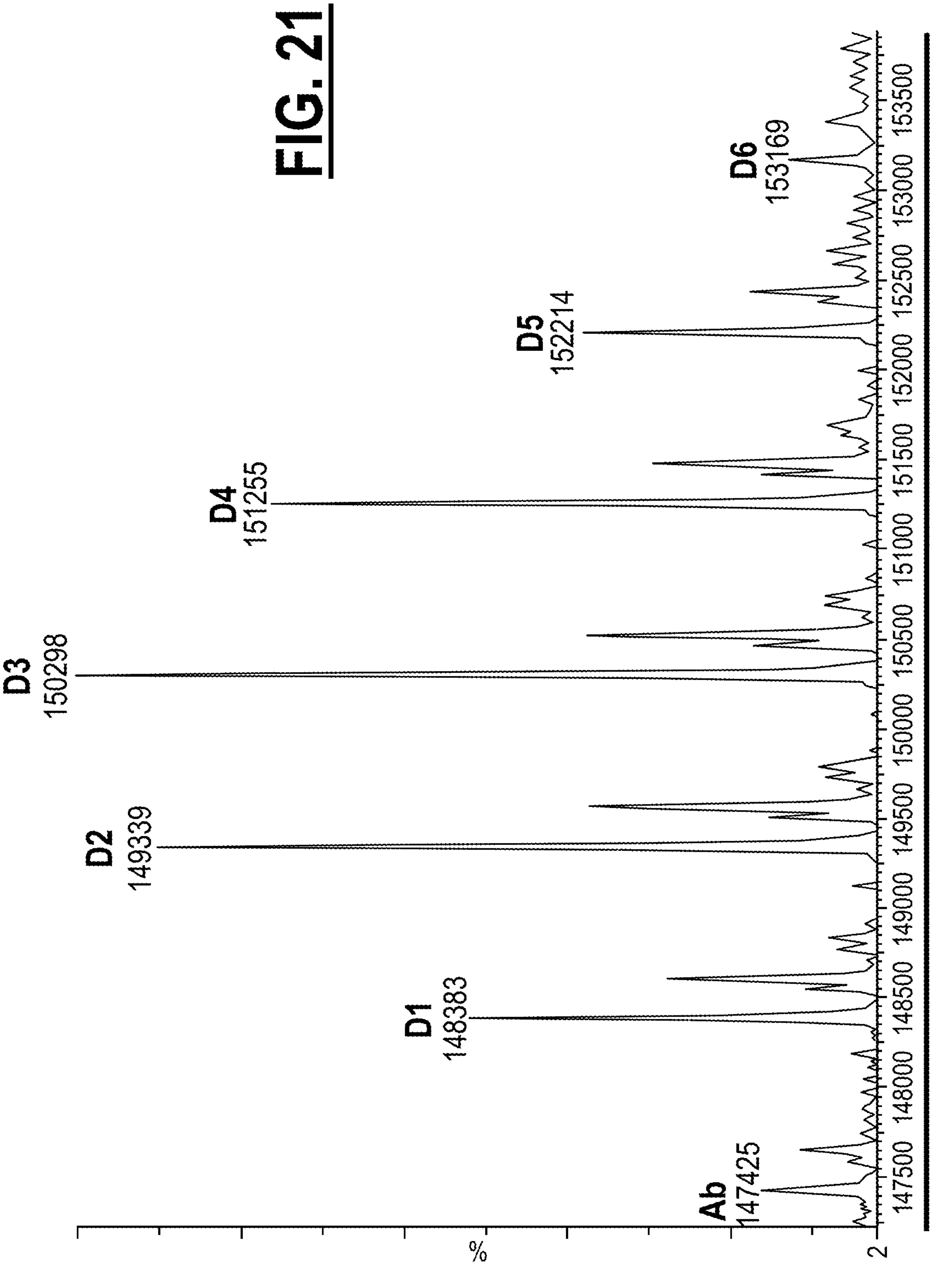
FIG. 21: HRMS analysis of huMAb2-3-SMCC-DM1.

9.5 ml of antiCEACAM5 huMAb2-3-SMCC-DM1 (c=1.73 mg/ml) was thus obtained as a colorless clear solution. The conjugate is then analyzed for final drug load and monomeric purity: DAR (UV)=2.7; DAR (SEC)=2.9; monomeric purity=99.6%; HRMS data see FIG. 21.

Example 10: Characterization of the Epitope and of the Paratope of CEACAM5-A3B3 in Complex with MAb2_VH1aVL1c Fab Using Hydrogen-Deuterium Exchange Associated with Mass Spectrometry (HDX MS)

Example 10.1: Principle of HDX MS

Amide hydrogen-deuterium exchange (HDX) associated with mass spectrometry (MS) enables identification of regions of proteins implied in conformational changes or interactions. This technique enables more specifically to identify the regions of an antigen showing, after incubation in a deuterated buffer and proteolysis, a decrease of deuterium incorporation in its form bound to an antibody compared to its free form.

The epitope belongs to these regions, the exchange of which is slowed down by the binding to the antibody. A recent article describes in detail the different steps to characterize epitopes using this approach (Zhang, Q., Willison, L. N., Tripathi, P., Sathe, S. K., Roux, K. H., Emmett, M. R., Blakney, G. T., Zhang, H. M. & Marshall, A. G. (2011). *Analytical Chemistry* 83, 7129-7136.).

Example 10.2: Materials

The variable domain coding sequences of MAb2_VH1aVL1c (SEQ ID NO:5 and SEQ ID NO:29) were cloned into a mammalian expression vector in fusion with the coding sequences of human CH1 domain (as found in papain cleaved IgG1 derived Fabs), followed by an hexa-Histidine tag or with the human Ckappa constant domain, respectively. A batch of MAb2_VH1aVL1c Fab was produced in suspension-cultivated HEK293-FS™ cells by transient transfection of two expression plasmids, encoding the two chains, complexed with 293fectin™ (Invitrogen). Culture supernatant containing the secreted protein was harvested seven days post-transfection, centrifuged and filtered on 0.22 μm membrane. The Fab was purified by affinity chromatography on IMAC (HisTrap, GE Healthcare) using imidazole gradient in PBS. Then, the pool of fractions containing the Fab was purified by size exclusion chromatography (SUPERDEX® 200, GE Healthcare) equilibrated with PBS.

His-tagged hCEACAM5-A3B3 domain (SEQ ID NO:67) was produced with HEK293-FS™ cells cultivated in flask by transient transfection of expression plasmid. Kifunensine (inhibitor of trimming glycosylation process) was added each day. Culture supernatant containing the secreted protein was harvested seven days post-transfection, centrifuged and filtered on 0.22 μm membrane. EndoH was added into supernatant up to 625 u/ml then incubated 3 h at 37° C. Deglycosylated hCEACAM5-A3B3 was purified by affinity chromatography on IMAC (HisTrap, GE Healthcare) using imidazole gradient in PBS. Then, the pool of fractions containing deglycosylated hCEACAM5-A3B3 was purified by size exclusion chromatography (SUPERDEX® 200, GE Healthcare) equilibrated with PBS. Mass spectrometry analysis of deglycosylated hCEACAM5-A3B3 showed two species (22 485 and 22 278 Da), indicating that the protein carries 7 or 8 N-acetylglucosamine residues (GlcNAc).

To build a complex, both proteins, were pooled with an excess of 1.5 moles of deglycosylated hCEACAM5-A3B3 for one mole of Fab. This excess was removed by size exclusion chromatography on SUPERDEX® 200 equilibrated with phosphate buffer saline. Fractions corresponding to complex Fab with the antigen were used for deuterium exchange study.

Example 10.3: Methods

Hydrogen/deuterium exchange (HDX) experiments were fully automated using a PAL autosampler (CTC Analytics). It enabled exchange start and quench, control of proteolysis temperature (4° C.), injection of the deuterated peptides, management of the injection and washing valves and triggering acquisition of the mass spectrometer and HPLC pumps. A Peltier-cooled box (4° C.) contained two RHEODYNE® automated valves (6-port for injection and 10-port for washing), a desalting cartridge (peptide MICRO TRAP™ from Bruker-Michrom) and a HPLC column (POROSHELL® 120 EC-C18, 1×50 mm, 2.7 μM from Agilent Technologies). Deuteration was initiated by a 5-fold dilution of CEACAM5, mAb or complex with PBS in $D_2O$. 2M GndHCl, 0.8 M TCEP, 1 M glycine was used to quench back-exchange and reduce the disulfide bridges for 2 min at 4° C.

The proteins were digested with pepsin and nepenthesin proteases and the peptides were desalted using an Agilent Technologies HPLC pump with TFA 0.03% in water at 100 μL/min. The peptides were then separated using another Agilent Technologies HPLC pump with a 15-100% B gradient in 20 min (A: TFA 0.03% in water; B: acetonitrile 90%, TFA 0.03% in water). The peptides masses were measured using an electrospray-TOF mass spectrometer (Agilent 6210).

The peptides were identified by tandem MS (MSMS), using a Bruker APEX-Q FTMS (9.4 T) and a Bruker 12 T SolariX.

Data Analysis (Bruker) and Mass Hunter (Agilent Technologies) softwares were used for data acquisitions. Data Analysis and Mascot (Matrix Science) were used to process the MSMS data. Mass Hunter and HD Examiner (Sierra Analytics) softwares were used for HDX data processing.

The HDX experiments were repeated at least three times.

Example 10.4: Results

Identification and Selection of the Peptides

The disulfide bridges remained intact during the deuteration to keep the structural information related to them. To favor proteolysis and peptides identification the bridges were reduced with TCEP after the quench step at low pH and low temperature. Using MSMS after digestion of the CEACAM5-Fab complex it was possible to identify a large number of peptides arising from the three protein chains. After the HDX experiments only the ones giving good quality signals were selected: 25, 30 and 20 peptides from the CEACAM5-A3-B3 antigen, MAb2_VH1aVL1c Fab heavy chain and MAb2_VH1aVL1c light chain, respectively. These peptides cover 89%, 77% and 68% of CEACAM5-A3-B3 antigen, MAb2_VH1aVL1c Fab heavy chain and MAb2_VH1aVL1c light chain sequences, respectively (Table 25). The uncovered regions of the Fab chains are mainly in their C-terminal parts.

TABLE 25

| sequence coverage with deuterated peptides | |
|---|---|
| Peptides | Sequence coverage |
| CEACAM5-A3-B3 | 1-18; 1-22; 1-23; 1-19: 23-35; 36-51; 35-49; 50-70; 36-43; 44-51; 36-51; 36-49; 50-67; 37-49; 44-49; 59-67; 71-89; 93-107; 108-115: 128-143; 128-142; 143-157; 130-143; 130-142; 140-143; 163-186 |
| MAb2_VH1aVL1c Fab heavy chain | 1-6; 1-20; 1-19; 1-17; 1-18; 4-18; 5-20; 5-18; 24-29; 27-32; 27-29; 34-46; 47-68; 48-68; 50-68; 69-86; 84-93; 88-98; 92-104; 100-109; 110-115; 116-136; 111-128; 149-158; 151-158; 159-177; 162-177; 167-177; 187-206 |
| MAb2_VH1aVL1c light chain | 1-11; 5-11; 22-46; 47-54; 55-70; 55-71; 72-82; 87-104; 105-115; 117-132; 124-131; 127-145; 133-144; 136-145; 136-143; 136-144; 143-161; 144-151; 146-151 |

All the 8 asparagine residues that are potential sites of glycosylations were identified within several peptides with an GlcNAc remaining from the endo H deglycosylation. In particular, N114 was found in peptide 108-115. In first experiments (not used for HDX), N166 was found in both forms (with and without GlcNAc). It might explain the heterogeneity observed in the mass spectrum of CEACAM5-A3B3 after deglycosylation, corresponding to 7 and 8 GlcNAc.

Epitope and Paratope Identification

The free antigen, the free Fab and their complex were deuterated during 2 min or 20 min at 4° C. or 20 min at room temperature (26° C.). Considering the exchange kinetics of amide hydrogens with temperature (about 3-fold exchange increase with 10° C.) the last condition is equivalent to 200 min deuteration at 4° C.

Epitope

The kinetics of deuterium incorporation for the 25 selected peptides of CEACAM5-A3B3 were compared when the antigen was deuterated in the free form and when it was in complex with the Fab. Several peptides did not show any significant HDX difference (ΔHDX) between both states. In contrast some of them (108-115 and 128-143), showed significant ΔHDX. The second region was covered with 5 different peptides: 128-142, 128-143, 130-142, 130-143 and 140-143 showing 13-15±2% (up to 1.6±0.2 D) ΔHDX after 2 min deuteration.

Comparing 128-142 with 130-142 and 128-143 with 130-143, we did not measure any significant ΔHDX change in each case (1.3-1.4 D for the first two peptides and 1.6 for the last two, after 2 min deuteration), meaning that the amides W129 and R130 are likely not involved in the epitope. In contrast, comparing 128-142 with 128-143 and 130-142 with 130-143, we measured a small ΔHDX change (about 0.2 D), meaning that the amide F143 is involved. The ΔHDX in peptide 140-143 (about 0.3 D) indicates that amides V141 or L142 might be also involved. Within the 9 amides from 1131 to Q140, several of them are involved in the epitope (about 1 ΔHDX shared on average).

These differences of deuterium incorporation indicate that the epitope belongs in particular to regions (amides), i.e. peptides of sequences SGANLNL (SEQ ID NO: 76) and INGIPQQHTQVLF (SEQ ID NO: 77).

Paratope

The kinetics of deuterium incorporation for the 30 selected peptides of the Fab heavy chain were compared when the Fab was deuterated in the free form and when it was in complex with the antigen. Almost all peptides did not show any significant ΔHDX between both states. Only one peptide (100-109) presented a ΔHDX after 200 min deuteration: 11±2% (0.7±0.2 D). The region (amides) 101-109 of MAb2_VH1aVL1c Fab heavy chain is implied in the paratope.

The kinetics of deuterium incorporation for the 20 selected peptides of the Fab light chain were compared when the Fab was deuterated in the free form and when it was in complex with the antigen. Almost all peptides did not show any significant ΔHDX between both states. Only two peptides (47-54 and 87-104) presented a difference. After 20 min deuteration, it was 10±2% (0.6±0.2 D) for the first one and 5±2% (0.9±0.2 D) for the second one, respectively. The regions 48-54 and 88-104 of MAb2_VH1aVL1c light chain are involved in the paratope.

The invention claimed is:

1. A method of treating a patient comprising administering to the patient an antibody or antigen binding fragment thereof which binds to human CEACAM5 (hCEACAM5) protein, wherein the patient has a hCEACAM5-expressing cancer, and wherein the antibody or antigen binding fragment thereof comprises:

a) a CDR1-H comprising an amino acid sequence of SEQ ID NO:1; a CDR2-H comprising an amino acid sequence of SEQ ID NO:2; a CDR3-H comprising an amino acid sequence of SEQ ID NO:3; a CDR1-L comprising an amino acid sequence of SEQ ID NO:4; a CDR2-L comprising an amino acid sequence of SAS; and a CDR3-L comprising an amino acid sequence of SEQ ID NO:6; or b) a CDR1-H comprising an amino acid sequence of SEQ ID NO:7; a CDR2-H comprising an amino acid sequence of SEQ ID NO:8; a CDR3-H comprising an amino acid sequence of SEQ ID NO:9; a CDR1-L comprising an amino acid sequence of SEQ ID NO:10; a CDR2-L comprising an amino acid sequence of NTK or NTR; and a CDR3-L comprising an amino acid sequence of SEQ ID NO:12; or c) a CDR1-H comprising an amino acid sequence of SEQ ID NO:13; a CDR2-H comprising an amino acid sequence of SEQ ID NO:14; a CDR3-H comprising an amino acid sequence of SEQ ID NO:15; a CDR1-L comprising an amino acid sequence of SEQ ID NO:16; a CDR2-L comprising an amino acid sequence SAS; and a CDR3-L comprising an amino acid sequence of-SEQ ID NO:18; or d) a CDR1-H comprising an amino acid sequence of SEQ ID NO:19; a CDR2-H comprising an amino acid sequence of SEQ ID NO:20; a CDR3-H comprising an amino acid sequence of SEQ ID NO:21; a CDR1-L comprising an amino acid sequence of SEQ ID NO:22; a CDR2-L comprising an amino acid sequence of NAK; and a CDR3-L comprising an amino acid sequence of SEQID NO:24; or e) a CDR1-H comprising an amino acid sequence of SEQ ID NO:25; a CDR2-H comprising an amino acid sequence of SEQ ID NO:26; a CDR3-H comprising an amino acid sequence of SEQ ID NO:27; a CDR1-L comprising an amino acid sequence of SEQ ID NO:28; a CDR2-L of sequence NAK; and a CDR3-L comprising an amino acid sequence of SEQ ID NO:30.

2. The method according to claim 1, wherein the cancer is selected from the group consisting of colorectal, stomach, lung, uterus, cervix, pancreas, esophagus, ovary, thyroid, bladder, endometrium, breast, liver, prostate and skin cancer.

3. The method according to claim 1, wherein the cancer is selected from the group consisting of stomach, lung, pancreas, prostate and colorectal cancer.

4. The method according to claim 1, wherein the antibody or antigen binding fragment thereof comprises a heavy chain variable domain comprising an amino acid sequence of sequence SEQ ID NO:33 and a light chain variable domain comprising an amino acid sequence of SEQ ID NO:34.

5. The method according to claim 1, wherein the antibody or antigen binding fragment thereof is a chimeric or a humanized antibody.

6. The method according to claim 1, wherein the antibody comprises a heavy chain comprising an amino acid sequence of SEQ ID NO:43 and a light chain comprising an amino acid sequence of SEQ ID NO:44.

7. The method according to claim 1, wherein the antibody or antigen binding fragment thereof comprises:

a) a heavy chain variable domain comprising an amino acid sequence of SEQ ID NO:51 and a light chain variable domain comprising an amino acid sequence of SEQ ID NO:17; or b) a heavy chain variable domain comprising an amino acid sequence of SEQ ID NO:5 and a light chain variable domain comprising an amino acid sequence of SEQ ID NO:23; or c) a heavy chain variable domain comprising an amino acid sequence of SEQ ID NO:5 and a light chain variable domain comprising an amino acid sequence of SEQ ID NO:29; or d) a heavy chain variable domain comprising an amino acid sequence of SEQ ID NO:51 and a light chain variable domain comprising an amino acid sequence of SEQ ID NO:55; or e) a heavy chain variable domain comprising an amino acid sequence of SEQ ID NO:74 and a light chain variable domain comprising an amino acid sequence of SEQ ID NO:75.

8. The method according to claim 1, wherein the antibody comprises:

a) a heavy chain comprising an amino acid sequence of SEQ ID NO:87 and a light chain comprising an amino acid of SEQ ID NO:88; or b) a heavy chain comprising an amino acid sequence of SEQ ID NO:89 and a light chain comprising an amino acid of SEQ ID NO:90.

9. A method of treating a patient comprising administering an immunoconjugate to the patient, wherein the immunoconjugate comprises an antibody or antigen binding fragment thereof linked to at least one growth inhibitory agent, wherein the patient has a hCEACAM5-expressing cancer, and wherein the antibody or antigen binding fragment thereof binds to human CEACAM5 protein and comprises:

a) a CDR1-H comprising an amino acid sequence of SEQ ID NO:1; a CDR2-H comprising an amino acid sequence of SEQ ID NO:2; a CDR3-H comprising an amino acid sequence of SEQ ID NO:3; a CDR1-L comprising an amino acid sequence of SEQ ID NO:4; a CDR2-L comprising an amino acid sequence of SAS; and a CDR3-L comprising an amino acid sequence of SEQ ID NO:6; or b) a CDR1-H comprising an amino acid sequence of SEQ ID NO:7; a CDR2-H comprising an amino acid sequence of SEQ ID NO:8; a CDR3-H comprising an amino acid sequence of SEQ ID NO:9; a CDR1-L comprising an amino acid sequence of SEQ ID NO:10; a CDR2-L comprising an amino acid sequence of NTK or NTR; and a CDR3-L comprising an amino acid sequence of SEQ ID NO:12; or c) a CDR1-H comprising an amino acid sequence of SEQ ID NO:13; a CDR2-H comprising an amino acid sequence of SEQ ID NO:14; a CDR3-H comprising an amino acid sequence of SEQ ID NO:15; a CDR1-L comprising an amino acid sequence of SEQ ID NO:16; a CDR2-L comprising an amino acid sequence SAS; and a CDR3-L comprising an amino acid sequence of-SEQ ID NO:18; or d) a CDR1-H comprising an amino acid sequence of SEQ ID NO:19; a CDR2-H comprising an amino acid sequence of SEQ ID NO:20; a CDR3-H comprising an amino acid sequence of SEQ ID NO:21; a CDR1-L comprising an amino acid sequence of SEQ ID NO:22; a CDR2-L comprising an amino acid sequence of NAK; and a CDR3-L comprising an amino acid sequence of SEQ ID NO:24; or e) a CDR1-H comprising an amino acid sequence of SEQ ID NO:25; a CDR2-H comprising an amino acid sequence of SEQ ID NO:26; a CDR3-H comprising an amino acid sequence of SEQ ID NO:27; a CDR1-L comprising an amino acid sequence of SEQ ID NO:28; a CDR2-L of sequence NAK; and a CDR3-L comprising an amino acid sequence of SEQ ID NO:30.

10. The method according to claim 9, wherein the cancer is selected from the group consisting of colorectal, stomach, lung, uterus, cervix, pancreas, esophagus, ovary, thyroid, bladder, endometrium, breast, liver, prostate, and skin cancer.

11. The method according to claim 9, wherein the cancer is selected from the group consisting of stomach, lung, pancreas, prostate and colorectal cancer.

12. The method according to claim 9, wherein the at least one growth inhibitory agent is a cytotoxic agent or a radioactive isotope.

13. The method according to claim 12, wherein the at least one growth inhibitory agent is selected from the group consisting of chemotherapeutic agents, enzymes, antibiotics, toxins, taxoids, vincas, taxanes, maytansinoid, maytansinoid analogs, tomaymycin derivatives, pyrrolobenzodiazepine derivatives, cryptophycin derivatives, leptomycin derivatives, auristatin analogs, dolastatin analogs, topoisomerase II inhibitors, DNA alkylating agents, anti-tubulin agents, and CC-1065 analogs.

14. The method according to claim 13, wherein the at least one growth inhibitory agent is (N2'-deacetyl-N2'-(3-mercapto-1-oxopropyl)-maytansine) (DM1) or N2'-deacetyl-N-2'(4-methyl-4-mercapto-1-oxopentyl)-maytansine (DM4).

15. The method according to claim 9, wherein the antibody is covalently attached via a cleavable or non-cleavable linker to the at least one growth inhibitory agent.

16. The method according to claim 15, wherein the linker is selected from the group consisting of N-succinimidyl pyridyldithiobutyrate (SPDB), 4-(Pyridin-2-yldisulfanyl)-2-sulfo-butyric acid (sulfo-SPDB), and succinimidyl (N-maleimidomethyl) cyclohexane-1-carboxylate (SMCC).

17. The method according to claim 16, wherein the at least one growth inhibitory agent is DM4 and the linker is SPDB.

18. The method according to claim 9, wherein the antibody or antigen binding fragment thereof comprises:

a) a heavy chain variable domain comprising an amino acid sequence of SEQ ID NO:51 and a light chain variable domain comprising an amino acid sequence of SEQ ID NO:17; or b) a heavy chain variable domain comprising an amino acid sequence of SEQ ID NO:5 and a light chain variable domain comprising an amino acid sequence of SEQ ID NO:23; or c) a heavy chain variable domain comprising an amino acid sequence of SEQ ID NO:5 and a light chain variable domain comprising an amino acid sequence of SEQ ID NO:29; or d) a heavy chain variable domain comprising an amino acid sequence of SEQ ID NO:51 and a light chain variable domain comprising an amino acid sequence of SEQ ID NO:55; or e) a heavy chain variable domain comprising an amino acid sequence of SEQ ID NO:74 and a light chain variable domain comprising an amino acid sequence of SEQ ID NO:75.

19. The method according to claim 9, wherein the antibody comprises:

a) a heavy chain comprising an amino acid sequence of SEQ ID NO:87 and a light chain comprising an amino acid of SEQ ID NO:88; or b) a heavy chain comprising an amino acid sequence of SEQ ID NO:89 and a light chain comprising an amino acid of SEQ ID NO:90.

20. The method according to claim 9, wherein the immunoconjugate is characterized by a drug-to-antibody ratio (DAR) ranging from 1 to 10.

21. A method of treating a patient comprising administering an immunoconjugate to the patient, wherein the immunoconjugate comprises an antibody linked to at least one growth inhibitory agent, wherein the patient has a hCEACAM5-expressing cancer, wherein the antibody binds to human CEACAM5 protein and comprises a heavy chain comprising the sequence of SEQ ID NO:87 and a light chain comprising the sequence of SEQ ID NO:88, wherein the antibody is covalently linked via N-succinimidyl pyridyldithiobutyrate (SPDB) to N2'-deacetyl-N-2'(4-methyl-4-mercapto-1-oxopentyl)-maytansine (DM4), and wherein the hCEACAM5-expressing cancer is selected from the group consisting of stomach, lung, pancreas, prostate and colorectal cancer.

* * * * *